(12) United States Patent
Parmee et al.

(10) Patent No.: US 7,572,922 B2
(45) Date of Patent: Aug. 11, 2009

(54) SUBSTITUTED PYRAZOLES, COMPOSITIONS CONTAINING SUCH COMPOUNDS AND METHODS OF USE

(75) Inventors: Emma Parmee, Scotch Plains, NJ (US); Subharekha Raghavan, Teaneck, NJ (US); Teresa Beeson, Pasadena, CA (US); Dong-Ming Shen, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 537 days.

(21) Appl. No.: 10/543,290

(22) PCT Filed: Jan. 23, 2004

(86) PCT No.: PCT/US2004/001927

§ 371 (c)(1),
(2), (4) Date: Jul. 25, 2005

(87) PCT Pub. No.: WO2004/069158

PCT Pub. Date: Aug. 19, 2004

(65) Prior Publication Data

US 2006/0084681 A1    Apr. 20, 2006

Related U.S. Application Data

(60) Provisional application No. 60/442,828, filed on Jan. 27, 2003.

(51) Int. Cl.
  C07D 257/00 (2006.01)
  C07D 231/10 (2006.01)
  A01N 43/64 (2006.01)
  A01N 43/56 (2006.01)

(52) U.S. Cl. .................. 548/377.1; 548/251; 514/381; 514/406

(58) Field of Classification Search .................. None
  See application file for complete search history.

(56) References Cited

U.S. PATENT DOCUMENTS

| | | | |
|---|---|---|---|
| 5,670,503 | A | 9/1997 | Kawai et al. |
| 5,776,954 | A | 7/1998 | de Laszlo et al. |
| 6,057,335 | A | 5/2000 | Fukami et al. |
| 6,218,431 | B1 | 4/2001 | Schoen et al. |
| 6,420,427 | B1 | 7/2002 | Takahashi et al. |
| 6,440,963 | B1 | 8/2002 | Leonardi et al. |
| 6,503,949 | B1 | 1/2003 | Lau et al. |
| 6,562,807 | B2 | 5/2003 | Jorgensen et al. |
| 6,613,942 | B1 | 9/2003 | Ling et al. |
| 6,762,318 | B2 | 7/2004 | Kodra et al. |
| 6,790,810 | B2 | 9/2004 | Yanagi et al. |
| 6,881,746 | B2 | 4/2005 | Lau et al. |
| 2005/0171196 | A1 | 8/2005 | Fujii et al. |
| 2005/0272794 | A1 | 12/2005 | Parmee et al. |
| 2006/0084681 | A1 | 4/2006 | Parmee et al. |
| 2007/0088070 | A1 | 4/2007 | Parmee et al. |

FOREIGN PATENT DOCUMENTS

| | | |
|---|---|---|
| EP | 1 400 243 A1 | 3/2004 |
| RU | 2124517 | 1/1999 |
| RU | 2001110360 | 3/2003 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/47509 | 10/1998 |
| WO | WO 99/32448 | 7/1999 |
| WO | WO 00/15229 | 3/2000 |
| WO | WO 00/39088 | 7/2000 |
| WO | WO 00/69810 | 11/2000 |
| WO | WO 02/00612 | 1/2002 |
| WO | WO 02/08188 A1 | 1/2002 |
| WO | WO 02/40444 A1 | 5/2002 |
| WO | WO 03/048109 | 6/2003 |
| WO | WO 03 051357 A1 | 6/2003 |
| WO | WO 03/053938 A1 | 7/2003 |
| WO | WO 03/064404 | 8/2003 |
| WO | WO 03/097619 | 11/2003 |
| WO | WO 2004/002480 | 1/2004 |
| WO | WO 2004/009158 | 1/2004 |
| WO | WO 2004/050039 A2 | 6/2004 |
| WO | WO 2004/069158 A2 | 8/2004 |
| WO | WO 2004/092146 A2 | 10/2004 |
| WO | WO 2004/100875 A2 | 11/2004 |
| WO | WO 2005/121097 A2 | 12/2005 |

OTHER PUBLICATIONS

Yellin et al, caplus an 1983:72126.*
Colarusso et al., caplus an 2002:777963 (2002).*
M. J. Burk et al., "Catalytic Asymmetric Reductive Amination of Keytones via Highly Enantioselective Hydrogenation ofth C=N Double Bond", Tetrahedron, vol. 50, No. 15, pp. 4399-4428 (1994).
Kurukulasuriya et al., "Biaryl amide glucagon receptor antagonists", Bioorganic & Medicinal Chemistry Letter, vol. 114, pp. 2047-2050 (2004).
Merck & Co., Inc., U. S. Appl. No. 60/442,828, filed Jan. 27, 2003.
Merck & Co., Inc., U. S. Appl. No. 60/577,116, filed Jun. 4, 2004.

* cited by examiner

*Primary Examiner*—Kamal A Saeed
*Assistant Examiner*—Sun Jae Y Loewe
(74) *Attorney, Agent, or Firm*—Richard C. Billups; Catherine D. Fitch

(57) ABSTRACT

The present invention relates to substituted pyrazoles, compositions containing such compounds and methods of treatment The compounds are glucagon receptor antagonists and thus are useful for treating, preventing or delaying the onset of type 2 diabetes mellitus.

16 Claims, No Drawings

SUBSTITUTED PYRAZOLES, COMPOSITIONS CONTAINING SUCH COMPOUNDS AND METHODS OF USE

CROSS REFERENCE TO RELATED APPLICATIONS

This application is the National Stage of International Application No. PCT/US04/001927, filed 23 Jan. 2004, which claims the benefit under 35 U.S.C. 119(e) of U.S. Provisional Application No. 60/442,828, filed 27 Jan. 2003.

BACKGROUND OF THE INVENTION

The present invention relates to substituted pyrazole derivatives, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level ≧126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure≧130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

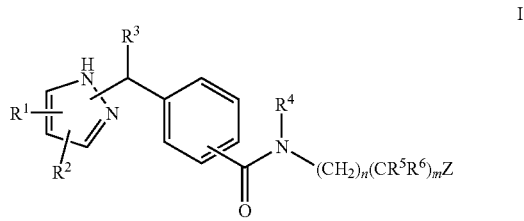

I or a pharmaceutically acceptable salt or solvate thereof, wherein:

$R^1$ is selected from the group consisting of:

(a) $C_{1-10}$alkyl, $C_{2-10}$alkenyl or $C_{2-10}$alkynyl optionally substituted with: (1) 1-5 halo groups up to a perhaloalkyl group; (2) 1 oxo group; (3) 1-2 OH groups; (4) 1-2 $C_{1-10}$alkoxy groups, each optionally substituted with: up to five halo or a perhaloalkoxy, 1 OH or $CO_2R^8$ group; (5) 1 $CO_2R^5$ or $S(O)_pR^7$; (6) 1-2 Aryl, Hetcy or HAR groups, each optionally substituted as follows: (i) 1-5 halo groups, (ii) 1OH, $CO_2R^5$, CN, $S(O)_pR^7$, $NO_2$ or $C(O)NR^9R^{10}$ group, (iii) 1-2 $C_{1-10}$alkyl or alkoxy groups, each optionally substituted with: 1-5 halo, up to perhaloalkyl, and 1-2 OH or $CO_2R^8$ groups; and (iv) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^8$ groups; (7) —$NR^8$—C(O)—$NR^9R^{10}$; (8) —$NR^8$—$CO_2R^{11}$; (9) —$NR^8$—C(O)$R^{11}$; (10) —$NR^9R^{10}$; (11) —$NR^8SO_2R^{11}$; (12) —$SO_2$—$NR^9R^{10}$; (13) —$C(O)NR^9R^{10}$ and (14) —OC(O)—$NR^9R^{10}$;

(b) Aryl, HAR or Hetcy, each optionally substituted as follows: (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 OH, phenyl, $CO_2R^8$, CN or $S(O)_pR^7$ groups; (3) 1-2 Aryl, HAR or Hetcy groups, each optionally substituted as follows: (i) 1-3 halo groups; (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 OH, phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

said Aryl, HAR or Hetcy group b) being further optionally substituted on carbon by a group selected from the group consisting of; (4) 1-5 halo groups; (5) 1-2 OH groups; (6) 1 $S(O)_pR^7$, $NO_2$ or CN group; (7) 1-2 $CO_2R^8$; (8) —$NR^8$—C(O)—$NR^9R^{10}$; (9) —$NR^8$—$CO_2R^{11}$; (10) —$NR^8$—C(O)$R^{11}$; (11) —$NR^9R^{10}$; (12)

—NR⁸SO₂R¹¹; (13) —SO₂—NR⁹R¹⁰; (14) —C(O)NR⁹R¹⁰ and (15) —OC(O)—NR⁹R¹⁰;

and when R¹ represents heterocyclyl containing a nitrogen atom, said nitrogen atom is optionally substituted with a member selected from the group consisting of: (a) —C(O)NR⁹R¹⁰; (b) —CO₂R¹¹; (c) —C(O)R¹¹; and (d) —SO₂R¹¹;

R² is H or R¹ as defined above;

R³ and R⁴ are H or $C_{1-10}$alkyl;

R⁵ represents H or F;

R⁶ represents H, OH, F or $C_{1-3}$alkyl, or R⁵ and R⁶ are taken in combination and represent oxo;

R⁷ represents a member selected from the group consisting of: $C_{1-10}$alkyl, Aryl or Ar—$C_{1-10}$alkyl, R⁸ is H, $C_{1-10}$alkyl, optionally substituted with phenyl, OH, $OC_{1-6}$alkyl, $CO_2H$, $CO_2C_{1-6}$alkyl and 1-3 halo groups;

R⁹ is H or $C_{1-10}$alkyl;

R¹⁰ is H or is independently selected from: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar—$C_{1-6}$alkyl, each optionally substituted with 1-5 halos and 1-3 members selected from the group consisting of: CN, OH, $C_{1-10}$alkyl and $OC_{1-10}$alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

R¹¹ is independently selected from the group consisting of: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar-$_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;

m is an integer selected from 0, 1 and 2;

n is an integer selected from 0 to 6;

p is an integer selected from 0, 1 and 2, and when at least one of m and n is other than 0, Z is selected from $CO_2Re$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

The present invention in its broadest aspect is directed to a compound represented by formula I:

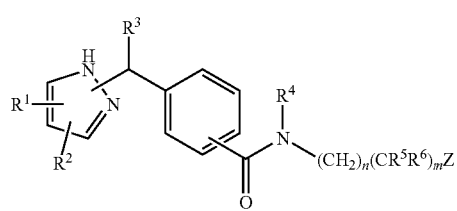

I or a pharmaceutically acceptable salt or solvate thereof, wherein:

$R^1$ is selected from the group consisting of:
(a) $C_{1-10}$alkyl, $C_{2-10}$alkenyl or $C_{2-10}$alkynyl optionally substituted with: (1) 1-5 halo groups up to a perhaloalkyl group; (2) 1 oxo group; (3) 1-2 OH groups; (4) 1-2 $C_{1-10}$alkyl groups, each optionally substituted with: up to five halo or a perhaloalkoxy, 1 OH or $CO_2R^8$ group; (5) 1 $CO_2R^8$ or $S(O)_pR^7$; (6) 1-2 Aryl, Hetcy or HAR groups, each optionally substituted as follows: (i) 1-5 halo groups, (ii) 1 OH, $CO_2R^8$, CN, $S(O)_pR^7$, $NO_2$ or $C(O)NR^9R^{10}$ group, (iii) 1-2 $C_{1-10}$alkyl or alkoxy groups, each optionally substituted with: 1-5 halo, up to perhaloalkyl, and 1-2 OH or $CO_2R^8$ groups; and (iv) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^8$ groups; (7) —$NR^8$—C(O)—$NR^9R^{10}$; (8) —$NR^8$—$CO_2R^{11}$; (9) —$NR^8$—C(O)$R^{11}$; (10) —$NR^9R^{10}$; (11) —$NR^8SO_2R^{11}$; (12) —$SO_2$—$NR^9R^{10}$; (13) —$C(O)NR^9R^{10}$ and (14) —OC(O)—$NR^9R^{10}$;
(b) Aryl, HAR or Hetcy, each optionally substituted as follows: (1) 1-3 $C_{1-10}$alkyl, $C_{2-10}$alkenyl or $C_{2-10}$alkanyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 OH, phenyl, $CO_2R^8$, CN or $S(O)_pR^7$ groups; (3) 1-2 Aryl, HAR or Hetcy groups, each optionally substituted as follows: (i) 1-3 halo groups; (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 OH, phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^7$, $NO_2$ or CN group; (7) 1-2 $CO_2R^8$; (8) —$NR^8$—C(O)—$NR^9R^{10}$; (9) —$NR^8$—$CO_2R^{11}$; (10) —$NR^8$—$C(O)R^{11}$; (11) —$NR^9R^{10}$; (12) —$NR^8SO_2R^{11}$; (13) —$SO_2$—$NR^9R^{10}$; (14) —C(O)$NR^9R^{10}$ and (15) —OC(O)—$NR^9R^{10}$;

and when $R^1$ represents heterocyclyl containing a nitrogen atom, said nitrogen atom is optionally substituted with a member selected from the group consisting of: (a) —$C(O)NR^9R^{10}$; (b) —$CO_2R^{11}$; (c) —$C(O)R^{11}$; and (d) —$SO_2R^{11}$;

$R^2$ is H or $R^1$ as defined above;
$R^3$ and $R^4$ are H or $C_{1-10}$alkyl;
$R^5$ represents H or F;
$R^6$ represents H, OH, F or $C_{1-3}$alkyl, or $R^5$ and $R^6$ are taken in combination and represent oxo;
$R^7$ represents a member selected from the group consisting of: $C_{1-10}$alkyl, Aryl or Ar—$C_{1-10}$alkyl,
$R^8$ is H, $C_{1-10}$alkyl, optionally substituted with phenyl, OH, $OC_{1-6}$alkyl, $CO_2H$, $CO_2C_{1-6}$alkyl and 1-3 halo groups;
$R^9$ is H or $C_{1-10}$alkyl;
$R^{10}$ is H or is independently selected from: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar—$C_{1-6}$alkyl, each optionally substituted with 1-5 halos and 1-3 members selected from the group consisting of: CN, OH, $C_{1-10}$alkyl and $OC_{1-10}$alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^{11}$ is independently selected from the group consisting of:
(a) $C_{1-10}$alkyl, optionally substituted with OH, $OC_{1-6}$alkyl, $CO_2H$, $CO_2C_{1-6}$alkyl, and 1-3 halo groups; (b) Aryl or Ar-$_{1-6}$alkyl, each optionally substituted with 1-5 halos and 1-3 members selected from the group consisting of: CN, OH, $C_{1-10}$alkyl and $OC_{1-10}$alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

m is an integer selected from 0, 1 and 2;
n is an integer selected from 0 to 6;
p is an integer selected from 0, 1 and 2, and
when at least one of m and n is other than 0, Z is selected from $CO_2R^8$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

One aspect of the invention that is of interest relates to compounds of formula Ia:

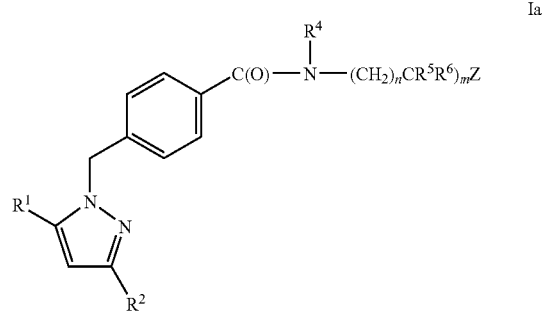

wherein all variables are as originally defined with respect to formula I.

Another aspect of the invention that is of interest relates to compounds of formula I, as well as pharmaceutically acceptable salts and solvates thereof, wherein:

$R^1$ is selected from the group consisting of:
a) $C_{1-10}$alkyl optionally substituted with: (1) 1-5 halo groups up to a perhaloalkyl group; (2) 1-2 OH groups; (3) 1-2 $C_{1-10}$alkoxy groups, each optionally substituted with up to five halo or a perhaloalkoxy group; (4) 1 $CO_2R^8$ or $S(O)_pR^7$; (5) 1-2 Aryl, Hetcy or HAR groups, each optionally substituted as follows: (i) 1-5 halo groups, (ii) 1 OH, $CO_2R^8$, CN, $S(O)_pR^7$, $NO_2$ or $C(O)NR^9R^{10}$ group, (iii) 1-2 $C_{1-10}$alkyl or alkoxy groups, each optionally substituted with: 1-5 halo, up to perhaloalkyl, and 1-2 OH or $CO_2R^8$ groups; and (iv) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^5$ groups; and b) Aryl, HAR or Hetcy, each optionally substituted as follows: (1) 1-3 $C_{1-10}$alkyl or $C_{2-10}$alkenyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 phenyl, CN or $S(O)_pR^7$ groups; (3) 1-2 Aryl, HAR or Hetcy groups, each optionally substituted as follows: (i) 1-3 halo groups; (ii) 1-2 $C_{1-10}$alkyl or $C_{2-10}$alkenyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

said Aryl, HAR or Hetcy group b) being further optionally substituted on carbon by a group selected from the group consisting of; (4) 1-5 halo groups; (5) 1-2 OH groups; (6) 1 $S(O)_pR^7$, $NO_2$ or CN group; (7) 1-2 $CO_2R'$; (8) $-NR^8-C(O)-NR^9R^{10}$; (9) $-NR^8-CO_2R^{11}$; (10) $-NR^8-C(O)R^{11}$; (11) $-NR^9R^{10}$; (12) $-NR^8SO_2R^{11}$; (13) $-SO_2-NR^9R^{10}$; (14) $-C(O)NR^9R^{10}$ and (15) $-OC(O)-NR^9R^{10}$;

and when $R^1$ represents heterocyclyl containing a nitrogen atom, said nitrogen atom can be optionally substituted with a member selected from the group consisting of: (a) $-CO_2R^{11}$; (b) $-C(O)R^{11}$; and (c) $-SO_2R^{11}$. Within this subset, all other variables are as originally defined with respect to formula I.

More particularly, compounds of formula I that are of interest can be described with respect to formula I wherein:

$R^1$ is selected from the group consisting of:

a) $C_{1-10}$alkyl optionally substituted with: (1) 1-2 halo groups; (2) 1-2 $C_{1-6}$alkoxy groups, each optionally substituted with up to 3 halo groups; (3) 1 Phenyl, Piperidinyl or Pyridinyl group, each optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups;

b) Phenyl, Pyridinyl, or Piperidinyl, each optionally substituted as follows: (1) 1 $C_{1-3}$alkyl group optionally substituted with 1-3 halo groups, 1 phenyl or $S(O)_pR^7$ group; (2) 1$C_{1-3}$alkoxy group, the alkyl portion of which is optionally substituted with 1-3 halo groups or 1 phenyl group; and (3) 1 phenyl, pyridinyl, isoxazolyl or piperidinyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group;

said Phenyl, Pyridinyl or Piperidinyl ring being further optionally substituted on carbon atoms by a group selected from the group consisting of: (4) 1-3 halo groups; (5) 1OH group; (6) 1 $S(O)_pR^7$, $NO_2$ or CN group; (7) 1 $CO_2R^8$; (8) $-NR^9R^{10}$; (9) $-C(O)NR^9R^{10}$ and (10) $-OC(O)-NR^9R^{10}$;

and when $R^1$ represents piperidinyl, the piperidine nitrogen atom can be optionally substituted with a member selected from the group consisting of: (a) $-CO_2R^{11}$; (b) $-C(O)R^{11}$; and (c) $-SO_2R^{11}$.

Within this subset, all other variables are as originally defined with respect to formula I.

Even more particularly, compounds of formula I that are of interest can be described with respect to formula I wherein $R^1$ is selected from the group consisting of:

a) $C_{1-10}$alkyl optionally substituted with: Phenyl, optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups; and b) Phenyl, Pyridinyl, or Piperidinyl, each optionally substituted as follows: (1) 1 $C_{1-3}$alkyl group optionally substituted with 1-3 halo groups or 1 phenyl group; (2) 1 $C_{1-3}$alkoxy group, the alkyl portion of which is optionally substituted with 1-3 halo groups or 1 phenyl group; (3) 1 phenyl, pyridinyl or isoxazolyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group;

said Phenyl, Pyridinyl or Piperidinyl group b) being further optionally substituted on carbon atoms by a group selected from the group consisting of: (4) 1-3 halo groups; (5) 1 OH group; (6) 1 $CO_2R^8$; and (7) $-NR^9R^{10}$;

and when $R^1$ represents piperidinyl, the piperidine nitrogen atom can be optionally substituted with a member selected from the group consisting of: (a) $-CO_2R^{11}$; (b) $-C(O)R^{11}$; and (c) $-SO_2R^{11}$. Within this subset, all other variables are as originally defined with respect to formula I.

Another aspect of the invention that is of interest relates to compounds of formula I, salts and solvates thereof, wherein $R^2$ is selected from the group consisting of:

(a) $C_{1-10}$alkyl optionally substituted with: (1) 1-5 halo groups up to a perhaloalkyl group; (2) 1-2 OH groups; (3) 1-2 $C_{1-10}$alkoxy groups, each optionally substituted with up to five halo or a perhaloalkoxy group; (4) 1 $CO_2R^5$ or $S(O)_pR^7$; (5) 1-2 Aryl, Hetcy or HAR groups, each optionally substituted as follows: i) 1-5 halo groups, (ii) 1OH, $CO_2R^8$, CN, $S(O)_pR^7$, $NO_2$ or $C(O)NR^9R^{10}$ group, (iii) 1-2 $C_{1-10}$alkyl or alkoxy groups, each optionally substituted with: 1-5 halo, up to perhaloalkyl, and 1-2 OH or $CO_2R^5$ groups; and (iv) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^8$ groups; and (b) Aryl, HAR or Hetcy, each optionally substituted as follows: (1) 1-3 $C_{1-10}$alkyl or $C_{2-10}$alkenyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 phenyl. CN or $S(O)_pR^7$ groups; (3) 1-2 Aryl, HAR or Hetcy groups, each optionally substituted as follows: (i) 1-3 halo groups; (ii) 1-2 $C_{1-10}$alkyl or $C_{2-10}$alkenyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^7$, $NO_2$ or CN group; (7) 1-2 $CO_2R^8$; (8) $-NR^8-C(O)-NR^9R^{10}$; (9) $-NR^8-CO_2R^{11}$; (10) $-NR^8-C(O)R^{11}$; (11) $-NR^9R^{10}$; (12) $-NR^8SO_2R^{11}$; (13) $-SO_2-NR^9R^{11}$; (14) $-C(O)NR^9R^{10}$ and (15) $-OC(O)-NR^9R^{10}$;

and when $R^2$ represents heterocyclyl containing a nitrogen atom, said nitrogen atom can be optionally substituted with a member selected from the group consisting of: (a) $-CO_2R^{11}$; (b) $-C(O)R^{11}$; and (c) $-SO_2R^{11}$. Within this subset, all other variables are as originally defined with respect to formula I.

More particularly, an aspect of the invention that is of interest relates to compounds of formula I as well as salts and solvates thereof wherein:

$R^2$ is selected from the group consisting of:

a) $C_{1-10}$alkyl optionally substituted with: (1) 1-2 halo groups; (2) 1-2 $C_{1-6}$alkoxy groups, optionally substituted with up to 3 halo groups; (3) 1 Phenyl, Piperidinyl or Pyridinyl group, each optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups; and b) Phenyl, Pyridinyl, or Piperidinyl, each optionally substituted as follows: (1) 1 $C_{1-3}$alkyl group optionally substituted with 1-3 halo groups, 1 phenyl or $S(O)_pR^7$ group; (2) 1 $C_{1-3}$alkoxy group, the alkyl portion of which is optionally substituted with 1-3 halo groups or 1 phenyl group; (3) 1 phenyl, pyridinyl, isoxazolyl or piperidinyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^1$, $S(O)_pR^7$, CN, $NR^9R^{10}$, $NO_2$ or OH group;

said Phenyl, Pyridinyl or Piperidinyl group b) being further optionally substituted on carbon atoms by a group selected from the group consisting of: (4) 1-3 halo groups; (5) 1 OH group; (6) 1 $S(O)_pR^7$, $NO_2$ or CN group; (7) 1 $CO_2R^8$; (8) $-NR^9R^{10}$; (9) $-C(O)NR^9R^{10}$ and (10) $-OC(O)-NR^9R^{10}$;

and when $R^2$ represents piperidinyl, the piperidine nitrogen atom can be optionally substituted with a member selected from the group consisting of: (a) $-CO_2R^{11}$; (b) $-C(O)R^{11}$; and (c) $-SO_2R^{11}$. Within this subset, all other variables are as originally defined with respect to formula I.

Even more particularly, compounds of formula I that are of interest can be described with respect to formula I wherein: $R^2$ is selected from the group consisting of:

a) $C_{1-10}$alkyl optionally substituted with: Phenyl, optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups; and b) Phenyl, Pyridinyl, or Piperidinyl, each optionally substituted as follows: (1) 1 $C_{1-3}$alkyl group optionally substituted with 1-3 halo groups or 1 phenyl group; (2) 1 $C_{1-3}$alkoxy group, the alkyl portion of which is optionally substituted with 1-3 halo groups or 1 phenyl group; (3) 1 phenyl, pyridinyl or isoxazolyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group;

said Phenyl, Pyridinyl or Piperidinyl group b) being further optionally substituted on carbon atoms by a group selected from the group consisting of: (4) 1-3 halo groups; (5) 1 OH group; (6) 1 $CO_2R^8$; and (7) $-NR^9R^{10}$;

and when $R^2$ represents piperidinyl, the piperidine nitrogen atom can be optionally substituted with a member selected from the group consisting of: (a) $-CO_2R^{11}$; (b) $-C(O)R^{11}$; and (c) $-SO_2R^{11}$. Within this subset, all other variables are as originally defined with respect to formula I.

Another aspect of the invention that is of interest relates to compounds of formula I wherein $R^3$ represents H or methyl. Within this subset, all other variables are as originally defined with respect to formula I.

More particularly, an aspect of the invention that is of interest relates to compounds of formula I wherein $R^3$ represents H. Within this subset, all other variables are as originally defined with respect to formula I.

Another aspect of the invention that is of interest relates to compounds of formula I wherein $R^4$ represents H or methyl. Within this subset, all other variables are as originally defined with respect to formula I.

More particularly, an aspect of the invention that is of interest relates to compounds of formula I wherein $R^4$ represents H. Within this subset, all other variables are as originally defined with respect to formula I.

In another aspect of the invention that is of interest, compounds of formula I are described wherein: n represents 0 or 1; m represents 0 and Z represents tetrazolyl. Within this subset, all other variables are as originally defined with respect to formula I.

In another aspect of the invention that is of interest, compounds of formula I are described wherein: n represents 1 or 2; m represents 0 and Z represents $CO_2R^8$. Within this subset, all other variables are as originally defined with respect to formula I.

In yet another aspect of the invention that is of interest, compounds of formula I are described wherein: n represents 1, m represents 1, $R^5$ represents H, $R^6$ represents OH, and Z represents $CO_2R^8$. Within this subset, all other variables are as originally defined with respect to formula I.

In yet another aspect of the invention that is of interest, compounds of formula I are described wherein $R^7$ represents a member selected from the group consisting of: $C_{1-6}$alkyl or Aryl. Within this subset, all other variables are as originally defined with respect to formula I.

In yet another aspect of the invention that is of interest, compounds of formula I are described wherein $R^8$ is H or $C_{1-10}$alkyl, optionally substituted with phenyl or 1-3 halo groups. Within this subset, all other variables are as originally defined with respect to formula I.

Species falling within the scope of the present invention that are of particular interest include the following:

| Cpd No. | Structure |
| --- | --- |
| 1 | 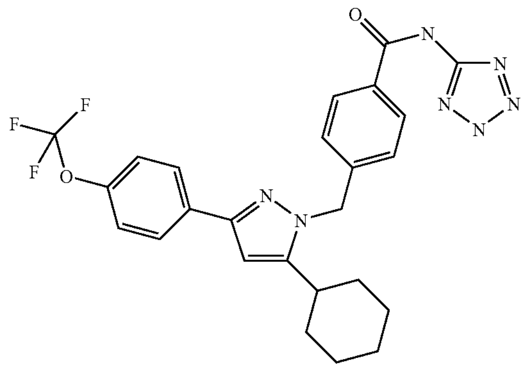 |
| 2 | 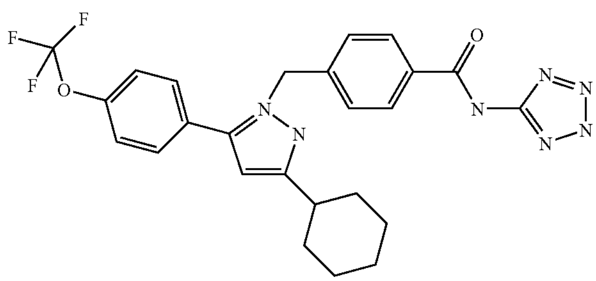 |
| 3 | 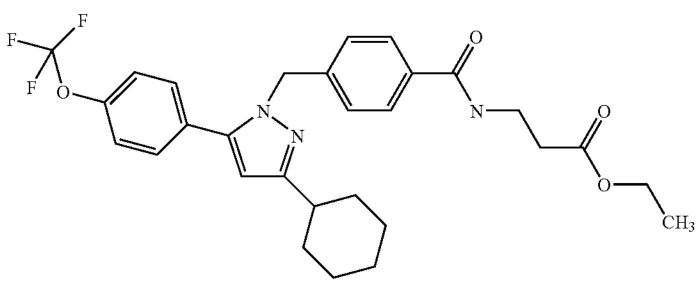 |
| 4 | 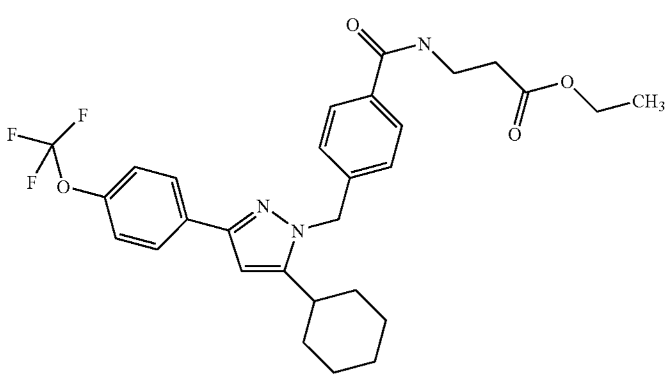 |

-continued

| Cpd No. | Structure |
|---|---|
| 5 | 3-{[4-({3-cyclohexyl-5-[4-(trifluoromethoxy)phenyl]-1H-pyrazol-1-yl}methyl)benzoyl]amino}propanoic acid |
| 6 | 3-{[4-({5-cyclohexyl-3-[4-(trifluoromethoxy)phenyl]-1H-pyrazol-1-yl}methyl)benzoyl]amino}propanoic acid |
| 7 | 3-{[4-({3-cyclohexyl-5-[4-(trifluoromethoxy)phenyl]-1H-pyrazol-1-yl}methyl)benzoyl]amino}-2-methylpropanoic acid |
| 8 | 4-({1-cyclohexyl-5-[4-(trifluoromethoxy)phenyl]-1H-pyrazol-3-yl}methyl)-N-(1H-tetrazol-5-yl)benzamide |

| Cpd No. | Structure |
|---|---|
| 9 | 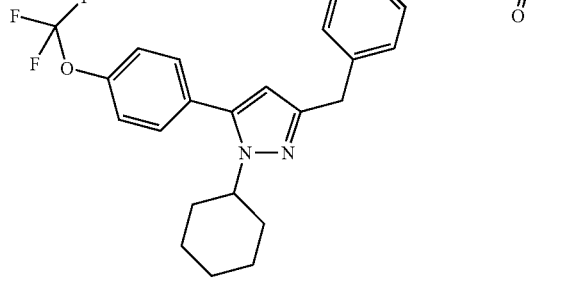 |
| 10 | 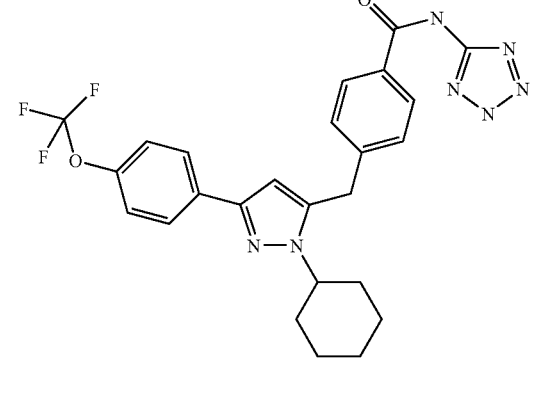 |
| 11 | 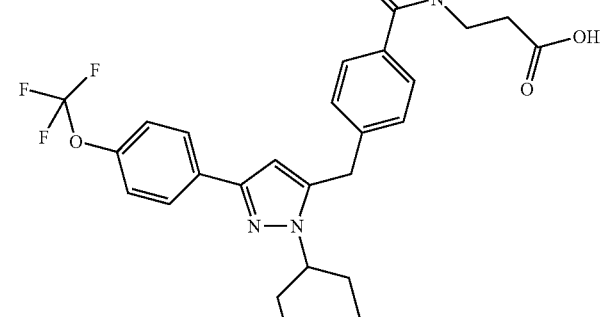 |

|Cpd No.|Structure|
|---|---|
|12|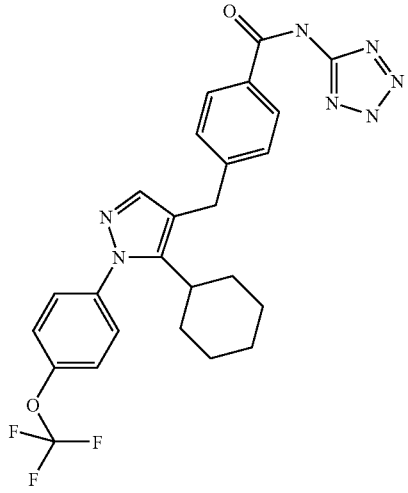|
|13|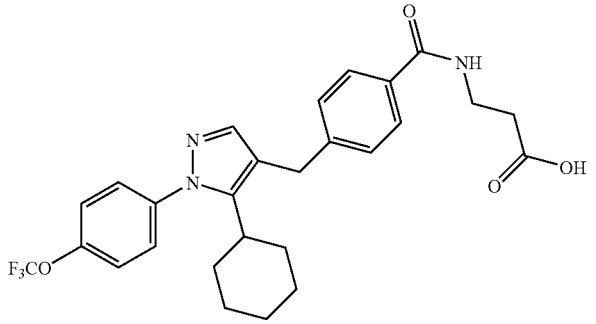|
|14|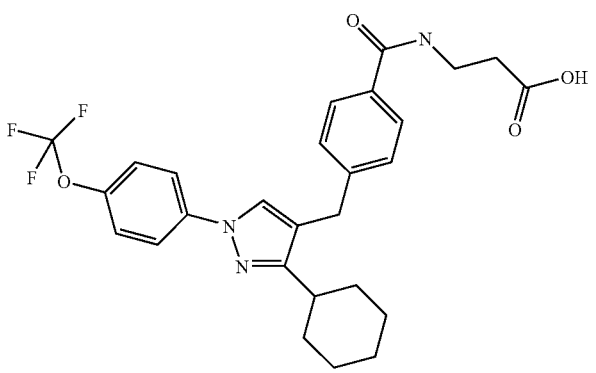|
|15|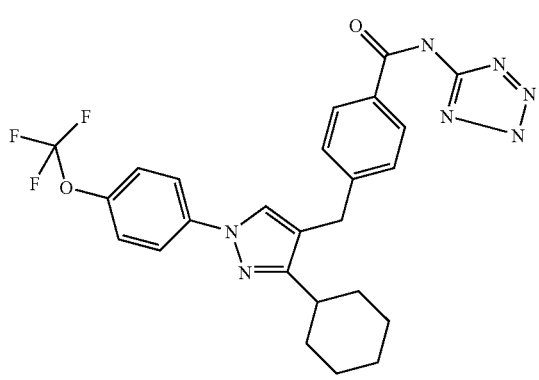|

-continued
| Cpd No. | Structure |
|---|---|
| 16 | 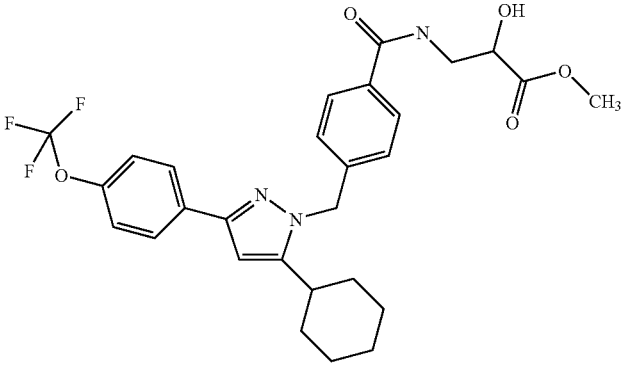 |
| 17 | 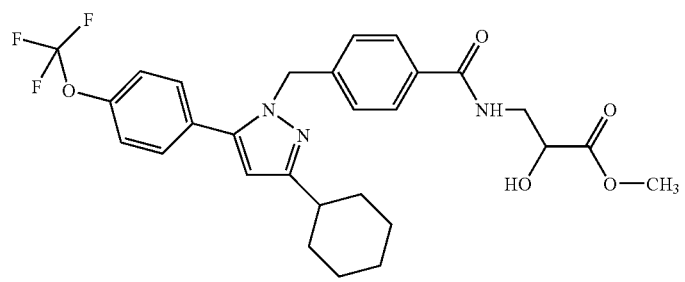 |
| 18 | 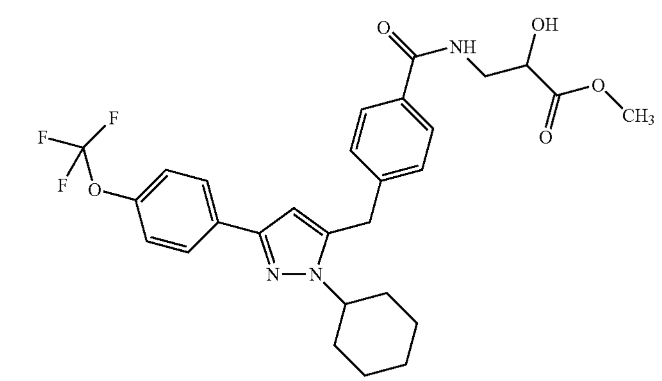 |
| 19 | 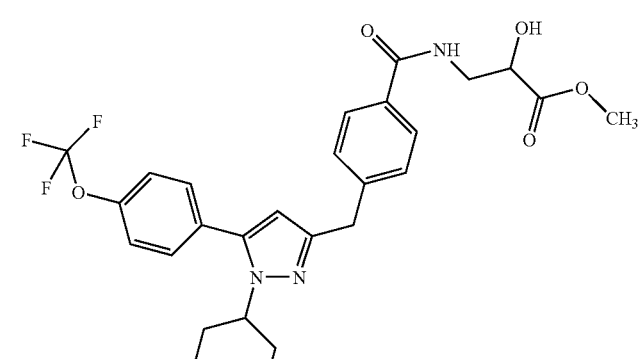 |

-continued
| Cpd No. | Structure |
|---|---|
| 20 | 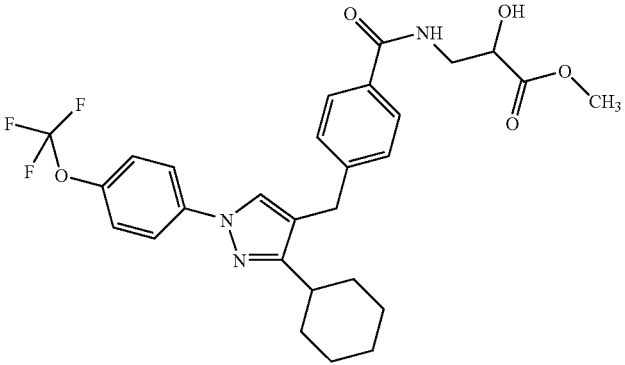 |
| 21 | 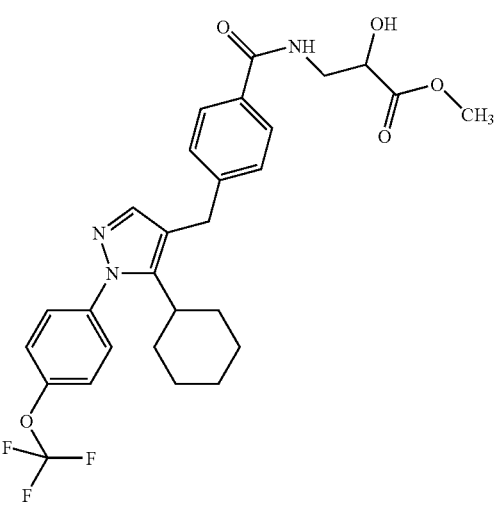 |
| 22 | 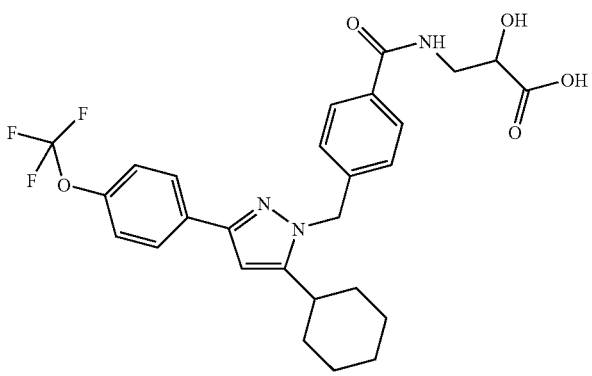 |
| 23 | 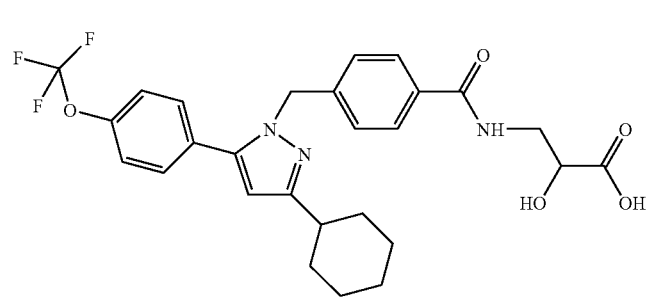 |

-continued
| Cpd No. | Structure |
|---|---|
| 24 | 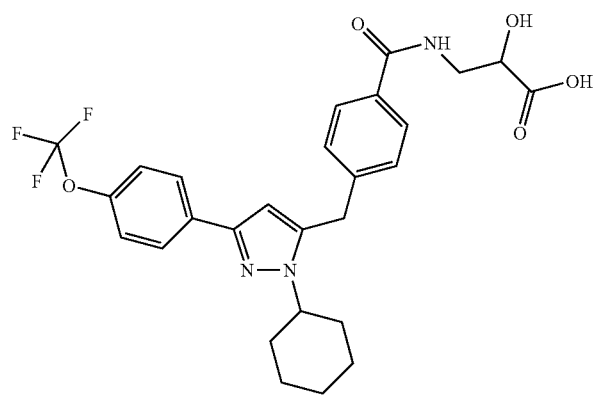 |
| 25 | 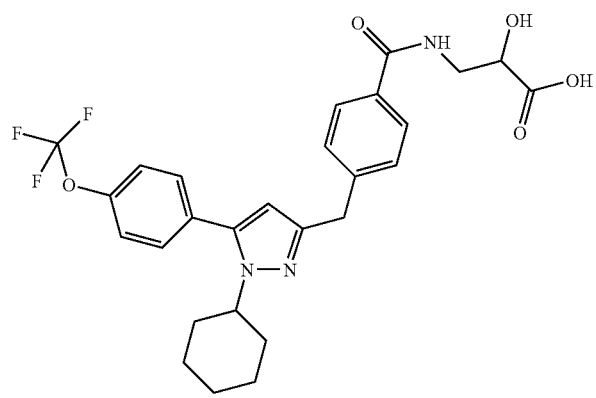 |
| 26 | 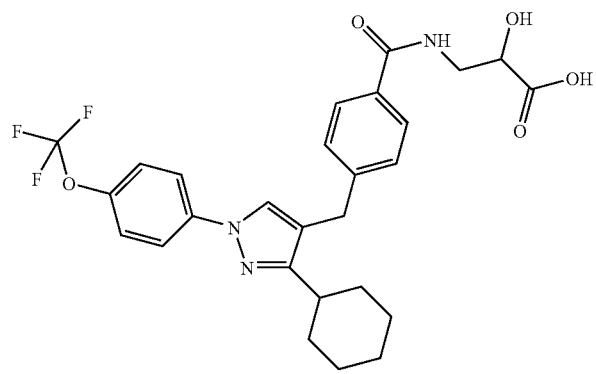 |

-continued
| Cpd No. | Structure |
|---------|-----------|
| 27 | 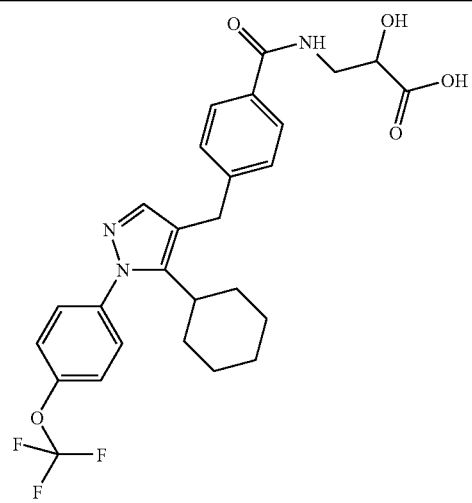 |
| 28 | 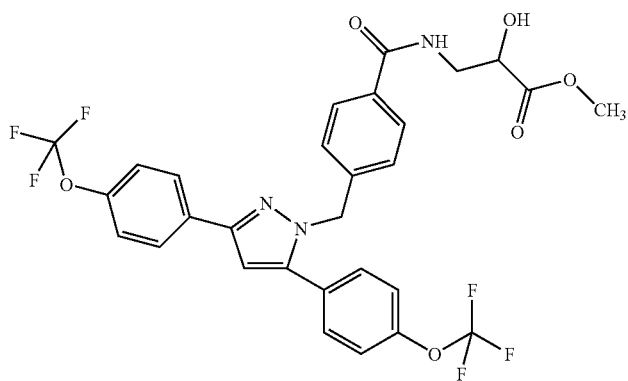 |
| 29 | 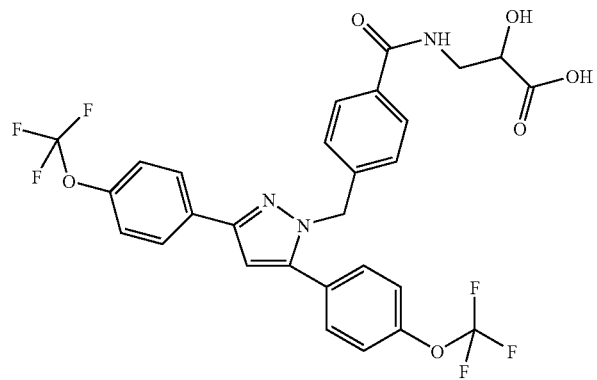 |

-continued
| Cpd No. | Structure |
|---------|-----------|
| 30 | 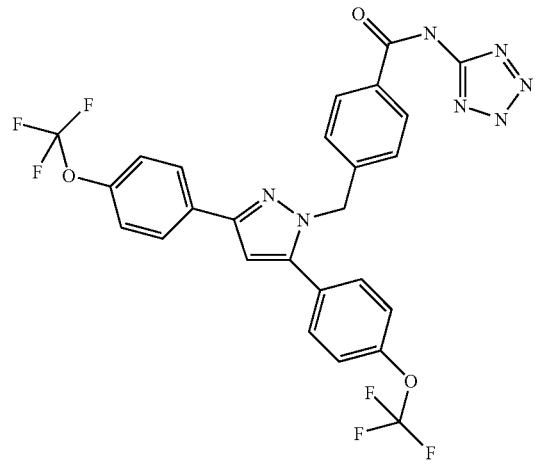 |
| 31 | 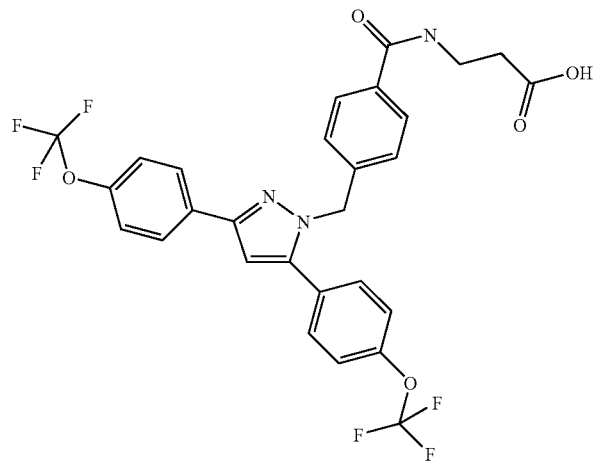 |
| 32 | 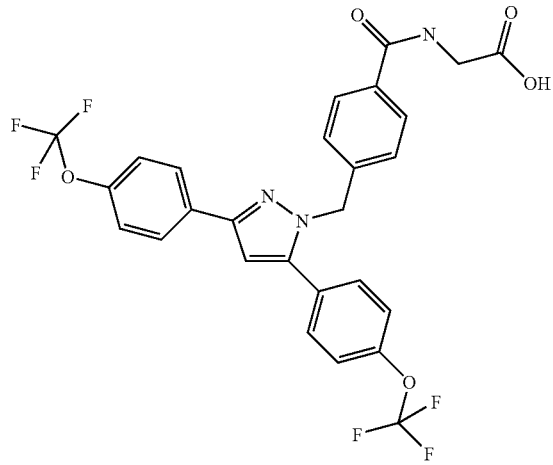 |

-continued

| Cpd No. | Structure |
|---|---|
| 33 | 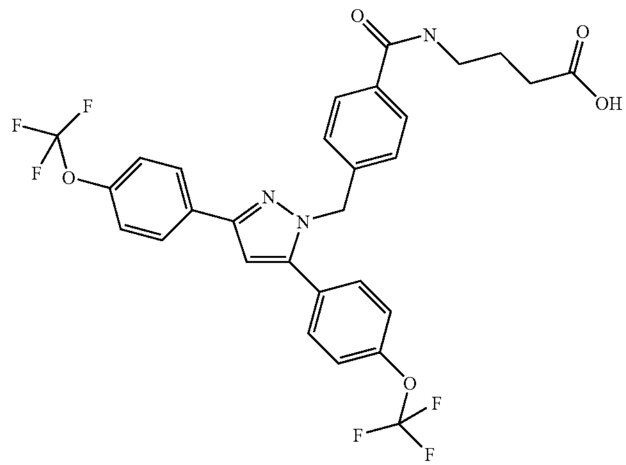 |
| 34 | 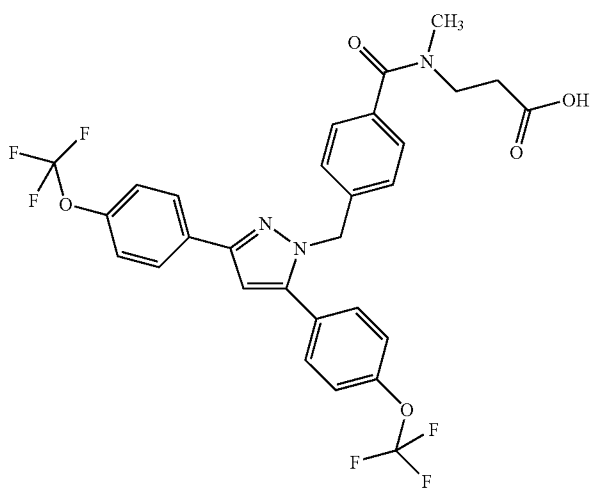 |
| 35 | 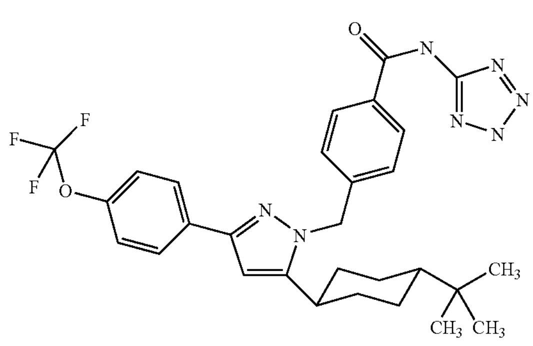 |

-continued
| Cpd No. | Structure |
|---|---|
| 36 | 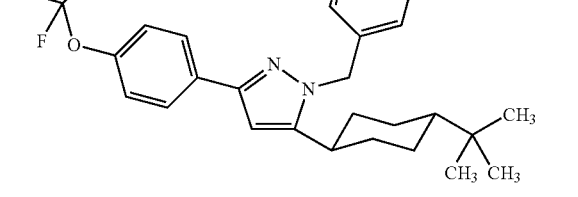 |
| 37 | 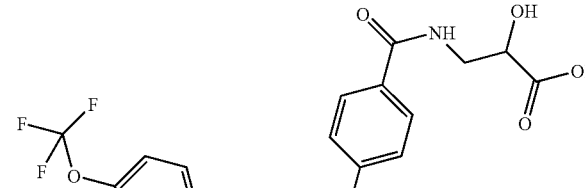 |
| 38 | 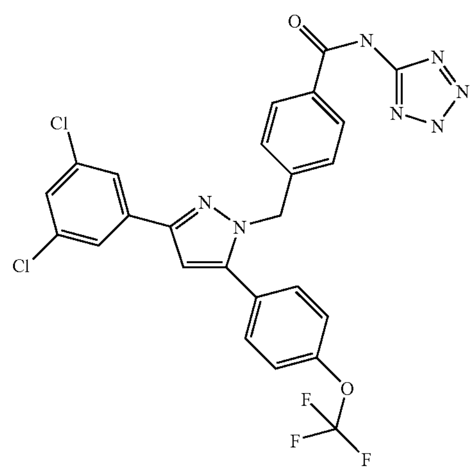 |
| 39 | 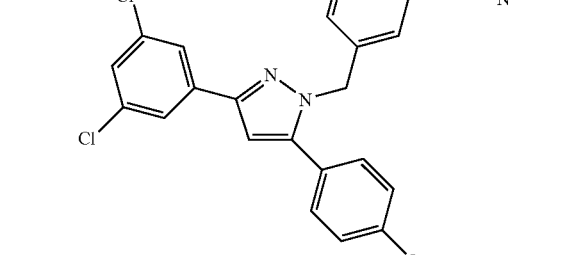 |

-continued
| Cpd No. | Structure |
|---|---|
| 40 | 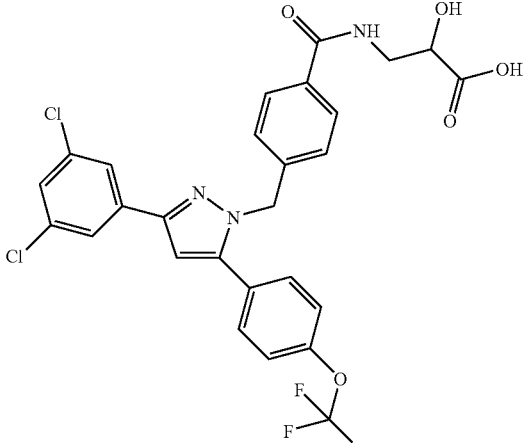 |
| 41 | 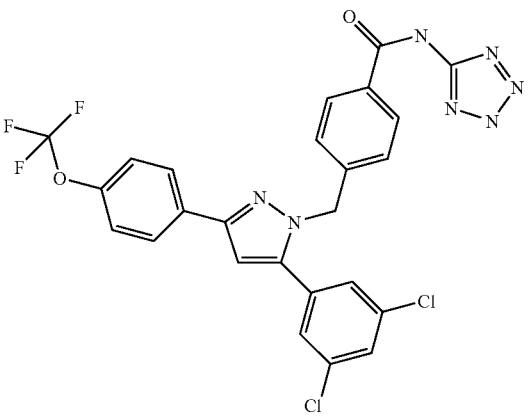 |
| 42 | 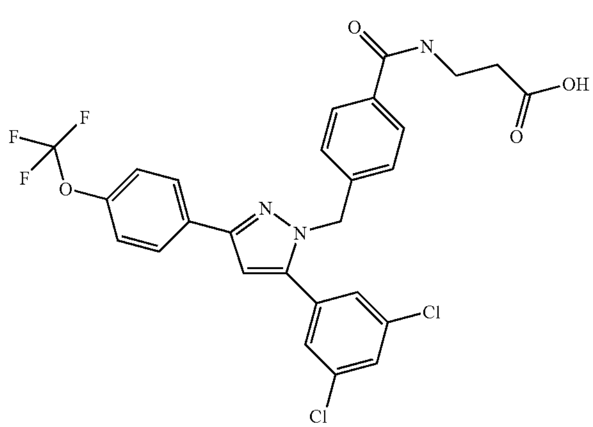 |

-continued
| Cpd No. | Structure |
|---|---|
| 43 | 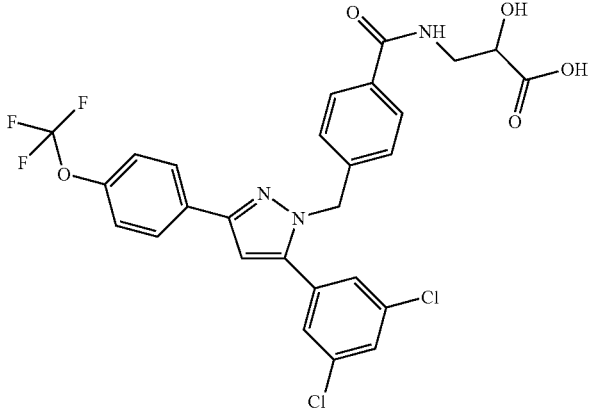 |
| 44 | 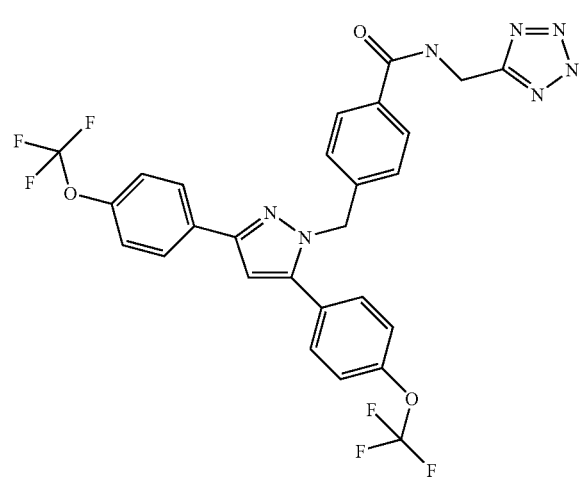 |
| 45 | 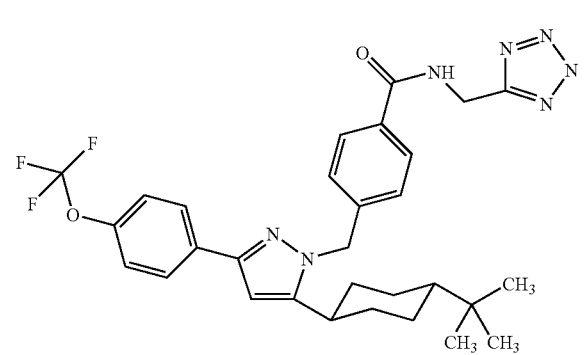 |

-continued
| Cpd No. | Structure |
|---|---|
| 46 | 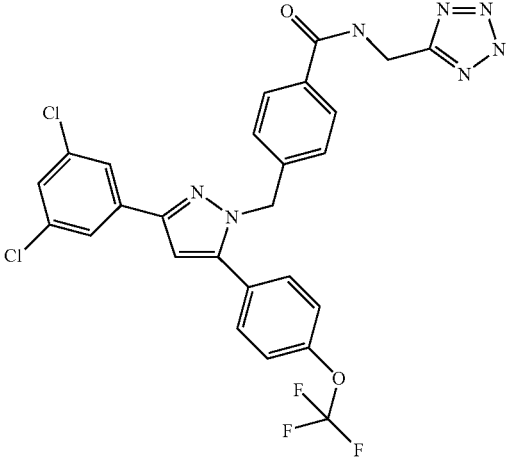 |
| 47 | 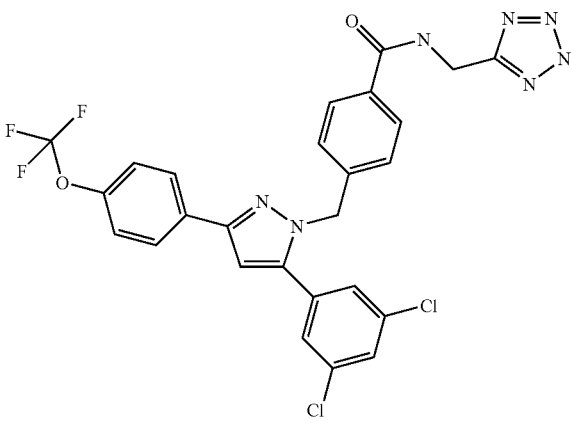 |
| 48 | 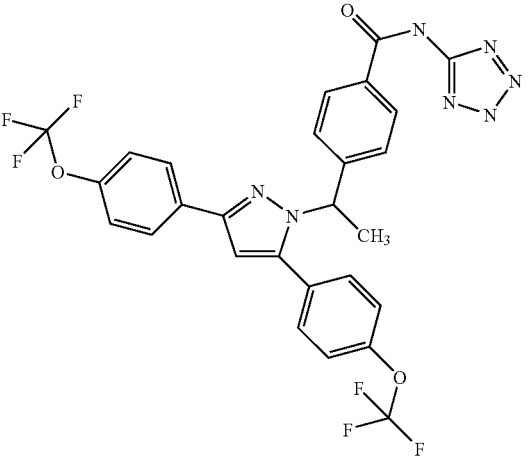 |

| Cpd No. | Structure |
|---|---|
| 49 | 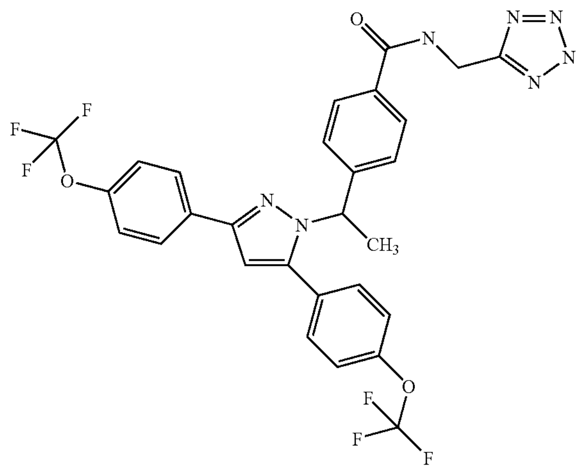 |
| 50 | 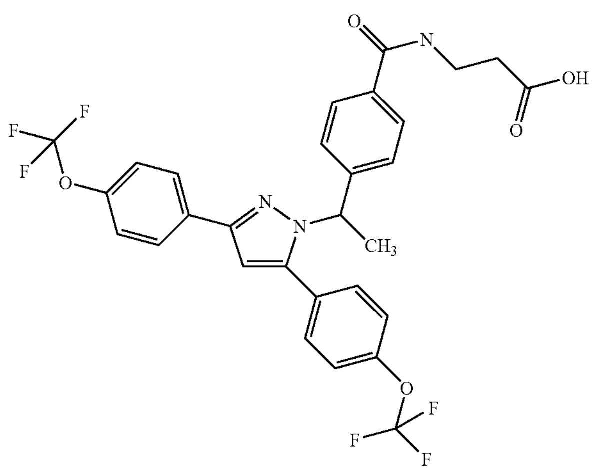 |
| 51 | 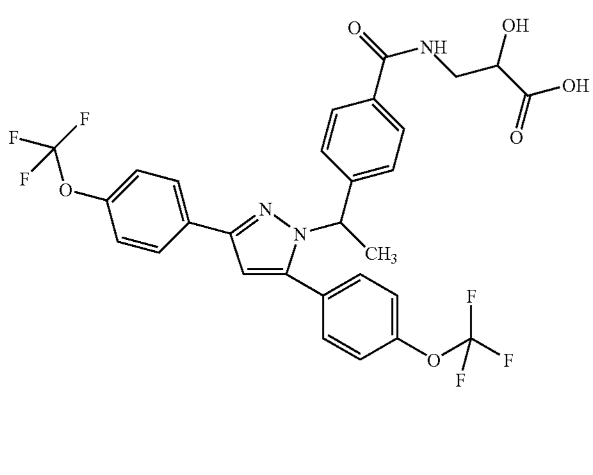 |

-continued
| Cpd No. | Structure |
|---|---|
| 52 | 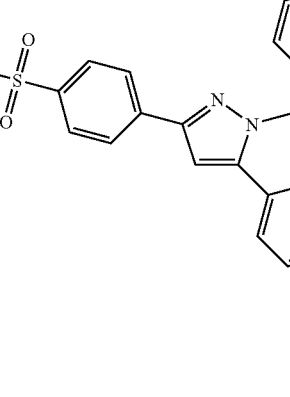 |
| 53 | 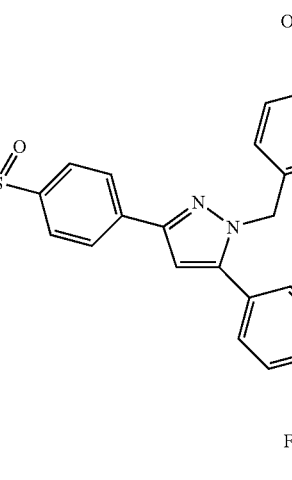 |
| 54 | 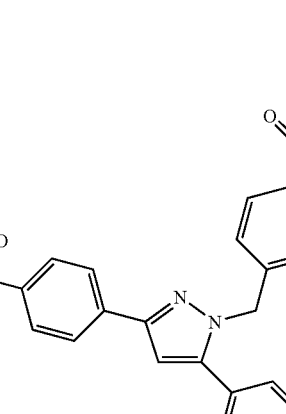 |

-continued
| Cpd No. | Structure |
|---|---|
| 55 | 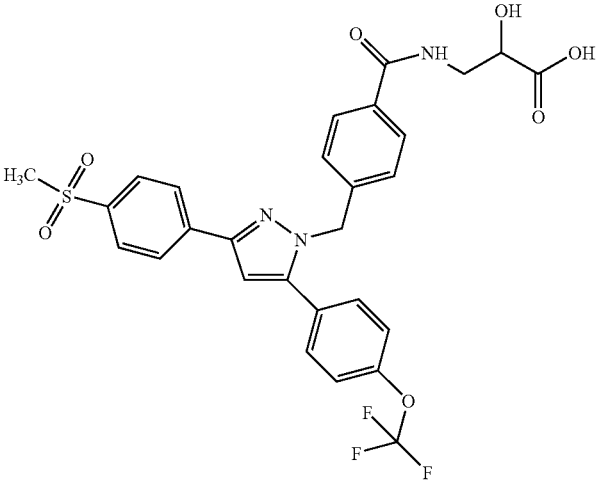 |
| 56 | 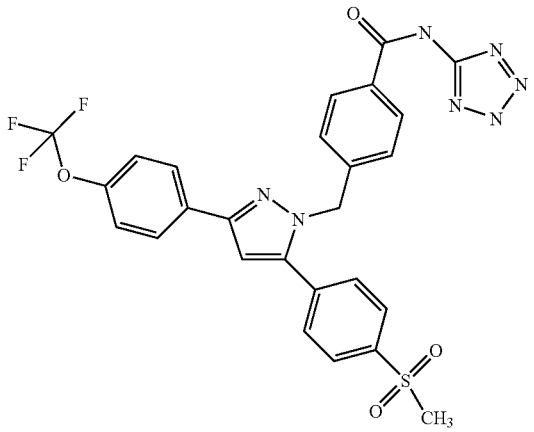 |
| 57 | 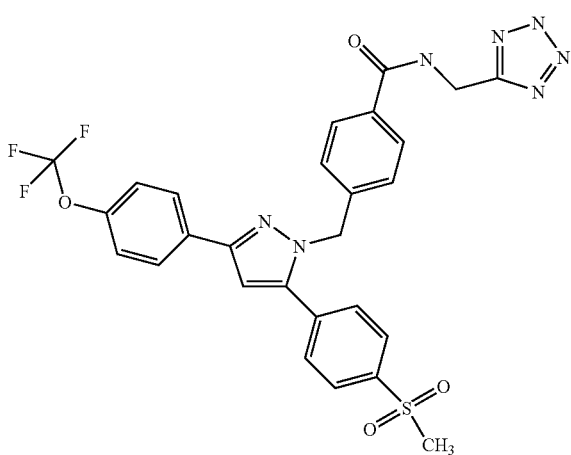 |

-continued
| Cpd No. | Structure |
|---|---|
| 58 | 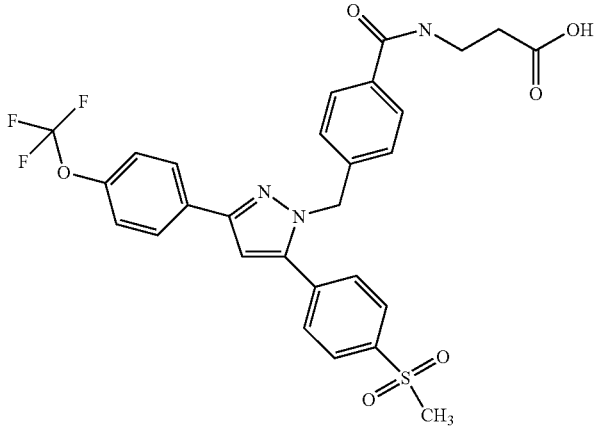 |
| 59 | 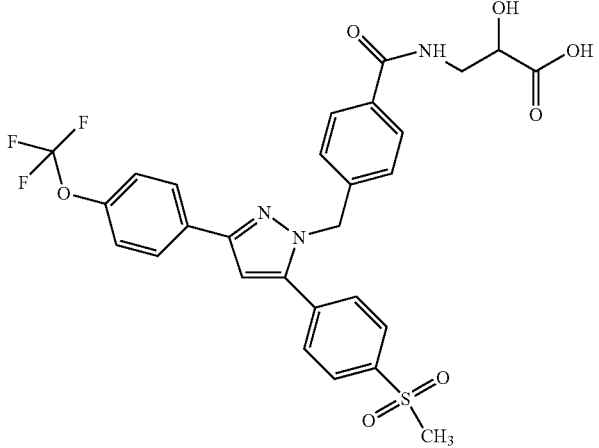 |
| 60 | 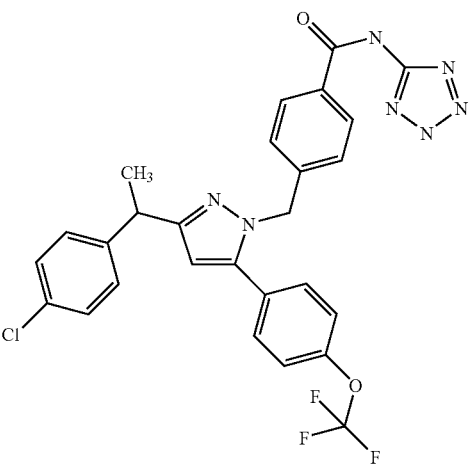 |

-continued
| Cpd No. | Structure |
|---|---|
| 61 | 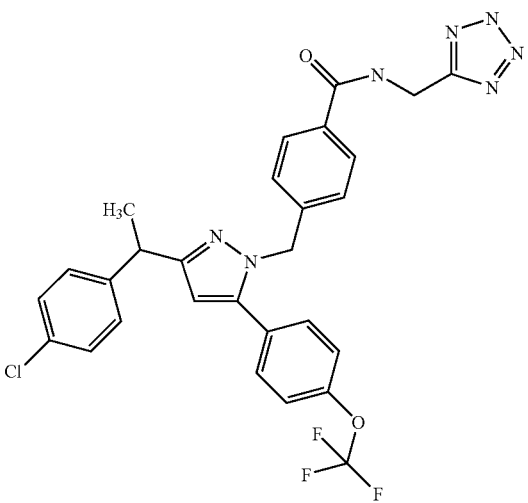 |
| 62 | 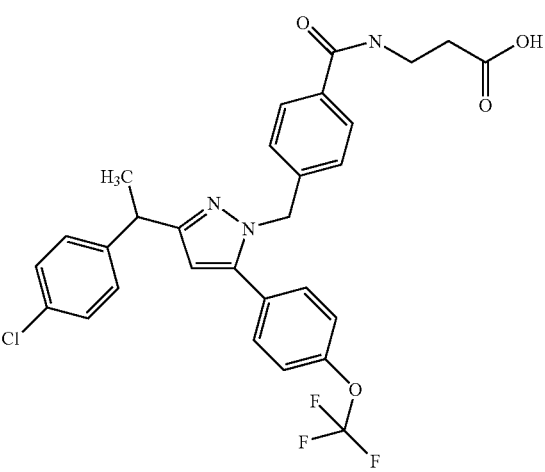 |
| 63 | 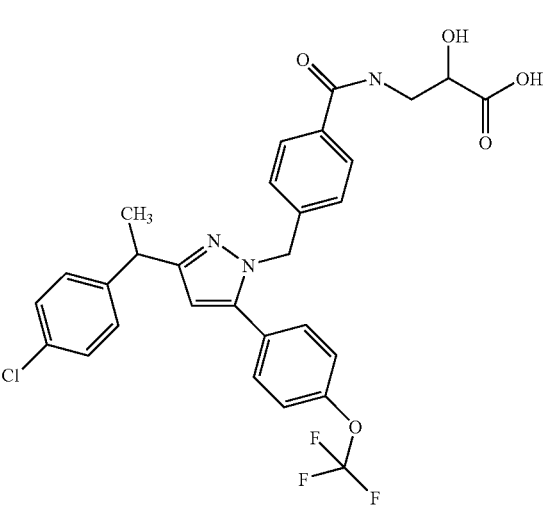 |

| Cpd No. | Structure |
|---|---|
| 64 | 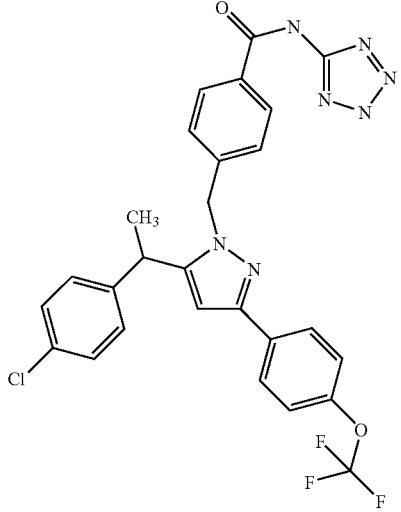 |
| 65 | 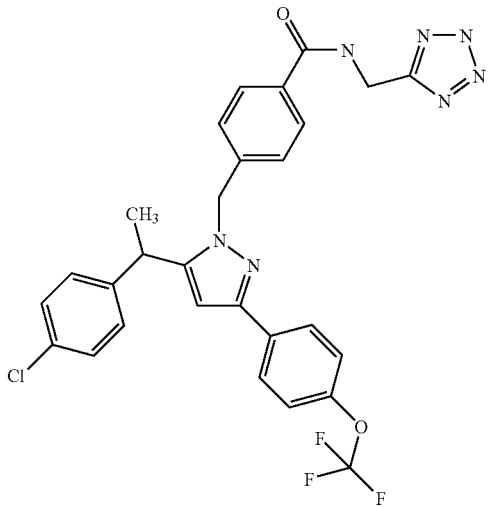 |
| 66 | 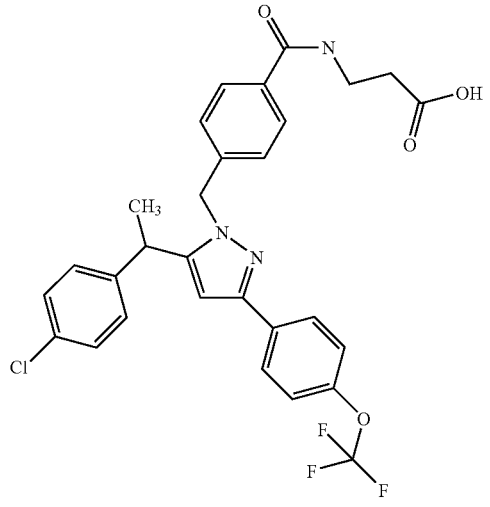 |

-continued

| Cpd No. | Structure |
|---|---|
| 67 | 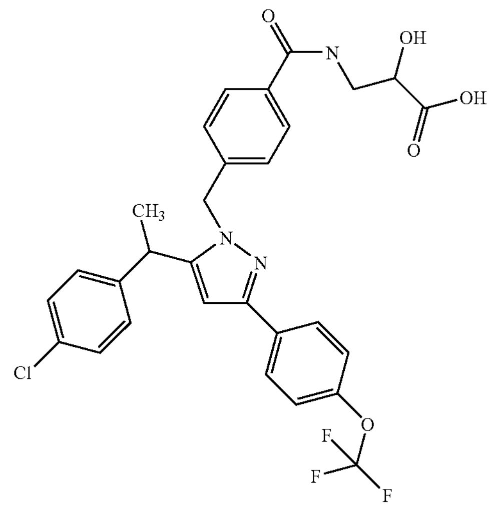 |
| 68 | 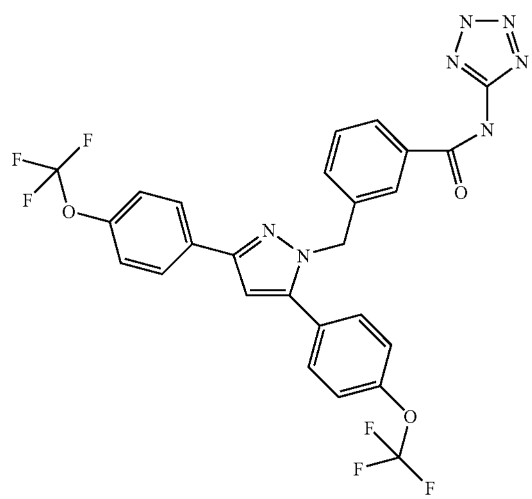 |
| 69 | 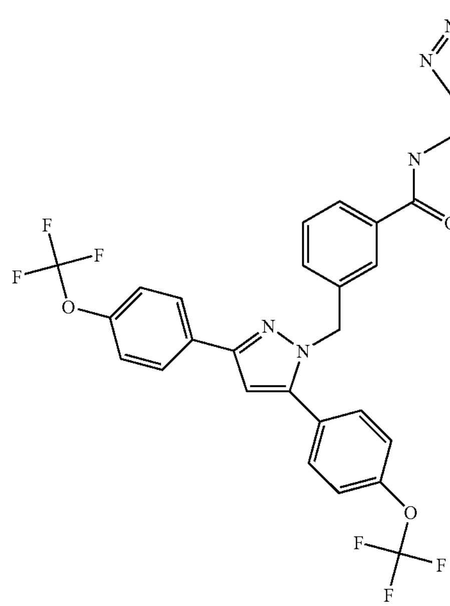 |

-continued
| Cpd No. | Structure |
|---|---|
| 70 | 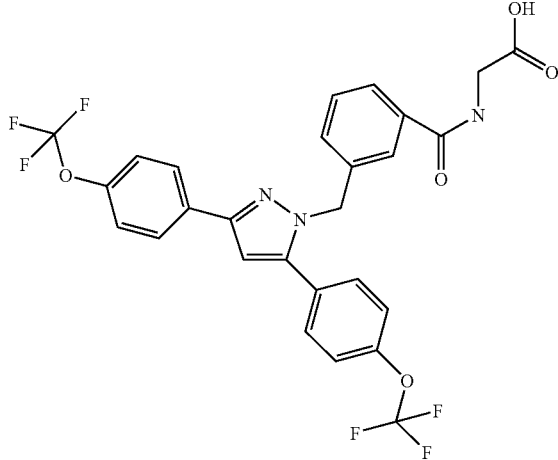 |
| 71 | 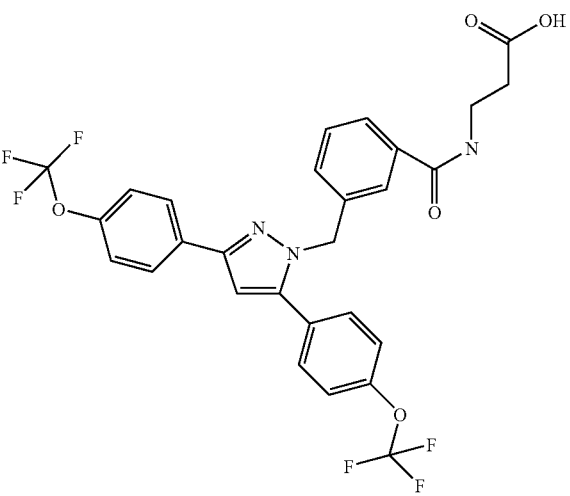 |
| 72 | 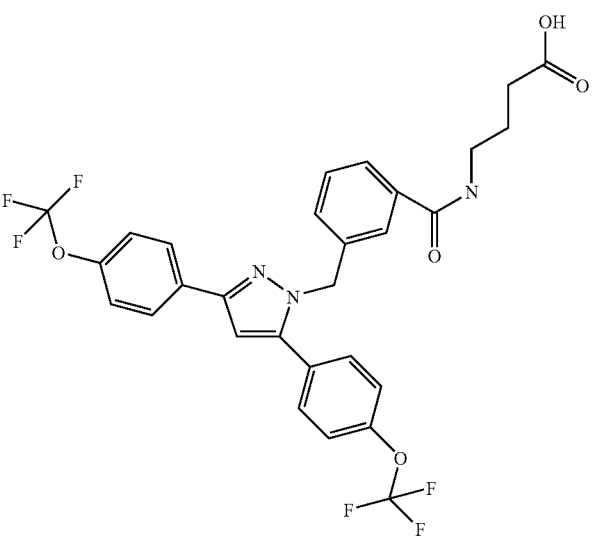 |

| Cpd No. | Structure |
|---|---|
| 73 | 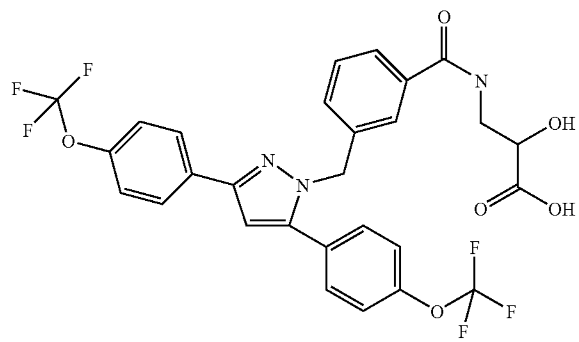 |
| 74 | 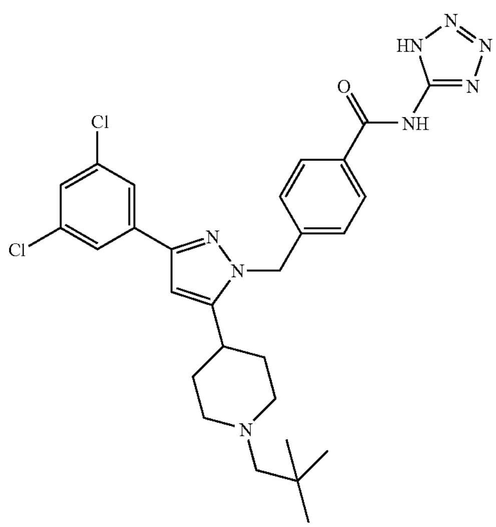 |
| 75 | 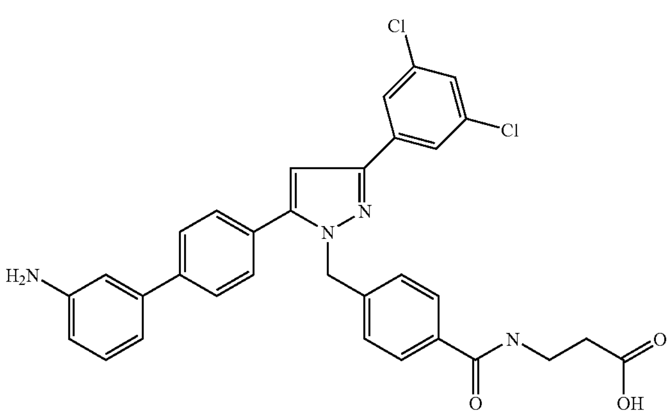 |

-continued
| Cpd No. | Structure |
|---|---|
| 76 | 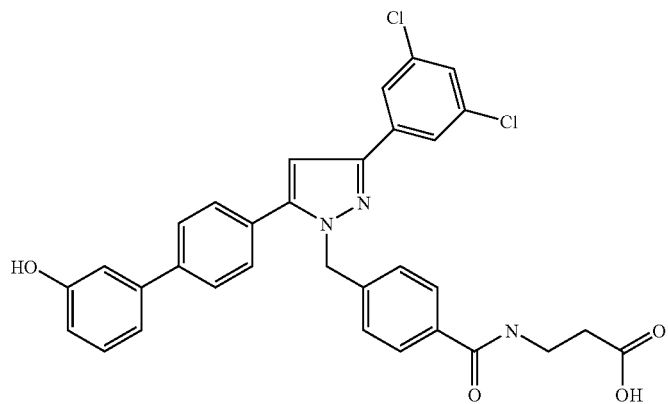 |
| 77 | 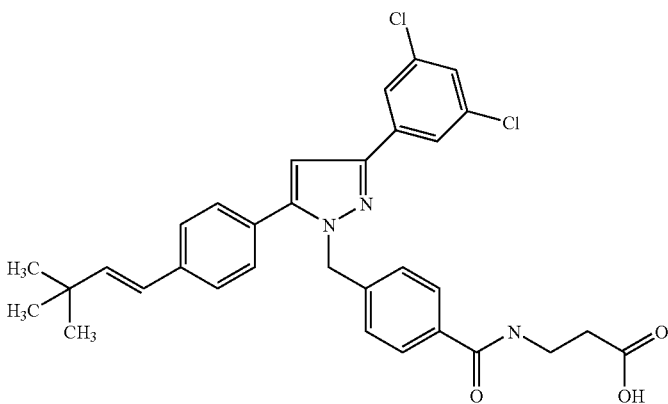 |
| 78 | 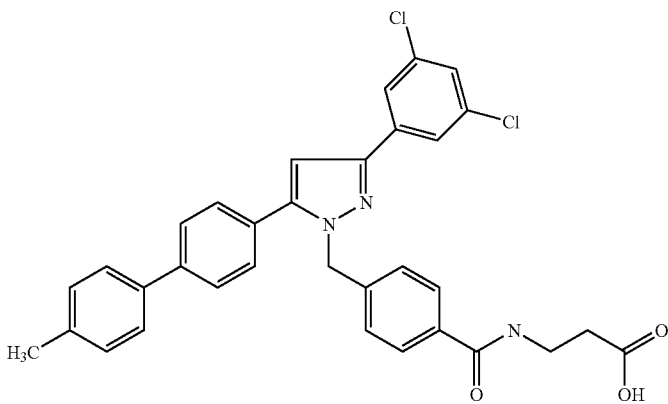 |

-continued
| Cpd No. | Structure |
|---|---|
| 79 | 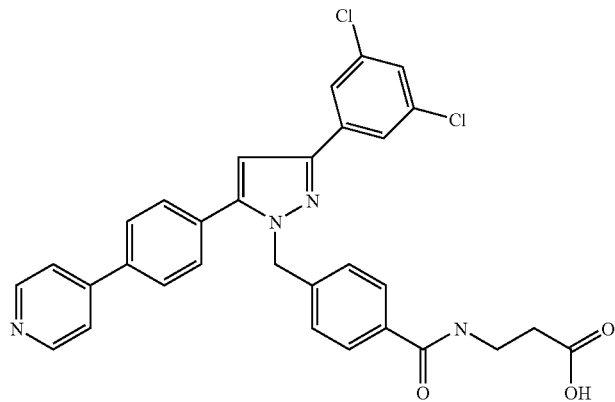 |
| 80 | 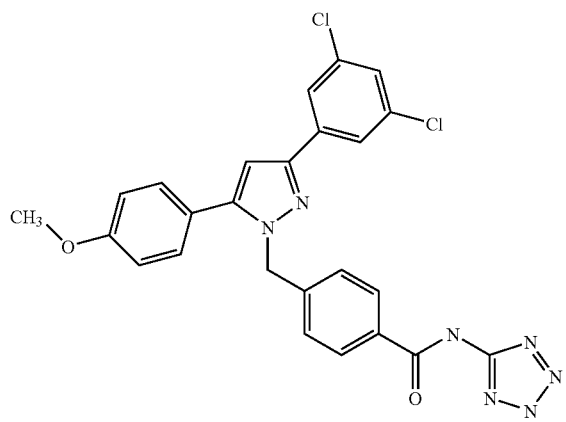 |
| 81 | 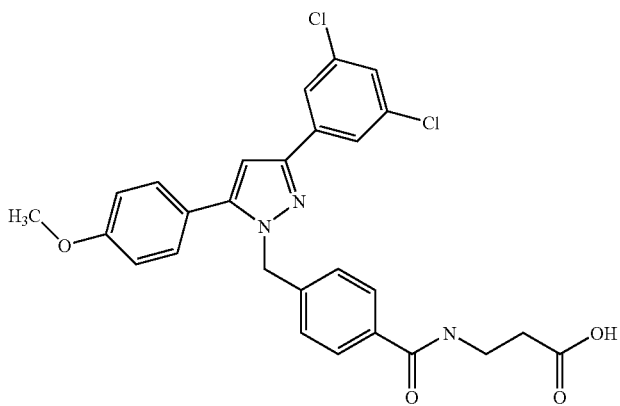 |

-continued
| Cpd No. | Structure |
|---|---|
| 82 | 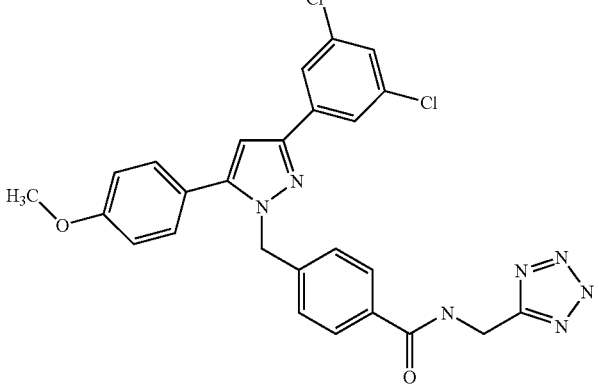 |
| 83 | 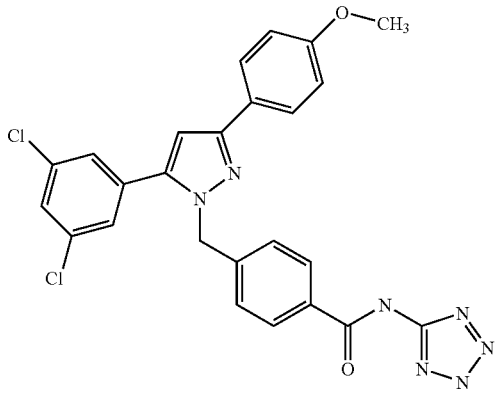 |
| 84 | 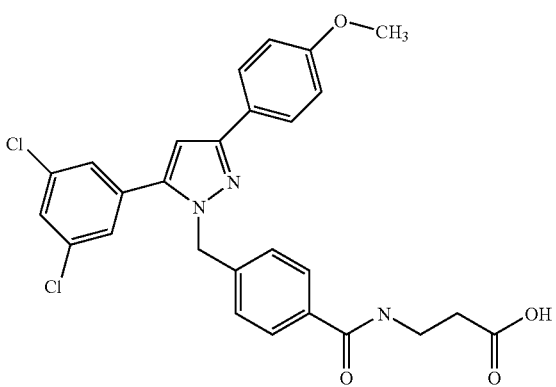 |
| 85 | 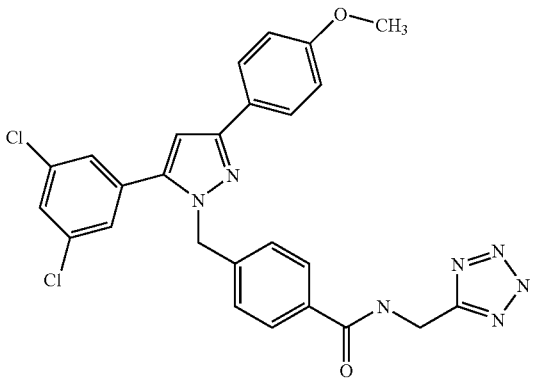 |

-continued

| Cpd No. | Structure |
|---|---|
| 86 | 3-(3,5-dichlorophenyl)-5-(3-(trifluoromethyl)phenyl)-1H-pyrazol-1-yl]methyl}benzamide with N-(1H-tetrazol-5-yl) |
| 87 | 3-(3,5-dichlorophenyl)-5-(3-(trifluoromethyl)phenyl)-1H-pyrazol-1-yl]methyl}benzamide with N-(2-carboxyethyl) |
| 88 | 5-(3,5-dichlorophenyl)-3-(3-(trifluoromethyl)phenyl)-1H-pyrazol-1-yl]methyl}benzamide with N-(1H-tetrazol-5-yl) |
| 89 | 5-(3,5-dichlorophenyl)-3-(3-(trifluoromethyl)phenyl)-1H-pyrazol-1-yl]methyl}benzamide with N-(2-carboxyethyl) |

-continued
| Cpd No. | Structure |
|---|---|
| 90 | 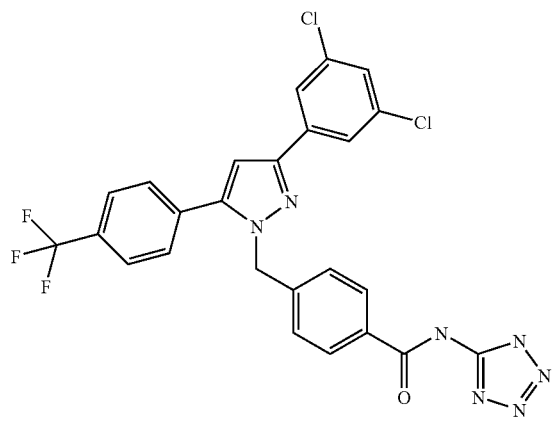 |
| 91 | 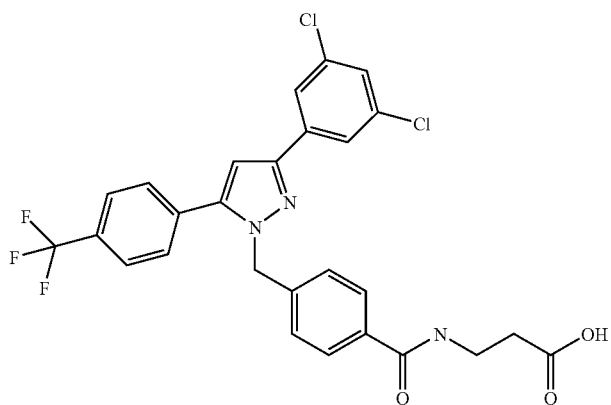 |
| 92 | 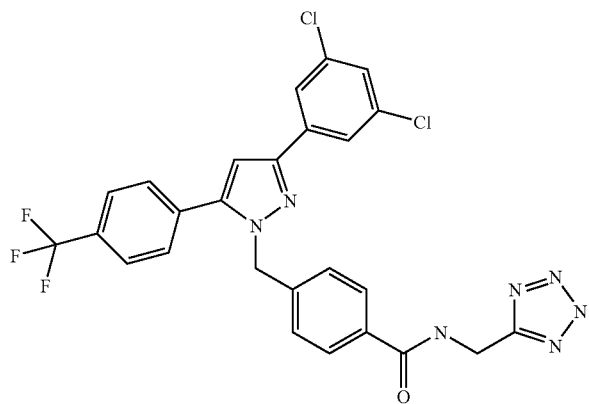 |

-continued
| Cpd No. | Structure |
|---|---|
| 93 | 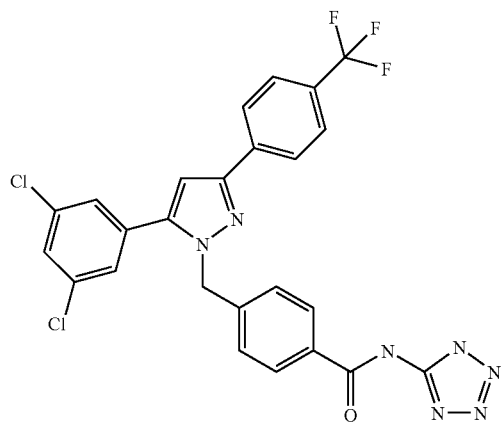 |
| 94 | 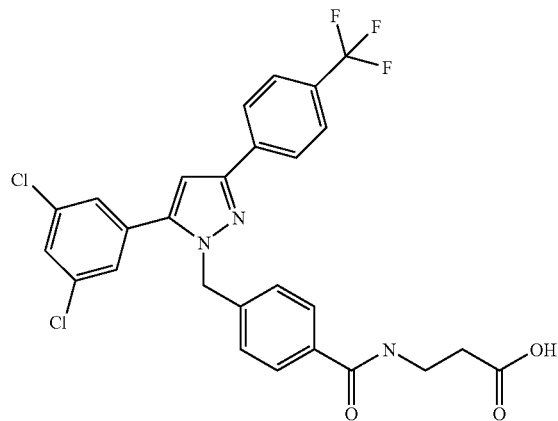 |
| 95 | 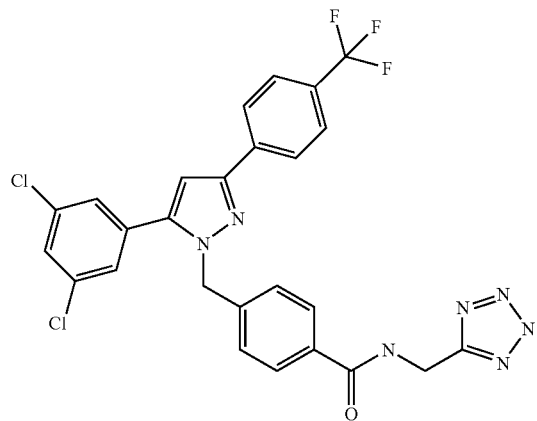 |

-continued

| Cpd No. | Structure |
|---|---|
| 96 | 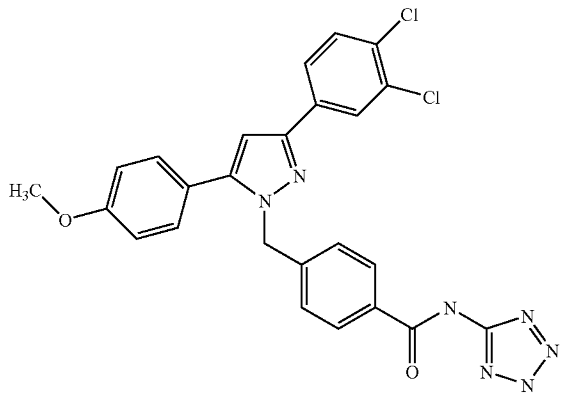 |
| 97 | 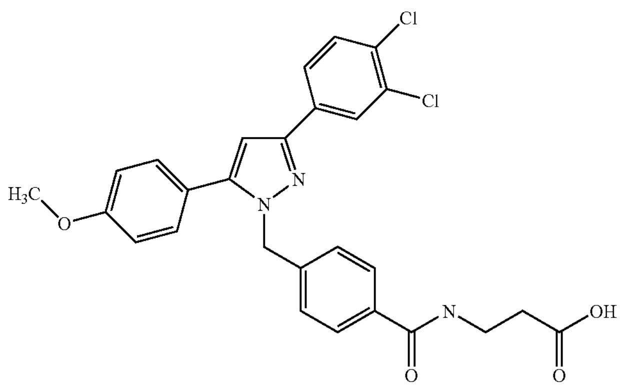 |
| 98 | 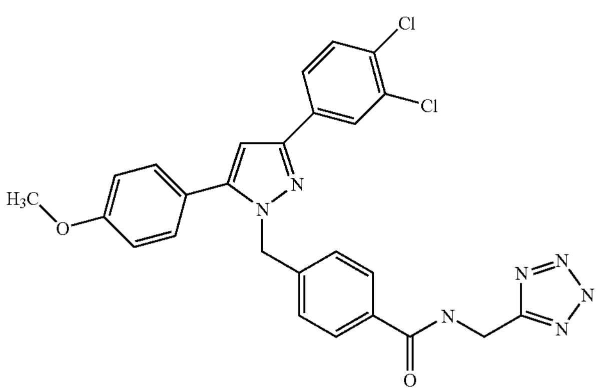 |
| 99 | 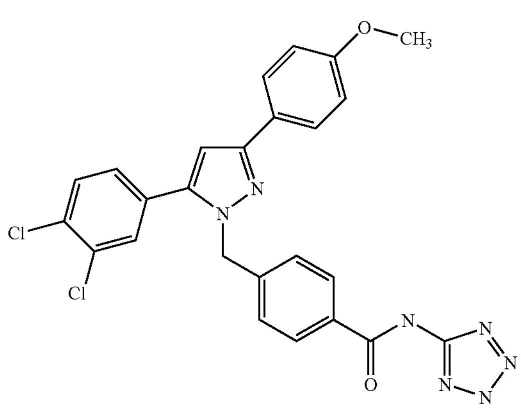 |

-continued

| Cpd No. | Structure |
|---|---|
| 100 | 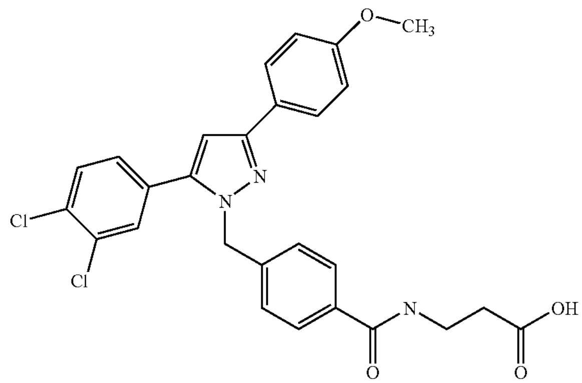 |
| 101 | 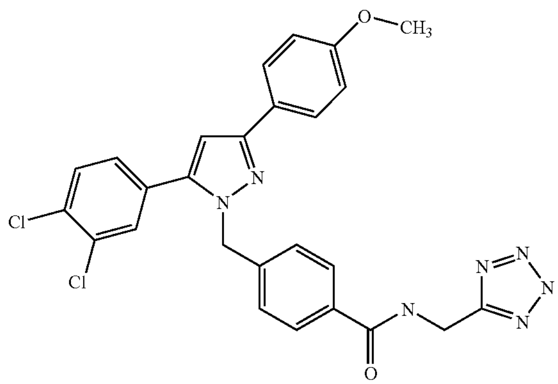 |
| 102 | 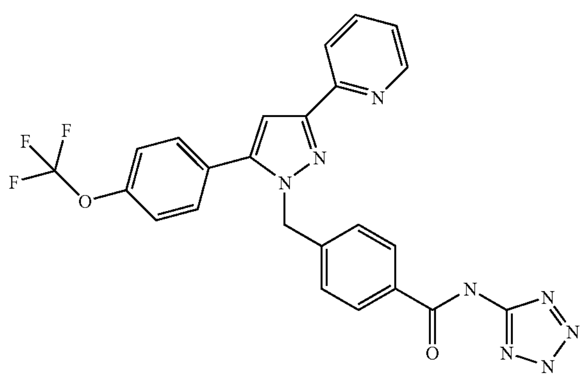 |
| 103 | 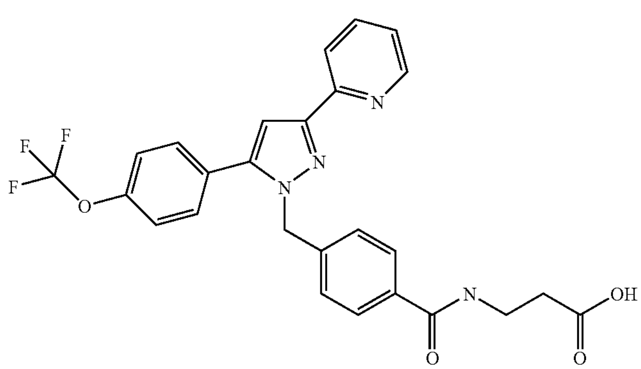 |

-continued
| Cpd No. | Structure |
|---|---|
| 104 | 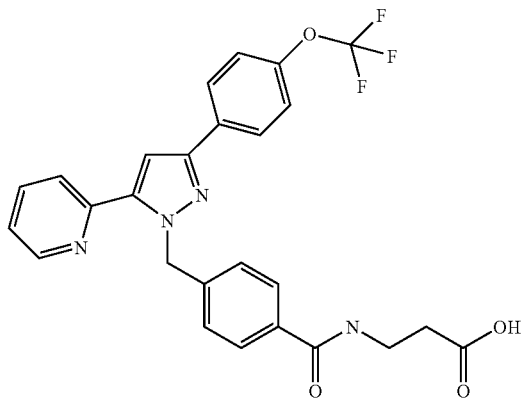 |
| 105 | 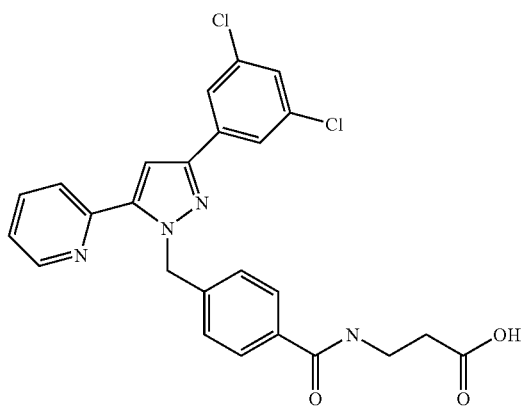 |
| 106 | 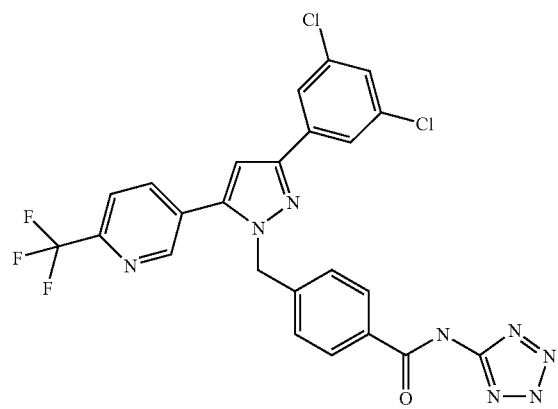 |

-continued
| Cpd No. | Structure |
| --- | --- |
| 107 | 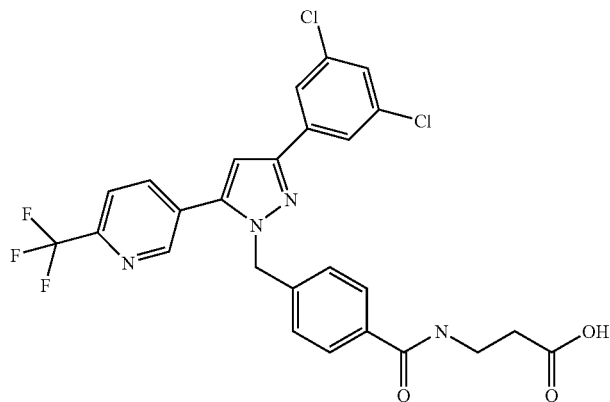 |
| 108 | 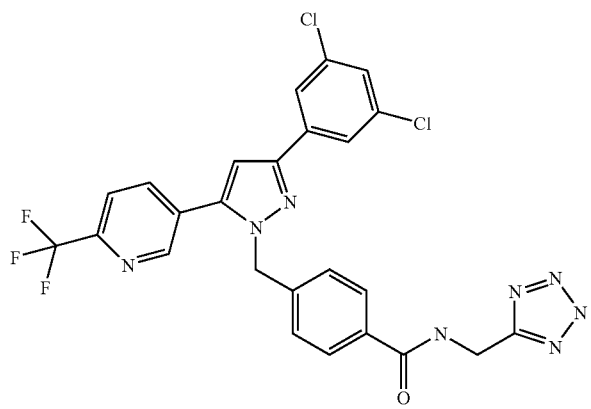 |
| 109 | 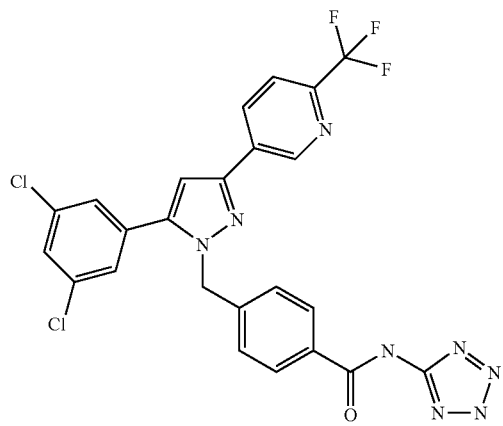 |

-continued
| Cpd No. | Structure |
|---|---|
| 110 | 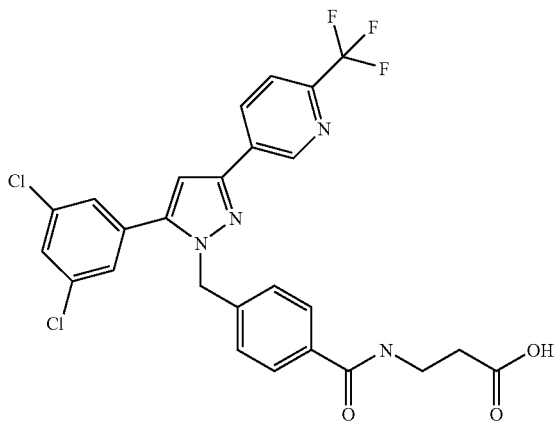 |
| 111 | 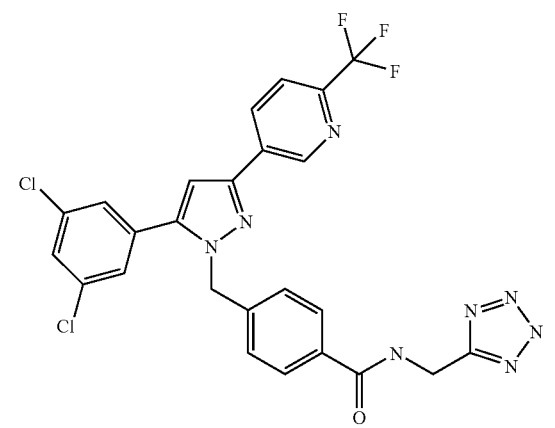 |
| 112 | 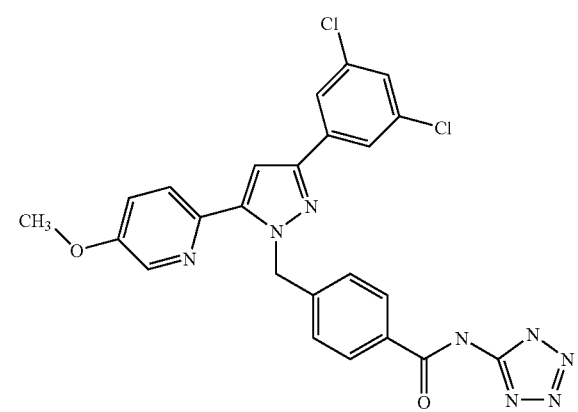 |

-continued
| Cpd No. | Structure |
|---|---|
| 113 | 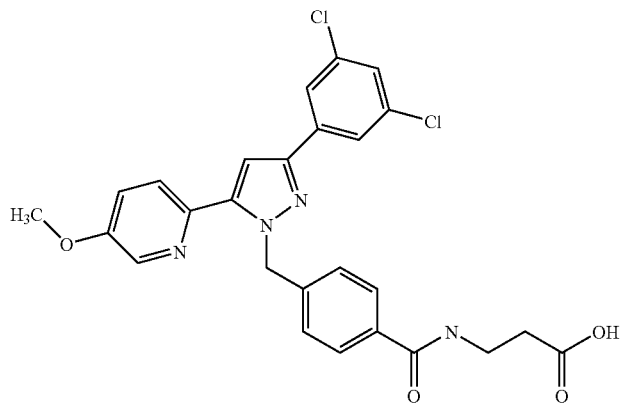 |
| 114 | 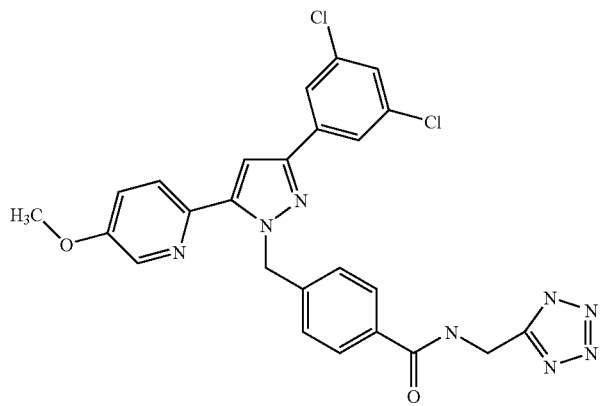 |
| 115 | 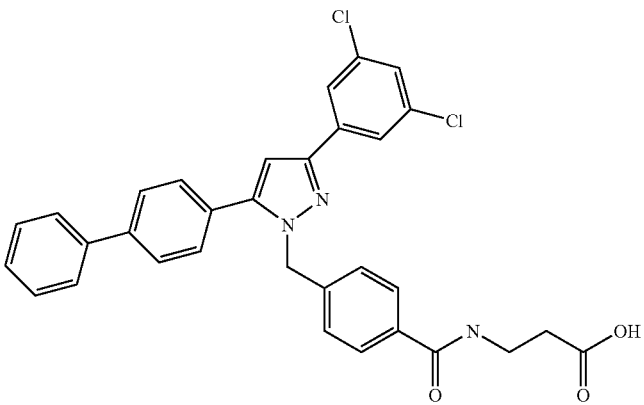 |

-continued
| Cpd No. | Structure |
|---|---|
| 116 | 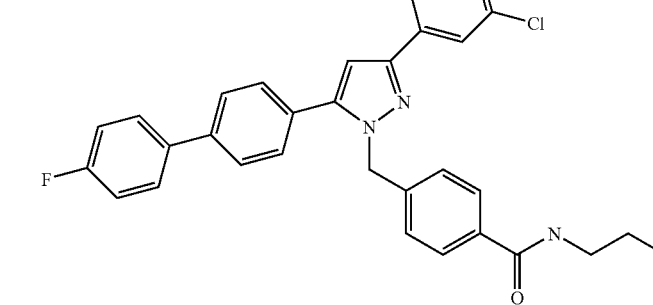 |
| 117 | 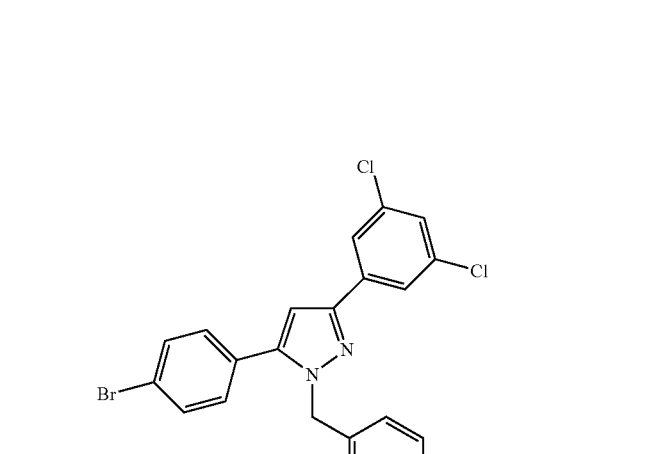 |
| 118 | 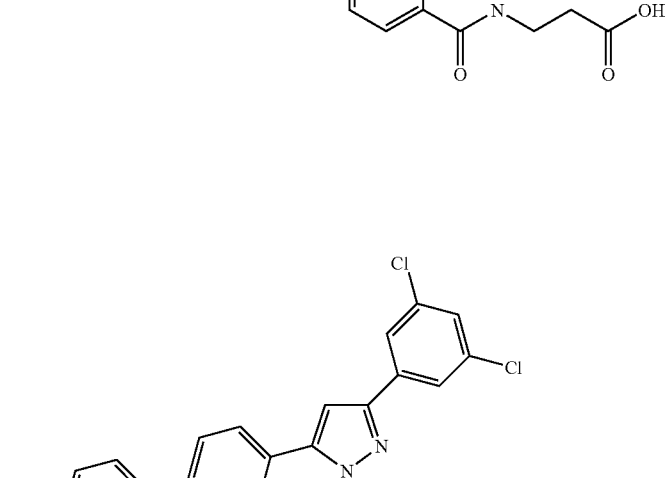 |

-continued

| Cpd No. | Structure |
|---|---|
| 119 | 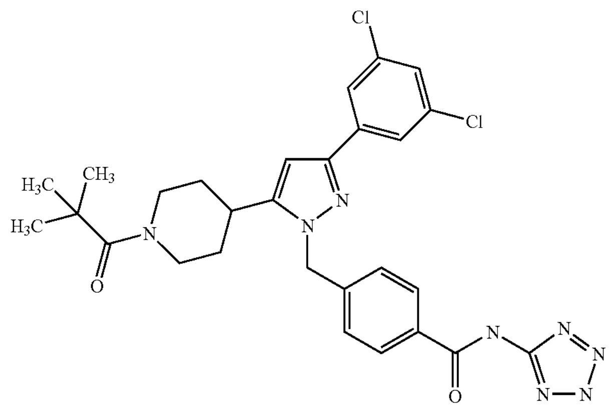 |
| 120 | 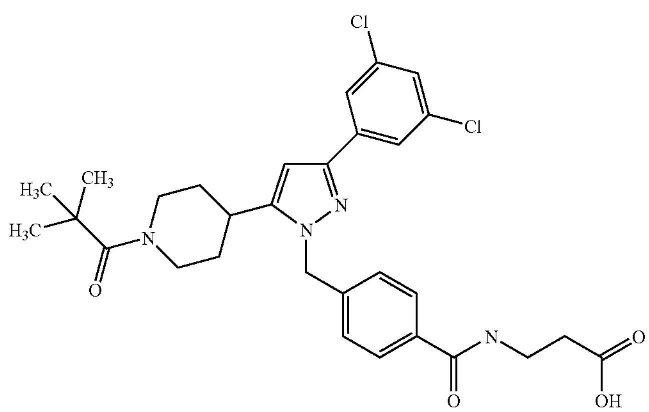 |
| 121 | 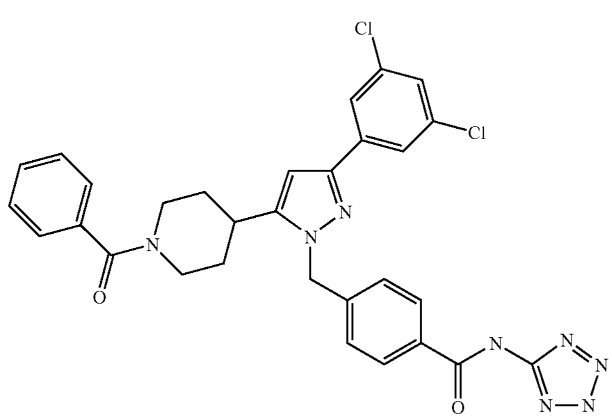 |

| Cpd No. | Structure |
|---|---|
| 122 | 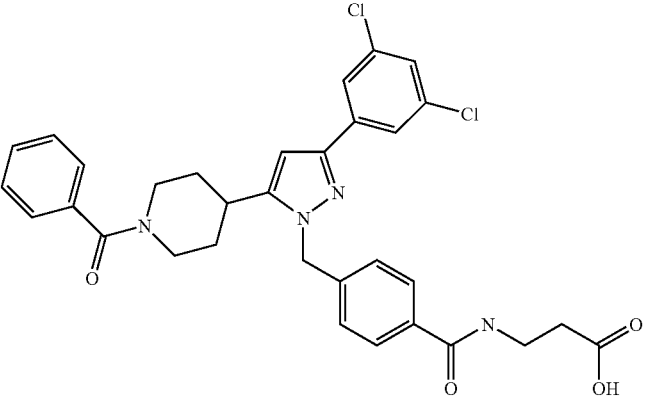 |
| 123 | 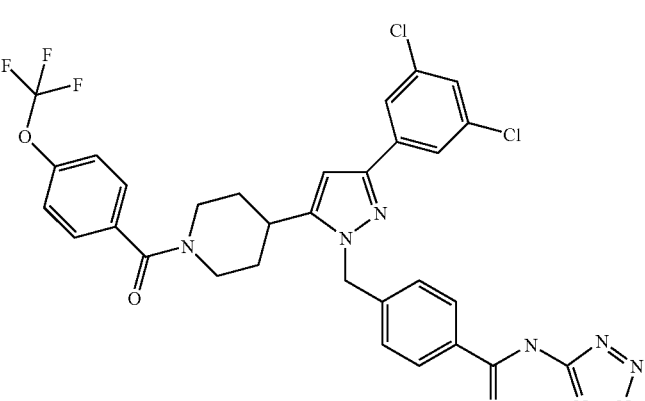 |
| 124 | 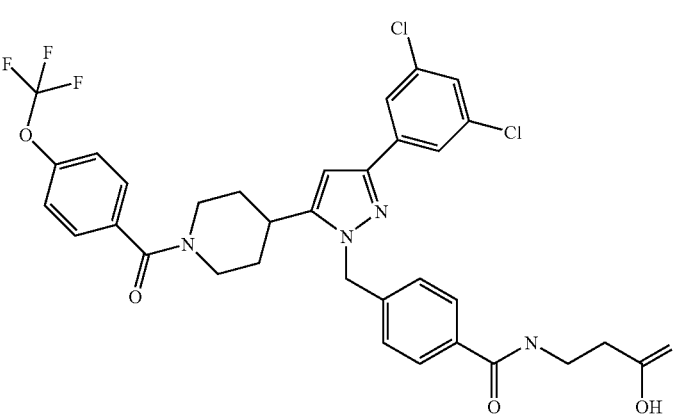 |

-continued
| Cpd No. | Structure |
|---|---|
| 125 | 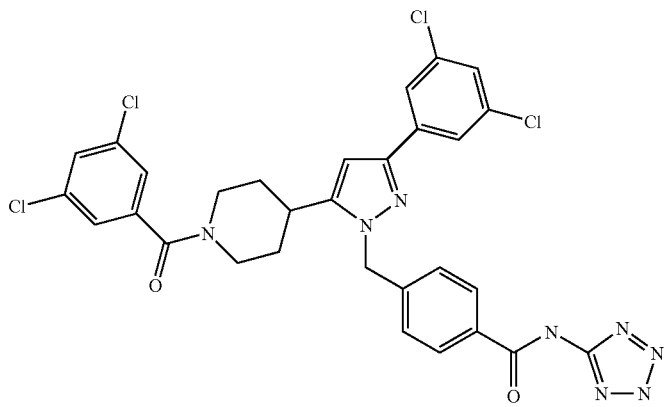 |
| 126 | 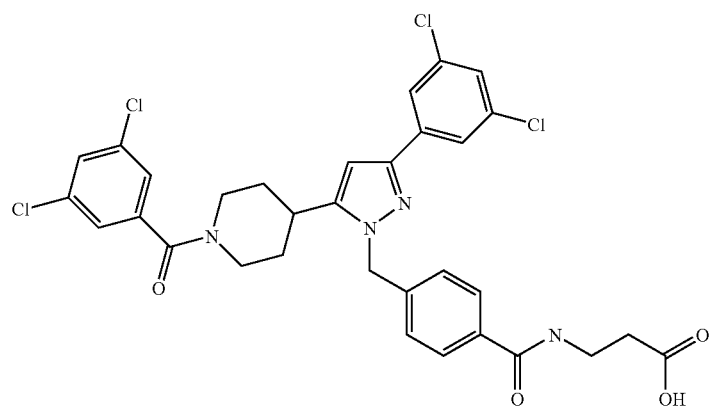 |
| 127 | 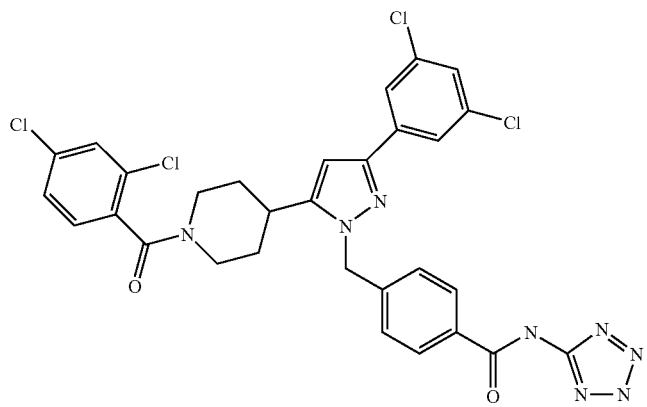 |

-continued
| Cpd No. | Structure |
|---|---|
| 128 | 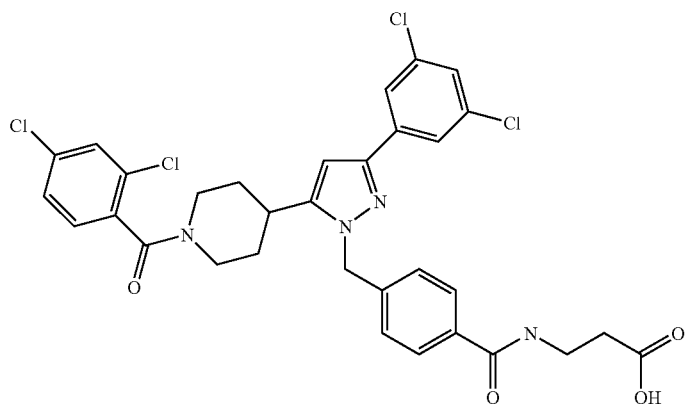 |
| 129 | 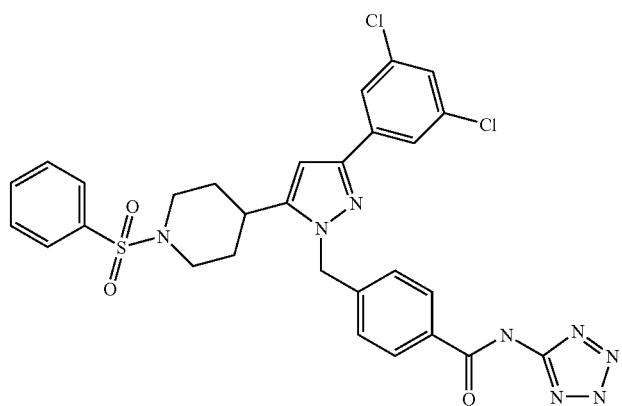 |
| 130 | 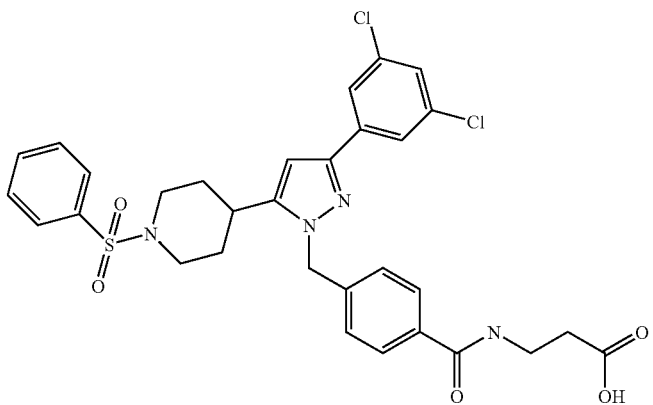 |

|Cpd No.|Structure|
|---|---|
|131|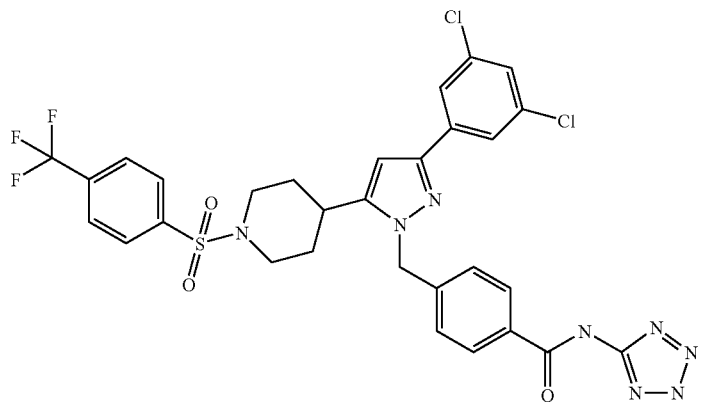|
|132|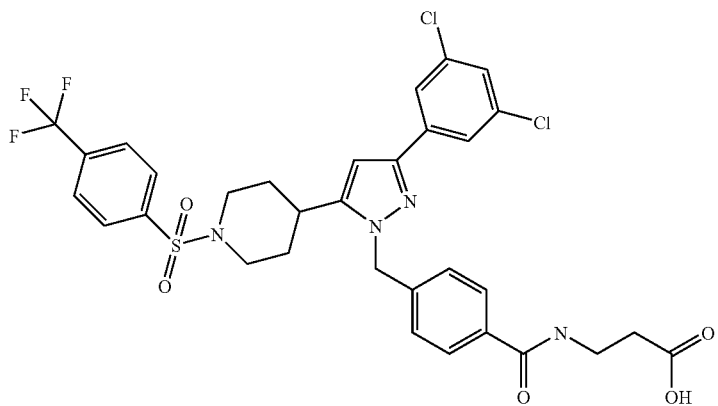|
|133|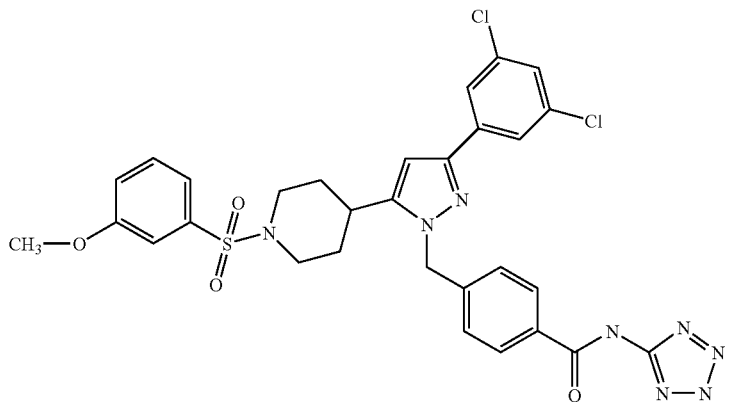|

-continued
| Cpd No. | Structure |
|---------|-----------|
| 134 | 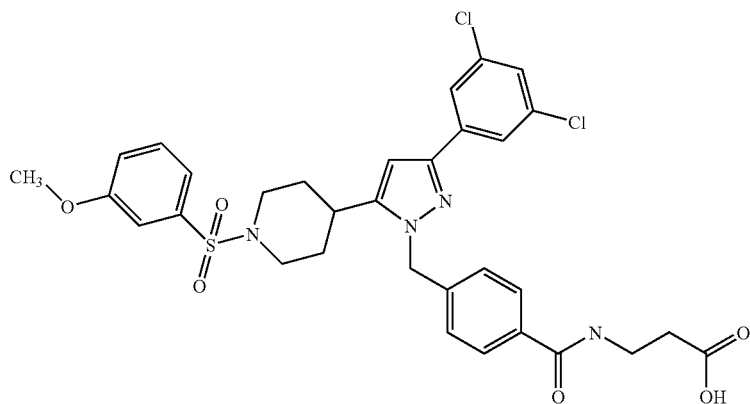 |
| 135 | 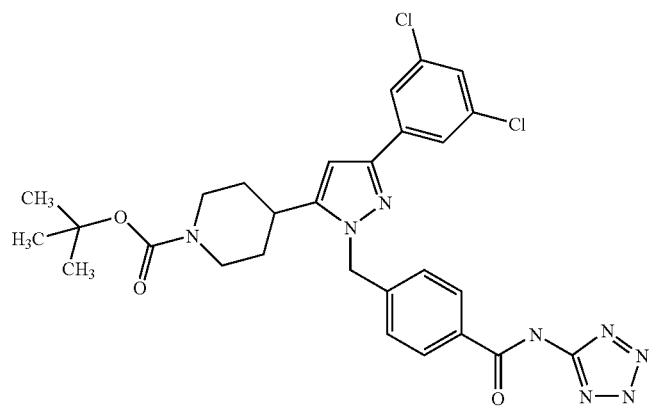 |
| 136 | 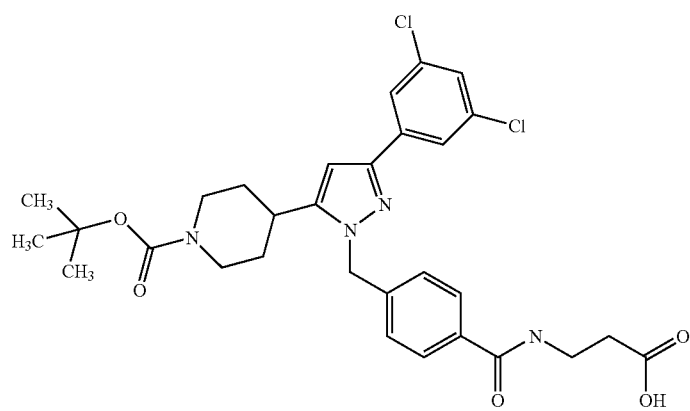 |

| Cpd No. | Structure |
|---|---|
| 137 | *[structure: 3-(4-trifluoromethylphenyl)-5-phenyl-1H-pyrazole linked via CH2 to pyridine-carboxamide-N-CH2CH2COOH]* |
| 138 | *[structure: 3-(4-trifluoromethylphenyl)-5-phenyl-1H-pyrazole linked via CH2 to benzamide-N-CH2-tetrazole]* |
| 139 | *[structure: 5-(4-trifluoromethylphenyl)-3-phenyl-1H-pyrazole linked via CH2 to benzamide-N-CH2CH2COOH]* |
| 140 | *[structure: 5-(4-trifluoromethylphenyl)-3-phenyl-1H-pyrazole linked via CH2 to benzamide-N-tetrazole]* |

| Cpd No. | Structure |
|---|---|
| 141 | *3-phenyl-5-[4-(trifluoromethyl)phenyl]-1-{[4-({[(1H-tetrazol-5-yl)methyl]carbamoyl})benzyl]}-1H-pyrazole* |
| 142 | *N-{4-[(5-biphenyl-3-yl-3-(3,5-dichlorophenyl)-1H-pyrazol-1-yl)methyl]benzoyl}-β-alanine* |
| 143 | *N-(4-{[3-(3,5-dichlorophenyl)-5-(4'-fluorobiphenyl-3-yl)-1H-pyrazol-1-yl]methyl}benzoyl)-β-alanine* |
| 144 | *N-(4-{[5-(3-bromophenyl)-3-(3,5-dichlorophenyl)-1H-pyrazol-1-yl]methyl}benzoyl)-β-alanine* |

| Cpd No. | Structure |
|---|---|
| 145 | 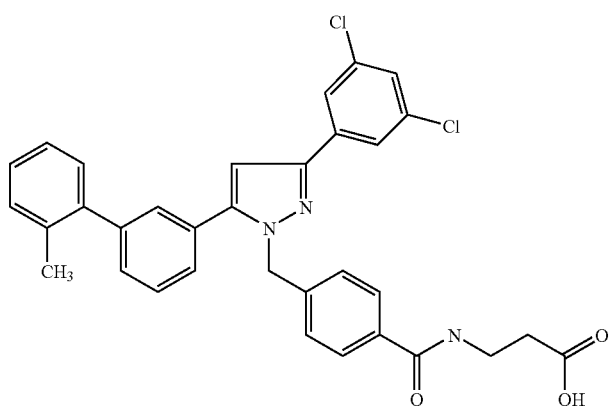 |
| 146 | 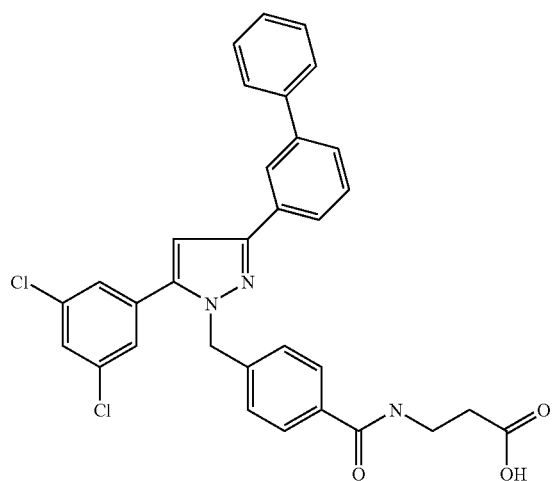 |
| 147 | 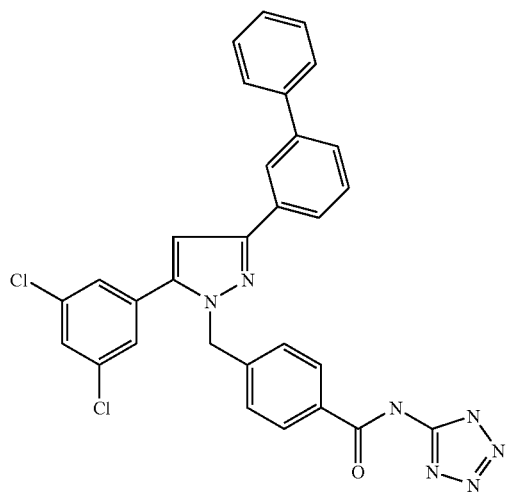 |

-continued
| Cpd No. | Structure |
|---|---|
| 148 | 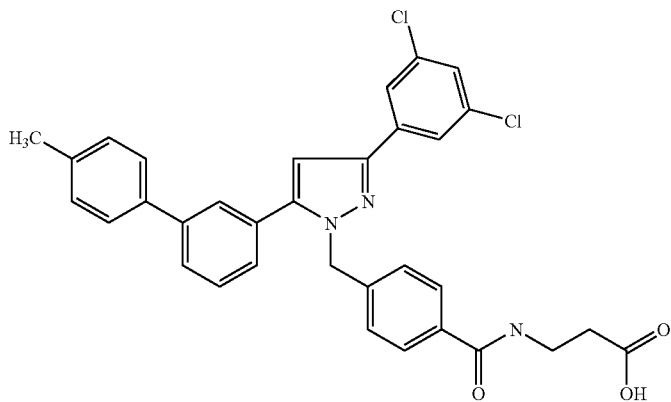 |
| 149 | 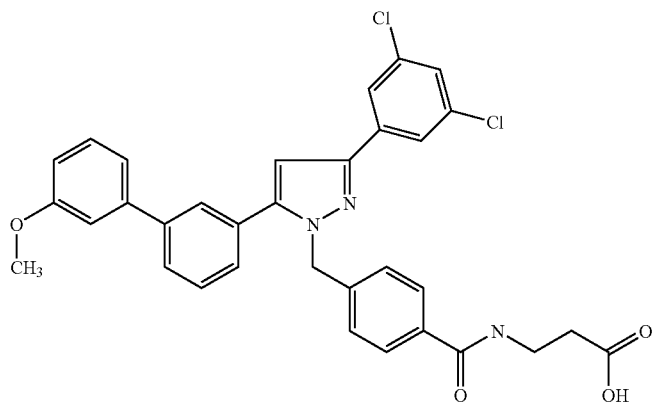 |
| 150 | 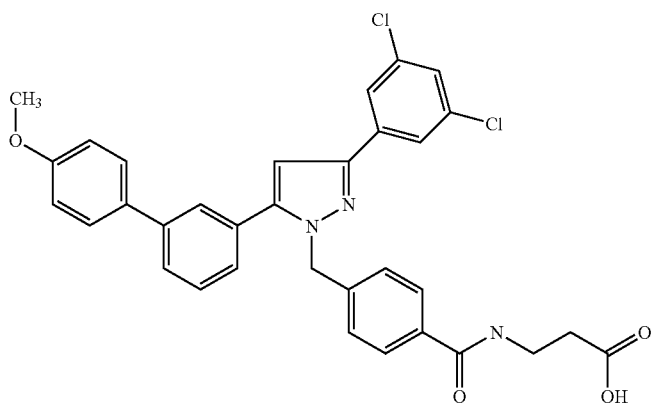 |

-continued
| Cpd No. | Structure |
|---|---|
| 151 | 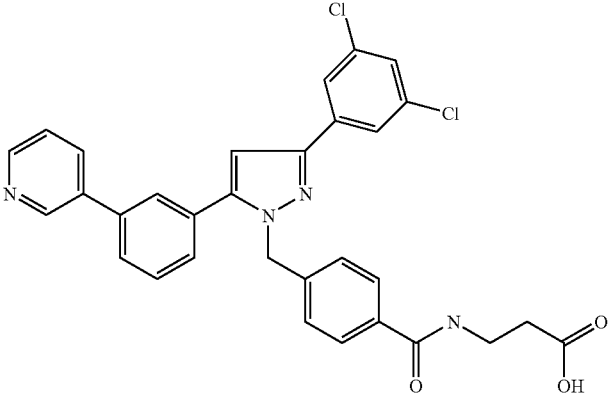 |
| 152 | 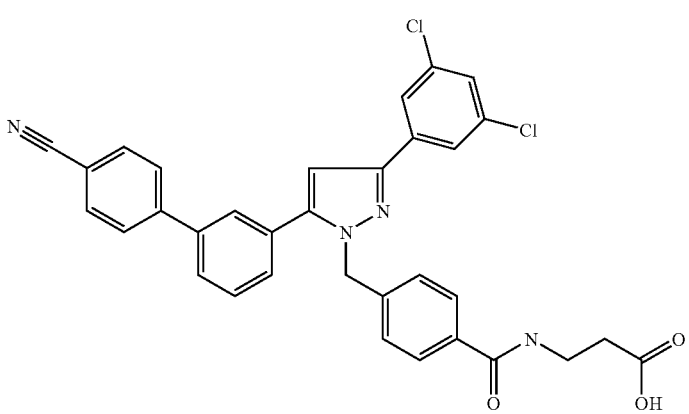 |
| 153 | 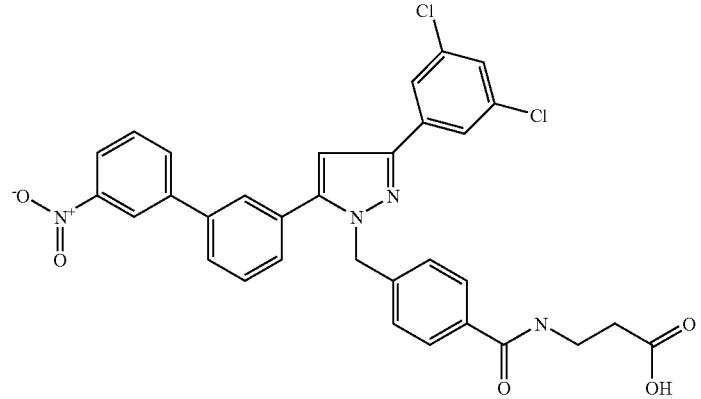 |

| Cpd No. | Structure |
|---|---|
| 154 | 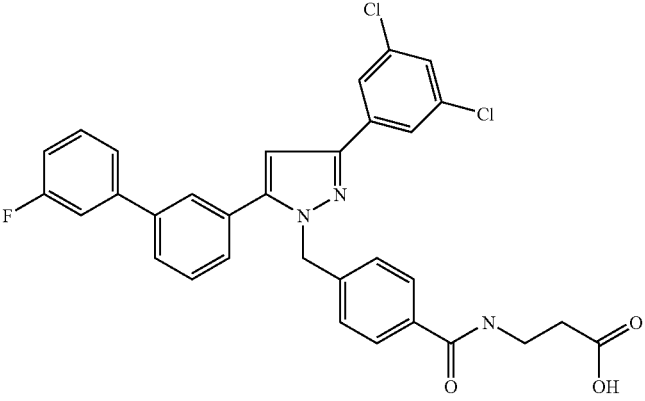 |
| 155 | 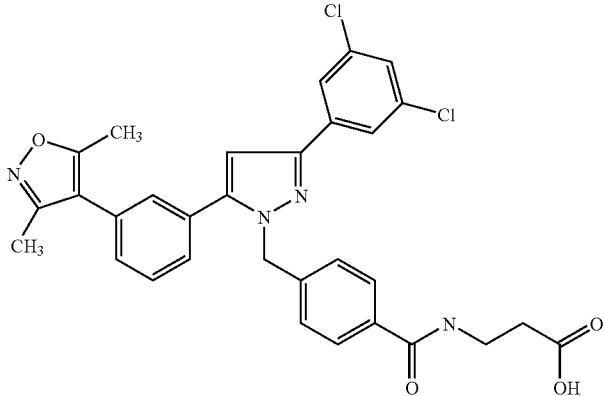 |
| 156 | 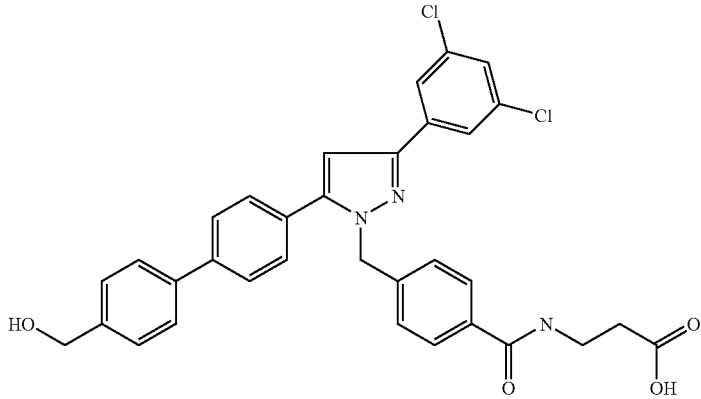 |

-continued
| Cpd No. | Structure |
|---|---|
| 157 | 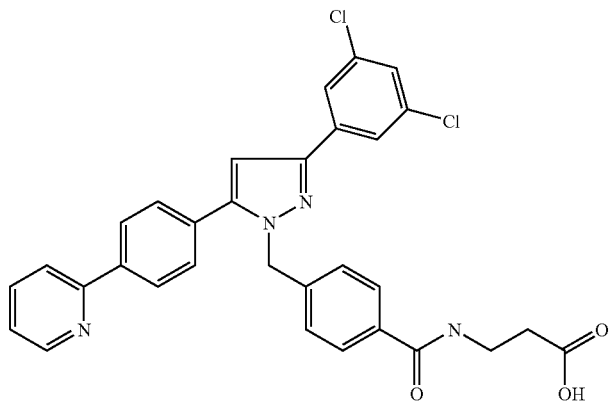 |
| 158 | 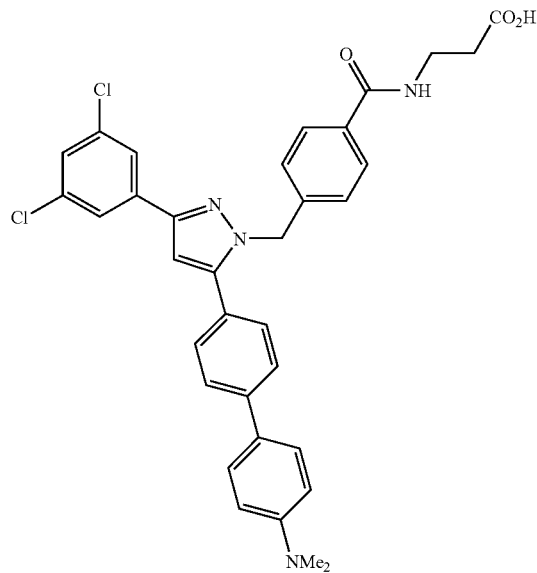 |
| 159 | 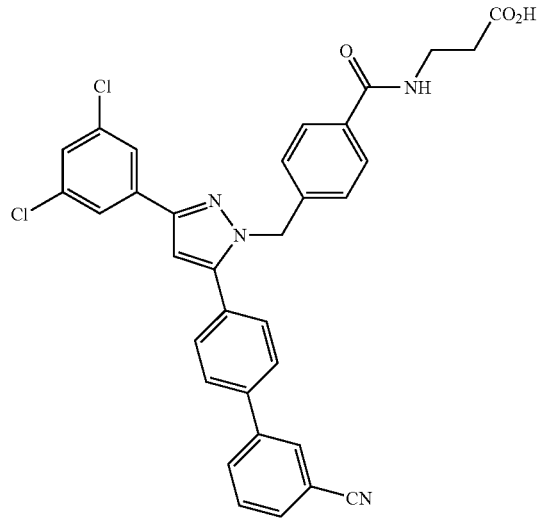 |

-continued
| Cpd No. | Structure |
|---|---|
| 160 | 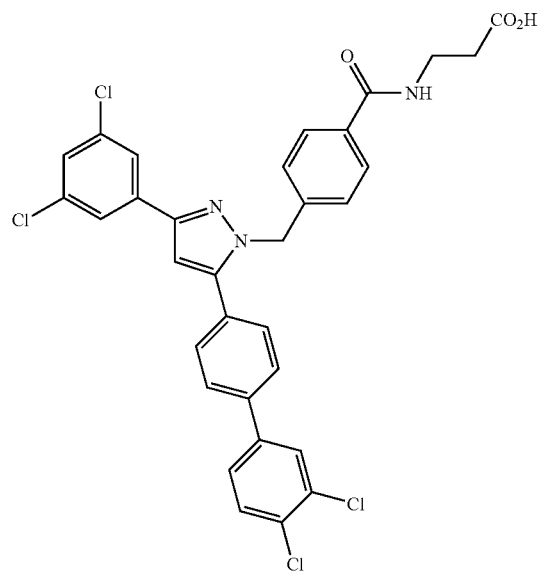 |
| 161 | 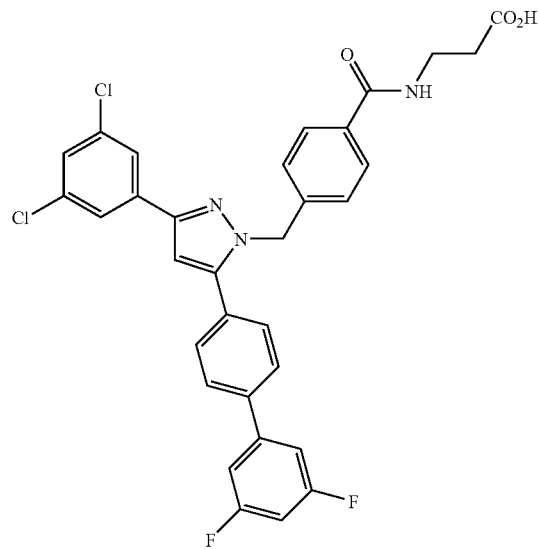 |

-continued
| Cpd No. | Structure |
|---|---|
| 162 | 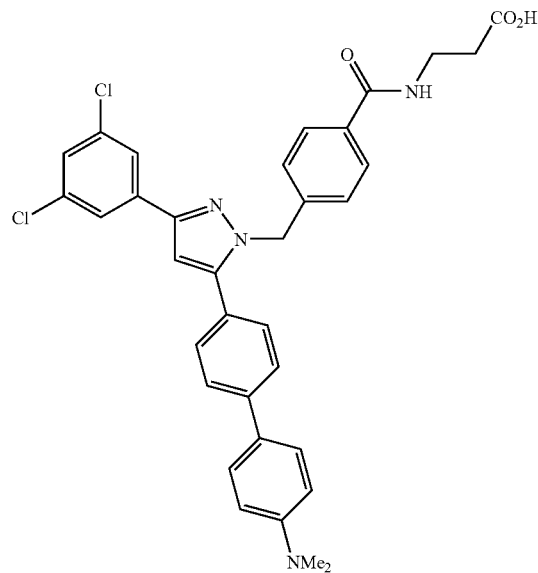 |
| 163 | 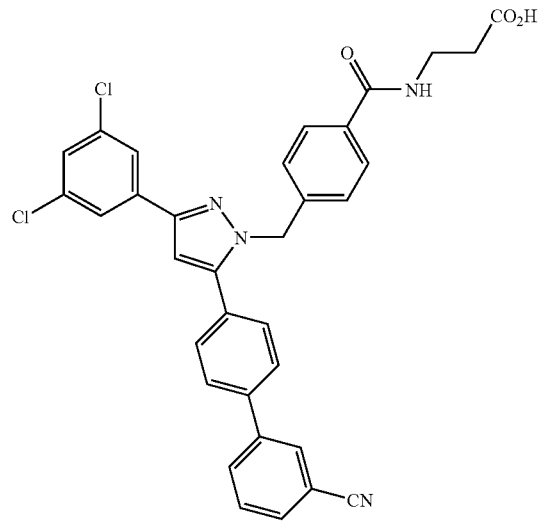 |

-continued
| Cpd No. | Structure |
|---|---|
| 164 | 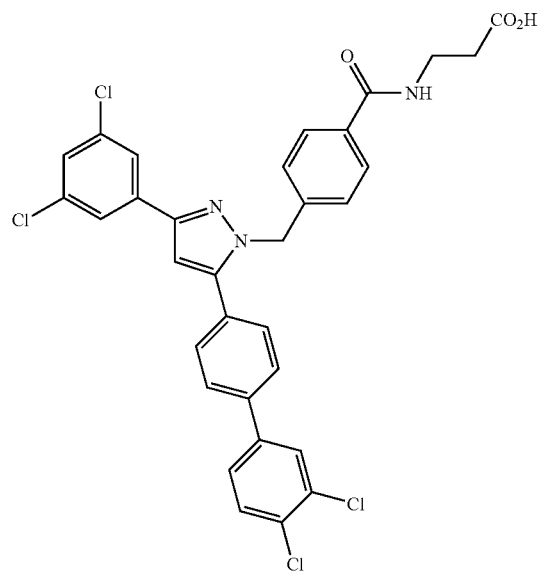 |
| 165 | 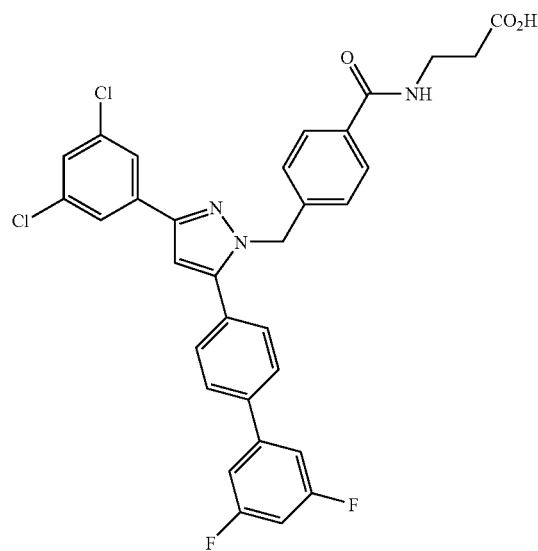 |

| Cpd No. | Structure |
|---|---|
| 166 | 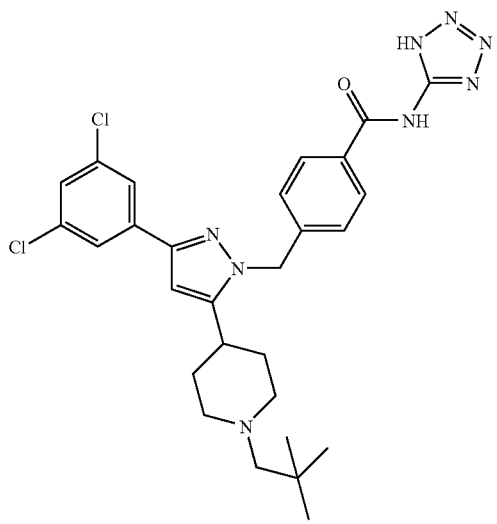 |
| 167 | 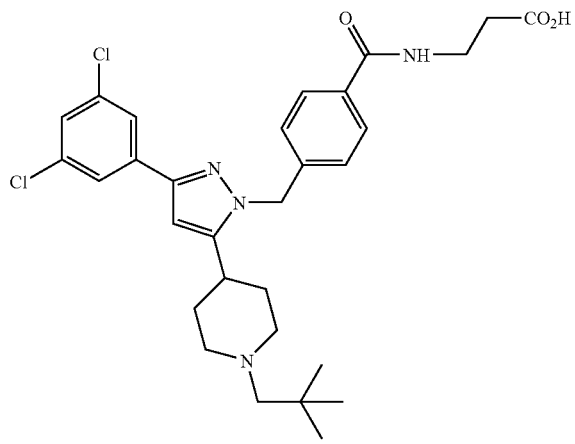 |
| 168 | 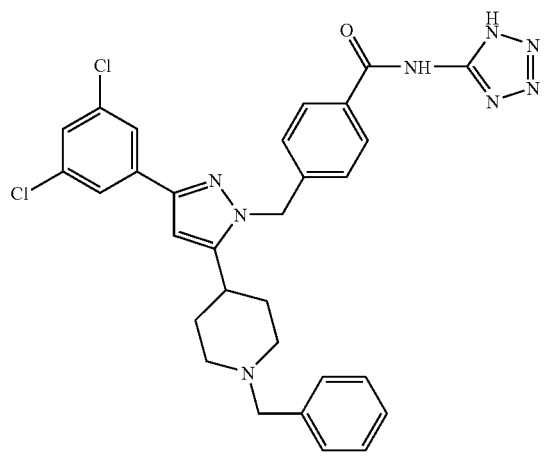 |

-continued

| Cpd No. | Structure |
|---|---|
| 169 | 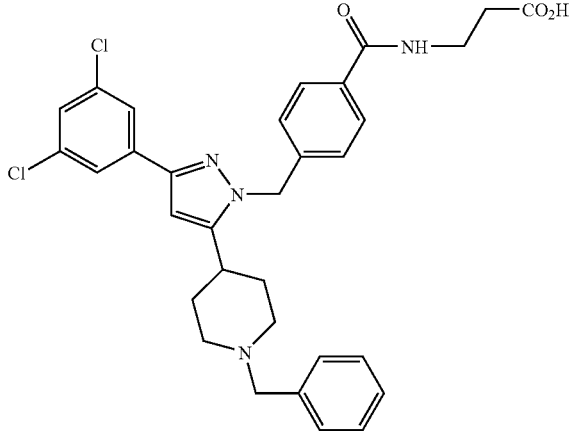 |
| 170 | 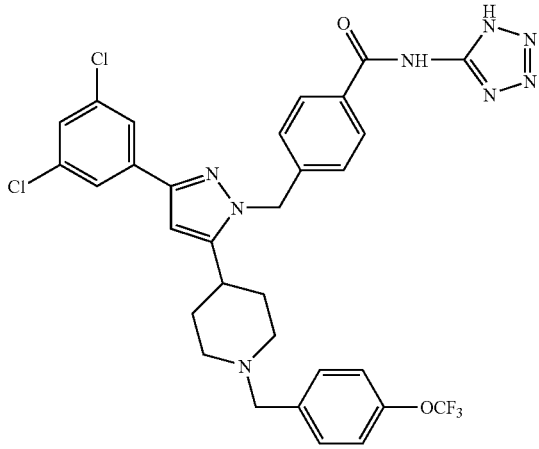 |
| 171 | 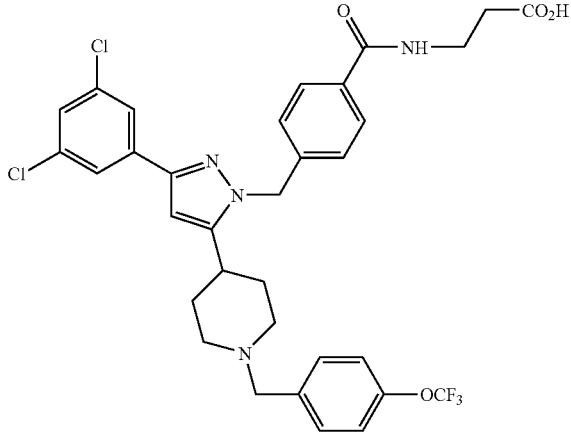 | as well as the pharmaceutically acceptable salts and solvates thereof. Some of the hydrogen atoms are implied on nitrogen atoms.

The invention further includes a pharmaceutical composition which is comprised of a compound of formula I in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included in the present invention is a method of treating hyperglycemia, diabetes or insulin resistance in a mammalian patient in need of such treatment which comprises administering to said patient an effective amount of a compound of formula I.

Also included in a method of treating, preventing or delaying the onset of diseases or conditions that are associated with type 2 diabetes mellitus. Examples include diseases and conditions selected from the group consisting of: dyslipidemias, (e.g., hyperlipidemia), such as elevated levels of cholesterol (hypercholesterolemia), triglycerides (hypertriglyceridemia) or low density lipoproteins (LDL) (high LDL levels), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Also included in the present invention is a method of treating atherosclerosis in a mammalian patient in need of such treatment, comprising administering to said patient a compound of formula I in an amount effective to treat atherosclerosis.

Also included in the present invention is a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I in an amount that is effective to treat said condition.

Also included in the present invention is a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to delay the onset of said condition.

Also included in the present invention is a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to reduce the risk of developing said condition.

More particularly, the present invention includes a method of treating, reducing the risk of developing, or delaying the onset of obesity in a mammalian patient in need of such treatment, comprising administering to the patient an amount of a compound of formula I that is effective for treating, preventing or delaying the onset of obesity.

Also more particularly, the present invention includes a method of treating, reducing the risk of developing, or delaying the onset of Syndrome X in a mammalian patient in need of such treatment, comprising administering to the patient an amount of a compound of formula I that is effective for treating, preventing or delaying the onset of Syndrome X.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine-resins, procaine, purines, theobromine, triethyl amine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose, comprised of combining the compound of formula I with the carrier materials to provide the medicament.

Dose Ranges

The prophylactic or therapeutic dose of a compound of formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount" "anti-diabetic effective amount" and the other terms appearing throughout the application addressing the amount of the compound to be used refer to the dosage ranges provided, taking into account any necessary variation outside of these ranges, as determined by the skilled physician. Similarly, when a compound is "administered" to the patient, this means that the compound is delivered as a conventional pharmaceutical preparation, or delivered systemically to the patient, such as via the administration of a pro-drug.

Representative dosages for adults thus range from about 0.1 mg to about 1.0 g per day, preferably about 1 mg to about 200 mg, in single or divided doses.

When intravenous or or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred. Thus, one aspect of the invention that is of interest is the use of a compound of formula I for preparing a pharmaceutical composition which is comprised of combining the compound of formula I with the carrier.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline | 415 |
| Tween 80 | 0.5 | Cellulose | |
| Benzyl alcohol | 9.0 | Povidone | 14.0 |
| Benzalkonium chloride | 1.0 | Pregelatinized | 43.5 |
| Water for injection to make | 1.0 mL | Starch | |
| | | Magnesium Stearate | 2.5 |
| | | Total | 500 mg |

| Capsule | mg/capsule | Aerosol | Per canister |
|---|---|---|---|
| Compound of Formula I | 25 | Compound of Formula I | 24 mg |
| | | Lecithin, NF Liq. Conc. | 1.2 mg |
| Lactose Powder | 573.5 | Trichlorofluoromethane, NF | 4.025 g |
| Magnesium Stearate | 1.5 | Dichlorodifluoromethane, NF | 12.15 g |
| Total | 600 mg | | |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical composition, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) α-glucosidase inhibitors (e.g., voglibose, miglitol, acarbose), (f) DP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include:

(1) a compound according to formula I, (2) a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; 0) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA: cholesterol acyltransferase inhibitors, (viii) anti-oxidants and (ix) LXR modulators; (k) PPARδ agonists; (l) antiobesity compounds; (m) an ileal bile acid transporter inhibitor; (n) anti-inflammatory agents other than glucocorticoids; and (O) protein tyrosine phosphatase-1B (PTP-1B) inhibitors; and (3) a pharmaceutically acceptable carrier.

In accordance with the methods described herein one method that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound of formula I and a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP,GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, (viii) anti-oxidants and (ix) LXR modulators; (k) PPARδ agonists; (1) antiobesity compounds; (m) an ileal bile acid transporter inhibitor (n) anti-inflammatory agents excluding glucocorticoids; and (o) protein tyrosine phosphatase-1B (PTP-1B) inhibitors, said compounds being administered to the patient in an amount that is effective to treat said condition.

More particularly, a method that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a therapeutically effective amount of a compound of formula I and an HMG-CoA reductase inhibitor.

Even more particularly, the method that is of interest comprises administering to the patient a therapeutically effective amount of a compound of formula I and an HMG-CoA reductase inhibitor wherein the HMG-CoA reductase inhibitor is a statin, and even more particularly, the statin is selected from the group consisting of lovastatin, simvastatin, pravastatin, fluvastatin, atorvastatin, itavastatin, 2D4522 and rivastatin.

A different aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and an HMG-CoA reductase inhibitor.

More particularly, another aspect of the invention relates to a method for delaying the onset or reducing the risk of developing atherosclerosis in a human patient in need of such treatment comprising administering to said patient an effective amount of a compound of formula I and an HMG-CoA reductase inhibitor. Even more particularly, the method comprises administering an effective amount of a compound of formula I and an HMG-CoA reductase inhibitor wherein the HMG-CoA reductase inhibitor is a statin. Even more particularly, the method comprises administering a compound of formula I and a statin selected from the group consisting of: lovastatin, simvastatin, pravastatin, fluvastatin, atorvastatin, itavastatin, ZD-4522 and rivastatin. Still more particularly, the method comprises administering a compound of formula I and the statin known as simvastatin.

Another aspect of the invention relates to a method of reducing the risk of developing a condition selected from the group consisting of hypercholesterolemia, atherosclerosis, low LDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and a cholesterol absorption inhibitor. In particular, the method comprises administering an effective amount of a compound of formula I and the cholesterol absorption inhibitor known as ezetimibe.

More particularly, a method for delaying the onset or reducing the risk of developing atherosclerosis in a human patient in need of such treatment is described which comprises administering to said patient an effective amount of a compound of formula I and a cholesterol absorption inhibitor. More particularly, the method comprises administering a compound of formula I and the cholesterol absorption inhibitor known as ezetimibe.

Throughout the instant application, the following abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DMF = N,N-dimethylformamide |
| DMAP = 4-Dimethylaminopyridine | Et = ethyl |
| EtOAc = ethyl acetate | EtOH = ethanol |
| eq. = equivalent(s) | FAB-mass spectrum = Fast atom bombardment-mass spectroscopy |
| HOAc = acetic acid | |
| HOBT, HOBt = Hydroxybenztriazole | HPLC = High pressure liquid chromatography |
| Me = methyl | |
| Ph = phenyl | LAH = Lithium aluminum hydride |
| THF = Tetrahydrofuran | PBS = phosphate buffer saline |
| $C_6H_{11}$ = cyclohexyl | TFA = Trifluoroacetic acid |
| iPr = isopropyl | TMS = Trimethylsilane |
| 2,4-diClPh = 2,4-dichlorophenyl | $Nme_2$ = dimethylamino |
| Py, Pyr = pyridyl | 2ClPh = 2-chlorophenyl |

Compounds of the present invention may be prepared according to the methodology outlined in the following general synthetic schemes.

Compounds (Ia) may be prepared by alkylation of pyrazole IIa:

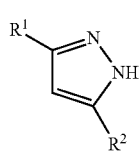

IIa where $R^1$ and $R^2$ are as defined above with respect to formula I.

Compounds IIa, where $R^1$ and $R^2$ represent either an alkyl or aryl group, are known in the literature or may be conveniently prepared by a variety of methods familiar to those skilled in the art such as described in Katritsky et al., Advances in Heterocyclic Chemistry, Vol. 6, pg 347-429. One route is illustrated in Scheme 1. Ester 1, which may be commercially available or readily prepared from the corresponding carboxylic acid by esterification using, for example, methanol or ethanol containing an acid such as sulphuric acid, is condensed with the anion of methyl ketone 2 to give diketone 3. The reaction is carried out using a base such as sodium hydride in a polar aprotic solvent such as tetrahydrofuran (THF) at 0 to 25° C. for 16 to 24 h, see March, Advanced Organic Chemistry, 3$^{rd}$ Ed., pg 439 and ref. therein. Compounds such as 2 are commercially available or can be prepared by a variety of methods familiar to those skilled in the art. Diketone 3 is then condensed with hydrazine in a polar solvent such as methanol which may contain an acid such as acetic or hydrochloric acid, for 16 to 24 h at a temperature of 0 to 25° C. As will be understood by those skilled in the art, for the preparation of enantiomerically pure compounds, enantiomerically pure starting materials 1 and 2 should be used.

SCHEME 1

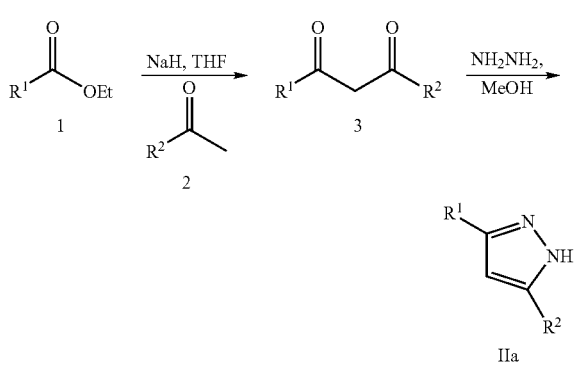

An alternate route to intermediate IIa involves condensation of alkynyl ketone 4 with hydrazine as shown in Scheme 2 and described in Cabarrocas et. al., Tetrahedron Asymmetry, Vol. 11, pg 2483-2493, 2000 and references therein. This is generally carried out in a polar solvent such as DMF at temperatures of from about 0 to 25° C. for about 16 to 24 h. Preparation of the intermediate 4 involves coupling of the alkyne 5 with the Weinreb amide of an appropriately functionalised carboxylic acid using a hindered base such as lithium diisopropylamide or butyl lithium in a polar aprotic solvent such as THF at about −78° C. This reaction is described in detail in Tetrahedron Lett., Vol. 22, pg 3815, 1981.

Alkynes 5 are either commercially available, or prepared from the corresponding halide and alkynyl magnesium iodide, see Negishi et. al., J. Org. Chem., Vol. 62, pg 8957-8960, 1997 and Org. Lett. Vol. 3, pg 3111-3113, 2001.

SCHEME 2

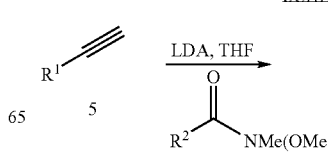

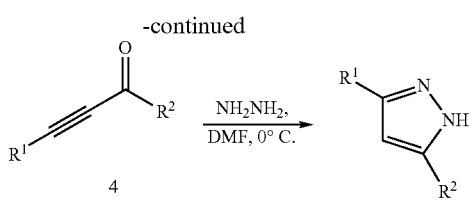

Intermediate IIa can then be converted to compounds of formula Ia-7 and Ia-8 as shown below in Scheme 3. Alkylation of pyrazole Ia with, for example, 4-carbomethoxy benzylbromide can be achieved following deprotonation of the pyrazole with a base such as sodium hydride or cesium carbonate in a polar solvent, generally dimethyl formamide (DMF), at about 0 to 25° C. for about 3 to 24 h. In some cases mixtures of isomers will be formed. These are generally separable by recrystallization, trituration, preparative thin layer chromatography, and flash chromatography on silica gel as described by W. C. Still et al, *J. Org. Chem.*, 43, 2923, (1978), or HPLC. Compounds purified by HPLC may be isolated as the corresponding salt.

Saponification of the methyl ester 6 is then achieved using a base such as aqueous lithium or sodium hydroxide in a polar solvent such as tetrahydrofuran, methanol, ethanol or a mixture of similar solvents. Coupling of the acid with an amine, generally 5-aminotetrazole 7 or a beta alanine derivative 8 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ia-7 and Ia-8.

The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner.

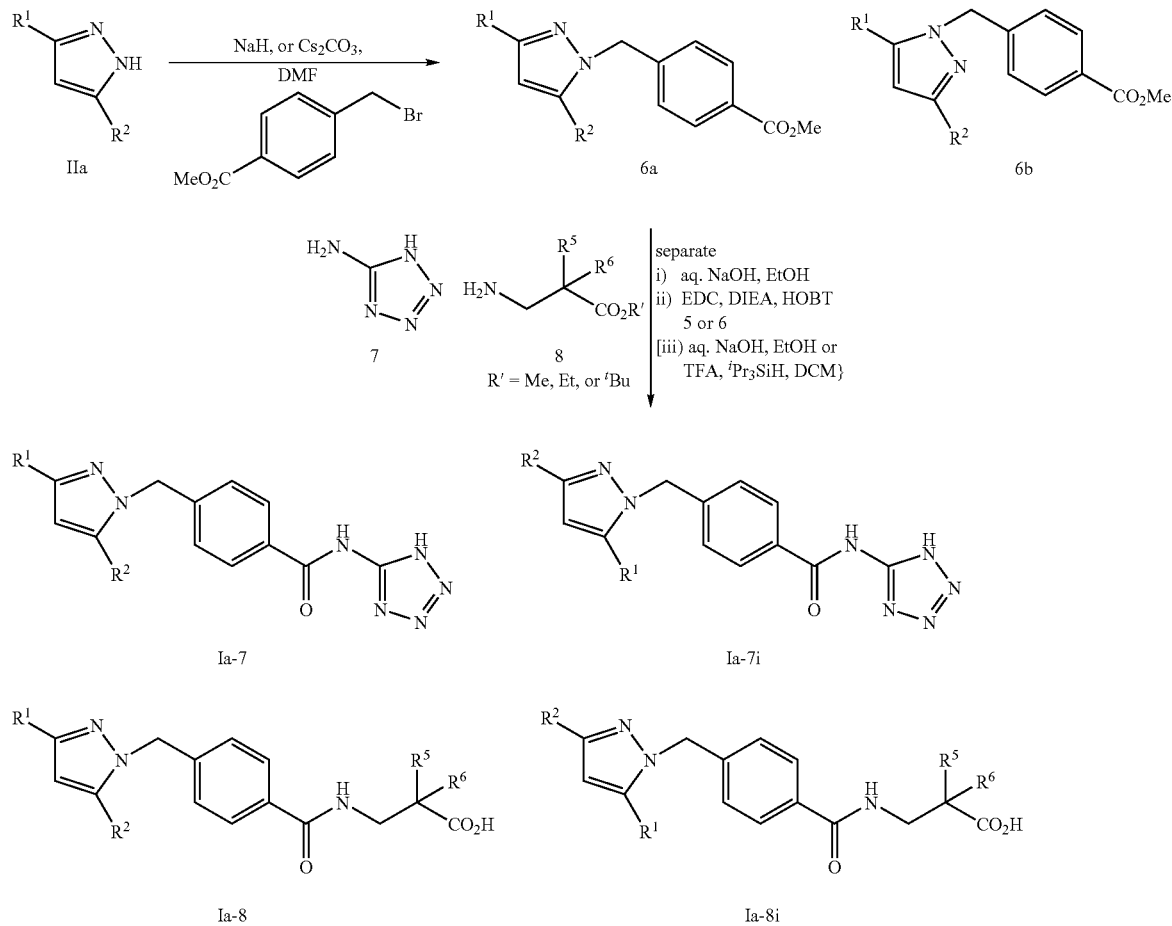

In some cases, the product from the reactions described in Scheme 3 will be further modified. These manipulations may include, but are not limited to substitution, reduction, oxidation, alkylation, acylation, and hydrolysis reactions, which are commonly known to those skilled in the art. One such modification is saponification of a methyl ester, as shown, this is achieved using a base such as aqueous lithium or sodium hydroxide in a polar solvent such as tetrahydrofuran, methanol, ethanol or a mixture of similar solvents.

Compounds of formulas Ib and Ic:

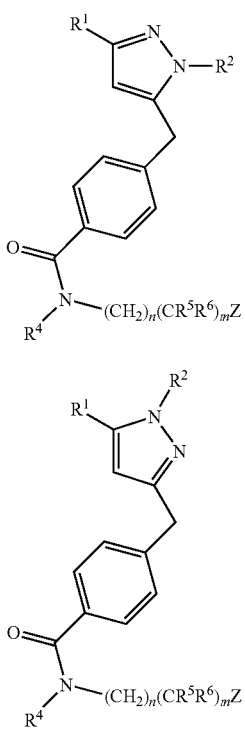

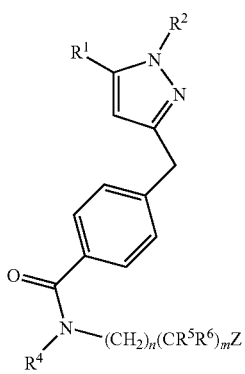

where $R^1$, $R^2$, $R^4$, $R^5$, $R^6$, and Z are as defined with respect to formula I, can be prepared as shown in Scheme 4 and 5. 4-Bromophenyl acetic acid 9 can be esterified using, e.g., methanol or ethanol containing an acid such as sulphuric acid, and is then condensed with the anion of methyl ketone 10 to give diketone 11. The reaction is carried out using a base such as sodium hydride in a polar aprotic solvent such as tetrahydrofuran (THF) at about 0 to 25° C. for about 16 to 24 h. Diketone 11 is condensed with a hydrazine 12 in a polar solvent such as methanol for about 16 to 24 h at a temperature of about 0 to 25° C. to give pyrazoles 13. The reaction may contain an acid such as acetic or hydrochloric acid, or a base such as DIEA or sodium methoxide. Hydrazines such as 12 are commercially available or can be prepared by those skilled in the art. In some cases mixtures of isomers will be formed, these are generally separable as described above (vide supra).

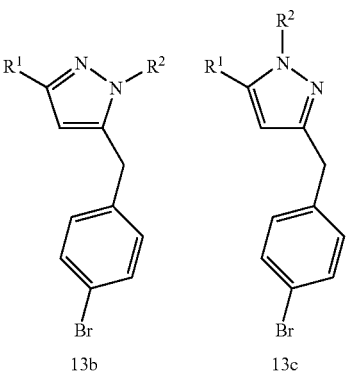

Installation of the carboxylic acid can be then achieved by a variety of methods using chemistry known to those skilled in the art. One such method, involves initial introduction of a cyano functionality, as shown in Scheme 5 and described by Tschaen et al., *Synth Commun,* 1994, 887. Treatment of bromide 13b with a cyanide source, usually zinc cyanide, and a palladium catalyst such as palladium tetrakis(triphenylphosphine), in a polar solvent such as DMF for about 2 to 24 h at about 25 to 80° C. yields the nitrile. Hydrolysis can then be achieved by heating to reflux in a solvent such as ethanol in the presence of an aqueous base such as potassium hydoxide. Coupling of acid 14 with an amine, generally 5-aminotetrazole 7 or a beta alanine derivative 8, which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compound Ib-7 or Ib-8. Products Ic can be similarly prepared from 13c. In some cases, the product Ib or c from the reactions described in Scheme 5 will be further modified. These manipulations may include, but are not limited to substitution, reduction, oxidation, alkylation, acylation, and hydrolysis reactions, which are commonly known to those skilled in the art. One such modification is saponification of an ester, as shown, this is achieved using a base such as aqueous lithium or sodium hydroxide in a polar solvent such as tetrahydrofuran, methanol, ethanol or a mixture of similar solvents.

SCHEME 4

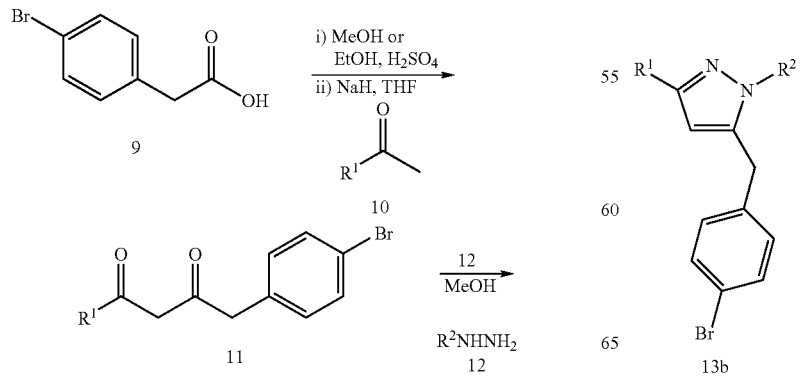

SCHEME 5

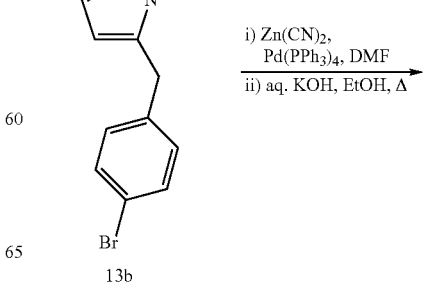

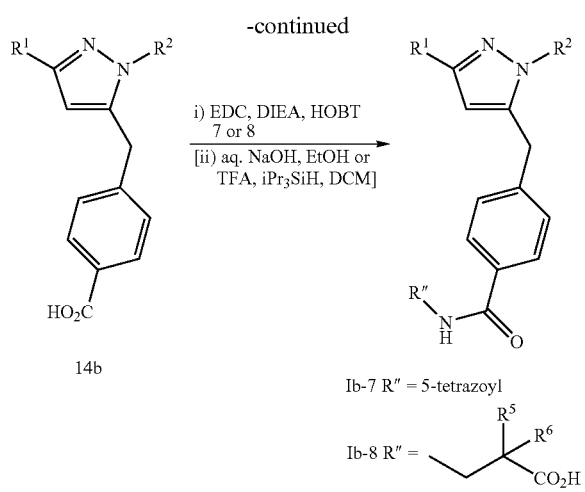

In another embodiment of the present invention, the compounds Id and Ie:

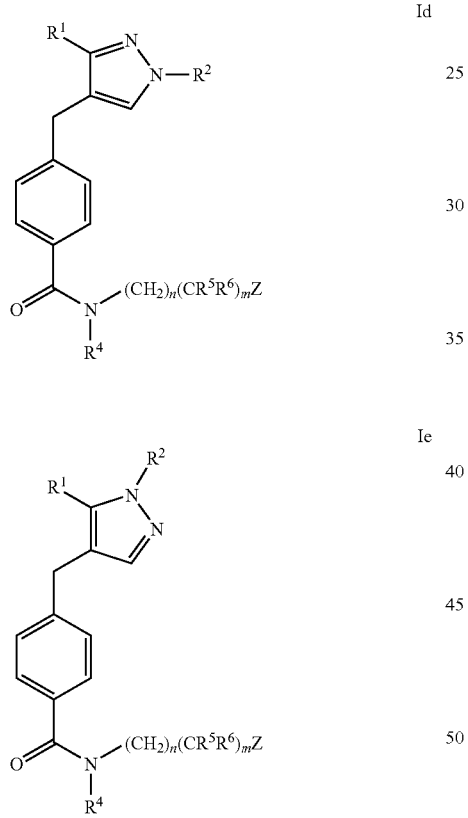

where $R^1$, $R^2$, $R^4$, $R^5$, $R^6$, and Z are as defined with respect to formula I, can be prepared as shown in Scheme 6 and 7. Ketone 15 can be prepared by methods described in the literature, or known to those skilled in the art. For example, formation of the Weinreb amide of 4-bromophenylpropionic acid is achieved using standard peptide coupling conditions such as 1-ethyl-3-(3-dimethylaminopropyl)-carbodiimide (EDC), 1-hydroxybenzotriazole (HOBT), and a base, generally diisopropylethylamine, in a solvent such as N,N-dimethylformamide (DMF) or methylene chloride for about 3 to 48 hours at ambient temperature, followed by the addition of an organometallic reagent, such as a Grignard reagent, in a polar aprotic solvent, usually THF, at temperatures of about 0 to 60° C.

Ketone 15 can then be deprotonated with, e.g., sodium hydride, in a polar solvent such as THF, and condensed with an ester such as ethyl formate for about 16 to 24 h at about 0 to 25° C., to give the dicarbonyl compound 16. Compound 16 can then be condensed with hydrazine 12 in a polar solvent such as methanol, which may contain an acid such as acetic or hydrochloric acid, or a base such as DIEA or sodium methoxide, for about 16 to 24 h at a temperature of about 0 to 25° C. to give pyrazoles 17. In some cases mixtures of isomers are formed. These are generally separable as described above.

SCHEME 6

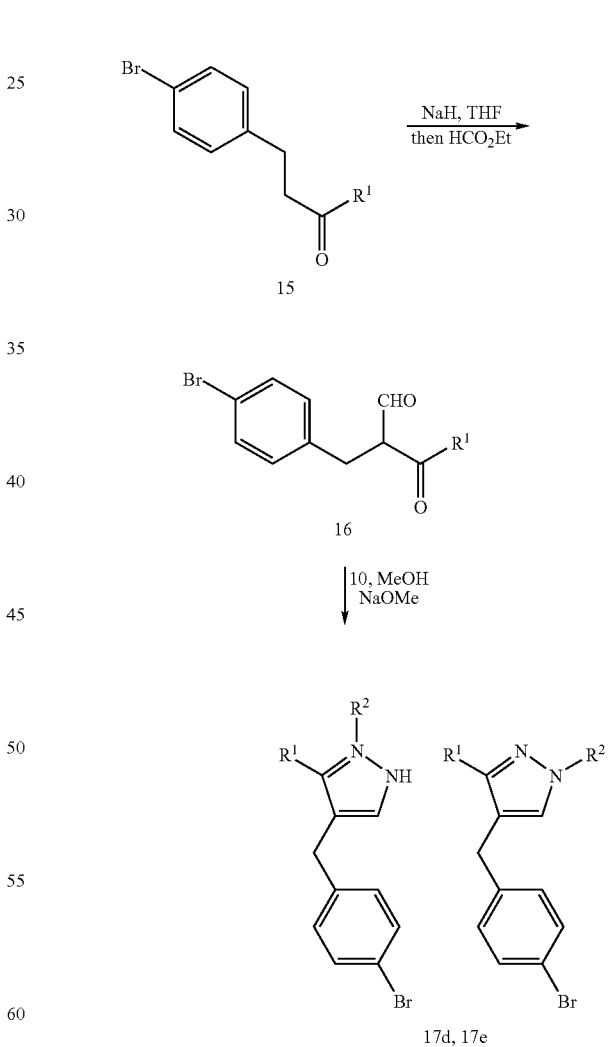

Installation of the carboxylic acid can be achieved by a variety of palladium coupling reactions using chemistry known to those skilled in the art. One such method involves the initial introduction of a cyano functionality, as shown in Scheme 7.

Treatment of bromide 17d with a cyanide source, usually zinc cyanide, and a palladium catalyst such as palladium tetrakis(triphenylphosphine), in a polar solvent such as DMF for about 2 to 24 h at about 25 to 80° C. yields the nitrite. Hydrolysis can then be achieved by heating to reflux in a solvent such as ethanol in the presence of an aqueous base such as potassium or sodium hydroxide. Coupling of acid 18d with an amine, generally 5-aminotetrazole 7 or a beta alanine derivative 8 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for about 3 to 48 hours at ambient temperature to yield the compound Id-7 and Id-8.

Product Ie can be similarly prepared from 17e. In some cases, the product Id or Ie from the reactions described in Scheme 7 will be further modified. These manipulations may include, but are not limited to substitution, reduction, oxidation, alkylation, acylation, and hydrolysis reactions, which are commonly known to those skilled in the art. One such modification is removal of a tert-butyl ester, as shown, this can be achieved using trifluoroactetic acid and triisopropylsilane in dichloromethane or similar solvent.

SCHEME 7

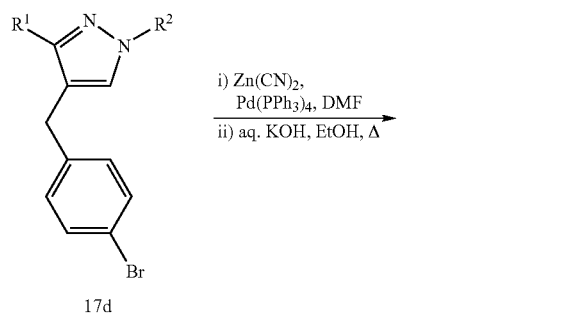

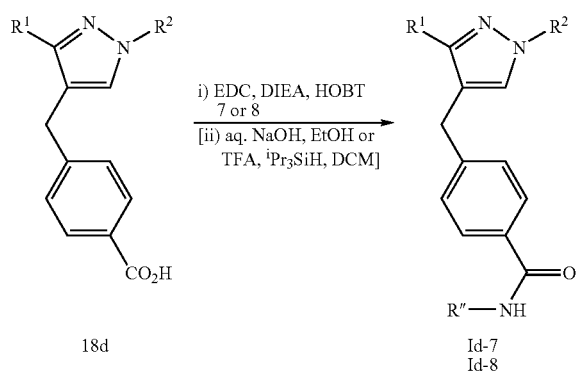

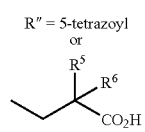

Other substitution patterns, such as If and Ig

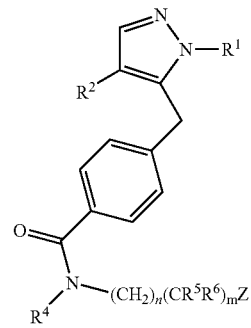

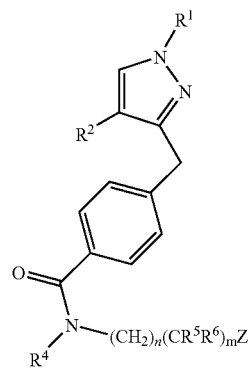

where $R^1$, $R^2$, $R^4$, $R^5$, $R^6$, and Z are as defined with respect to compound I can be prepared from the appropriate hydrazine and dicarbonyl derivative, using chemistry analogous to that described above.

In some cases further modification of intermediates such as 6a can be undertaken in one of several different ways. Firstly, if one of $R^1$ and $R^2$ in 6a contains a protected amino group such as the BOC protected carbamate 19, Scheme 8, the BOC group can be removed to reveal the amine 20. This can be achieved by treatment of the compound with trifluoroacetic acid in an aprotic solvent such as methylene chloride at ambient temperature for about 0.25-6 h. Further manipulation of this amine can then be readily performed. Acylation or sulphonylation of the nitrogen can be carried out by treatment with an electrophile such as an acid chloride, isocyanate or sulphonyl chloride. The reaction is performed in a non polar aprotic solvent such as methylene chloride or THF, in the presence of an organic base, generally pyridine or triethylamine, or an inorganic base such as aqueous sodium hydroxide solution, to give the products 21.

Conversion of products 21 to the desired compounds is carried out as described vide supra. Alternately, amine 20 can be alkylated by reductive amination with an aldehyde and a reducing agent such as sodium triacetoxycyanoborohydride in a solvent such as dichloroethane at ambient temperatures, Scheme 8. Conversion of 22 to the final products is carried out as previously described.

SCHEME 8

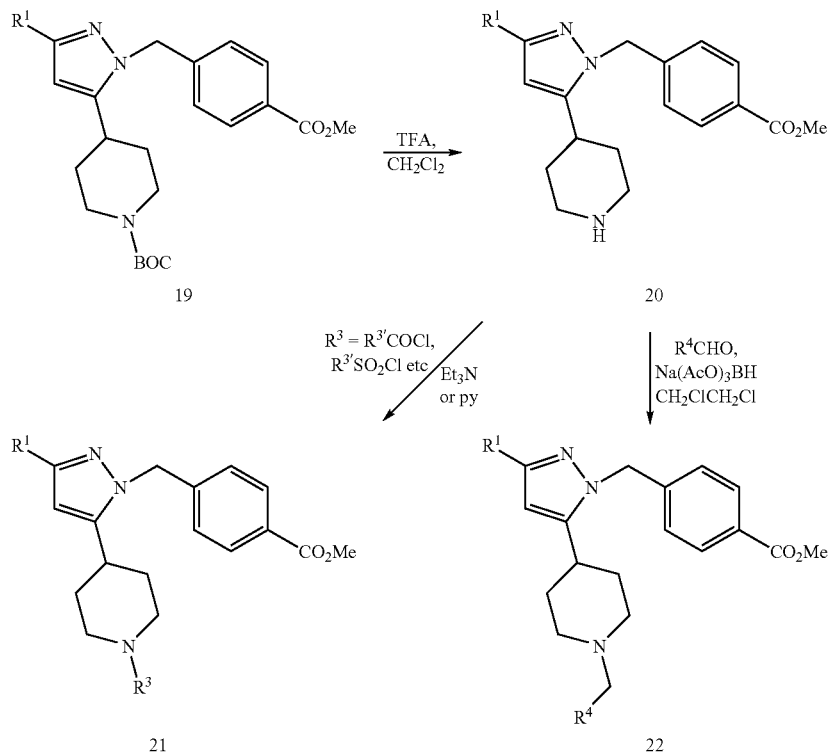

An alternative modification of intermediates such as 6, where $R^1$ or $R^2$ contain an aryl halide as in 23 is described in Scheme 9. The aryl halide moiety can be further coupled with a boronic acid using a palladium catalyst such as palladium 2-(di-t-butylphosphino)biphenyl or palladium tetrakis triphenylphosphine. The solvent is generally either ethanol or toluene, and aqueous sodium carbonate or potassium fluoride is also added to the reaction, which is performed at elevated temperatures. The products of the reaction 24 can be converted to the desired compounds is carried out as described vide supra.

SCHEME 9

The following examples are provided so that the invention might be more fully understood. They should not be construed as limiting the invention in any way.

EXAMPLE 1

4-({5-CYCLOHEXYL-3-[4-(TRIFLUO-ROMETHOXY)PHENYL]-1H-PYRAZOL-1-YL}METHYL)-N-(1H-TETRAZOL-5-YL)BENZA-MIDE

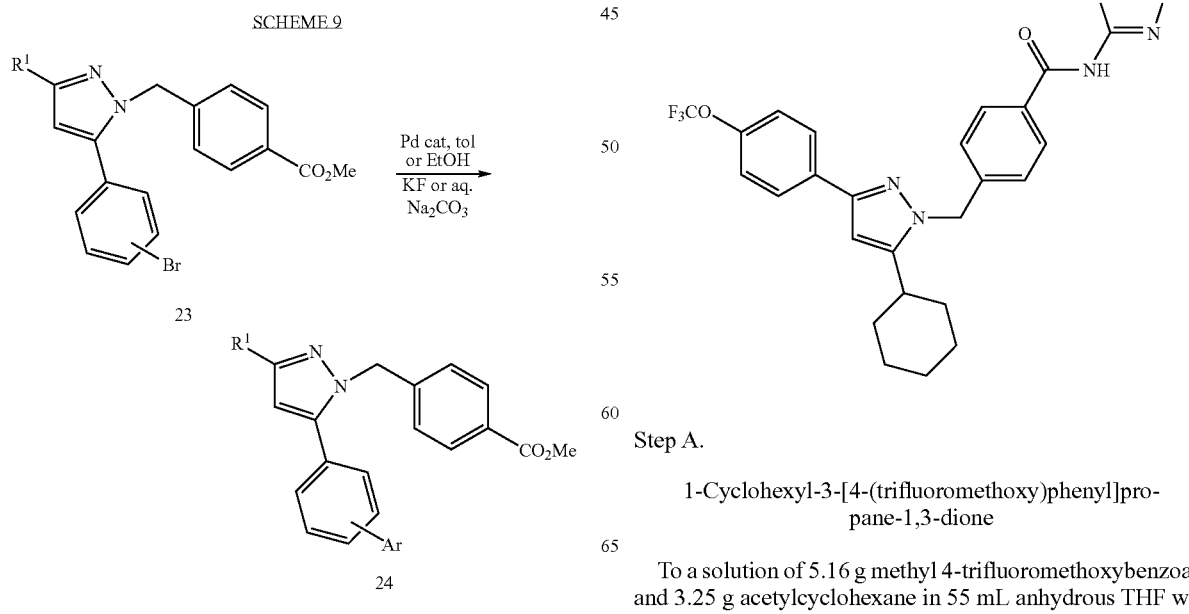

Step A.

1-Cyclohexyl-3-[4-(trifluoromethoxy)phenyl]propane-1,3-dione

To a solution of 5.16 g methyl 4-trifluoromethoxybenzoate and 3.25 g acetylcyclohexane in 55 mL anhydrous THF was added 1.17 g 60% sodium hydride oil dispersion. The resulting mixture was stirred at room temperature under nitrogen over night. The reaction mixture was poured into 200 mL ice water with 3.5 mL concentrated HCl and extracted with 3×150 mL ether. The combined organic layer was washed with 100 mL saturated brine, dried over anhydrous sodium sulfate, and evaporated to give a crude product. It was purified on silica gel using 5-20% EtOAc in hexanes to give a 2:1 molar mixture of the title compound and the starting ketone as a red liquid based on NMR. This material was used in the next step without further purification. $^1$H NMR of the title compound (CDCl$_3$, 500 MHz) δ 7.93~7.96 (m, 2H), 7.29 (d, J=8.3 Hz, 2H), 6.16 (s, 1H), 2.34 (tt, J=3.4 & 11.5 Hz, 1H), 1.93~1.97 (m, 2H), 1.72~1.91 (m, 31), 1.44~1.52 (m, 2H), 1.20~1.39 (m, 4H).

Step B.

5-Cyclohexyl-3-[4-(trifluoromethoxy)phenyl]-1H-pyrazole

A solution of 1.19 g of the product from Step A Example 1 in 20 mL methanol was treated with 0.15 mL anhydrous hydrazine overnight. After evaporating the solvent under vacuum, the crude product was purified on silica gel using 25-35% EtOAc in hexanes with 1% Et$_3$N to give title compound as a colorless solid. $^1$H NMR (CDCl$_3$, 500 MHz), 7.77~7.79 (m, 2H), 7.23 (d, J=8.2 Hz, 2H), 6.37 (s, 1H), 5.00 (v br s, ~3H), 2.71 (tt, J=3.6 & 11.7 Hz, 1H), 2.02~2.07 (m, 2H), 1.82~1.86 (m, 2H), 1.44~1.52 (m, 2H), 1.33~1.41 (m, 2H), 1.23~1.31 (m, 1H). LC-MS: 2.24 min. (M+H=311.2).

Step C.

Methyl 4-({5-cyclohexyl-3-[4-(trifluoromethoxyphenyl]-1H-pyrazol-1-yl}methyl)benzoate and methyl 4-([3-cyclohexyl-5-[4-(trifluoromethoxy)phenyl]-1H-pyrazol-1-yl]methyl)benzoate A solution of 0.93 g of the product from Step B Example 1 and 0.721 g methyl 4-bromomethylbenzoate in 20 mL anhydrous DMF was treated with 0.150 g 60% sodium hydride oil dispersion at room temperature under nitrogen over night. After removing solvent under reduced pressure, the crude product was separated into two isomers on silica gel using 1.5~4% MeCN in dichloromethane as colorless gels. The faster-eluting isomer was methyl 4-({5-cyclohexyl-3-[4-(trifluoromethoxy)phenyl]-1H-pyrazol-1-yl}methyl)benzoate. $^1$H NMR (CDCl$_3$, 500 MHz) δ 7.99~8.01 (m, 2H), 7.82~7.85 (m, 2), 7.24 (d, J=8.0 Hz, 2H), 7.17 (d, J=8.3 Hz, 2H), 6.40 (s, 1H), 5.43 (s, 2H), 3.92 (s, 3H), 2.47 (tt, J=3.0 & 11.7 Hz, 1H), 1.77~1.82 (m, 4H), 1.71~1.74 (m, 1H), 1.35~1.43 (m, 2H), 1.20~1.32 (m, 3H). The slower-eluting isomer is methyl 4-({3-cyclohexyl-5-[4-(trifluoromethoxy)phenyl]-1H-pyrazol-1-yl}methyl)benzoate. $^1$H NMR (CDCl$_3$, 500 MHz) δ 7.95~7.98 (m, 2H), 7.27~7.31 (m, 2H), 7.21 (d, J=8.2 Hz, 2H), 7.06 (d, J=8.5 Hz, 2H), 6.20 (s, 1H), 5.32 (s, 2H), 3.92 (s, 3H), 2.72 (tt, J=3.5 & 11.3 Hz, 1H), 2.04~2.08 (m, 2H), 1.82~1.87 (m, 2H), 1.73~1.77 (m, 1H), 1.38~1.53 (m, 4H), 1.25-1.34 (m, 1H). The structures of these isomers were confirmed using NOE difference spectra.

Step D.

4-({5-Cyclohexyl-3-[4-(trifluoromethoxy)phenyl]-1H-pyrazol-1-yl}methyl)benzoic acid A solution of 0.55 g methyl 4-({5-cyclohexyl-3-[4-(trifluoromethoxy)phenyl]-1H-pyrazol-1-yl}methyl)benzoate from Step C Example 1 in 16 mL ethanol and 6 mL water was treated with 2.4 equivalents of 5 N NaOH solution till the hydrolysis was complete based on HPLC. After evaporating ethanol under reduced pressure, the residue was acidified with 20% molar excess of 2 N HCl to precipitate the acid product. Extract the reaction mixture with 2×35 mL EtOAc. Wash the combined organic layer with saturated brine, dry over anhydrous Na$_2$SO$_4$, and evaporate to give the title compound as a white solid. It can be recrystallized from 5:3 MeCN and water to give fine crystalline needles. $^1$H NMR (CDCl$_3$, 500 MHz) δ 7.95~7.97 (m, 2H), 7.84~7.87 (m, 2H), 7.28 (d, J=8.1 Hz, 2H), 7.19 (d, J=8.2 Hz, 2H), 6.56 (s, 1H), 5.48 (s, 2H), 2.60 (tt, J=3.0 & 11.8 Hz, 1H), 1.72~1.78 (m, 4H), 1.68~1.72 (m, 1H), 1.37~1.44 (m, 2H), 1.23~1.35 (m, 3H).

Step E.

4-({5-Cyclohexyl-3-[4-(trifluoromethoxy)phenyl]-1H-pyrazol-1-yl}methyl)-N-(1H-Tetrazol-5-yl)benzamide A solution of 128 mg product from Step D above, 66.3 mg 1-(3-dimethylaminopropyl)-3-ethylcarbodiimide hydrochloride (EDC), 46.8 mg 1-hydroxybenzotriazole hydrate (HOBt) in 1 mL DMF was stirred at room temperature for 30 minutes. 5-Aminotetrazole monohydrate (35.7 mg) was added and the mixture stirred for additional 16 hours. Precipitate the product by adding 1 mL water to the reaction mixture. Collect the product by filtration, wash it with 1:1 DMF and water, water, and MeCN, and dry to give the title compound as a white solid. $^1$H NMR (CD$_3$OD, 500 MHz) δ 7.995 (d, J=8.2 Hz, 2H), 7.86 (d, J=8.6 Hz, 2H), 7.27~7.29 (m, 4H), 6.58 (s, 1H), 5.52 (s, 2H), 2.59~2.65 (m, 1H), 1.75~1.81 (m, 4H), 1.69~1.73 (m, 1H), 1.39~1.46 (m, 2H), 1.24~1.37 (m, 3H). LC-MS: 2.32 min. (M+H=512.3).

EXAMPLE 2

ETHYL N-[4-({5-CYCLOHEXYL-3-[4-(TRIFLUOROMETHOXY)PHENYL]-1H-PYRAZOL-1-YL}METHYL)BENZOYL]-β-ALANINATE

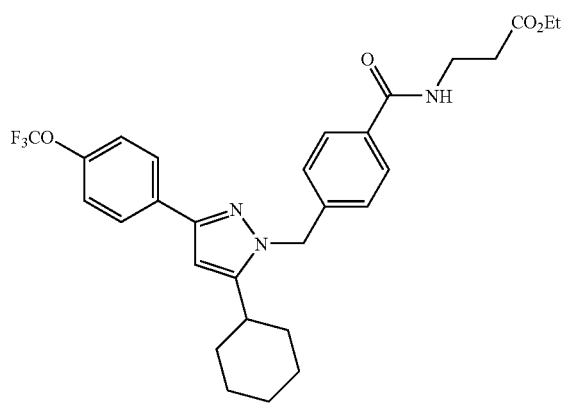

A solution of 177.8 mg product from Step D Example 1, 92.0 mg EDC, 64.9 mg HOBt in 1.5 mL DMF was stirred at room temperature for 30 minutes. Diisopropylethylamine (DIEA, 84 μL) and β-amino-alanine ethyl ester hydrochloride (73.7 mg) were added and the mixture stirred for additional 16 hours. The solvent was removed under reduced pressure. Some crystalline product precipitated after dissolving the residue in 14 mL 3:2 MeCN and water with 0.1% TFA. More title compound was isolated by preparative HPLC of the filtrate using 60-80% MeCN gradient over 10 minutes at 8.0 mL per minute with 0.1% TFA on a 9.4×250 mm SB-C18 Zorbax column. $^1$H NMR (CD$_3$OD, 600 MHz) δ 7.84~7.87 (m, 2H), 7.75 (d, J=8.4 Hz, 2H), 7.28 (d, J=8.3 Hz, 2H), 7.18 (d, J=8.2 Hz, 2H), 6.56 (s, 1H), 5.46 (s, 2), 4.12 (q, J=7.1 Hz, 2H), 3.60 (t, J=6.8 Hz, 2H), 2.62 (t, J=6.8 Hz, 2H), 2.60 (tt, J=11.7 & 3.3 Hz, 1H), 1.73~1.77 (m, 4H), 1.68~1.71 (m, 1H), 1.37~1.43 (m, 2H), 1.24~1.35 (m, 3H), 1.21 (t, J=7.1 Hz, 3H). LC-MS: 2.47 min. (M+H=544.4).

EXAMPLE 3

N-[4-({5-CYCLOHEXYL-3-[4-(TRIFLUOROMETHOXY)PHENYL]-1H-PYRAZOL-1-YL}METHYL)BENZOYL]-β-ALANINE

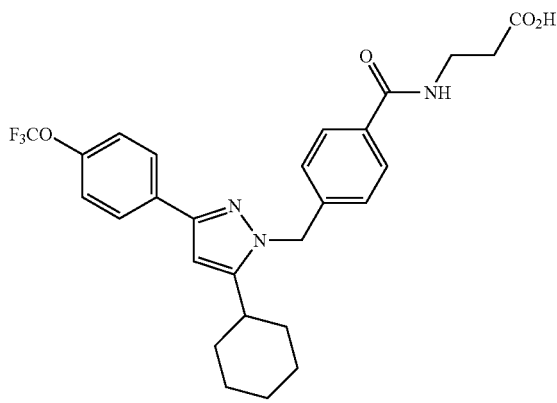

Dissolve 135.8 mg of product from Example 2 in 5 mL ethanol and 0.15 mL water and treat the solution with 0.50 mL 5 N NaOH solution over night at room temperature. Remove solvents under reduced pressure. Dissolve the residue in water and acidify with 2 N HCl to pH ~1. Filter to collect the white solid, wash with water, and dry to give title compound as a white solid. $^1$H NMR (CD$_3$OD, 500 MHz) δ 8.51 (t, J=5.7 Hz, 1NH), 7.86~7.89 (m, 2H), 7.775 (d, J=8.3 Hz, 2H), 7.30 (d, J=8.0 Hz, 2H), 7.20 (d, J=8.2 Hz, 2H), 6.57 (s, 1H), 5.48 (s, 2H), 3.59~3.64 (m, 2H), 2.59~2.66 (m, 3H), 1.76~1.81 (m, 4H), 1.69-1.74 (m, 1H), 1.38~1.47 (m, 2H), 1.24~1.38 (m, 3I). LC-MS: 2.25 min. (M+H=516.3).

EXAMPLE 4

METHYL (2R)-3-{[4-({5-CYCLOHEXYL-3-[4-(TRIFLUOROMETHOXY)PHENYL]-1H-PYRAZOL-1-YL}METHYL)BENZOYL]AMINO}-2-HYDROXYPROPANOATE

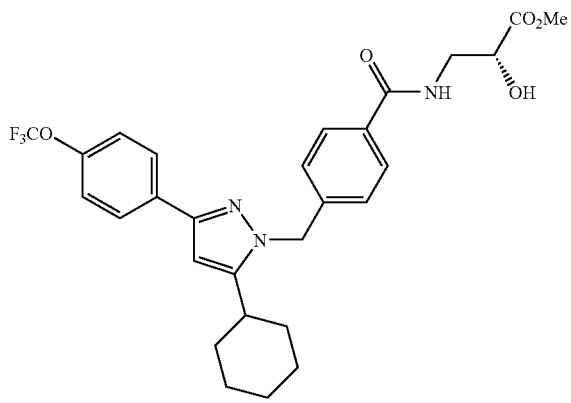

Step A.

[(4R)-2,2-Dimethyl-5-oxo-1,3-dioxolan-4-yl]acetic acid

A solution of 25.05 g D-malic acid and 68.1 g 2,2-dimethoxypropane in 200 mL toluene was refluxed for 2 hours under nitrogen. The solvent was removed under reduced pressure to give the title compound as a white solid. $^1$H NMR (CDCl$_3$, 500 MHz) δ 4.76 (dd, J=3.9 & 6.6 Hz, 1H), 3.02 (dd, J=3.9 & 17.2 Hz, 1H), 2.88 (dd, J=6.6 & 17.2 Hz, 1H), 1.64 (s, 3H), 1.59 (s, 3H).

Step B.

Benzyl [(4R)-2,2-dimethyl-5-oxo-1,3-dioxolan-4-yl] methylcarbamate

A solution of 5.25 g intermediate from Step A above, 8.88 g diphenylphosphoryl azide, and 3.34 g triethyl amine in 100 mL toluene was refluxed under nitrogen for 75 minutes. Benzyl alcohol (2.92 g) was added and reflux continued for additional 15 hours. The reaction mixture was cooled, diluted with ethyl acetate, washed with 5% NaHCO$_3$ and saturated brine, dried over anhydrous Na$_2$SO$_4$, and evaporated under vacuum to give a crude product. It was purified on silica gel with 20-45% ethyl acetate in hexanes to give the title compound as a yellow oil. $^1$H NMR (CDCl$_3$, 500 MHz) δ 7.33~7.40 (m, 5H), 5.175 (d, J=12.1 Hz, 1H), 5.11 (d, J=11.9 Hz, 1H), 4.50~4.52 (m, 1H), 3.69~3.75 (m, 1H), 3.60~3.66 (m, 1H), 1.59 (s, 3H), 1.57 (s, 3H).

Step C.

Methyl (2R)-3-amino-2-hydroxypropanoate hydrochloride

Benzyl [(4R)-2,2-dimethyl-5-oxo-1,3-dioxolan-4-yl]methylcarbamate (7.76 g) prepared by the method described in Step B above was dissolve in methanol (70 mL) with 0.62 g 10% Pd/C. A 1 M HCl in ether solution was added (25 mL). This mixture was hydrogenated using a hydrogen balloon for 22 hours. The reaction mixture was purged with nitrogen, filtered though a pad of Celite, and evaporated under vacuum to give the title compound as a yellowish solid. $^1$H NMR (CD$_3$OD, 500 MHz) δ 4.45 (dd, J=4 and 8 Hz, 1H), 3.82 (s, 3H), 3.31 (dd, 1H), 3.15 (dd, J=8 and 13 Hz, 1H).

Step D.

Methyl (2R)-3-{[4-({5-cyclohexyl-3-[4-(trifluoromethoxy)phenyl]-1H-pyrazol-1-yl}methyl)benzoyl]amino}-2-hydroxypropanoate A solution of 44.4 mg product from Step D Example 1, 28.8 mg EDC, 20.3 mg HOBt, 31.1 mg methyl (2R)-3-amino-2-hydroxypropanoate hydrochloride from Step C above and 70 μL DIEA in 1 mL DMF was stirred at room temperature over night. The title compound was isolated by preparative HPLC using 55-75% MeCN gradient over 10 minutes at 8.0 mL per minute with 0.1% TFA on a 9.4×250 mm SB-C18 Zorbax column as a white solid after lyophilization. LC-MS: 2.55 min. (M+H=546.3).

EXAMPLE 5

(2R)-3-{[4-({5-CYCLOHEXYL-3-[4-(TRIFLUO-ROMETHOXY)PHENYL]-1H-PYRAZOL-1-YL}METHYL)BENZOYL]AMINO}-2-HYDROX-YPROPANOIC ACID

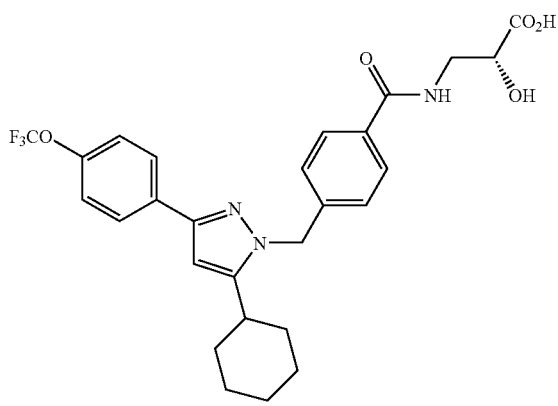

A solution of the product from Example 4 above (42.9 mg) in 0.937 mL methanol and 0.156 mL water was treated with 0.078 mL 5 N NaOH over night. The title compound was isolated by preparative HPLC using 50~70% MeCN gradient over 10 minutes at 8.0 mL per minute with 0.1% TPA on a 9.4×250 mm SB-C18 Zorbax column as a white solid after lyophilization. LC-MS: 2.44 min. (M+H=532.3).

EXAMPLE 6

4-({3-CYCLOHEXYL-5-[(4-(TRIFLUO-ROMETHOXY)PHENYL]-1H-PYRAZOL-1-YL}METHYL)-N-(1H-TETRAZOL-5-YL)BENZA-MIDE

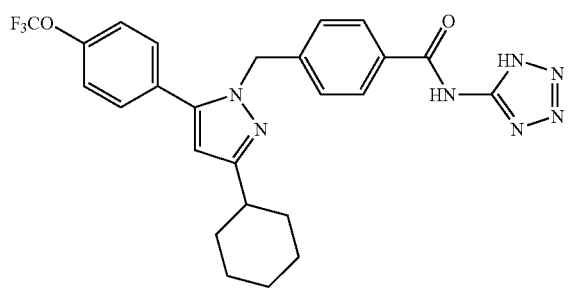

Step A.

4-({3-Cyclohexyl-5-[4-(trifluoromethoxyphenyl]-1H-pyrazol-1-yl}methyl) benzoic acid A solution of 0.19 g methyl 4-({3-cyclohexyl-5-[4-(trifluoromethoxy)phenyl]-1H-pyrazol-1-yl}methyl)benzoate from Step C Example 1 in 6 mL ethanol and 2.5 mL water was treated with 2.4 equivalents of 5 N NaOH solution till the hydrolysis was complete based on HPLC. After evaporating ethanol under reduced pressure, the residue was acidified with 20% molar excess of 2 N HCl to precipitate the acid product. Extract the reaction mixture with 2×35 mL EtOAc. Wash the combined organic layer with saturated brine, dry over anhydrous $Na_2SO_4$, and evaporate to give the title compound as a white solid. It can be recrystallized from 5:3 MeCN and water to give fine crystalline needles. $^1$H NMR ($CDCl_3$, 500 MHz) δ 7.89 (d, J=8.3 Hz, 2H), 7.39~7.42 (m, 2H), 7.29 (d, J=8.1 Hz, 2H), 7.00 (d, J=8.3 Hz, 2H), 6.30 (s, 1H), 5.38 (s, 2H), 2.67 (tt, J=3.5 & 11.5 Hz, 1H), 1.97~2.01 (m, 2H), 1.80~1.85 (m, 2H), 1.71~1.75 (m, 1H), 1.38~1.53 (m, 4H), 1.26~1.33 (m, 1H). LC-MS: 2.47 min. (M+H=445.3).

Step B.

4-({3-Cyclohexyl-5-[4-(trifluoromethoxy phenyl]-1H-pyrazol-1-yl}methyl)-N-(1H-tetrazol-5-yl)benza-mide A solution of 70 mg product from Step A above, 38.1 mg EDC, 26.9 mg HOBt in 1 mL DMF was stirred at room temperature for 30 minutes. 5-Aminotetrazole monohydrate (20.5 mg) was added and the mixture stirred for additional 16 hours. Precipitate the product by adding 1 mL water to the reaction mixture. Collect the product by filtration, wash it with 1:1 DMF and water, water, and MeCN, and dry to give the title compound as a white solid. $^1$H NMR ($CD_3OD$, 600 MHz) δ 7.92 (d, J=8.4 Hz, 2H), 7.42~7.45 (m, 2H), 7.30 (d, J=8.2 Hz, 2H), 7.08 (d, J=8.4 Hz, 2H), 6.32 (s, 1H), 5.42 (s, 2H), 2.67 (tt, J=3.5 & 11.5 Hz, 1H), 1.97~2.01 (m, 2H), 1.81~1.85 (m, 2H), 1.72~1.76 (m, 1H), 1.46~1.53 (m, 2H), 1.38~1.47 (m, 2H), 1.26~1.35 (m, 1H). LC-MS: 2.30 min. (M+H=512.3).

EXAMPLE 7

ETHYL N-[4-({3-CYCLOHEXYL-5-[4-(TRIF-LUOROMETHOXY)PHENYL]-1H-PYRAZOL-1-YL}METHYL)BENZOYL]-β-ALANINATE

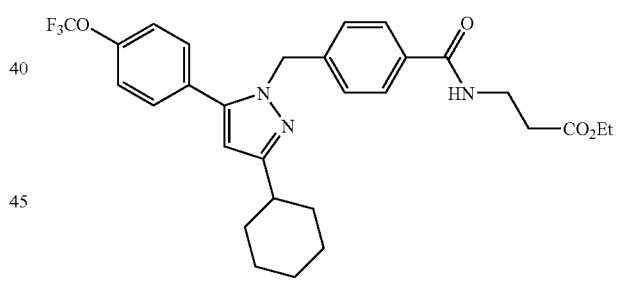

A solution of 66.7 mg product from Step A Example 6, 34.5 mg EDC, 24.3 mg HOBt in 0.5 mL DMF was stirred at room temperature for 30 minutes. DIEA (31 μL) and β-amino-alanine ethyl ester hydrochloride (27.6 mg) were added and the mixture stirred for additional 16 hours. The solvent was removed under reduced pressure. The title compound was isolated as a white solid by preparative HPLC using 60~80% MeCN gradient over 10 minutes at 8.0 mL per minute with 0.1% TFA on a 9.4×250 mm SB-C18 Zorbax column followed by lyophilization. $^1$H NMR ($CD_3OD$, 600 MHz) δ 7.68 (d, J=8.4 Hz, 2H), 7.39~7.42 (m, 2H), 7.28 (d, J=8.1 Hz, 2H), 6.99 (d, J=8.3 Hz, 2H), 6.31 (s, 1H), 5.37 (s, 2H), 4.11 q, J=7.1 Hz, 2H), 3.59 (t, J=6.8 Hz, 2H), 2.66 (tt, J=11.6 & 3.5 Hz, 1), 2.61 (t, J=6.8 Hz, 2H), 1.96-2.00 (m, 2H), 1.80~1.84 (m, 2H), 1.71~1.75 (m, 1H), 1.45~1.52 (m, 2H), 1.37~1.45 (m, 2H), 1.25~1.33 (m, 1H), 1.21 (t, J=7.1 Hz, 3H). LC-MS: 2.44 min. (M+H=544.4).

EXAMPLE 8

N-[4-({3-CYCLOHEXYL-5-[4-(TRIFLUOROMETHOXY)PHENYL]-1H-PYRAZOL-1-YL}METHYL)BENZOYL]-β-ALANINE

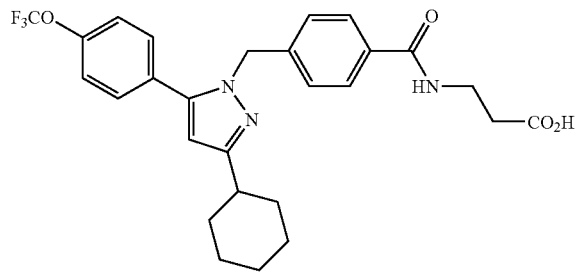

Dissolve 71.1 mg of product from Example 7 in 2.5 mL ethanol and 0.075 mL water and treat the solution with 0.26 mL 5 N NaOH solution over night at room temperature. Remove solvents under reduced pressure. Dissolve the residue in water and acidify with 2 N HCl to pH ~1. Filter to collect the white solid, wash with water, and dry to give the title compound as a white solid. $^1$H NMR (CD$_3$OD, 500 MHz) δ 8.48 (t, 1NH), 7.71 (d, J=8.5 Hz, 2H), 7.41~7.45 (m, 2H), 7.31 (d, J=8.3 Hz, 2H), 7.035 (d, J=8.4 Hz, 2), 6.32 (s, 1H), 5.38 (s, 2H), 3.60 (t, J=7.0 Hz, 2H), 2.68 (tt, J=3.5 & 11.6 Hz, 1H), 2.62 (t, J=6.9 Hz, 3H), 1.98~2.04 (m, 2H), 1.82~1.87 (m, 2H), 1.73~1.78 (m, 1H), 1.40~1.56 (m, 4H), 1.27~1.36 (m, 1H). LC-MS: 2.23 min. (M+H=516.3).

EXAMPLE 9

METHYL (2R)-3-{[4-({3-CYCLOHEXYL-5-[4-(TRIFLUOROMETHOXY)PHENYL]-1H-PYRAZOL-1-YL}METHYL)BENZOYL]AMINO}-2-HYDROXYPROPANOATE

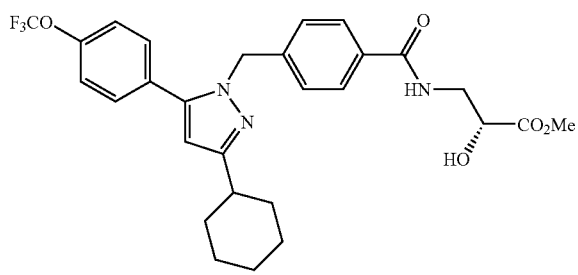

A solution of 24.6 mg product from Step A Example 6, 15.9 mg EDC, 11.2 mg HOBt, 17.2 mg methyl (2R)-3-amino-2-hydroxypropanoate hydrochloride from Step C Example 4 and 39 μL DIEA in 0.5 mL DMF was stirred at room temperature over night. The title compound was isolated by preparative HPLC using 55~75% MeCN gradient over 10 minutes at 8.0 mL per minute with 0.1% TFA on a 9.4×250 mm SB-C18 Zorbax column as a white solid after lyophilization. LC-MS: 2.55 min. (M+H=546.3).

EXAMPLE 10

(2R)-3-{[4-({3-CYCLOHEXYL-5-[4-(TRIFLUOROMETHOXY)PHENYL]-1H-PYRAZOL-1-YL}METHYL)BENZOYL]AMINO}-2-HYDROXYPROPANOIC ACID

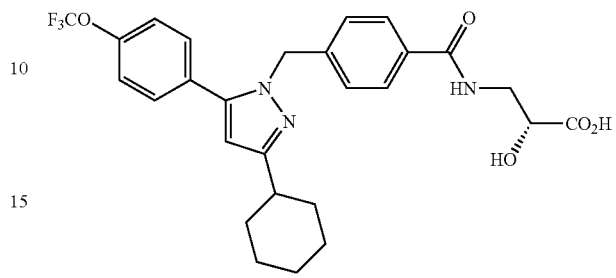

A solution of the product from Example 9 above (18.8 mg) in 0.411 mL methanol and 0.068 mL water was treated with 0.034 mL 5 N NaOH over night. The title compound was isolated by preparative HPLC using 50~70% MeCN gradient over 10 minutes at 8.0 mL per minute with 0.1% TFA on a 9.4×250 mm SB-C18 Zorbax column as a white solid after lyophilization. LC-MS: 2.41 min. (M+H=532.3).

EXAMPLE 11

4-({1-CYCLOHEXYL-5-[4-(TRIFLUOROMETHOXY)PHENYL]-1H-PYRAZOL-3-YL}METHYL)-N-(1H-TETRAZOL-5-YL)BENZAMIDE

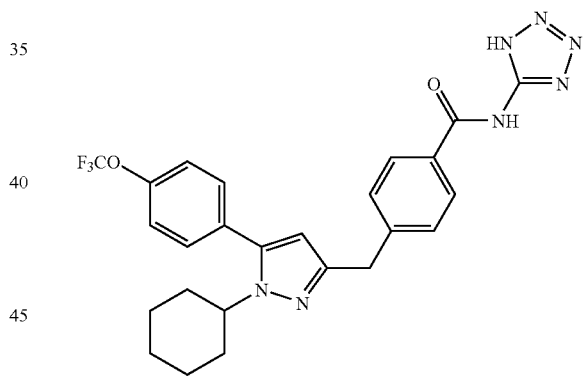

Step A.

Methyl 4-bromophenylacetate

A solution of 202.78 g 4-bromophenylacetic acid in 1.5 L methanol was treated with 15 mL concentrated sulfuric acid and the resulting mixture refluxed under nitrogen for 3 hours. Almost all of the methanol was removed by distillation. Dilute the residue with 1 L ether. Separate the bottom layer and extract that with 2×100 mL ether. Wash the combined ether solution with 3×250 mL 5% NaHCO$_3$ and 250 mL saturated brine, dried over Na$_2$SO$_4$, and concentrated under reduced pressure to give a crude product as light tan oil. Filter that through 300 g silica gel with 10% EtOAc in hexanes and concentrated under reduced pressure to give the title compound as colorless oil. $^1$H NMR (CDCl$_3$, 500 MHz) δ 7.46~7.48 (m, 2H), 7.16~7.19 (m, 2H), 3.72 (s, 3H), 3.60 (s, 2H).

Step B.

4-(4-Bromophenyl)-1-[4-(trifluoromethoxy)phenyl]butane-1,3-dione

A solution of 5.40 g 4-trifluoromethoxyacetophenone and 7.57 g methyl 4-bromophenylacetate in 60 mL anhydrous THF was treated with 1.59 g 60% NaH for 60 hours. After removing the solvent under reduced pressure, the reaction mixture was diluted with 250 mL ether and washed with 250 mL 0.2 M HCl, 2×100 mL 5% NaHCO$_3$ and 100 mL saturated brine, dried over anhydrous Na$_2$SO$_4$, and evaporated to give a crude product. It was purified on silica gel using 0-25% EtOAc in hexanes to give title compound as red oil. $^1$H NMR (CDCl$_3$, 500 MHz) δ 7.86~7.89 (m, 2H), 7.48~7.51 (m, 2H), 7.27 (d, J=7 Hz, 2H), 7.17~7.19 (m, 2H), 6.07 (s, 1H), 3.70 (s, 2H).

Step C.

3-(4-Bromobenzyl)-1-cyclohexyl-5-[4-(trifluoromethoxy)phenyl]-1H-pyrazole and 5-(4-bromobenzyl)-1-cyclohexyl-3-[4-(trifluoromethoxy)phenyl]-1H-pyrazole A solution of 1.20 g 4-(4-bromophenyl)-1-[4-(trifluoromethoxy)phenyl]-butane-1,3-dione from Step B above, 0.497 g cyclohexylhydrazine hydrochloride, and 0.575 mL DIEA in 20 mL methanol was refluxed over night. The solvent was removed under reduced pressure. The crude products were separated on silica gel eluting with methylene chloride to give yellow oils. The fast-eluting isomer was 5-(4-bromobenzyl)-1-cyclohexyl-3-[4-(trifluoromethoxy)phenyl]-1H-pyrazole based on NOE difference, COSY, and NOESY spectra. $^1$H NMR (CDCl$_3$, 600 MHz) δ 7.78~7.81 (m, 2H), 7.44~7.47 (m, 2H), 7.21 (d, J=8.1 Hz, 2H), 7.07~7.10 (m, 2H), 6.22 (s, 1H), 3.97 (s, 2H), 3.88 (tt, J=3.9 & 11.7 Hz, 1H), 1.95~2.03 (m, 2H), 1.85~1.89 (m, 2H), 1.75~1.79 (m, 2H), 1.68~1.71 (m, 1H), 1.24~1.33 (m, 3H). LC-MS: 2.86 min. (M+H=479.2/481). The slow-eluting isomer was 3-(4-bromobenzyl)-1-cyclohexyl-5-[4-(trifluoromethoxy)-phenyl]-1H-pyrazole. $^1$H NMR (CDCl$_3$, 600 MHz) δ 7.40~7.43 (m, 2H), 7.33~7.36 (m, 2H), 7.28 (d, J=8.2 Hz, 2H), 7.16~7.19 (m, 2H), 5.90 (s, 1H), 3.99 (tt, J=3.7 & 11.7 Hz, 1H), 3.97 (s, 2H), 2.02~2.10 (m, 2H), 1.85~1.92 (m, 4H), 1.66~1.70 (m, 1H), 1.24~1.35 (m, 3H). LC-MS: 2.79 min. (M+H-479/481.1).

Step D 4-({1-Cyclohexyl-5-[4-(trifluoromethoxy)phenyl]-1H-pyrazol-3-yl}methyl)benzonitrile A mixture of 526 mg 3-(4-bromobenzyl)-1-cyclohexyl-5-[4-(trifluoromethoxy)phenyl]-1H-pyrazole from Step C above, 79.9 mg zinc cyanide, 50.8 mg tetrakis(triphenylphosphine)palladium(0) in 2 mL DMF was heated under nitrogen in 80° C. oil bath for 20 hours. Evaporate most of DMF. The residue was purified on silica gel using 1 and 3% MeCN in methylene chloride to give the title compound as a yellowish solid. $^1$H NMR (CDCl$_3$, 500 MHz) δ 7.61 (d, J=8.2 Hz, 2H), 7.42 (d, J=8.3 Hz, 2H), 7.35~7.38 (m, 2H), 7.31 (d, J=8.3 Hz, 2H), 5.94 (s, 1H), 4.09 (s, 2H), 4.02 (tt, J=2.75 & 11.7 Hz, 1H), 2.03~2.11 (m, 2H), 1.87~1.94 (m, 4H), 1.69~1.72 (m, 1H), 1.25~1.35 (m, 3H); LC-MS: 2.55 min. (M+H=426.2).

Step E 4-({1-Cyclohexyl-5-[4-(trifluoromethoxy)phenyl]-1H-pyrazol-3-yl}methyl)benzoic acid To a warm solution of 0.45 g 4-({1-cyclohexyl-5-[4-(trifluoromethoxy)phenyl]-1H-pyrazol-3-yl}methyl)benzonitrile from Step D above in 10 mL ethanol and 2.5 mL water was added 0.70 g potassium hydroxide pellets. The resulting solution was refluxed under nitrogen over night. Ethanol was removed under reduced pressure. The product was precipitated by adding 11.5 mL 1 N HCl to the residue. The title compound was collected by filtrated, washed with water several times, and dried to give a slightly yellowish solid. $^1$H NMR (CD$_3$OD, 500 MHz) δ 7.94~7.96 (m, 2H), 7.47~7.49 (m, 2H), 7.37~7.41 (m, 4H), 6.09 (s, 1H), 4.06 (s, 2H), 4.05 (tt, J=3.8 & ~11.9 Hz, 1H), 1.97~2.05 (m, 2H), 1.85~1.93 (m, 4H), 1.67~1.71 (m, 1H), 1.26~1.36 (m, 3H). LC-MS: 2.38 min. (M+H=445.2).

Step F 4-({1-Cyclohexyl-5-[4-(trifluoromethoxy)phenyl]-1H-pyrazol-3-yl}methyl)-N-(1H-tetrazol-5-yl)benzamide A solution of 55.6 mg product from Step E above, 28.8 mg EDC, 20.3 mg HOBt in 1 mL DMF was stirred at room temperature for 45 minutes. 5-Aminotetrazole monohydrate (15.5 mg) was added and the mixture stirred for additional 22 hours. DIEA (26 μL) and more EDC (13.8 mg) were added and the reaction continued for another day. The title compound was isolated on preparative HPLC using 75~90% MeCN gradient over 10 minutes at 8.0 mL per minute with 0.1% TFA as a white solid following lyophilization. LC-MS: 2.26 min. (M+H=512.1).

EXAMPLE 12

4-({1-CYCLOHEXYL-3-[4-(TRIFLUOROMETHOXY)PHENYL]-1H-PYRAZOL-5-YL}METHYL)-N-(1H-TETRAZOL-5-YL)BENZAMIDE

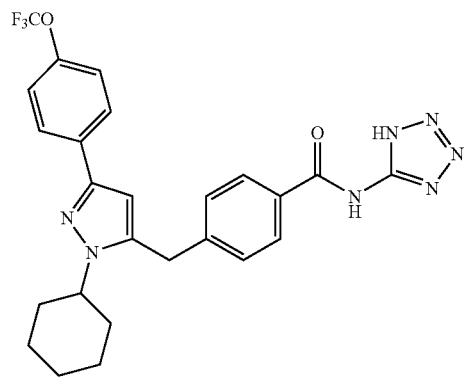

Step A 4-({1-Cyclohexyl-3-[4-(trifluoromethoxy)phenyl]-1H-pyrazol-5-yl}methyl)benzonitrile A mixture of 651 mg 5-(4-bromobenzyl)-1-cyclohexyl-3-[4-(trifluoromethoxy)phenyl]-1H-pyrazole from Step C Example 11, 95.7 mg zinc cyanide, 62.9 mg tetrakis(triphenylphosphine)palladium(0) in 2.5 mL DMF was heated under nitrogen in 80° C. oil bath for 24 hours. Evaporate most of DMF. The residue was purified on silica gel using 1 and 3% MeCN in methylene chloride to give the title compound as a yellow foam. $^1$H NMR (CDCl$_3$, 600 MHz) δ 7.78~7.81 (m, 2H), 7.63 (d, J=8.3 Hz, 2H), 7.33 (d, J=8.2 Hz, 2H), 7.215 (d, J=8.3 Hz, 2H), 6.25 (s, 1H), 4.09 (s, 2H), 3.83 (tt, J=3.9 & 11.7 Hz, 1H), 1.96~2.03 (m, 2H), 1.85~1.89 (m, 2H), 1.73~1.77 (m, 2H), 1.68~1.71 (m, 1H), 1.23~1.33 (m, 3H). LC-MS: 2.63 min. (M+H=426).

Step B 4-({1-Cyclohexyl-3-[4-(trifluoromethoxy)phenyl]-1H-pyrazol-5-yl}methyl)benzoic acid To a mixture of 0.395 g 4-({1-cyclohexyl-3-[4-(trifluoromethoxy)phenyl]-1H-pyrazol-5-yl}methyl)benzonitrile from Step A above in 9 mL ethanol and 3 mL water was added 0.80 g potassium hydroxide pellets. The resulting solution was refluxed under nitrogen over night. Ethanol was removed under reduced pressure. The product was precipitated by adding 14 mL 1 N HCl to the residue. The title compound was collected by filtrated, washed with water several times, and dried to give a off-white solid. $^1$H NMR (CD$_3$OD, 600 MHz) δ 7.97 (d, J=8.2 Hz, 2H), 7.81~7.84 (m, 2H), 7.35 (d, J=8.2 Hz, 2H), 7.25 (d, J=8.2 Hz, 2H), 6.425 (s, 1H), 4.165 (s, 2H), 4.01 (tt, J=3.9 & 11.8 Hz, 1H), 1.86~1.93 (m, 2H), 1.78~1.83 (m, 2H), 1.64~1.68 (m, 3H), 1.20~1.35 (m, 3H). LC-MS: 2.49 min. (M+H=445.2).

Step C 4-({1-Cyclohexyl-3-[4-(trifluoromethoxy)phenyl]-1H-pyrazol-5-yl}methyl)-N-(1H-tetrazol-5-yl)benzamide A mixture of 44.4 mg product from Step B above, 28.8 mg EDC, 20.3 mg HOBt and 13.4 mg aminotetrazole monohydrate was dissolved in 1 mL DMF. DIEA (44 μL) was added immediately and the resulting solution was stirred at room temperature for five days. The reaction mixture was diluted with a mixture of DMF, MeCN, and water and purified on preparative HPLC using 70~80% MeCN gradient over 10 minutes at 8.0 mL per minute with 0.1% TFA. The title compound was obtained as a white solid following lyophilization. $^1$H NMR (CD$_3$OD, 500 MHz) δ 8.03 (d, J=8.3 Hz, 2H), 7.84~7.86 (m, 2H), 7.46 (d, J=8.2 Hz, 2H), 7.28 (d, J=8.2 Hz, 2H), 6.47 (s, 1H), 4.23 (s, 2H), 4.055 (tt, J=3.7 & 11.7 Hz, 1H), 1.88~1.97 (m, 2H), 1.81~1.85 (m, 2H), 1.67~1.73 (m, 3H), 1.25~1.39 (m, 3H). LC-MS: 2.34 min. (M+H=512.2).

EXAMPLE 13

4-({15-CYCLOHEXYL-1-[4-(TRIFLUOROMETHOXY)PHENYL]-1H-PYRAZOL-4-YL}METHYL)-N-(1H-TETRAZOL-5-YL)BENZAMIDE

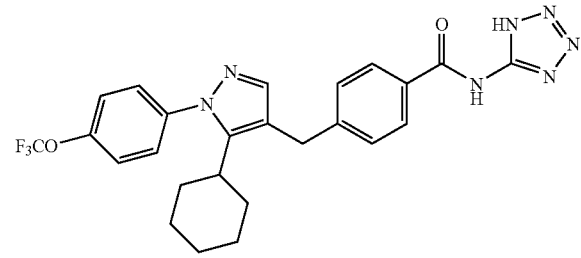

Step A.

3-(4-Bromophenyl)-N-methoxy-N-methylpropanamide

To a mixture of 24.95 g 3-(4-bromophenyl)propionic acid, 12.75 g N,O-dimethylhydroxylamine hydrochloride, 27.14 g EDC, and 17.66 g HOBt were added 300 mL DMF and 47.4 mL DIEA. The reaction mixture was stirred at room temperature for 17 hours and then poured into 700 mL ice water, extracted with 5×200 mL EtOAc. The combined EtOAc solution was washed with 200 mL 5% NaHCO$_3$, 4×200 mL water, and 200 mL saturated brine, dried over Na$_2$SO$_4$, and concentrated under reduced pressure to give crude product as a yellow oil. It was purified on silica gel using 35-55% EtOAc in hexanes to give the title compound as yellowish oil. $^1$H NMR (CDCl$_3$, 500 MHz) δ 7.40~7.43 (m, 2H), 7.11~7.14 (m, 2H), 3.63 (s, 3), 3.19 (s, 3H), 2.93 (t, J=7.8 Hz, 2H), 2.73 (t, J=7.7 Hz, 2H). LC-MS: 1.77 min. (M+H=272.1/274).

Step B.

3-(4-Bromophenyl)-1-cyclohexylpropan-1-one

To a solution of 25.02 g 3-(4-Bromophenyl)-N-methoxy-N-methylpropanamide from Step A above in 500 mL anhydrous ether cooled in an ice bath was added 115 mL 2 M cyclohexylmagnesium bromide in ether over 30 minutes. The cooling bath was removed after finishing addition. After 75 minutes, an additional 30 mL 2 M cyclohexylmagnesium bromide in ether was added. The reaction mixture was stirred for 40 minutes and poured into a mixture containing 500 mL ether, 500 mL cold water, 200 mL saturated brine, and 175 mL 2 N HCl. The layers were separated. The aqueous layer was extracted with 4×75 mL ether. The combined ether solution was washed with 200 mL 1:1 5% NaHCO$_3$ and saturated brine followed by 200 mL saturated brine, dried over anhydrous Na$_2$SO$_4$, and evaporated to give a crude product. It was purified on silica gel using 20-100% EtOAc in hexanes and re-purified using 5-10% EtOAc in hexanes to give the title compound as yellow oil. $^1$H NMR (CDCl$_3$, 500 MHz) δ 7.39~7.42 (m, 2H), 7.06~7.09 (m, 2H), 2.84~2.87 (m, 2H), 2.74~2.78 (m, 2H), 2.32 (tt, J=3.3 & 11.3 Hz, 1H), 1.76~1.84 (m, 4H), 1.65~1.70 (m, 1H), 1.15~1.36 (m, 5H).

Step C.

2-(4-Bromobenzyl)-3-cyclohexyl-3-oxopropanal

To a solution of 2.84 g 3-(4-bromophenyl)-1-cyclohexylpropan-1-one from Step B above in 50 mL anhydrous THF was added 1.15 g 60% sodium hydride followed by one 6.2 mL and five 3.2 mL portions of ethyl formate over one day. The resulting mixture was stirred at room temperature under nitrogen for another day. The solvent was removed under reduced pressure and the residue was partitioned between cold 0.1 N HCl and ether. The combined ether extract was washed with water (2×), 5% NaHCO$_3$ (3×), water, and saturated brine, dried over anhydrous Na$_2$SO$_4$, and evaporated to give crude product as orange solid. It was purified on silica gel using 10~15% EtOAc in hexanes to give the title compounds as pink oily solid. $^1$H NMR (CDCl$_3$, 500 MHz) δ 15.43 (d, J=7.1 Hz, 1H), 8.01 (d, J=7.1 Hz, 1H), 7.43~7.45 (m, 2H), 7.07 (d, J=8.3 Hz, 2H), 3.52 (s, 2H), 2.32 (tt, J=11.5 & Hz, 1H), 1.73~1.77 (m, 2H), 1.63~1.68 (m, 1H), 1.49~1.53 (m, 2H), 1.39~1.47 (m, 2H), 1.07~1.25 (m, 4H).

Step D.

4-(4-Bromobenzyl)-5-cyclohexyl-1-[4-(trifluoromethoxy)phenyl]-1H-pyrazole and 4-(4-bromobenzyl)-3-cyclohexyl-1-[4-(trifluoromethoxy)phenyl]-1H-pyrazole To a solution of 3.17 g 2-(4-bromobenzyl)-3-cyclohexyl-3-oxopropanal from Step C above and 2.47 g 4-trifluoromethoxyphenylhydrazine hydrochloride in 100 mL methanol was added 21.6 mL 0.5 M sodium methoxide in methanol. The resulting mixture was refluxed under nitrogen for two days. The solvent was removed under reduced pressure. The resulting crude product was subjected to repeated chromatography on silica gel using 0~10% MeCN in methylene chloride, 0~2% MeCN in methylene chloride, or 7~10% EtOAc in hexanes. Pure 4-(4-bromobenzyl)-5-cyclohexyl-1-[4-(trifluoromethoxy)phenyl]-1H-pyrazole was obtained as the major product by recrystallization of chromatographic fractions from methanol. $^1$H NMR (CDCl$_3$, 500 MHz) δ 7.64~7.67 (m, 2H), 7.43~7.46 (m, 2H), 7.44 (s, 1H), 7.23~7.27 (m, 2H), 7.10~7.13 (m, 2H), 3.82 (s, 2H), 2.63 (tt, J=3.3 & 11.8 Hz, 1H), 1.83~1.89 (m, 4H), 1.72~1.76 (m, 1H), 1.60~1.69 (m, 2H), 1.27~1.40 (m, 3H). LC-MS: 2.91 min. (M+H=479). Pure 4-(4-bromobenzyl)-3-cyclohexyl-1-[4-(trifluoromethoxy)phenyl]-1H-pyrazole was obtained as the minor product following preparative HPLC of the silica gel chromatography fractions. $^1$H NMR (CDCl$_3$, 500 MHz) δ 7.59~7.63 (m, 2H), 7.44~7.47 (m, 2H), 7.41 (s, 1H), 7.25~7.28 (m, 2H), 7.10~7.13 (m, 2H), 3.82 (s, 2H), 2.64 (tt, J=3.2 & 12.1 Hz, 1H), 1.83~1.89 (m, 4H), 1.72~1.76 (m, 1H), 1.57~1.66 (m, 2H), 1.27~1.39 (m, 3H). LC-MS: 2.70 min. (M+H=479.1/481). The identity of the isomers were confirmed by NOE difference spectra.

Step E.

4-({5-Cyclohexyl-1-[4-(trifluoromethoxy)phenyl]-1H-pyrazol-4-yl}methyl)benzonitrile A mixture of 782 mg 4-(4-bromobenzyl)-5-cyclohexyl-1-[4-(trifluoromethoxy)phenyl]-1H-pyrazole from Step D above, 115 mg zinc cyanide, and 94 mg tetrakis(triphenylphosphine)palladium(0) in 5 mL DMF was heated under nitrogen in a 75° C. oil bath over night. Evaporate most of DMF. The residue was purified on silica gel using 10-40% EtOAc in hexanes to give the title compound as a yellowish solid. $^1$H NMR (CDCl$_3$, 500 MHz) δ 7.61~7.64 (m, 2H), 7.40~7.44 (m, 2H), 7.33~7.37 (m, 4), 7.31 (s, 1H), 4.06 (s, 2H), 2.70 (tt, J=3.1 & 12.5 Hz, 1H), 1.73~1.79 (m, 4H), 1.66~1.71 (m, 1H), 1.50~1.58 (m, 2H), 1.09~1.24 (m, 3H). LC-MS: 2.46 min. (M+H=426.2).

Step F.

4-({5-Cyclohexyl-1-[4-(trifluoromethoxy)phenyl]-1H-pyrazol-4-yl}methyl)benzoic acid To a hot solution of 0.73 g 4-({5-cyclohexyl-1-[4-(trifluoromethoxy)phenyl]-1H-pyrazol-4-yl}methyl)benzonitrile From Step E above in 15 mL ethanol and 6 mL water was added 1.11 g potassium hydroxide. The resulting solution was refluxed under nitrogen over night. The solvents were removed under reduced pressure. The residue was re-suspended in 10 mL water and acidified with 9.0 mL 2 N HCl. The resulting solid was filtered, washed with water, and dried to give the title compound as a white solid. $^1$H NMR (CD$_3$OD, 500 MHz) δ 7.95 (d, J=8.2 Hz, 2H), 7.48~7.50 (m, 2H), 7.45 (d, J=8.6 Hz, 2H), 7.36 (s, 1H), 7.32 (d, J=8.2 Hz, 2H), 4.06 (s, 2H), 2.66 (tt, J=3.0 & 12.7 Hz, 1H), 1.69~1.73 (m, 4H), 1.53~1.64 (m, 3H), 1.09~1.19 (m, 3). LC-MS: 2.29 min. (M+H=445.2).

Step G.

4-({5-Cyclohexyl-1-[4-(trifluoromethoxy)phenyl]-1H-pyrazol-4-yl}methyl)-N-(1H-tetrazol-5-yl)benzamide A mixture of 66.7 mg product from Step F above, 71.9 mg EDC, 30.4 mg HOBt and 23.2 mg aminotetrazole monohydrate was dissolved in 1 mL DMF. DIEA (92 μL) was added immediately and the resulting solution was stirred at room temperature for 17 hours. The reaction mixture was diluted with a mixture of DMSO, MeCN, and water and purified on preparative HPLC using 65~80% MeCN gradient over 10 minutes at 8.0 mL per minute with 0.1% TFA. The title compound was obtained as a white solid following lyophilization. $^1$H NMR (DMSO-d$_6$, 500 MHz) δ 8.045 (d, J=8.2 Hz, 2H), 7.50~7.54 (m, 4H), 7.41 (d, J=8.2 Hz, 2H), 7.33 (s, 1H), 4.06 (s, 2H), 2.64 (tt, J=3.0 & 12.2 Hz, 1H), 1.62~1.72 (m, 4H), 1.48~1.48 (m, 3H), 1.05~1.15 (m, 3H). LC-MS: 1.97 min. (M+H=512.2).

EXAMPLE 14

4-({3-CYCLOHEXYL-1-[4-(TRIFLUOROMETHOXY)PHENYL]-1H-PYRAZOL-4-YL}METHYL)-N-(1H-TETRAZOL-5-YL)BENZAMIDE

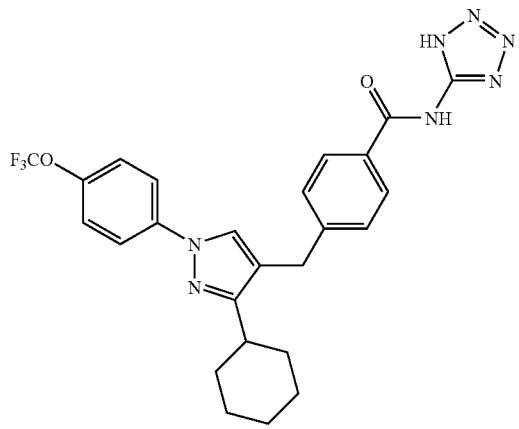

Step A.

4-({3-Cyclohexyl-1-[4-(trifluoromethoxy)phenyl]-1H-pyrazol-yl}methyl)benzonitrile A mixture of 0.75 g 4-(4-bromobenzyl)-3-cyclohexyl-1-[4-(trifluoromethoxy)phenyl]-1H-pyrazole from Step D Example 13, 110 mg zinc cyanide, and 90 mg tetrakis(triphenylphosphine)palladium(0) in 5 mL DMF was heated under nitrogen in a 75° C. oil bath over night. Evaporate most of DMF. The residue was purified on silica gel using 10~40% EtOAc in hexanes to give the title compound as a colorless gel. $^1$H NMR (CDCl$_3$, 500 MHz) δ 7.64~7.65 (m, 2H), 7.62~7.64 (m, 2H), 7.50 (s, 1H), 7.35 (d, J=8.2 Hz, 2H), 7.26~7.29 (m, 2H), 3.94 (s, 2H), 2.58 (tt, J=3.1 & 11.9 Hz, 1H), 1.82~1.87 (m, 4H), 1.72~1.76 (m, 1H), 1.58~1.67 (m, 2H), 1.28~1.38 (m, 3H). LC-MS: 2.67 min. (M+H=426).

Step B.

4-({3-Cyclohexyl-1-[4-(trifluoromethoxy)phenyl]-1H-pyrazol-4-yl}methyl)benzoic acid To a hot solution of 0.63 g 4-({3-cyclohexyl-1-[4-(trifluoromethoxy)phenyl]-1H-pyrazol-4-yl}methyl)benzonitrile From Step A above in 20 mL ethanol and 6 mL water was added 0.96 g potassium hydroxide. The resulting solution was refluxed under nitrogen for one day. HPLC showed some amide intermediate remaining. Add 1.05 g potassium hydroxide in 2 mL water and 4 mL ethanol. Reflux continued for another 17 hours. The solvents were removed under reduced pressure. The residue was re-suspended in 5 mL water and acidified with 18.0 mL 2 N HCl. The resulting solid was filtered, washed with water, and dried to give the title compound as a white solid. $^1$H NMR (CD$_3$OD, 500 MHz) δ 7.93~7.95 (m, 2), 7.91 (s, 1H), 7.75~7.79 (m, 2H), 7.32~7.36 (m, 4H), 3.95 (s, 2H), 2.60 (tt, J=3.2 & 11.8 Hz, 1H), 1.68~1.81 (m, 5H), 1.51~1.60 (m, 2H), 1.22~1.36 (m, 3H). LC-MS: 2.51 min. (M+H=445.2).

Step C.

4-({3-Cyclohexyl-1-[4-(trifluoromethoxy)phenyl]-1H-pyrazol-4-yl}methyl)-N-(1H-tetrazol-5-yl)benzamide A mixture of 66.7 mg product from Step B above, 71.9 mg EDC, 30.4 mg HOBt and 23.2 mg aminotetrazole monohydrate was dissolved in 1 mL DMF. DIEA (92 µL) was added immediately and the resulting solution was stirred at room temperature for 17 hours. The reaction mixture was diluted with about 2:1 mixture of DMF and water and purified on preparative HPLC using 70~80% MeCN gradient over 10 minutes at 8.0 mL per minute with 0.1% TFA. The title compound was obtained as a white solid following lyophilization. $^1$H NMR (DMSO-d$_6$, 500 MHz) δ 8.26 (s, 1H), 8.02 (d, J=8.2 Hz, 2H), 7.84~7.87 (m, 2), 7.40~7.45 (m, 4H), 3.92 (s, 2H), 2.58 (tt, J=3.4 & 11.9 Hz, 1H), 1.62~1.74 (m, 5H), 1.41~1.50 (m, 2H), 1.17~1.31 (m, 3H). LC-MS: 2.41 min. (M+H=512.3).

Following the procedures outlined for Examples 1-14 the compounds listed in Table 1-9 were prepared

TABLE 1

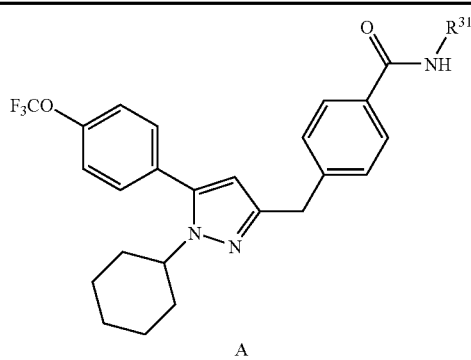

A

TABLE 1-continued

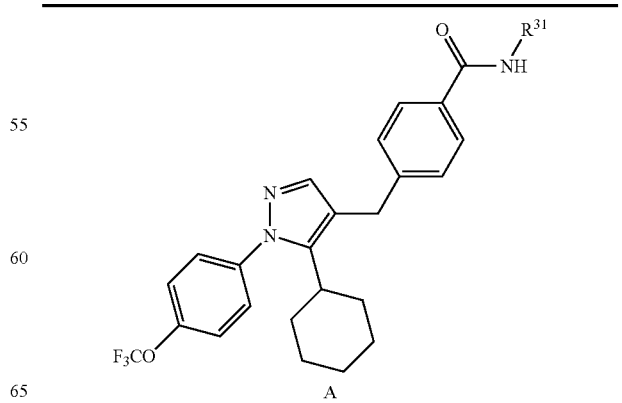

B

| Example | $R^{31}$ | LC-MS, min.(M + H) and NMR |
|---|---|---|
| 15 | A | ~CO$_2$H  2.17(516.2) |
| 16 | A | ~CO$_2$Me  2.47(546.3), OH |
| 17 | A | ~CO$_2$H  2.36(532.3), OH |
| 18 | B | ~CO$_2$H  2.28(516.3); $^1$H NMR(CD$_3$OD, 500MHz) δ 7.82~7.85(m, 2H), 7.785(d, 8.2Hz, 2H), 7.35(d, 8.2Hz, 2H), 7.27(d, 8.0Hz, 2H), 6.44(s, 1H), 4.165(s, 2H), 4.035(tt, 3.8 & 11.8Hz, 1H), 3.62(t, 7.0Hz, 2H), 2.64(t, 7.0Hz, 2H), 1.87~1.95(m, 2H), 1.79~1.84(m, 2H), 1.65~1.71(m, 3H), 1.21~1.37(m, 3H). |
| 19 | B | ~CO$_2$Me  2.58(546.3), OH |
| 20 | B | ~CO$_2$H  2.47(532.3), OH |

TABLE 2

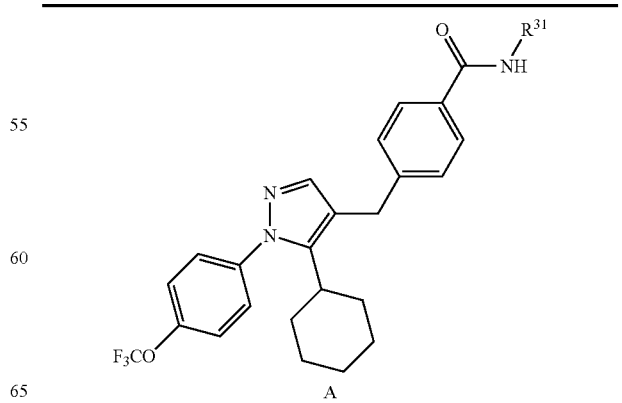

A

TABLE 2-continued

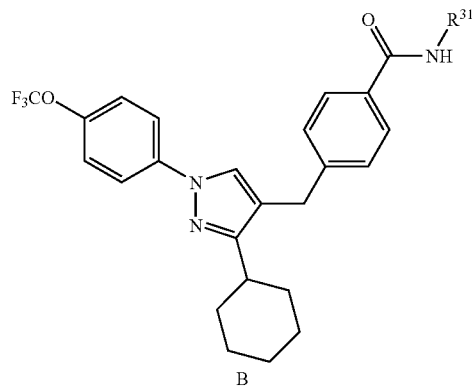

| Example | R³¹ | | LC-MS, min.(M + H) and NMR |
|---|---|---|---|
| 21 | A | ~~~CO₂H | 2.00(516.3); ¹H NMR(CD₃OD, 500MHz) δ 7.76(d, 8.2Hz, 2H), 7.46~7.51(m, 4H), 7.36(s, 1H), 7.32(d, 8.3Hz, 2H), 4.06(s, 2H), 3.62(t, 6.9Hz, 2H), 2.61~2.70(m, 3H), 1.69~1.74(m, 4H), 1.54~1.65(m, 3H), 1.12~1.20(m, 3H). |
| 22 | A | ~~CH(OH)CO₂Me | 2.41(546.3) |
| 23 | A | ~~CH(OH)CO₂H | 2.30(532.3) |
| 24 | B | ~~~CO₂H | 2.22(516.3); ¹H NMR(CD₃OD, 500MHz) δ 7.91(s, 1H), 7.73~7.78(m, 4H), 7.32~7.36(m, 4H), 3.94(s, 2H), 3.61(t, 7.0Hz, 2H), 2.63(t, 6.9Hz, 2H), 2.59(tt, 3.2 & 11.9Hz, 1H), 1.68~1.81(m, 5H), 1.51~1.59(m, 2H), 1.25~1.36(m, 3H). |
| 25 | B | ~~CH(OH)CO₂Me | 2.69(546.3) |
| 26 | B | ~~CH(OH)CO₂H | 2.58(532.3) |

TABLE 3

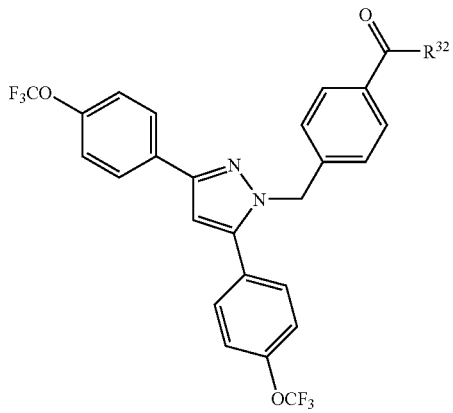

| Example | R³² | LC-MS, min.(M + H) and NMR |
|---|---|---|
| 27 | HN-tetrazolyl | 2.58(590.2) |
| 28 | HN~~CO₂H | 2.53(594.2) |
| 29 | HN~CH(OH)CO₂Me | 2.58(624.2) |
| 30 | HN~CH(OH)CO₂H | 2.47(610.2) |
| 31 | HN~CO₂H | 2.53(580.3) |
| 32 | HN~~~CO₂H | 2.53(608.3) |
| 33 | MeN~~CO₂H | 2.57(608.3) |
| 34 | HN-CH₂-tetrazolyl | 2.48(604.2); ¹H NMR(dioxane-d₈, 500MHz) δ 8.13(br t, 1NH), 7.92~7.95(m, 2H), 7.75(d, 8.2Hz, 2H), 7.47~7.50(m, 2H), 7.40(d, 8.2Hz, 2H), 7.37(d, 8.2Hz, 2H), 7.18(d, 8.2Hz, 2H), 6.85(s, 1H), 5.48(s, 2H), 4.80(d, 5.7Hz, 2H). |

TABLE 4

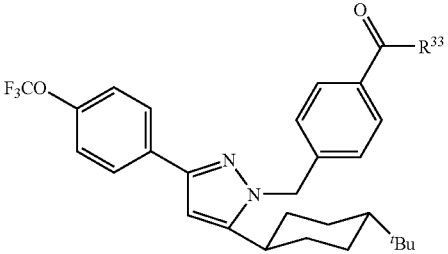

| Example | R³³ | LC-MS, min.(M + H) and NMR |
|---|---|---|
| 35 |  | 2.81(568.3) |
| 36 | 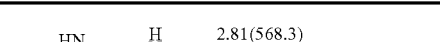 | 2.77(572.3) |
| 37 |  | 2.71(588.3) |
| 38 | 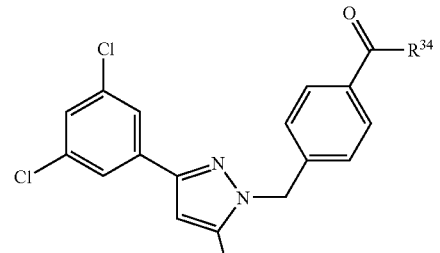 | 2.48(604.2); ¹H NMR(dioxane-d₈, 500MHz) δ 8.13(br t, 1NH), 7.92~7.95(m, 2H), 7.75(d, 8.2Hz, 2H), 7.47~7.50(m, 2H), 7.40(d, 8.2Hz, 2H), 7.37(d, 8.2Hz, 2H), 7.18(d, 8.2Hz, 2H), 6.85(s, 1H), 5.48(s, 2H), 4.80(d, 5.7Hz, 2H). |

TABLE 5

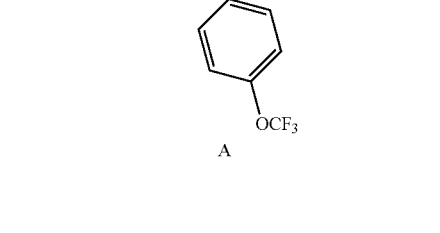
A

TABLE 5-continued

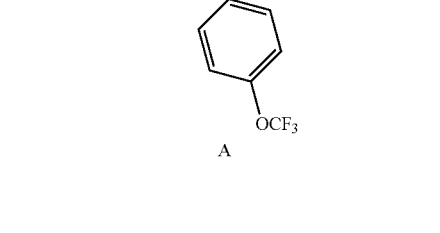
B

| Example | R³⁴ | | LC-MS, min.(M + H) and NMR |
|---|---|---|---|
| 39 | A | 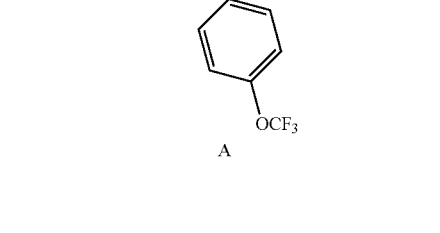 | 2.68(574.1/576.2); ¹H NMR(CD₃OD, 500MHz) δ 7.99(d, 8.3Hz, 2H), 7.87(d, 2.1Hz, 2H), 7.53~7.57(m, 2H), 7.425(t, 1.8Hz, 1H), 7.39(d, 8.3Hz, 2H), 7.25(d, 8.2Hz, 2H), 6.98(s, 1H), 5.58(s, 2H). |
| 40 | A | 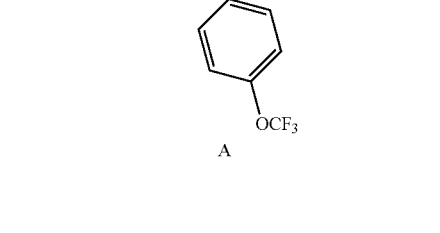 | 2.63(578.2/580.1); ¹H NMR(CD₃OD, 500MHz) δ 7.84(d, 1.9Hz, 2H), 7.71~7.74(m, 2H), 7.49~7.52(m, 2H), 7.40(t, 2.0Hz, 1H), 7.36(d, 8.0Hz, 2H), 7.13(d, 8.3Hz, 2H), 6.94(s, 1H), 5.51(s, 2H), 3.60(t, 7.0Hz, 2H), 2.61(t, 6.9Hz, 2H). |
| 41 | A | 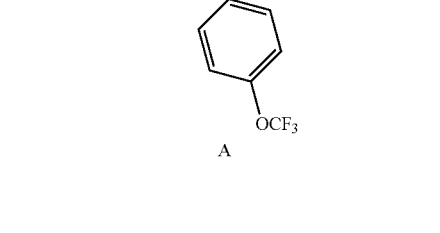 | 2.57(594.1/596.2); ¹H NMR(CD₃OD, 500MHz) δ 7.84(m, 1.9Hz, 2H), 7.76(d, 8.2Hz, 2H), 7.50~7.53(m, 2H), 7.40(t, 2.0Hz, 1H), 7.36(d, 8.2Hz, 2H), 7.14(d, 8.0Hz, 2H), 6.94(s, 1H), 5.51(s, 2H), 4.36(br s, 1H), 3.70~3.80(m, 1H), 3.15~3.47(m, 1H). |
| 42 | A | 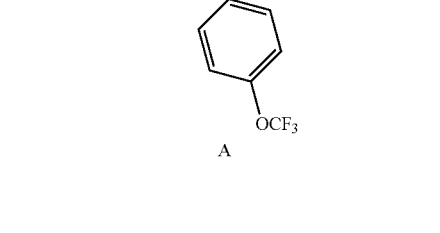 | 2.60(588.1/590.1); ¹H NMR(dioxane-d₈, 500MHz) δ 8.13(br s, 1NH), 7.83(d, 2.0Hz, 2H), 7.76(d, 8.2Hz, 2H), 7.52(t, 1.9Hz, 1H), 7.46~7.49(m, 2H), 7.40(d, 8.3Hz, 2H), 7.17(d, 8.3Hz, 2H), 6.93(s, 1H), 5.48(s, 2H), 4.81(d, 6.0Hz, 2H). |
| 43 | B | 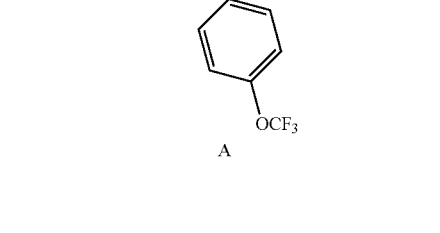 | 2.61(574.1/576.1); ¹H NMR(CD₃OD, 500MHz) δ 7.97~8.01(m, 4H), 7.535(t, 1.9Hz, 1H), 7.41(d, 1.9Hz, 2H), 7.34(d, 8.0Hz, 2H), 7.26(d, 8.3Hz, 2H), 6.97(s, 1H), 5.58(s, 2H). |

TABLE 5-continued

| 44 | B | HN-CH2CH2-CO2H | 2.57(578.1/580.1) |
| 45 | B | HN-CH2-CH(OH)-CO2H | 2.51(594.2/596.2) |
| 46 | B | HN-CH2-(tetrazole) | 2.54(588.1/590.1); ¹H NMR(dioxane-d₈, 500MHz) δ 8.13(br s, 1NH), 7.91~7.95(m, 2H), 7.77(d, 8.2Hz, 2H), 7.64(t, 1.9Hz, 1H), 7.44(d, 1.8Hz, 2H), 7.38(d, 8.5Hz, 2H), 7.21(d, 8.2Hz, 2H), 6.92(s, 1H), 5.50(s, 2H), 4.80(d, 5.7Hz, 2H). |

TABLE 6

Structure: F₃CO-phenyl-pyrazole-N-CH(CH₃)-phenyl-C(O)-R³⁵, with OCF₃-phenyl substituent

| Example | R³⁵ | LC-MS, min.(M + H) |
|---|---|---|
| 47 | HN-(tetrazole) | 2.67(604.3) |
| 48 | HN-CH2CH2-CO2H | 2.62(608.3) |
| 49 | HN-CH2-CH(OH)-CO2H | 2.56(624.3) |
| 50 | HN-CH2-(tetrazole) | 2.60(618.3) |

TABLE 7

Structure A: MeO₂S-phenyl-pyrazole-N-CH2-phenyl-C(O)-R³⁶, with OCF₃-phenyl substituent Structure B: F₃CO-phenyl-pyrazole-N-CH2-phenyl-C(O)-R³⁶, with SO₂Me-phenyl substituent

| Example | | R³⁶ | LC-MS, min.(M + H) |
|---|---|---|---|
| 51 | A | HN-(tetrazole) | 2.19(584.3) |
| 52 | A | HN-CH2CH2-CO2H | 2.12(588.3) |
| 53 | A | HN-CH2-CH(OH)-CO2H | 2.07(604.3) |
| 54 | A | HN-CH2-(tetrazole) | 2.11(598.3) |
| 55 | B | HN-(tetrazole) | 2.11(584.3) |
| 56 | B | HN-CH2CH2-CO2H | 2.07(588.3) |
| 57 | B | HN-CH2-CH(OH)-CO2H | 1.99(604.3) |

TABLE 7-continued

| | | | |
|---|---|---|---|
| 58 | B | (aminomethyl-1H-tetrazole) | 2.05(598.3) |

TABLE 8

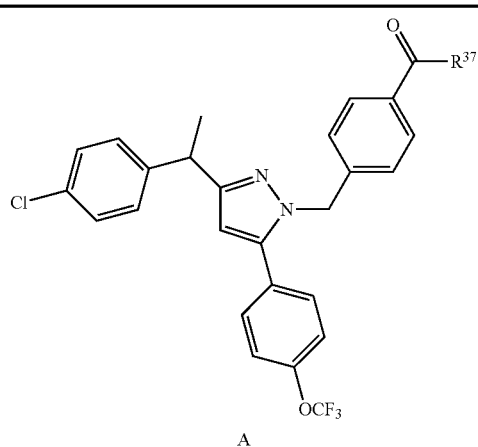

A

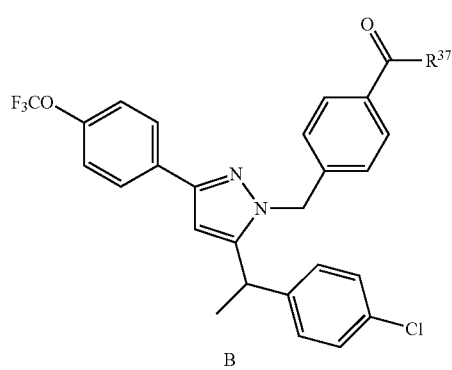

B

| Example | R³⁷ | | LC-MS, min.(M + H) |
|---|---|---|---|
| 59 | A | 5-amino-1H-tetrazole | 2.53(568.3/570.3) |
| 60 | A | HN-CH₂-CH₂-CO₂H | 2.48(572.3/574.3) |
| 61 | A | HN-CH₂-CH(OH)-CO₂H | 2.41(588.3/590.3) |
| 62 | A | aminomethyl-1H-tetrazole | 2.46(582.3/584.3) |
| 63 | B | 5-amino-1H-tetrazole | 2.54(568.3/570.3) |
| 64 | B | HN-CH₂-CH₂-CO₂H | 2.49(572.3/574.3) |

TABLE 8-continued

| 65 | B | HN-CH₂-CH(OH)-CO₂H | 2.44(588.3/590.3) |
|---|---|---|---|
| 66 | B | aminomethyl-1H-tetrazole | 2.48(582.3/584.3) |

TABLE 9

[Structure: F₃CO-phenyl-pyrazole-CH₂-phenyl-C(O)-R³⁸, with OCF₃-phenyl substituent]

| Example | R³⁸ | LC-MS, min.(M + H) and NMR |
|---|---|---|
| 67 | 5-amino-1H-tetrazole | 2.55(590.3); ¹H NMR(dioxane-d₈, 500MHz) δ 7.92~7.95(m, 2H), 7.90(d, 7.8Hz, 1H), 7.84(s, 1H), 7.52~7.55(m, 2H), 7.48(dd, 7.8 & 7.6Hz, 1H), 7.42(d, 8.0Hz, 2H), 7.38(d, 8.2Hz, 2H), 7.31(d, 7.8Hz, 1H), 6.86(s, 1H), 5.53(s, 2H). |
| 68 | HN-CH₂-CH₂-CO₂H | 2.50(594.3) |
| 69 | HN-CH₂-CH(OH)-CO₂H | 2.44(610.3) |
| 70 | HN-CH₂-CO₂H | 2.49(580.3) |
| 71 | HN-(CH₂)₃-CO₂H | 2.52(608.3) |
| 72 | aminomethyl-1H-tetrazole | 2.48(604.3) |

EXAMPLE 73

4-{[3-(3,5-DICHLOROPHENYL)-5-(4-METHOX-YPHENYL)-1H-PYRAZOL-1-YL]METHYL}-N-(1H-TETRAAZOL-5-YL)BENZAMIDE

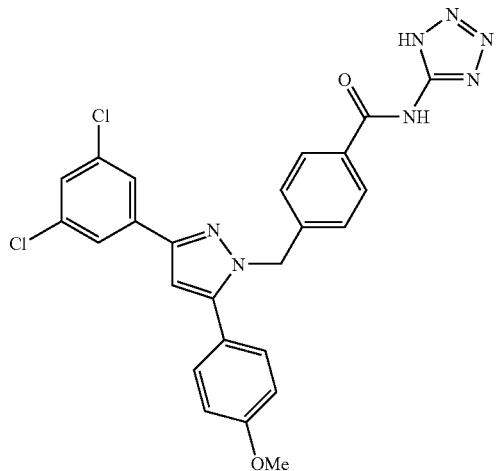

Step A.

1-(3,5-dichlorophenyl)-3-(4-methoxyphenyl)prop-2-yn-1-one

To a solution of 4-methoxy-1-ethynyl benzene (0.57 g, 4.27 mmol) in 20 mL of anhydrous THF cooled to −78° C. under a $N_2$ atmosphere was added nButLi (3.2 mL, 5.12 mmol). After 5 minutes a solution of 3,5-dichloro-N-methoxy-N-methylbenzamide (1.0 g, 4.27 mmol) in THF (10 mL) was added to the reaction. The reaction was slowly warmed to −40° C. over 30 minutes and then quenched with saturated $NH_4Cl$ solution. The resulting bi-phasic mixture was extracted with EtOAc (3×). The organic layer was washed with brine, dried over anhydrous $Na_2SO4$, filtered and concentrated in vacuo. The residue was purified by flash chromatography using 1:10 ethyl acetate-hexanes to give the title compound as a yellow solid. $^1H$ NMR ($CDCl_3$, 500 MHz): δ 8.09(d, J=2.0 Hz, 2H), 7.7(d, J=7.1 Hz, 2H), 7.64(t, J=1.8 Hz, 1H), 7.0(d, J=8.7 Hz, 1H), 3.91(s, 3H).

Step B.

3-(3,5-dichlorophenyl)-5-(4-methoxyphenyl)-1H-pyrazole

To a solution of the intermediate from step A (1.13 g, 3.7 mmol) in DMF (20 mL) was added hydrazine (0.37 mL, 4.07 mmol, 35% aqueous solution). After 2 hours the reaction mixture was concentrated in vacuo. The residue was suspended in $H_2O$ (20 mL). A white precipitate crashed out. The aqueous layer was extracted with ethyl acetate (2×). The organic layer was dried over anhydrous $Na_2SO_4$, filtered and concentrated in vacuo. An off-white solid was obtained. This material was used in the next step without any further purification. $^1H$ NMR ($CDCl_3$, 500 MHz): δ 7.7(d, J=1.8 Hz, 2H), 7.66(d, J=8.4 Hz, 2H), 7.35(s, 1H), 7.03(d, J=8.7 Hz, 2H), 6.8(s, 1H), 3.91(s, 3H). LC-MS: 2.92 min. (M+H)=319.

Step C.

Methyl 4-{[3-(3,5-dichlorophenyl)-5-(4-methoxyphenyl)-1H-pyrazol-1-yl]methyl}benzoate To a solution of the intermediate from step B (1.1 g, 3.44 mmol) in DMF (20 mL) was added $Cs_2CO_3$ (1.68 g, 5.15 mmol) and Methyl 4-(bromomethyl)-benzoate (0.94 g. 4.13 mmol). The resulting solution was stirred at room temperature for 48 hours. The reaction mixture was quenched by the addition of $H_2O$ (50 mL). The resulting solution was extracted with ethyl acetate (3×50 mL). The combined organic layers were washed with brine, dried over anhydrous $Na_2SO_4$, filtered and concentrated in vacuo to give a yellow oil. This material was purified by flash chromatography using 15% ethyl acetate-hexanes. A white solid was obtained. This material was re-purified by flash chromatography using DCM to give the two pyrazole isomers A and B in a 2:1 ratio. The pyrazole isomers were assigned by NOE difference spectroscopy. $^1H$ NMR ($CDCl_3$, 500 MHz): Isomer A (first compound off column); δ 8.06(d, J=8.2 Hz, 2H), 7.78(d, J=1.8 Hz, 2H), 7.32(t, J=1.9 Hz, 1H), 7.26(d, J=8.7 Hz, 2H), 7.19(d, J=8.3 Hz, 2H), 6.96(d, J=8.7 Hz, 2H), 6.63(s, 1H), 5.44(s, 2H), 3.94(s, 3H), 3.87(s, 3H). LC-MS: 2.94 min; (M+H)=467.2. Isomer B (second compound off column); δ 8.03(d, J=8.3 Hz, 2H), 7.82(d, J=8.7 Hz, 2H), 7.42(t, J=1.9 Hz, 1H), 7.22(d, J=1.9 Hz, 2H), 7.21(s, 1H), 7.01(d, J=8.9 Hz, 2H), 6.6(s, 1H), 5.49(s, 2H), 3.94(s, 3H), 3.85(s, 3H).

Step D.

4-{[3-(3,5-dichlorophenyl)-5-(4-methoxyphenyl)-1H-pyrazol-1-yl]methyl}benzoic acid To a solution of the intermediate from step C (Isomer A, 0.99 g, 2.13 mmol) in THF (30 mL) was added methanol (10 mL) followed by sodium hydroxide solution (2N, 2 mL, 4 mmol). The reaction was stirred at room temperature overnight. The reaction mixture was concentrated in vacuo to remove the organic solvents. The residue was acidified with 1N HCl until the pH was less than 2. The resulting solution was extracted with ethyl acetate (3×) dried over anhydrous $Na_2SO_4$, filtered and concentrated in vacuo to give the title compound as a white solid. This material was used in the next step without any further purification. $^1H$ NMR (DMSO, 500 MHz): δ 7.89(d, J=8.2 Hz, 2H), 7.88(d, J=1.8 Hz, 2H), 7.55 (d, J=1.9 Hz, 1H), 7.38(d, J=8.7 Hz, 2H), 7.15(d, J=8.3 Hz, 2H), 7.11(s, 1H), 7.04(d, J=8.7 Hz, 2H), 5.5(s, 2H), 3.79(s, 3H). LC-MS: 2.69 min. (M+H)=453.

Step E.

4-{[3-(3,5-dichlorophenyl)-5-(4-methoxyphenyl)-1H-pyrazol-1-yl]methyl}-N-(1H-tetraazol-5-yl)benzamide To a solution of the intermediate from step D (100 mg, 0.22 mmol) in 1:1 DMF/DCM (0.54 mL) was added 1-hydroxy-7-azabenzo-triazole (35 mg, 0.264 mmol), N,N-diisopropyl-ethyl amine (92 μL, 0.53 mmol) amino tetrazole (56 mg, 0.66 mmol) and 1-(3-(Dimethylamino)propyl-3-ethyl carbodiimide hydrochloride (51 mg, 0.26 mmol). The reaction was left stirring at room temperature for 18 hours. The reaction was checked by LC-MS and was found to have not gone to completion. An additional equivalent of amino tetrazole was added followed by Bromo-tris-pyrrolidino-phosphonium hexafluorophosphate (51 mg, 0.11 mmol). The reaction was complete in 3 hours. It was diluted with DCM (10 mL) and washed with 1N HCl, dried over anhydrous Na₂SO₄, filtered and concentrated in vacuo. The residue was purified by reverse phase HPLC (Gilson) to give the title compound. ¹H NMR (DMSO, 500 MHz): δ 8.04(d, J=8.5 Hz, 2H), 7.89(d, J=2.1 Hz, 2H), 7.56(t, J=1.9 Hz, 1H), 7.41(d, J=8.7 Hz, 2H), 7.21(d, J=8.4 Hz, 2H), 7.14(s, 1H), 7.05(d, J=8.7 Hz, 2H), 5.53(s, 2H), 3.79(s, 3H). LC-MS: 2.53 min; (M+H)=520.2.

EXAMPLE 74

N-(4-{[3-(3,5-DICHLOROPHENYL)-5-(4-METH-OXYPHENYL)-1H-PYRAZOL-1-YL]METHYL}BENZOYL)-β-ALANINE

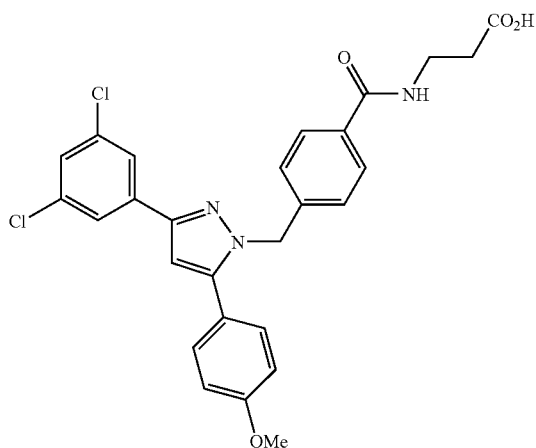

Step A.

N-4-{[3-(3,5-dichlorophenyl)-5-(4-methoxyphenyl)-1H-pyrazol-1-yl]methyl}benzoyl)-β-alanine To a solution of the intermediate from example 73 step D (100 mg, 0.22 mmol) in 1:1 DMF/DCM (0.54 mL) was added 1-hydroxy-7-azabenzo-triazole (35 mg, 0.264 mmol), N,N-diisopropylethyl amine (92 μL, 0.53 mmol) β-alanine-t-butyl ester hydrochloride (48 mg, 0.26 mmol) and 1-(3-(Dimethylamino)propyl-3-ethyl carbodiimide hydrochloride (51 mg, 0.26 mmol). The reaction was left stirring at room temperature for 18 hours. The reaction was diluted with DCM, washed with 1N HCl, dried over anhydrous Na₂SO₄, filtered and concentrated in vacuo. The residue was purified by flash chromatography using 2:5 ethyl acetate-hexanes to give a colorless oil. LC-MS: 4.5 min; (M+H)=580.2. This material was dissolved in 1:1 TFA/DCM (4 mL) and stirred at room temperature for 18 hours. The reaction mixture was concentrated in vacuo and azeotroped with toluene (1×). The residue was purified by reverse phase HPLC (Gilson) to give the title compound. ¹H NMR (DMSO, 500 MHz): δ 8.49(t, J=5.5 Hz, 1H), 7.88(d, J=2.1 Hz, 2H), 7.76(d, J=8.3 Hz, 2H), 7.55(t, J=1.8 Hz, 1H), 7.39(d, J=8.7 Hz, 2H), 7.1(s, 1H), 7.09(d, J=8.9 Hz, 2H), 7.04(d, J=9.0 Hz, 2H), 5.47(s, 2H), 3.79(s, 3H), 3.45(q, J=7.1 Hz, 2H), 2.49(t, J=7.1 Hz, 2H). LC-MS: 3.85 min; (M+H)=524.1.

EXAMPLE 75

4-{[3-(3,5-DICHLOROPHENYL)-5-(4-METHOXYPHENYL)-1H-PYRAZOL-1-YL]METHYL}-N-(1H-TETRAAZOL-5-YL)BENZAMIDE

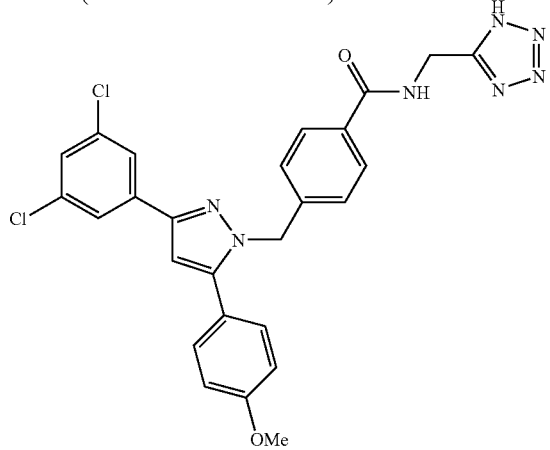

Step A.

4-{[3-(3,5-dichlorophenyl)-5-(4-methoxyphenyl)-1H-pyrazol-1-yl]methyl}-N-(1H-tetraazol-5-ylmethyl)benzamide To a solution of the intermediate from example 73 step D (100 mg, 0.22 mmol) in 1:1 DMF/DCM (0.54 mL) was added 1-hydroxy-7-azabenzo-triazole (35 mg, 0.264 mmol), N,N-diisopropylethyl amine (92 μL, 0.53 mmol) amino methyl tetrazole (26 mg, 0.26 mmol) and 1-(3-(Dimethylamino)propyl-3-ethyl carbodiimide hydrochloride (51 mg, 0.26 mmol). The reaction was left stirring at room temperature for 18 hours. The reaction was diluted with DCM, washed with 1N HCl, dried over anhydrous Na₂SO₄, filtered and concentrated in vacuo. The residue was purified by reverse phase HPLC (Gilson) to give the title compound. ¹H NMR (DMSO, 500 MHz): δ 9.21(t, J=5.3 Hz, 1H), 7.88(d, J=2.1 Hz, 2H), 7.83(d, J=8.5 Hz, 2H), 7.56(t, J=2.1 Hz, 1H), 7.39(d, J=8.7 Hz, 2H), 7.15(d, J=8.3 Hz, 2H), 7.12(s, 1H), 7.04(d, J=8.7 Hz, 2H), 5.49(s, 2H), 4.74(d, J=5.4 Hz, 2H), 3.79(s, 3H). LC-MS: 3.82 min; (M+H)=534.1.

EXAMPLE 76

4-{[5-(3,5-DICHLOROPHENYL)-3-(4-METHOXYPHENYL)-1H-PYRAZOL-1-YL]METHYL}-N(1H-TETRAAZOL-5-YL)BENZAMIDE

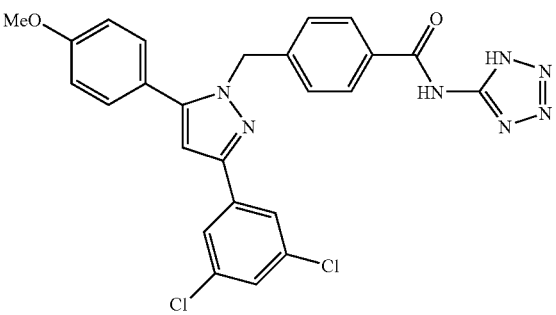

Step A

4-{[5-(3,5-dichlorophenyl)-3-(4-methoxyphenyl)-1H-pyrazol-1-yl]methyl}benzoic acid To a solution of the intermediate from example 73 step C (Isomer B, 0.43 g, 0.92 mmol) in THF (30 mL) was added methanol (10 mL) followed by sodium hydroxide solution (2N, 2 mL, 4 mmol). The reaction was stirred at room temperature overnight. The reaction mixture was concentrated in vacuo to remove the organic solvents. The residue was acidified with 1N HCl until the pH was less than 2. The resulting solution was extracted with ethyl acetate (3×) dried over anhydrous $Na_2SO_4$, filtered and concentrated in vacuo to give the title compound as a white solid. This material was used in the next step without any further purification. $^1$H NMR (DMSO, 500 MHz): δ 7.86(d, J=8.5 Hz, 2H), 7.77(d, J=8.7 Hz, 2H), 7.67(s, 1H), 7.5(d, J=1.8 Hz, 2H), 7.14(d, J=8.3 Hz, 2H), 7.04(s, 1H), 6.98(d, J=8.9 Hz, 2H), 5.52(s, 2H), 3.77(s, 3H). LC-MS: 2.55 min; (M+H)=453.1.

Step B.

4-{[5-(3,5-dichlorophenyl)-3-(4-methoxyphenyl)-1H-pyrazol-1-yl]methyl}-N-(1H-tetraazol-5-yl)benzamide To a solution of the intermediate from step A (100 mg, 0.22 mmol) in 1:1 DMF/DCM (0.54 mL) was added 1-hydroxy-7-azabenzo-triazole (35 mg, 0.264 mmol), NAN-diisopropylethyl amine (92 μL, 0.53 mmol) amino tetrazole (56 mg, 0.66 mmol) and 1-(3-(Dimethylamino)propyl-3-ethyl carbodiimide hydrochloride (51 mg, 0.26 mmol). The reaction was left stirring at room temperature for 18 hours. The reaction was checked by LC-MS and was found to have not gone to completion. An additional equivalent of amino tetrazole was added followed by Bromo-tris-pyrrolidino-phosphonium hexafluorophosphate (51 mg, 0.11 mmol). The reaction was complete in 3 hours. It was diluted with DCM (10 mL) and washed with 1N HCl, dried over anhydrous $Na_2SO_4$, filtered and concentrated in vacuo. The residue was purified by reverse phase HPLC (Gilson) to give the title compound. $^1$H NMR (DMSO, 500 MB): δ 8.04(d, J=8.2 Hz, 2H), 7.8(d, J=8.6 Hz, 2H), 7.7(s, 1H), 7.56(d, J=1.8 Hz, 2H), 7.23(d, J=8.2 Hz, 1H), 7.07(s, 1H), 7.01(d, J=9.0 Hz, 2H), 5.56(s, 2H), 3.79(s, 3H). LC-MS: 3.8 min; (M+H)=520.1.

EXAMPLE 77

4-{[5-(3,5-DICHLOROPHENYL)-3-(4-METHOXYPHENYL)-1H-PYRAZOL-1-YL]METHYL}BENZOYL)-β-ALANINE

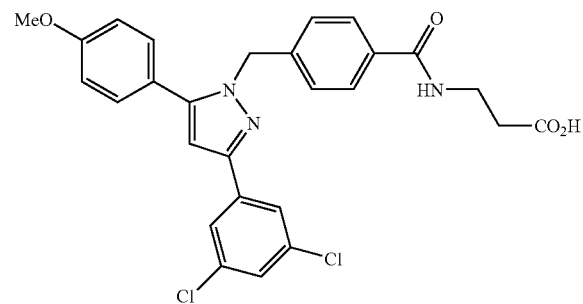

Step A.

4-{[5-(3,5-dichlorophenyl)-3-(4-methoxyphenyl)-1H-pyrazol-1-yl]methyl}benzoyl)-β-alanine To a solution of the intermediate from example 76 step A (100 mg, 0.22 mmol) in 1:1 DMF/DCM (0.54 mL) was added 1-hydroxy-7-azabenzo-triazole (35 mg, 0.264 mmol), N,N-diisopropylethyl amine (92 μL, 0.53 mmol) β-alanine-t-butyl ester hydrochloride (48 mg, 0.26 mmol) and 1-(3-(Dimethylamino)propyl-3-ethyl carbodiimide hydrochloride (51 mg, 0.26 mmol). The reaction was left stirring at room temperature for 18 hours. The reaction was diluted with DCM, washed with 1N HCl, dried over anhydrous $Na_2SO_4$, filtered and concentrated in vacuo. The residue was dissolved in 1:1 TFA/DCM (4 mL) and stirred at room temperature for 18 hours. The reaction mixture was concentrated in vacuo and azeotroped with toluene (1×). The residue was purified by reverse phase HPLC (Gilson) to give the title compound. $^1$H NMR (DMSO, 500 MHz): δ 8.49(t, J=5.5 Hz, 1H), 7.79(d, J=8.9 Hz, 2H), 7.76(d, J=8.5 Hz, 2H), 7.69(t, J=1.9 Hz, 1H), 7.53(d, J=1.8 Hz, 2H), 7.12(d, J=8.4 Hz, 2H), 7.05(s, 1H), 7.01(d, J=8.7 Hz, 2H), 5.51(s, 2H), 3.79(s, 3H), 3.45(q, J=7.1 Hz), 2.49(t, J=7.1 Hz, 2H). LC-MS: 2.35 min; (M+H)=524.2.

EXAMPLE 78

4-{[5-(3,5-DICHLOROPHENYL)-3-(4-METHOXYPHENYL)-1H-PYRAZOL-1-YL]METHYL}-N-(1H-TETRAAZOL-5-YLMETHYL)BENZAMIDE

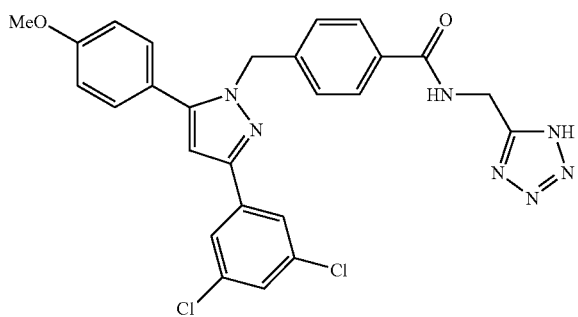

4-{[5-(3,5-dichlorophenyl)-3-(4-methoxyphenyl)-1H-pyrazol-1-yl]methyl}-N-(1-tetraazol-5-ylmethyl)benzamide To a solution of the intermediate from example 76 step A (100 mg, 0.22 mmol) in 1:1 DMF/DCM (0.54 mL) was added 1-hydroxy-7-azabenzo-triazole (35 mg, 0.264 mmol), N,N-diisopropylethyl amine (92 μL, 0.53 mmol) amino methyl tetrazole (26 mg, 0.26 mmol) and 1-(3-(Dimethylamino)propyl-3-ethyl carbodiimide hydrochloride (51 mg, 0.26 mmol). The reaction was left stirring at room temperature for 18 hours. The reaction was diluted with ethyl acetate, washed with 1N HCl, dried over anhydrous $Na_2SO_4$, filtered and concentrated in vacuo. The residue was purified by reverse phase HPLC (Gilson) to give the title compound. $^1$H NMR (DMSO, 500 MHz): δ 9.22(t, J=5.5 Hz, 1H), 7.84(d, J=8.5 Hz, 2H), 7.79(d, J=8.9 Hz, 2H), 7.69(t, J=1.9 Hz, 1H), 7.54(d, J=1.8 Hz, 2H), 7.17(d, J=8.2 Hz, 2H), 7.06(s, 1H), 7.0(d, J=8.7 Hz, 2H), 5.53(s, 2H), 4.74(d, J=5.5 Hz, 2H), 3.79(s, 3H). LC-MS: 2.32 min; (M+H)=534.3.

EXAMPLE 79

N-(4-{[5-(4-BROMOPHENYL)-3-(3,5-DICHLOROPHENYL)-1H-PYRAZOL-1-YL]METHYL}BENZOYL)-β-ALANINE

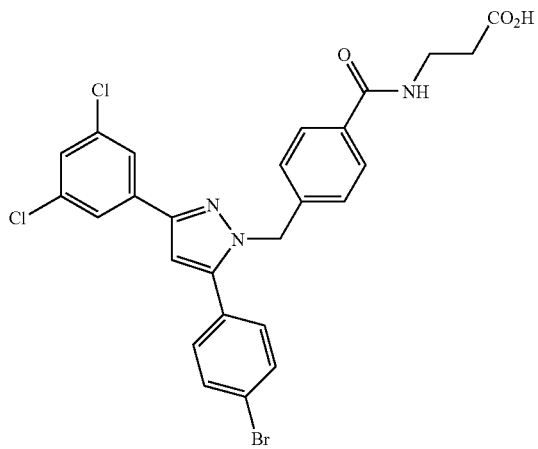

Step A.

1-bromo-4-ethynyl benzene

To a solution of zinc bromide (9.0 g, 40 mmol) in anhydrous THF (100 mL) at room temperature under a nitrogen atmosphere was added a solution of ethynyl magnesium bromide (0.5 M in THF, 60 mL, 30 mmol). After 5 minutes 4-bromo-iodobenzene was added (5.64 g, 20 mmol) followed by tetrakis triphenyl phosphine palladium (0) (1.15 g, 1.0 mmol). The reaction was stirred at room temperature for 18 hours. The reaction mixture was poured into brine and extracted with ether (4×100 mL). The ether layer was washed with brine, dried over anhydrous MgSO$_4$, filtered and concentrated in vacuo. The residue was purified by flash chromatography with hexanes to give the title compound as a yellow solid. $^1$H NMR (CDCl$_3$, 500 MHz): δ 7.51(d, J=8.5 Hz, 2H), 7.4(d, J=8.5 Hz, 1H), 3.16(s, 1H).

Step-B.

3-(4-bromophenyl)-1-(3,5-dichlorophenyl)prop-2-yn-1-one

To a solution of the intermediate from step A (2.1 g, 11.6 mmol) in anhydrous THF (80 mL) cooled to −78° C. under a N$_2$ atmosphere was added LHMDS (1.0 M solution in THF, 11.6 mL). After 5 minutes a solution of 3,5-dichloro-N-methoxy-N-methyl benzamide (2.71 g, 11.6 mmol) in THF (20 mL) was added to the reaction. The reaction was slowly warmed to 0° C. over 30 minutes and then quenched with saturated NH$_4$Cl solution. The resulting bi-phasic mixture was extracted with EtOAc (3×). The organic layer was washed with brine, dried over anhydrous Na$_2$SO$_4$, filtered and concentrated in vacuo. The residue was purified by flash chromatography using 1:10 ethyl acetate-hexanes to give the title compound as a bright yellow solid. $^1$H NMR (CDCl$_3$, 500 MHz): δ 8.07(d, J=1.8 Hz, 2H), 7.66(t, J=1.9 Hz, 1H), 7.64(d, J=8.5 Hz, 2H), 7.6(d, J=8.7 Hz, 2H).

Step C.

5-(4-bromophenyl)-3-(3,5-dichlorophenyl)-1H-pyrazole

The title compound was prepared from the intermediate in step B using the procedure described in example 73 step B.

Step D.

Methyl4-{[5-(4-bromophenyl)-3-(3,5-dichlorophenyl)-1H-pyrazole-1-yl]methyl}benzoate To a solution of the intermediate from step C (1.65 g, 4.66 mmol) in DMF (50 mL) was added Cs$_2$CO$_3$ (2.27 g, 6.99 mmol) and Methyl-4-(bromomethyl)-benzoate (1.12 g, 5.12 mmol). The resulting solution was stirred at room temperature for 2 hours. The reaction mixture was quenched by the addition of H$_2$O (50 mL). The resulting solution was extracted with ethyl acetate (3×50 mL). The combined organic layers were washed with brine, dried over anhydrous Na$_2$SO$_4$, filtered and concentrated in vacuo to give a oil. This material was purified by flash chromatography using 1:5 ethyl acetate-hexanes. The white solid was obtained was re-purified by flash chromatography using 1:4 hexanes-DCM, then 2:5 ethyl acetate-DCM to give the two pyrazole isomers A and B. $^1$H NMR (CDCl$_3$, 500 MHz): δ Isomer A (first compound off column), 8.02 (d, J=8.5 Hz, 2H), 7.77 (d, J=1.9 Hz, 2H), 7.58 (d, J=8.5 Hz, 2H), 7.34 (t, J=1.8 Hz, 1H), 7.2 (d, J=8.5 Hz, 2H), 7.17 (d, J=8.3 Hz, 2H), 6.68 (s, 1H), 5.43 (s, 2H), 3.9 (s, 3H).

Step E.

4-{[5-(4-bromophenyl)-3-(3,5-dichlorophenyl)-1H-pyrazole-1-yl]methyl}benzoic acid The title compound was prepared from the intermediate in step D using the procedure described in example 73 step D. LC-MS: 2.59 min; (M+H)=573.9.

Step F.

tert-butyl N-(4-{[5-(4-bromophenyl)-3-(3,5-dichlorophenyl)-1H-pyrazol-1-yl]methyl}benzoyl)-β-alaninate To a solution of the intermediate from step E (1.07 g, 2.13 mmol) in DMF (20 mL) was added 1-hydroxy-7-azabenzotriazole (435 mg, 3.19 mmol), N,N-diisopropylethyl amine (557 µL, 3.19 mmol) β-alanine-t-butyl ester hydrochloride (465 mg, 2.55 mmol) and 1-(3-(Dimethylamino)propyl-3-ethyl carbodiimide hydrochloride (489 mg, 2.55 mmol). The reaction was left stirring at room temperature for 18 hours. The reaction was diluted with EtOAc (150 mL), washed with 1N HCl, saturated NaHCO$_3$ solution, brine, dried over anhydrous Na$_2$SO$_4$, filtered and concentrated in vacuo. The yellow foam obtained was purified by flash chromatography using 2:5 ethylacetate-hexanes to give the title compound as a white solid. $^1$H NMR (CDCl$_3$, 500 MHz): δ 7.75 (d, J=1.6 Hz, 2H), 7.73 (d, J=8.2 Hz, 2H), 7.56 (d, J=8.4 Hz, 2H), 7.31 (t, J=1.6 Hz, 1H), 7.18 (d, J=8.3 Hz, 2H), 7.15 (d, J=8.3 Hz, 2H), 6.92 (t, J=5.7 Hz, 1H), 6.65 (s, 1H), 5.39 (s, 2H), 3.7 (q, J=5.9 Hz, 2H), 2.57 (t, J=6.1 Hz, 2H), 1.47 (s, 9H). LC-MS: 2.95 min; (M-56)=572.1.

Step G.

N-(4-{[5-(4-bromophenyl)-3-(3,5-dichlorophenyl)-1H-pyrazol-1-yl]methyl}benzoyl)-β-alanine To a solution of the intermediate from step F (30 mg, 0.047 mmol) in DCM (2 mL) was added trifluroacetic acid (2 mL). The reaction was stirred at room temperature for 1 hour. The reaction mixture was concentrated in vacuo and lyophilized from acetonitrile-water to give the title compound. $^1$H NMR (DMSO, 500 MHz): δ 8.49(t, J=5.5 Hz, 1H), 7.89 (d, J=1.8 Hz, 2H), 7.75 (d, J=8.2 Hz, 2H), 7.7 (d, J=8.5 Hz, 2H), 7.43 (d, J=8.4 Hz, 2H), 7.22 (s, 1H), 7.11 (d, J=8.2 Hz, 2H), 5.5 (s, 2H), 3.45 (q, J=7.1 Hz, 2H), 2.49 (t, J=6.8 Hz, 2H). LC-MS: 2.59 min; (M+H)=571.9.

EXAMPLE 80

N-(4-{[5-(1,1'-BIPHENYL-4-YL)-3-(3,5-DICHLOROPHENYL)-1H-PYRAZOL-1-YL]METHYL}BENZOYL)-β-ALANINE

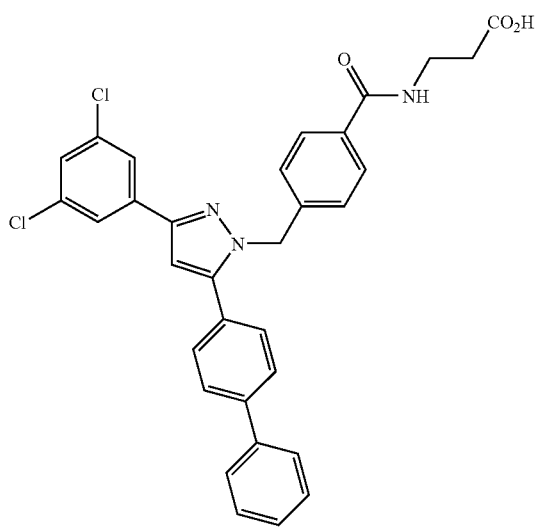

N-(4-{[5-(1,1'-biphenyl-4-yl)-3-(3,5-dichlorophenyl)-1H-pyrazol-1-yl]methyl}benzoyl)-β-alanine To a solution of the intermediate from example 79 step F (50 mg, 0.079 mmol) in toluene (1 mL) was added phenyl boronic acid (10 mg, 0.079 mmol), Na$_2$CO$_3$ solution (2.0M, 79 uL) and tetrakis triphenyl phosphine palladium (0) (5 mg, 0.003 mmol). The resulting mixture was placed in the CEM microwave instrument for 10 min at a temperature of 100° C. and power 150 W. The reaction mixture was diluted with ethyl acetate and washed with saturated NaHCO$_3$, dried over anhydrous Na$_2$SO$_4$, filtered and concentrated in vacuo. The residue was purified by flash chromatography using 3:10 ethyl acetate-hexanes to give the desired product, a colorless oil. To a solution of this material in DCM (2 mL) was added trifluroacetic acid (2 mL). The reaction was stirred at room temperature for 1 hour. The reaction mixture was concentrated in vacuo and lyophilized from acetonitrile-water to give the title compound. $^1$H NMR (DMSO, 500 MHz): δ 8.5(t, J=5.5 Hz, 1H), 7.91(d, J=1.9 Hz, 2H), 7.81(d, J=8.2 Hz, 2H), 7.78(d, J=8.5 Hz, 2H), 7.74(d, J=7.3 Hz, 2H), 7.58(m, 3H), 7.51(t, J=7.6 Hz, 2H), 7.42(t, J=7.6 Hz, 1H), 7.25(s, 1H), 7.15(d, J=8.2 Hz, 2H), 5.56(s, 2H), 3.45(q, J=7.1 Hz, 2H), 2.47(t, J=7.1 Hz, 2H). LC-MS: 2.73 min; (M+H)=570.1.

Following the procedures outlined for Examples 73-80 the compounds listed in Table 10-12 were prepared.

TABLE 10

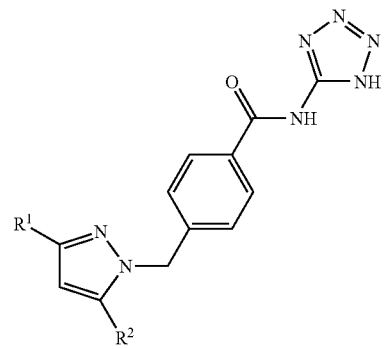

| Example | R$^1$ | R$^2$ | LC-MS data |
|---|---|---|---|
| 81 | 3,5-diClPh | 3-CF$_3$Ph | 2.64 min; (M + H) = 558.1 |
| 82 | 3-CF$_3$Ph | 3,5-diClPh | 2.58 min; (M + H) = 558.1 |
| 83 | 3,5-diClPh | 4-CF$_3$Ph | 2.64 min; (M + H) = 558.1 |
| 84 | 4-CF$_3$Ph | 3,5-diClPh | 2.59 min; (M + H) = 558.2 |
| 85 | 3,4-diClPh | 4-MeOPh | 2.47 min; (M + H) = 520.1 |
| 86 | 4-MeOPh | 3,4-diClPh | 2.37 min; (M + H) = 520.1 |
| 87 | 2-Py | 4-CF$_3$OPh | 1.75 min; (M + H) = 507.2 |
| 88 | 3,5-diClPh | ![F$_3$C-pyridyl-methyl] | 2.48 min; (M + H) = 559.0 |
| 89 | ![F$_3$C-pyridyl-methyl] | 3,5-diClPh | 2.40 min; (M + H) = 559.0 |
| 90 | 3,5-diClPh | ![MeO-pyridyl-methyl] | 2.34 min; (M + H) = 521.0 |
| 91 | Ph | 4-CF$_3$Ph | 2.33 min; (M + H) = 490.3 |
| 92 | Ph-[methylphenyl] | 3,5-diClPh | 2.68 min; (M + H) = 566.2 |

TABLE 11

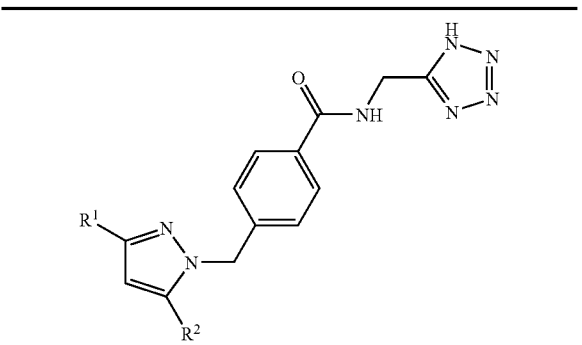

| Example | R¹ | R² | LC-MS data |
|---|---|---|---|
| 93 | 3,5-diClPh | 4-CF₃Ph | 4.11 min; (M + H) = 572.0 |
| 94 | 4-CF₃Ph | 3,5-diClPh | 2.52 min; (M + H) = 572.1 |
| 95 | 3,4-diClPh | 4-MeOPh | 2.39 min; (M + H) = 534.1 |
| 96 | 4-MeOPh | 3,4-diClPh | 2.30 min; (M + H) = 534.1 |
| 97 | 3,5-diClPh | 5-methyl-2-(trifluoromethyl)pyridinyl | 2.41 min; (M + H) = 573 |

TABLE 11-continued

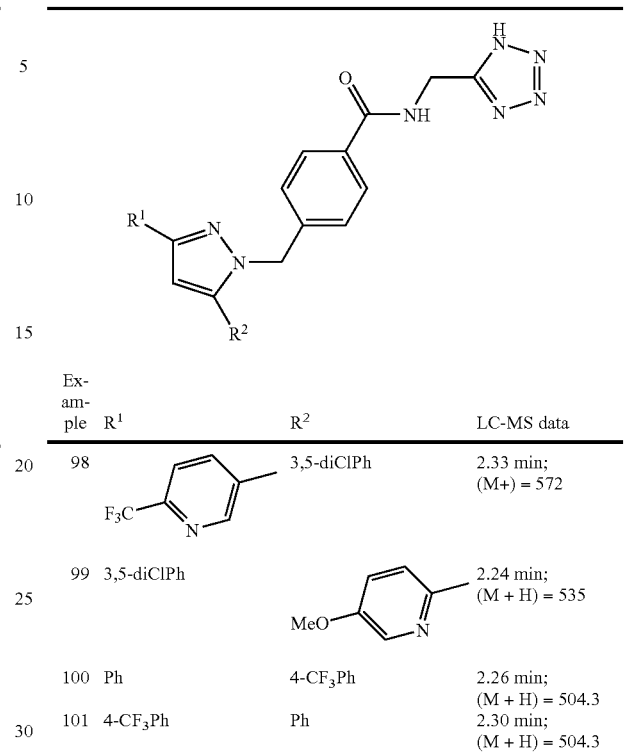

| Example | R¹ | R² | LC-MS data |
|---|---|---|---|
| 98 | 5-methyl-2-(trifluoromethyl)pyridinyl | 3,5-diClPh | 2.33 min; (M+) = 572 |
| 99 | 3,5-diClPh | 5-methoxypyridin-2-yl | 2.24 min; (M + H) = 535 |
| 100 | Ph | 4-CF₃Ph | 2.26 min; (M + H) = 504.3 |
| 101 | 4-CF₃Ph | Ph | 2.30 min; (M + H) = 504.3 |

TABLE 12

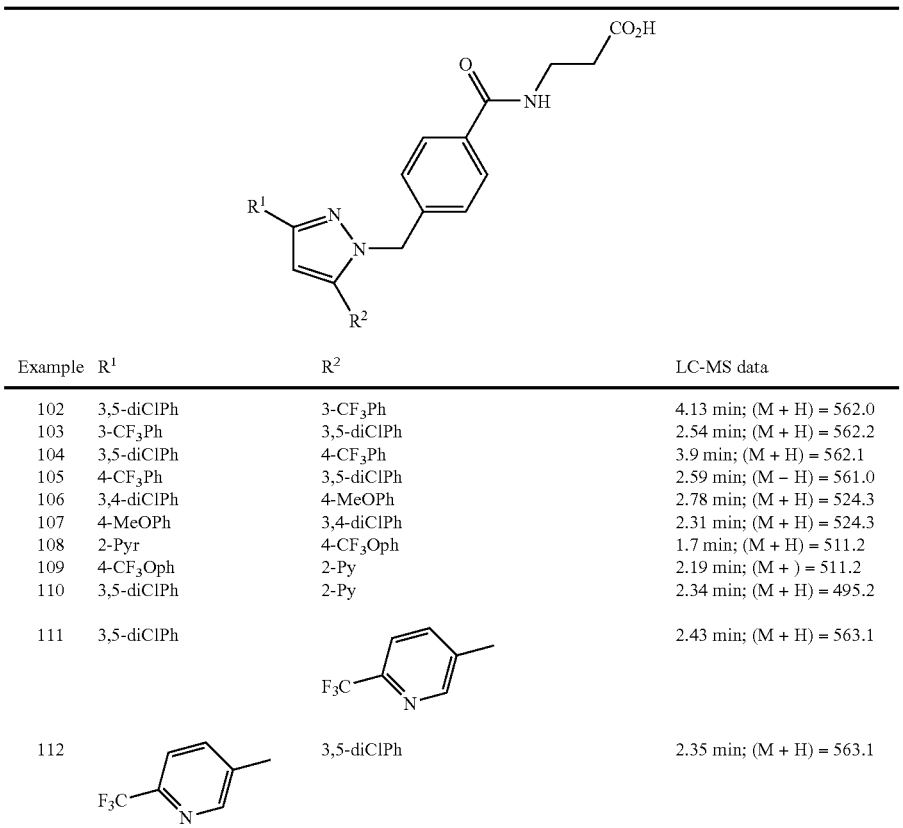

| Example | R¹ | R² | LC-MS data |
|---|---|---|---|
| 102 | 3,5-diClPh | 3-CF₃Ph | 4.13 min; (M + H) = 562.0 |
| 103 | 3-CF₃Ph | 3,5-diClPh | 2.54 min; (M + H) = 562.2 |
| 104 | 3,5-diClPh | 4-CF₃Ph | 3.9 min; (M + H) = 562.1 |
| 105 | 4-CF₃Ph | 3,5-diClPh | 2.59 min; (M − H) = 561.0 |
| 106 | 3,4-diClPh | 4-MeOPh | 2.78 min; (M + H) = 524.3 |
| 107 | 4-MeOPh | 3,4-diClPh | 2.31 min; (M + H) = 524.3 |
| 108 | 2-Pyr | 4-CF₃Oph | 1.7 min; (M + H) = 511.2 |
| 109 | 4-CF₃Oph | 2-Py | 2.19 min; (M + ) = 511.2 |
| 110 | 3,5-diClPh | 2-Py | 2.34 min; (M + H) = 495.2 |
| 111 | 3,5-diClPh | 5-methyl-2-(trifluoromethyl)pyridinyl | 2.43 min; (M + H) = 563.1 |
| 112 | 5-methyl-2-(trifluoromethyl)pyridinyl | 3,5-diClPh | 2.35 min; (M + H) = 563.1 |

TABLE 12-continued
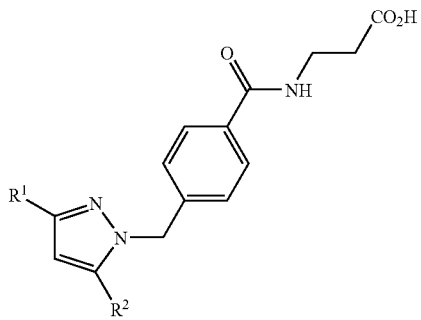
| Example | R¹ | R² | LC-MS data |
|---|---|---|---|
| 113 | 3,5-diClPh | 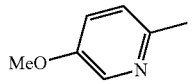 | 2.27 min; (M + H) = 525.1 |
| 114 | 3,5-diClPh | 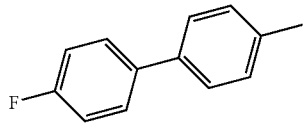 | 2.72 min; (M + H) = 588 |
| 115 | 3,5-diClPh | 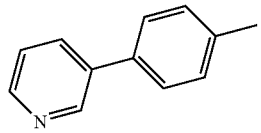 | 2.01 min; (M + H) = 571 |
| 116 | 4-CF₃Ph | Ph | 2.31 min; (M + H) = 494.3 |
| 117 | Ph | 4-CF₃Ph | 2.28 min; (M + H) = 494.3 |
| 118 | 3,5-diClPh | 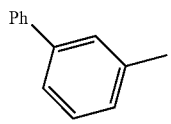 | 2.73 min; (M + H) = 570.3 |
| 119 | 3,5-diClPh | 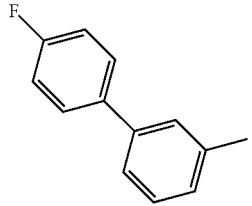 | 2.73 min; (M + H) = 588.3 |
| 120 | 3,5-diClPh | 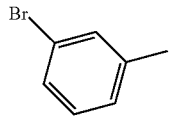 | 2.62 min; (M + H) = 572.2 |
| 121 | 3,5-diClPh | 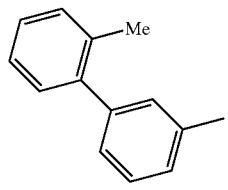 | 2.81 min; (M + H) = 584.2 |

TABLE 12-continued
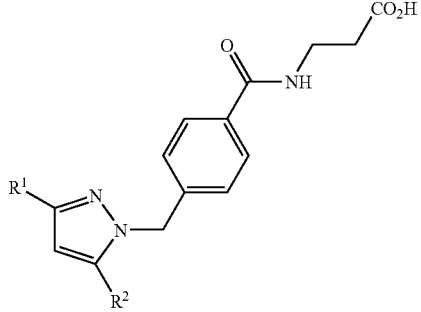
| Example | R¹ | R² | LC-MS data |
|---|---|---|---|
| 122 | 3,5-diClPh | 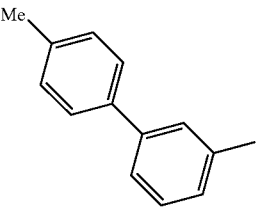 | 2.81 min; (M + H) = 584.2 |
| 123 | 3,5-diClPh | 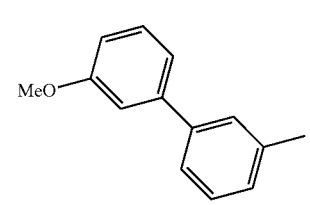 | 2.70 min; (M + H) = 600.2 |
| 124 | 3,5-diClPh | 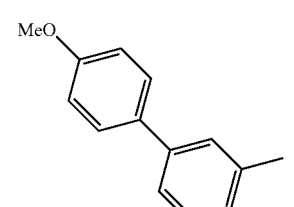 | 2.72 min; (M + H) = 600.2 |
| 125 | 3,5-diClPh | 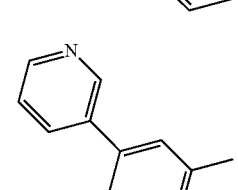 | 2.04 min; (M + H) = 571.2 |
| 126 | 3,5-diClPh | 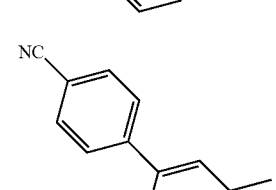 | 2.61 min; (M + H) = 595.2 |
| 127 | 3,5-diClPh | 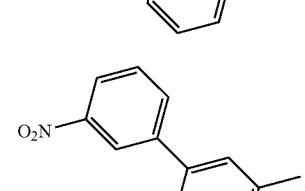 | 2.66 min; (M + H) = 615.2 |

TABLE 12-continued
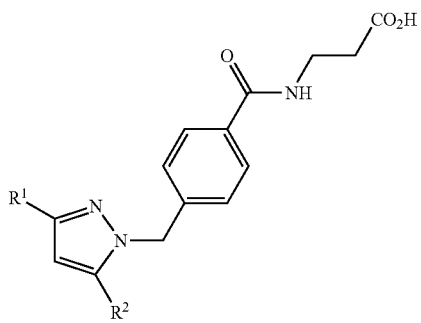
| Example | R¹ | R² | LC-MS data |
|---|---|---|---|
| 128 | 3,5-diClPh | 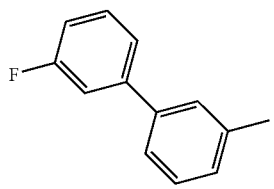 | 2.72 min; (M + H) = 588.2 |
| 129 | 3,5-diClPh | 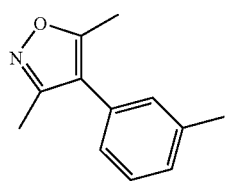 | 2.51 min; (M + H) = 589.2 |
| 130 | 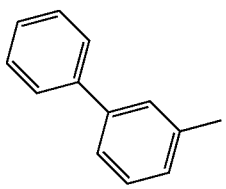 | 3,5-diClPh | 4.16 min; (M + H) = 570.1 |
| 131 | 3,5-diClPh | 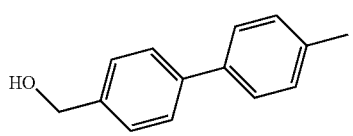 | 2.47 min; (M + H) = 600.2 |
| 132 | 3,5-diClPh | 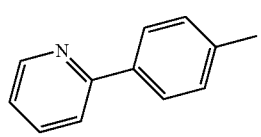 | 2.17 min; (M + H) = 571.1 |
| 133 | 3,5-diClPh | 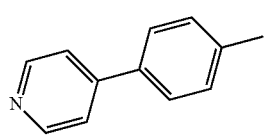 | 1.97 min; (M + H) = 571.1 |
| 134 | 3,5-diClPh | 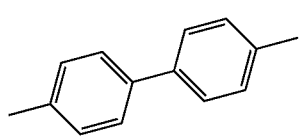 | 4.49 min; (M + H) = 584.1 |

TABLE 12-continued

| Example | R¹ | R² | LC-MS data |
|---|---|---|---|
| 135 | 3,5-diClPh | (E)-4-(3,3-dimethylbut-1-en-1-yl)phenyl | 2.92 min; (M + H) = 576.2 |
| 136 | 3,5-diClPh | 3'-hydroxy-[1,1'-biphenyl]-4-yl | 2.50 min; (M + H) = 586.1 |
| 137 | 3,5-diClPh | 3'-amino-[1,1'-biphenyl]-4-yl | 2.17 min; (M + H) = 585.1 |
| 138 | 3,5-diClPh | 4'-(dimethylamino)-[1,1'-biphenyl]-4-yl | 2.37 min; (M + H) = 613.2 |
| 139 | 3,5-diClPh | 3'-cyano-[1,1'-biphenyl]-4-yl | 2.62 min; (M + H) = 595.1 |
| 140 | 3,5-diClPh | 3',4'-dichloro-[1,1'-biphenyl]-4-yl | 2.92 min; (M + H) = 638.1 |
| 141 | 3,5-diClPh | 3',5'-difluoro-[1,1'-biphenyl]-4-yl | 2.77 min; (M + H) = 606.1 |

EXAMPLE 142

4-({3-(3,5-DICHLOROPHENYL)-5-[1-(2,2-DIMETHYLPROPANOYL)PIPERIDIN-4-YL]-1H-PYRAZOL-1-YL}METHYL)-N-(1H-TETRAAZOL-5-YL)BENZAMIDE

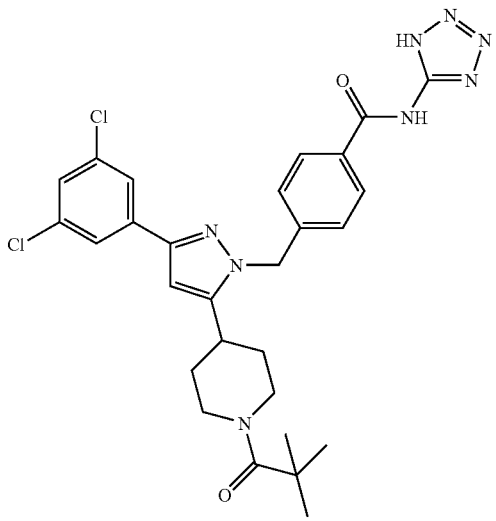

Step A.

1,3-dichloro-5-ethynyl benzene

To a solution of zinc bromide (5.0 g, 22.2 mmol) in anhydrous THF (100 mL) at room temperature under a nitrogen atmosphere was added a solution of ethynyl magnesium bromide (0.5 M in THF, 44.4 mL, 44.4 mmol). After 5 minutes 3,5-dichloro-iodobenzene was added (4.03 g, 14.8 mmol) followed by tetrakis-triphenyl phosphine palladium (0) (855 mg, 0.74 mmol). The reaction was stirred at room temperature for 18 hours. The reaction mixture was poured into brine and extracted with ether (4×100 mL). The ether layer was washed with brine, dried over anhydrous MgSO$_4$, filtered and concentrated in vacuo. The residue was purified by flash chromatography with hexanes to give the title compound as a yellow solid. $^1$H NMR (CDCl$_3$, 500 MHz): δ 7.4 (d, J=1.6 Hz, 2H), 7.3 (d, J=1.6 Hz, 1H), 3.19 (s, 1H).

Step B.

tert-butyl 4-{[methoxy(methyl)amino]carbonyl}piperidine-1-carboxylate

To a solution of 1-(tert-Butoxycarbonyl)-4-piperidine carboxylic acid (2.29 g, 10 mmol) and 4-methyl morpholine (1.2 mL, 11 mmol) in THF (60 mL) cooled to −15° C. was added isobutyl chloroformate (1.36 mL, 10.5 mmol). To this solution was added N-methoxy-N-methyl amine (1.07 g, 11 mmol) in DMF (20 mL) followed by triethyl amine (1.53 mL, 11 mmol). The resulting reaction was warmed to room temperature. The reaction was quenched after 1 hour by adding a solution of saturated NaHCO$_3$ (400 mL). The resulting mixture was extracted with EtOAc (3×). The organic layer was washed with brine, dried over anhydrous Na$_2$SO$_4$, filtered and concentrated in vacuo. The crude material was purified on the Biotage flash 40 M column using 1:1 ethyl acetate-hexanes as the solvent to give the title compound a colorless oil. $^1$H NMR (CDCl$_3$, 500 M): δ 4.16(bm, 2H), 3.73(s, 31), 3.21(s, 3H), 2.79(m, 3H), 1.7(m, 4H), 1.48(s, 9H). LC-MS: 1.75 min; (M-56)=217.

Step C.

tert-butyl 4-[3-(3,5-dichlorophenyl)prop-2-ynol]piperidine-1-carboxylate

The title compound was prepared from the intermediate in step B using the procedure described in example 73 step A. $^1$H NMR (CDCl$_3$, 500 MHz): δ 7.48(s, 1H), 7.47(d, J=1.6 Hz, 2H), 4.1 (bm, 2H), 2.92(t, J=11.7 Hz, 2H), 2.63(m, 1H), 2.03(d, J=11.7 Hz, 2), 1.72(dq, J=4.4, 11.5 Hz, 2H), 1.48(s, 91).

Step D.

tert-butyl 4-[3-(3,5-dichlorophenyl)-1H-pyrazol-5-yl]piperidine-1-carboxylate

The title compound was prepared from the intermediate in step C using the procedure described in example 73 step B.

Step E.

tert-butyl 4-{3-(3,5-dichlorophenyl)-1-[4-(methoxycarbonyl)benzyl]-1H-pyrazol-5-yl}piperidine-1-carboxylate To a solution of the intermediate from step D (1.88 g, 4.76 mmol) in DMF (20 mL) was added Cs$_2$CO$_3$ (2.32 g, 7.14 mmol) and Methyl 4-(bromomethyl)-benzoate (1.2 g. 5.14 mmol). The resulting solution was stirred at room temperature for 2 hours. The reaction mixture was quenched by the addition of H$_2$O (50 mL). The resulting solution was extracted with ethyl acetate (3×50 mL). The combined organic layers were washed with brine, dried over anhydrous Na$_2$SO$_4$, filtered and concentrated in vacuo to give an oil. This material was purified by flash chromatography using 1:5 ethyl acetate-hexanes. The white solid was obtained was repurified by flash chromatography using 1:20 acetonitrile-DCM, then 1:5 acetonitrile-DCM to give the two pyrazole isomers A and B. $^1$H NMR (CDCl$_3$, 500 MHz): Isomer A (first compound off column), δ 8.02(d, J=8.2 Hz, 2H), 7.69(d, J=2.1 Hz, 2H), 7.28(t, J=1.8 Hz, 1H), 7.16 (d, J=8.2 Hz, 2H), 6.41(s, 1H), 5.44 (s, 2H), 4.16(bm, 2H), 3.92 (s, 3H), 2.6(m, 4H), 1.6(m, 3H), 1.47 (s, 9H).

Step F.

Methyl 4-{[3-(3,5-dichlorophenyl)-5-piperidin-4-yl-1H-pyrazol-1-yl]methyl}benzoate To a solution of the intermediate from step D (1.75 g, 3.2 mmol) in DCM (50 mL) was added methane sulfonic acid (0.625 mL, 9.6 mmol). After 1 hour the reaction was washed with saturated solution of sodium carbonate to give the title compound as a white solid. $^1$H NMR (CDCl$_3$, 500 MHz): δ 8.04(d, J=8.3 Hz, 2H), 7.73(d, J=1.9 Hz, 1H), 7.72(d, J=1.8 Hz, 1H), 7.3(t, J=1.9 Hz, 1H), 7.19(d, J=8.2 Hz, 2H), 6.45(d, J=1.8 Hz, 1H), 5.45 (s, 2H), 3.96(s, 3H), 3.07 (d, J=11.6 Hz, 2H), 2.91(s, 1H), 2.68(m, 1H), 2.5(m, 1H), 1.95(m, 1H), 1.6-1.8(m, 5H).

Step H.

4-({3-(3,5-dichlorophenyl)-5-[1-(2,2-dimethylpropanoyl)piperidin-4-yl]-1H-pyrazol-1-yl}methyl)benzoic acid To a solution of the intermediate from step F (100 mg, 0.225 mmol) in DCM (3 mL) was added triethyl amine (94 µl, 0.675 mmol) followed by trimethyl acetyl chloride (33.25 µL, 0.27 mmol). After 2 hours the reaction was diluted with DCM (10 mL) and washed with 1N HCl, saturated $Na_2CO_3$, dried over brine and concentrated in vacuo to give a colorless oil. This material was dissolved in THF (2 mL) and MeOH (1 mL) and 2N NaOH (2 mL) were added and the reaction left stirring at room temperature for 16 hours. The reaction was concentrated in vacuo. The residue was suspended in 1N HCl (until the pH was less then 2). The resulting suspension was extracted with EtOAc (3×), dried over anhydrous $Na_2SO_4$, filtered and concentrated in vacuo to give the title compound as a white solid. $^1$H NMR (DMSO, 500 MHz): δ 7.93(d, J=8.2 Hz, 2H), 7.81(d, J=1.8 Hz, 2H), 7.51(t, J=2.1 Hz, 1H), 7.26(d, J=8.3 Hz, 2H), 6.94(s, 1H), 5.54(s, 2H), 4.34(d, J=13.3 Hz, 2H), 3.0(m, 1H), 2.86(t, J=12.9 Hz, 2H), 2.51(t, J=1.6 Hz, 1H), 1.74 (d, J=1 Hz, 2H), 1.44 (dq, J=3.4, 12.8 Hz, 2H), 1.2(s, 9H).

Step G. 4-({3-(3,5-dichlorophenyl)-5-[1-(2,2-dimethylpropanoyl)piperidin-4-yl]-1H-pyrazol-1-yl}methyl)-N-(1H-tetraazol-5-yl)benzamide The title compound was prepared from the intermediate in step H using the procedure described in example 76 step B. $^1$H NMR (DMSO, 500 MHz): δ 8.08(d, J=8.1 Hz, 2H), 7.82(d, J=1.8 Hz, 2H), 7.52(t, J=2.1 Hz, 1H), 7.32(d, J=8.2 Hz, 2H), 6.97(s, 1H), 5.57(s, 2H), 4.35(d, J=13.2 Hz, 2H), 3.07(m, 1H), 2.85(t, J=12.1 Hz, 2H), 1.77(d, J=11.7 Hz, 2H), 1.47(dq, J=3.5, 12.8 Hz, 2H), 1.21(s, 9H). LC-MS: 2.39 min. (M+H)=581.2.

EXAMPLE 143

N-[4-({3-(3,5-DICHLOROPHENYL)-5-[1-(2,2-DIMETHYLPROPANOYL)PIPERIDIN-4-YL]-1H-PYRAZOL-1-YL}METHYL)BENZOYL]-BETA-ALANINE

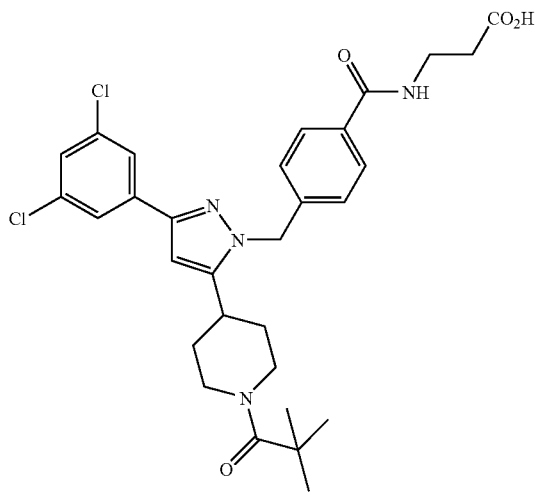

N-[4-({3-(3,5-dichlorophenyl)-5-[1-(2,2-dimethylpropanoyl)piperidin-4-yl]-1H-pyrazol-1-yl}methyl)benzoyl]-β-alanine The title compound was prepared from the intermediate in Example 142 step H using the procedure described in example 77 step A. $^1$H NMR (DMSO, 500 MHz): δ 8.51(bt, 1H), 7.81(d, J=1.6 Hz, 2H) 7.79 (d, J=8.1 Hz, 2H), 7.50(t, J=1.6 Hz, 1H), 7.23 (d, J=7.3 Hz, 2H), 6.94(d, J=1.1 Hz, 1H), 5.50(s, 2H), 4.33(d, J=12.8 Hz, 2H), 3.45 (m, 2H), 3.07(t, J=11.2 Hz, 1H), 2.86(t, J=12.6 Hz, 2H), 2.5(m, 2H), 1.74(d, J=12.4 Hz, 2H), 1.44(q, J=12.8 Hz, 2H), 1.21(s, 9H). LC-MS: 3.73 min; (M+H)=585.1.

EXAMPLE 144

4-({3-(3,5-DICHLOROPHENYL)-5-[1-(PHENYLSULFONYL)PIPERIDIN-4-YL]-1H-PYRAZOL-1-YL}METHYL)-N-(1H-TETRAAZOL-5-YL)BENZAMIDE

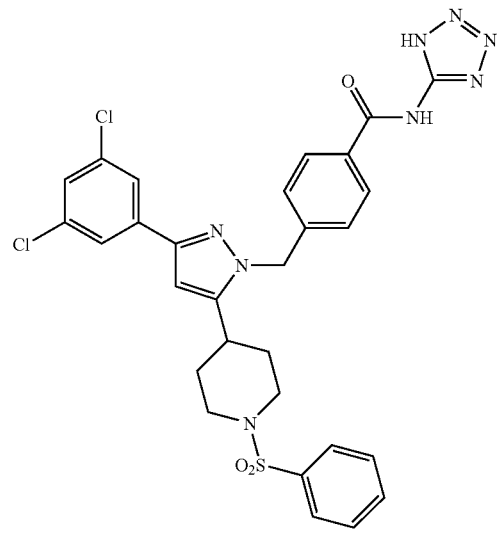

Step A.

Methyl 4-({3-(3,5-dichlorophenyl)-5-[1-(phenylsulfonyl)piperidin-4-yl]-1H-pyrazol-1-yl}methyl)benzoate To a solution of the intermediate from Example 142 step F (156 mg, 0.35 mmol) in DCM (5 mL) was added pyridine (5 mL) and benzene sulfonyl chloride (68 µL, 0.53 mmol). After 4 hours the reaction was diluted with DCM and washed with 1N HCl (3×), dried over anhydrous $Na_2SO_4$ filtered and concentrated in vacuo. The residue was purified by flash chromatography using 1:5 ethyl acetate-hexanes to give the title compound a white foam. $^1$H NMR (CDCl$_3$, 500 MHz): δ 7.99(d, J=8.3 Hz, 2H), 7.8(d, J=8.7 Hz, 2H), 7.7(d, J=1.9 Hz, 2H), 7.67(t, J=7.3 Hz, 1H), 7.58(t, J=8.0 Hz, 2H), 7.32(t, J=1.8 Hz, 1H), 7.1(d, J=8.2 Hz, 2H), 6.42(s, 1H), 5.55(s, 2H), 3.93(s, 3H), 3.90(d, J=12.2 Hz, 2H), 2.46(m, 1H), 2.31(m, 2H), 1.77(m, 3H).

Step B.

4-({3-(3,5-dichlorophenyl)-5-[1-(phenylsulfonyl)piperidinyl]-1H-pyrazol-1-yl}methyl)benzoic acid The title compound was prepared from the intermediate in step A using the procedure described in example 73 step D. $^1$H NMR (DMSO, 500 MHz): δ 7.88(d, J=8.4 Hz, 2H), 7.78(d, J=1.8 Hz, 2H), 7.76(t, J=7.1 Hz, 1H), 7.72(t, J=7.3 Hz, 1H), 7.68(t, J=7.8 Hz, 2H), 7.51(t, J=1.8 Hz, 1H), 7.19(d, J=8.2 Hz, 2H), 6.9(s, 1H), 5.44(s, 2H), 3.71(d, J=11.7 Hz, 2H), 2.8(m, 1H), 2.51(t, J=1.9 Hz, 1H), 2.3(t, J=12.2 Hz, 2H), 1.78(d, J=11.2 Hz, 2H), 1.67(dq, J=3.9, 12.6 Hz, 2H).

Step C.

4-({3-(3,5-dichlorophenyl)-5-[1-(phenylsulfonyl)piperidin-4-yl]-1H-pyrazol-1-yl}methyl)-N-(1H-tetraazol-5-yl)benzamide The title compound was prepared from the intermediate in step B using the procedure described in example 76 step B. $^1$H NMR (DMSO, 500 MHz): δ 8.03(d, J=8.3 Hz, 2H), 7.79(d, J=1.8 Hz, 2H), 7.76(m, 4), 7.65(t, J=7.8 Hz, 2H), 7.52(t, J=2.0 Hz, 1H), 7.26(d, J=8.5 Hz, 2H), 6.92(s, 1H), 5.47(s, 3H), 3.73(d, J=11.6 Hz, 2H), 2.87(m, 1H), 2.32(t, J=12.1 Hz, 2H), 1.81(d, J=11.2 Hz, 2H), 1.69(dq, J=3.7, 12.6 Hz, 2H). LC-MS: 3.93 min; (M+H)=637.1.

EXAMPLE 145

4-{[3-(3,5-DICHLOROPHENYL)-5-(1-NEOPENTYLPIPERIDIN-4-YL)-1H-PYRAZOL-1-YL]METHYL}-N-(1H-TETRAAZOL-5-YL)BENZAMIDE

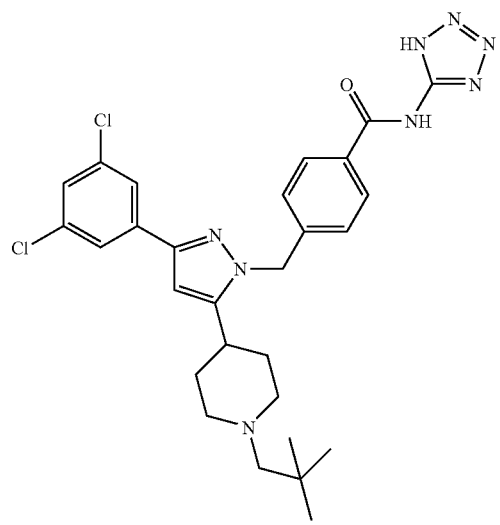

Step A. Methyl 4-{[3-(3,5-dichlorophenyl)-5-(1-neopentylpiperidin-4-yl)-1H-pyrazol-1-yl]methyl}benzoate To a solution of the intermediate from Example 142 step F (100 mg, 0.225 mmol) in 1,2-dichloroethane (3 mL) was added trimethyl acetaldehyde (29 mg, 0.337 mmol) and sodium triacetoxy borohydride (71 mg, 0.337 mmol). After 16 hours the reaction was diluted with DCM (10 mL) and washed with saturated NaHCO$_3$ solution, dried over anhydrous Na$_2$SO$_4$, filtered and concentrated in vacuo. This material was used in the next step without any further purification. LC-MS: 3.44 min; (M+H)=514.2.

Step B.

4-{[3-(3,5-dichlorophenyl)-5-(1-neopentylpiperidin-4-yl)-1H-pyrazol-1-yl]methyl}benzoic acid The title compound was prepared from the intermediate in step A using the procedure described in example 73 step D.

Step C.

4-{[3-(3,5-dichlorophenyl)-5-(1-neopentylpiperidin-4-yl)-1H-pyrazol-1-yl]methyl}-N-(1H-tetraazol-5-yl)benzamide The title compound was prepared from the intermediate in step B using the procedure described in example 76 step B. $^1$H NMR (DMSO, 500 MHz): δ 8.09(d, J=8.2 Hz, 2H), 7.82(bs, 2H), 7.55(s, 1H), 7.33(d, J=8.3 Hz, 2H), 5.57(s, 2H), 3.6(m, 2H), 3.42(s, 2H), 3.1 (m, 4H), 2.5(s, 2H), 2.04(m, 2H), 1.87 (m, 2H), 1.05(s, 9H). LC-MS: 1.92 min; (M+H)=567.2.

Following the procedures outlined for Examples 142-145 the compounds listed in Table 13 were prepared

TABLE 13

| Example | R$^{21}$ | R$^{22}$ | LC-MS data |
|---|---|---|---|
| 146 | PhCO | tetrazole-NH | 2.33 min; (M + H) = 601.2 |
| 147 | PhCO | HN-CH$_2$CH$_2$-CO$_2$H | 3.65 min; (M + H) = 605.2 |
| 148 | 4-CF$_3$PhCO | tetrazole-NH | 2.52 min; (M + H) = 685.1 |
| 149 | 4-CF$_3$PhCO | HN-CH$_2$CH$_2$-CO$_2$H | 3.94 min; (M + H) = 689.1 |
| 150 | 3,5-diClPhCO | tetrazole-NH | 2.55 min; (M + H) = 669.0 |
| 151 | 3,5-diClPhCO | HN-CH$_2$CH$_2$-CO$_2$H | 3.98 min; (M + H) = 673.1 |
| 152 | 2,4-diClPhCO | tetrazole-NH | 2.53 min; (M + H) = 669.1 |
| 153 | 2,4-diClPhCO | HN-CH$_2$CH$_2$-CO$_2$H | 3.96 min; (M + H) = 673 |
| 154 | PhSO$_2$ | HN-CH$_2$CH$_2$-CO$_2$H | 3.85 min; (M + H) = 641.1 |

TABLE 13-continued

| Example | R²¹ | R²² | LC-MS data |
|---|---|---|---|
| 155 | 4-CF₃PhSO₂ | (tetrazole-NH) | 2.56 min; (M + H) = 705.2 |
| 156 | 4-CF₃PhSO₂ | HN~CO₂H | 2.52 min; (M + 23) = 731 |
| 157 | 3-MeOPhSO₂ | (tetrazole-NH) | 2.47 min; (M + H) = 667.1 |
| 158 | 3-MeOPhSO₂ | HN~CO₂H | 2.43 min; (M + H) = 671.1 |
| 159 | t-BuOCO | (tetrazole-NH) | 2.58 min; (M − 56) = 541.1 |
| 160 | t-BuOCO | HN~CO₂H | 3.99 min; (M + H) = 601.2 |
| 161 | (neopentyl) | HN~CO₂H | 1.91 min; (M + H) = 571.2 |
| 162 | Bnzl | (tetrazole-NH) | 1.89 min; (M − 56) = 587.1 |
| 163 | Bnzl | HN~CO₂H | 1.84 min; (M + H) = 591.2 |
| 164 | 4-CF₃OBnzl | (tetrazole-NH) | 2.08 min; (M + H) = 671.0 |
| 165 | 4-CF₃OBnzl | HN~CO₂H | 2.06 min; (M + H) = 675.1 |

Biological Assays

The ability of the compounds of the present invention to inhibit the binding of glucagon and their utility in treating or preventing type 2 diabetes mellitus and the related condition be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM $MgCl_2$, 2 mM EDTA, 12% Glycerol, and 0.200 mg WGA coated PVT SPA beads (Amersham), +/−compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prismo from GraphPad. The $IC_{50}$ were calculated using non-linear regression analysis assuming single site competition.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in cell suspension buffer [75 mM Tris-HCl pH7.5, 250 mM Sucrose, 25 mM $MgCl_2$, 1.5 mM EDTA, 0.1 mM Ro-20-1724 (Biomol, Inc.), 0.2% bovine serum albumin and one tablet of complete™ (Boehringer), which contains a cocktail of protease inhibitors, for each 50 ml of buffer]. An adenylate cyclase assay was setup using an Adenylate Cyclase Assay kit (SMP-004B) from New England Nuclear (NEN) as per manufacturer instructions. Briefly, compounds were diluted from stocks in a cell stimulation buffer supplied with the kit. Cells prepared as above were preincubated in flash plates coated with anti-cAMP antibodies (NEN) in presence of compounds or DMSO controls for 40 minutes, and then stimulated with glucagon (250 pM) for an additional 40 minutes. The cell stimulation was stopped by addition of equal amount of a detection buffer containing lysis buffer as well as $^{125}$I-labeled cAMP tracer (NEN). After 3-6 h of incubation at room temperature the bound radioactivity was determined in a liquid scintillation counter (TopCount-Packard Instruments). Activity of test compounds was calculated by comparing to the total scintillation signal (CPM) of control samples with no compound and with 0.001 mM unlabeled-glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

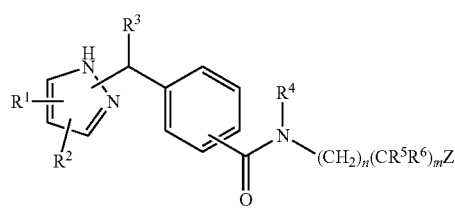

or a pharmaceutically acceptable salt thereof, wherein:

R¹ is selected from the group consisting of:
(a) $C_{1-10}$alkyl optionally substituted with: (1) 1-5 halo groups up to a perhaloalkyl group; (2) 1 oxo group; (3)

1-2 OH groups; (4) 1-2 $C_{1-10}$alkoxy groups, each optionally substituted with: up to five halo or a perhaloalkoxy, 1 OH or $C_2R^8$ group; (5) 1 $C_2R^8$ or $S(O)_pR^7$; (6) 1-2 Arl, Tetcy or HAR groups, each optionally substituted as follows: (i) 1-5 halo groups, (ii) 1 OH, $CO_2R^8$, CN, $S(O)_pR^7$, $NO_2$ or $C(O)NR^9R^{10}$ group, (iii) 1-2 $C_{1-10}$alkyl or alkoxy groups, each optionally substituted with: 1-5 halo, up to perhaloalkyl, and 1-2 OH or $CO_2R_8$ groups; and (iv) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^8$ groups; (7) —$NR^8$—$C(O)$—$NR^9R^{10}$; (8) —$NR^8$—$CO_2R^{11}$; (9) —$NR^8$—$C(O)R^{11}$; (10) —$NR^9R^{10}$; (11) —$NR^8SO_2R^{11}$; $NR^9R^{10}$; (13) —$C(O)NR^9R^{10}$ and (14) —$OC(O)$—$NR^9R^{10}$;

(b) Aryl optionally substituted as follows: (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 OH, phenyl, $CO_2R^8$, CN or $S(O)_pR^7$ groups; (3) 1-2 Aryl, HAR or Hetcy groups, each optionally substituted as follows: (i) 1-3 halo groups; (ii) 1-2 $C_{1-10}$alkyl, $C_{2-10}$alkenyl or $C_{2-10}$aykynyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 OH, phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

said Aryl being further optionally substituted on carbon by a group selected from the group consisting of; (4) 1-5 halo groups; (5) 1-2 OH groups; (6) 1 $S(O)_pR^7$, $NO_2$ or CN group; (7) 1-2 $CO_2R^8$; (8) —$NR^8$—$C(O)NR^9R^{10}$; (9) —$NR^8$—$CO_2R^{11}$; (10) —$NR^8$—$C(O)R^{11}$; (11) —$NR^9R^{10}$; (12) —$NR^8SO_2R^{11}$; (13) —$SO_2$—$NR^{910}$; (14) —$C(O)NR^9R^{10}$ and (15) —$OC(O)$—$NR^9R^{10}$;

$R^2$ is H or $R^I$ as defined above;

$R^3$ and $R^4$ are H or $C_{1-10}$alkyl;

$R^5$ represents H or F;

$R^6$ represents H, OH, F or $C_{1-3}$alkyl, or $R^5$ and $R^6$ are taken in combination and represent oxo;

$R^7$ represents a member selected from the group consisting of: $C_{1-10}$alkyl, Aryl or Ar-$C_{1-10}$alkyl, $R^8$ is H, $C^{1-10}$alkyl, optionally substituted with phenyl, OH, $OC_{1-6}$alkyl, $CO_2H$, $CO_2C_{1-6}$alkyl and 1-3 halo groups;

$R^9$ is H or $C_{1-10}$alkyl;

$R^{10}$ is H or is independently selected from: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar-$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^{11}$ is independently selected from the group consisting of: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar-$_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

m is an integer sclectcd from 0, 1 and 2;

n is an integer selected from 0 to 6;

p is an integer selected from 0, 1 and 2, and when at least one of m and n is other than 0, Z is selected from $C_2R^8$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

2. A compound in accordance with claim 1 or a pharmaceutically acceptable salt thereof wherein: $R^1$ is Aryl optionally substituted as set forth below:

(1) 1-3 $C_{1-10}$alkyl or $C_{2-10}$alkenyl groups optionally substituted with 1-5 halo groups, 1-2 OH, phenyl, $CO_2R^8$, CN or $S(O)_pR^7$ groups;

(2) 1-3 $C_{1-10}$alkoxy groups, the alkyl portion of which is optionally substituted with 1-5 halo groups, 1-2 phenyl, CN or $S(O)_p,R^7$ groups;

(3) 1-2 Aryl, HAR or Hetcy groups, each optionally substituted as follows: (i) 1-3 halo groups; (ii) 1-2 $C_{1-10}$alkyl or $C_{2-10}$alkenyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups;

(4) 1-5 halo groups;

(5) 1-2 OH groups;

(6) 1 $S(O)_pR^7$, $NO_2$ or CN group;

(7) 1-2 $CO_2R^8$;

(8) —$NR^8$—$C(O)$—$NR^9R^{10}$;

(9) —$NR^8$—$CO_2R^{11}$;

(10) —$NR^8$—$C(O)R^{11}$;

(11) —$NR^9R^{10}$;

(12) —$NR^8SO_2R^{11}$;

(13) —$SO_2$—$NR^9R^{10}$;

(14) —$C(O)NR^9R^{10}$ and

(15) —$OC(O)$—$NR^9R^{10}$.

3. A compound in accordance with claim 2 or a pharmaceutically acceptable salt thereof wherein $R^1$ is Phenyl optionally substituted as follows: (1) 1 $C^{1-3}$alkyl group optionally substituted with 1-3 halo groups, 1 phenyl or $S(O)_pR^7$ group; (2) 1 $C^{1-3}$alkoxy group, the alkyl portion of which is optionally substituted with 1-3 halo groups or 1 phenyl group; (3) 1 phenyl, pyridinyl, isoxazolyl or piperidinyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group; (4) 1-3 halo groups; (5) 1 OH group; (6) 1 $S(O)_p R^7$, $NO_2$ or CN group; (7) 1 $CO_2R^8$; (8) —$NR^9R^{10}$; (9) —C(O)$NR^9R^{10}$ and (10) —OC(O)—$NR^9R^{10}$.

4. A compound in accordance with claim 3 or a pharmaceutically acceptable salt thereof wherein $R^1$ is Phenyl optionally substituted as follows:
(1) 1 $C^{1-3}$alkyl group optionally substituted with 1-3 halo groups or 1 phenyl group; (2) 1 $C_{1-3}$alkoxy group, the alkyl portion of which is optionally substituted with 1-3 halo groups or 1 phenyl group; (3) 1 phenyl, pyridinyl or isoxazolyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group; (4) 1-3 halo groups; (5) 1 OH group; (6) 1 $CO_2R^8$; and (7) —$NR^9R^{10}$.

5. A compound in accordance with claim 1 or a pharmaceutically acceptable salt thereof wherein $R^1$, $R^3$ through $R^{11}$, m, n, p and Z are as defined therein, and
$R^2$ is selected from the group consisting of:
a) $C_{1-10}$alkyl optionally substituted with: (1) 1-5 halo groups upto a perhaloalkyl group; (2) 1-2 OH groups; (3) 1-2 $C_{1-10}$alkoxy groups, each optionally substituted with up to five halo or a perhaloalkoxy group; (4) 1 $CO_2R^8$ or $S(O)_pR^7$; (5) 1-2 Aryl, Hetcy or HAR, groups, each optionally substituted as follows: (a) 1-5 halo groups, (b) 1 OH, $CO_2R^8$, CN, $S(O)_pR^7$, $NO_2$ or C(O)$NR^9R^{10}$ group, (c) 1-2 $C_{1-10}$alkyl or alkoxy groups, each optionally substituted with: 1-5 halo, up to perhaloalkyl, and 1-2 OH or $CO_2R^8$ groups; and (d) 1-2 phenyl rings, each of which is optionally substituted as follows: 1-3 $C_{1-10}$alkyl or alkoxy groups, each being further optionally substituted with 1-5 halo up to perhalo, or 1-2 hydroxy or $CO_2R^8$ groups; and
b) Aryl optionally substituted as follows: (1) 1-3 $C_{1-10}$alkyl or $C_{2-10}$alkenyl groups optionally substituted with 1-5 halo groups, 1-2 OH, phenyl, $CO_2R^8$, CN or $S(O)_pR^7$ groups; (2) 1-3 $C_{1-10}$alkoxy groups, the alkyl portion of which is optionally substituted with 1-5 halo groups, 1-2 phenyl, CN or $S(O)_pR^7$ groups; (3) 1-2 Aryl, HAR or Hetcy groups, each optionally substituted as follows: (i) 1-3 halo groups; (ii) 1-2 $C_{1-10}$alkyl or $C_{2-10}$alkenyl groups each optionally substituted with 1-5 halo groups, 1-2 OH, phenyl, $CO_2R^{11}$, CN or $S(O)_pR^7$ groups; (iii) 1-2 $C_{1-10}$alkoxy groups the alkyl portion of which being optionally substituted with 1-5 halo groups, 1-2 phenyl, $CO_2R^{11}$, CN or $S(O)_pR^7$ groups; and (iv) 1-2 $CO_2R^{11}$, $S(O)_pR^7$, CN, $NR^9R^{10}$, $NO_2$ or OH groups; (4) 1-5 halo groups; (5) 1-2 OH groups; (6) 1 $S(O)_pR_7$, $NO_2$ or CN group; (7) 1-2 $CO_2R^8$; (8) —$NR^8$—C(O)—$NR^9R^{10}$; (9) —$NR^8$—$CO_2R^{11}$; (10) —$NR^8$—C(O)$R^{11}$; (11) —$NR^9{}^{10}$; (12) —$NR^8SO_2R^{11}$; —$SO_2$—$NR^9R^{10}$; (14) —C(O)$NR^9R^{10}$ and (15) —OC(O)—$NR^9R^{10}$.

6. A compound in accordance with claim 5 or a pharmaceutically acceptable salt thereof wherein $R^2$ is selected from the group consisting of:
a) $C_{1-10}$ alkyl optionally substituted with: (1) 1-2 halo groups; (2) 1-2 $C_{1-6}$alkoxy groups, each optionally substituted with up to 3 halo groups; (3) 1 Phenyl, Piperidinyl or Pyridinyl group, each optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups; and
b) Phenyl optionally substituted as follows: (1) 1 $C_{1-3}$alkyl group optionally substituted with 1-3 halo groups, 1 phenyl or $S(O)_pR^7$ group; (2) 1 $C_{1-3}$alkoxy group, the alkyl portion of which is optionally substituted with 1-3 halo groups or 1 phenyl group; (3) 1 phenyl, pyridinyl, isoxazolyl or piperidinyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_pR^7$, CN, $NR^9R^{10}$, $NO_2$ or OH group; (4) 1-3 halo groups; (5) 1 OH group; (6) 1 $S(O)_p R^7$, $NO_2$ or CN group; (7) 1 $CO_2R^8$; (8) —$NR^9R^{10}$; (9) —C(O)$NR^9R^{10}$ and (10) —OC(O)—$NR^9R^{10}$.

7. A compound in accordance with claim 6 or a pharmaceutically acceptable salt thereof wherein:
$R^2$ is selected from the group consisting of:
a) $C_{1-10}$alkyl optionally substituted with: Phenyl, optionally substituted as follows: (i) 1-2 halo groups, (ii) 1-2 $C_{1-3}$alkyl or alkoxy groups, each optionally substituted with: 1-3 halo groups; and (iii) 1 phenyl ring, optionally substituted with 1-3 $C_{1-3}$alkyl or alkoxy groups, each being further optionally substituted with 1-3 halo groups;
b) Phenyl optionally substituted as follows: (1) 1 $C_{1-3}$alkyl group optionally substituted with 1-3 halo groups or 1 phenyl group; (2) 1 $C_{1-3}$alkoxy group, the alkyl portion of which is optionally substituted with 1-3 halo groups or 1 phenyl group; (3) 1 phenyl, pyridinyl or isoxazolyl group, each optionally substituted as follows: (i) 1-3 halo groups; (ii) 1 $C_{1-6}$alkyl group optionally substituted with 1-3 halo or 1 hydroxy group; (iii) 1 $C_{1-6}$alkoxy group the alkyl portion of which being optionally substituted with 1-3 halo groups; and (iv) 1 $CO_2R^{11}$, $S(O)_p R^7$, CN, $NR^9R^{10}$, $NO_2$ or OH group; (4) 1-3 halo groups; (5) 1 OH group; (6) 1 $CO_2R^8$; and (7) —$NR^9R^{10}$.

8. A compound in accordance with claim 1 or a pharmaceutically acceptable salt thereof wherein $R^3$ represents H or methyl.

9. A compound in accordance with claim 1 or a pharmaceutically acceptable salt thereof wherein $R^4$ represents H or methyl.

10. A compound in accordance with claim 9 or a pharmaceutically acceptable salt thereof wherein $R^4$ represents H.

11. A compound in accordance with claim 1 or a pharmaceutically acceptable salt thereof wherein n represents 1 or 2; m represents 0 and Z is selected from $CO_2R^8$ and 5-tetrazolyl.

12. A compound in accordance with claim 11 or a pharmaceutically acceptable salt thereof wherein n represents 1 or 2; m represents 0 and Z represents 5-tetrazolyl.

13. A compound in accordance with claim 11 or a pharmaceutically acceptable salt thereof wherein: n represents 1 or 2; m represents 0 and Z represents $CO_2R^8$.

14. A compound in accordance with claim 1 or a pharmaceutically acceptable salt thereof wherein $R^8$ is H or $C_{1-10}$alkyl, optionally substituted with phenyl or 1-3 halo groups.

15. A compound in accordance with claim 1 selected from the group consisting of:

| Cpd No. | Structure |
|---|---|
| 1 | 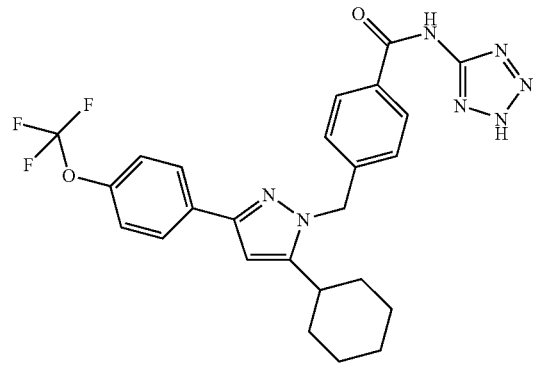 |
| 2 | 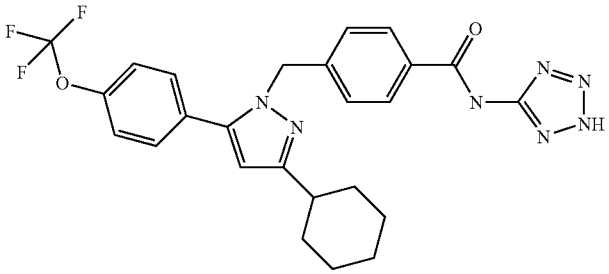 |
| 3 | 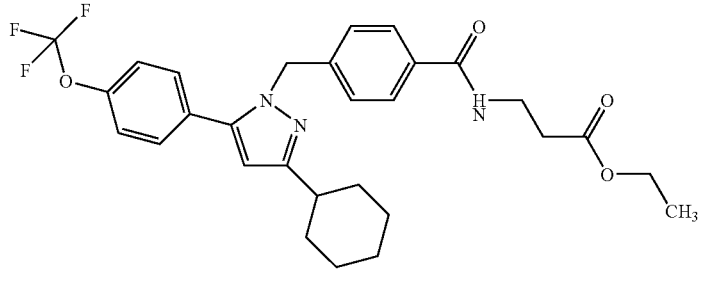 |
| 4 | 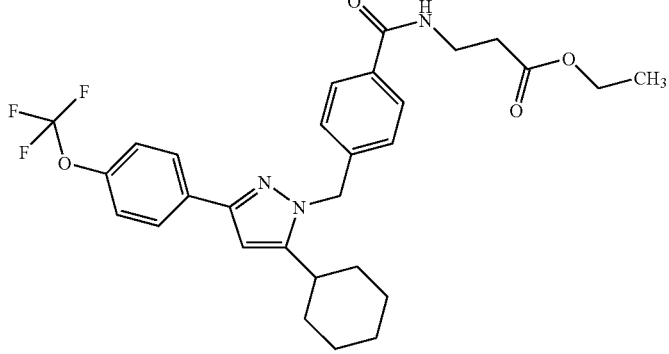 |

-continued
| Cpd No. | Structure |
|---|---|
| 5 | 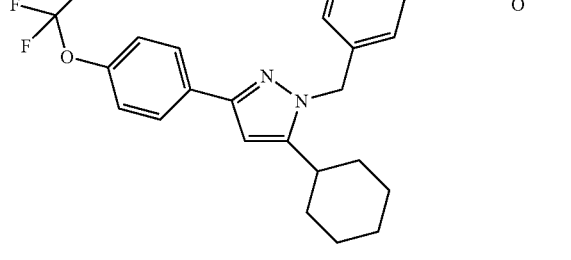 |
| 6 | 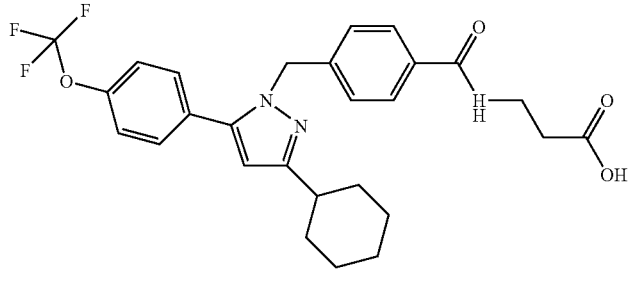 |
| 7 | 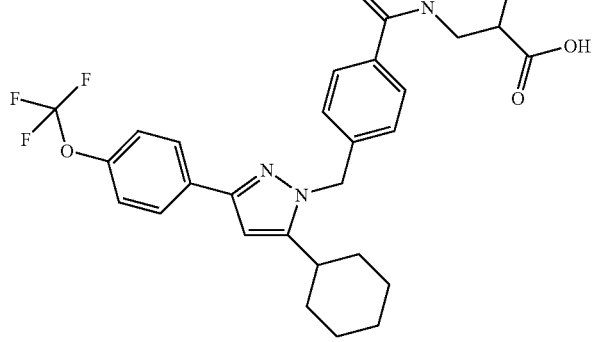 |
| 8 | 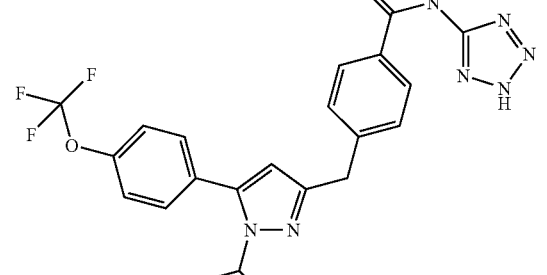 |

-continued
| Cpd No. | Structure |
|---|---|
| 9 | 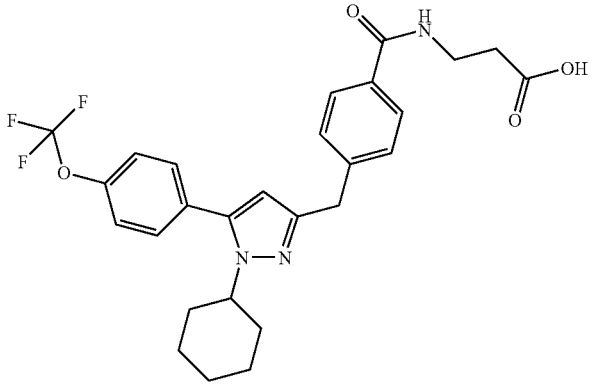 |
| 10 | 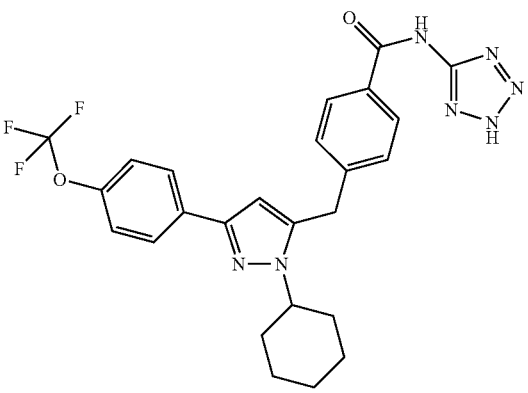 |
| 11 | 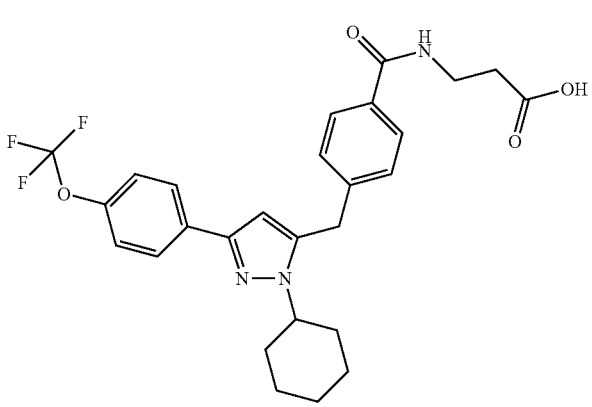 |

-continued
| Cpd No. | Structure |
|---|---|
| 12 | 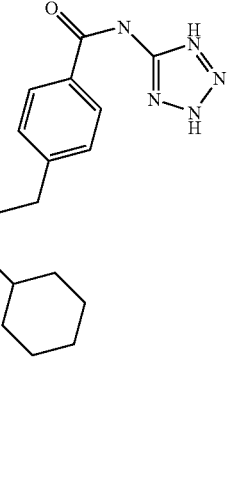 |
| 13 | 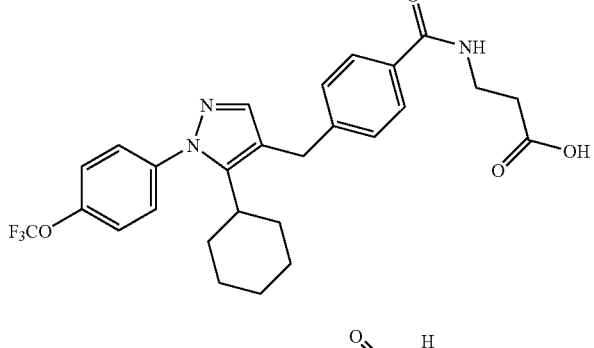 |
| 14 | 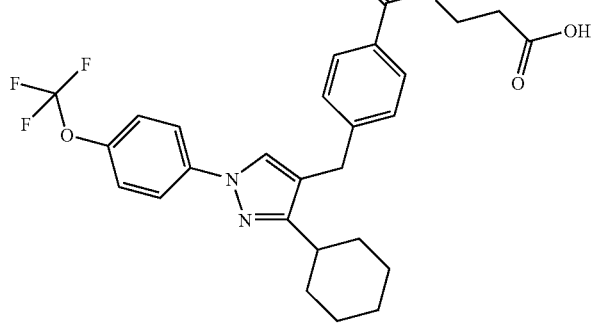 |
| 15 | 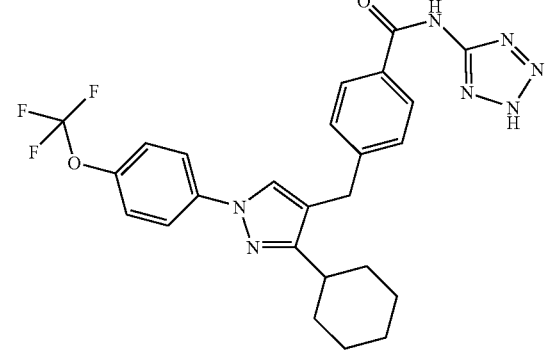 |

-continued
| Cpd No. | Structure |
|---|---|
| 16 | 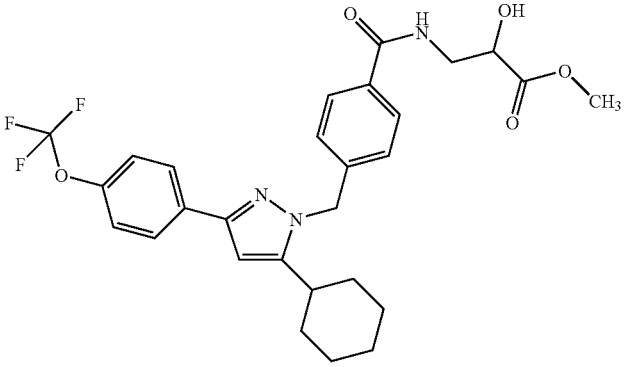 |
| 17 | 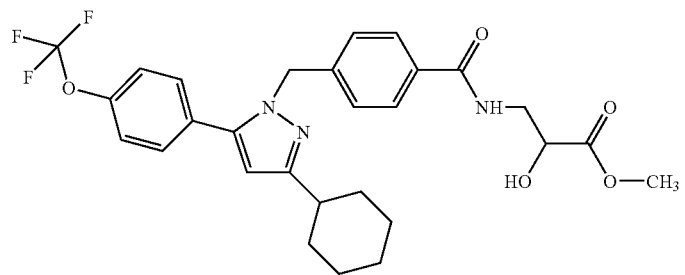 |
| 18 | 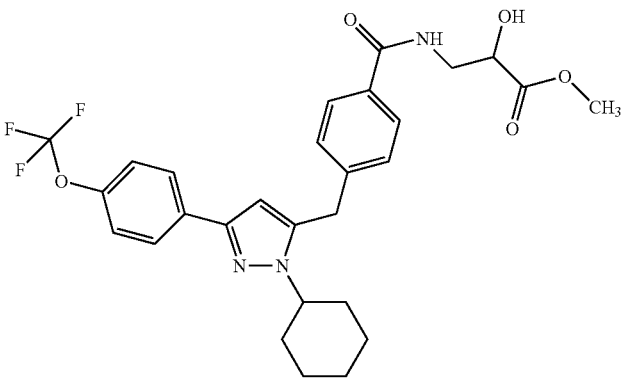 |
| 19 | 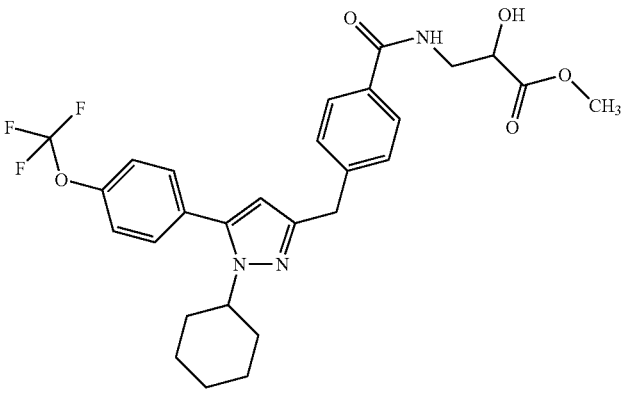 |

-continued

| Cpd No. | Structure |
|---|---|
| 20 | 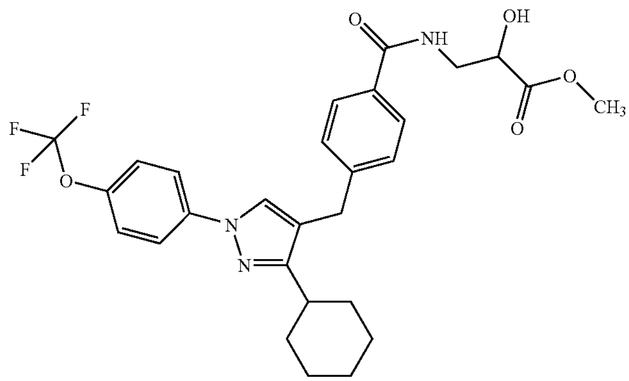 |
| 21 | 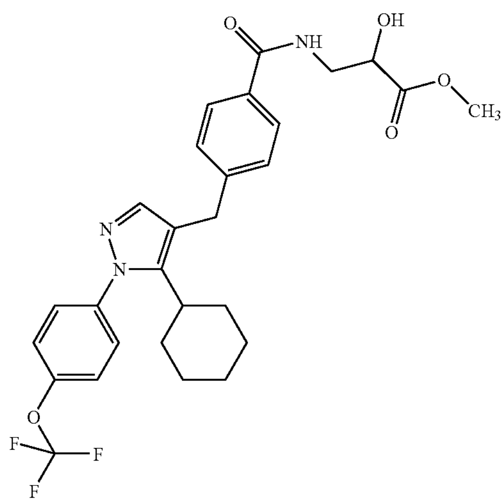 |
| 22 | 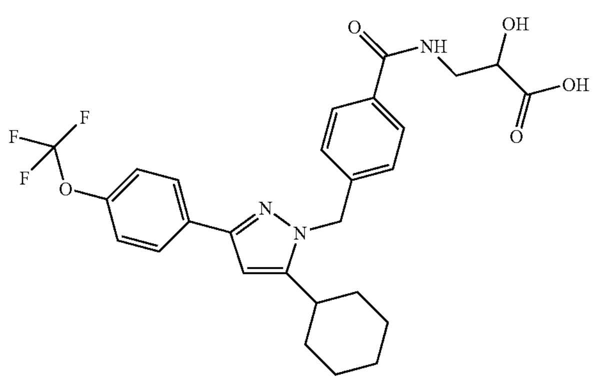 |
| 23 | 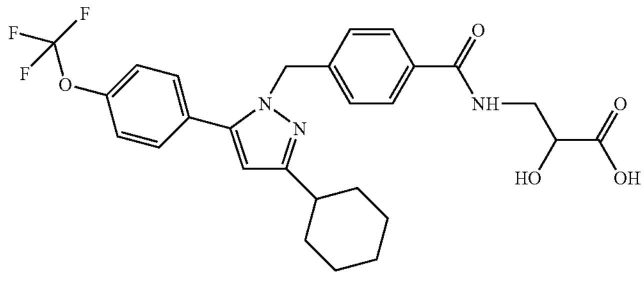 |

| Cpd No. | Structure |
|---|---|
| 24 | *(structure)* |
| 25 | *(structure)* |
| 26 | *(structure)* |

-continued
| Cpd No. | Structure |
|---|---|
| 27 | 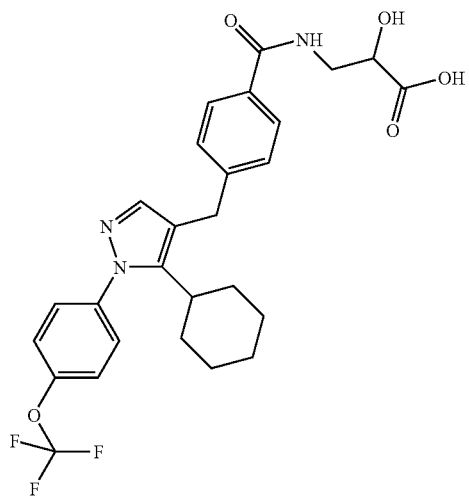 |
| 28 | 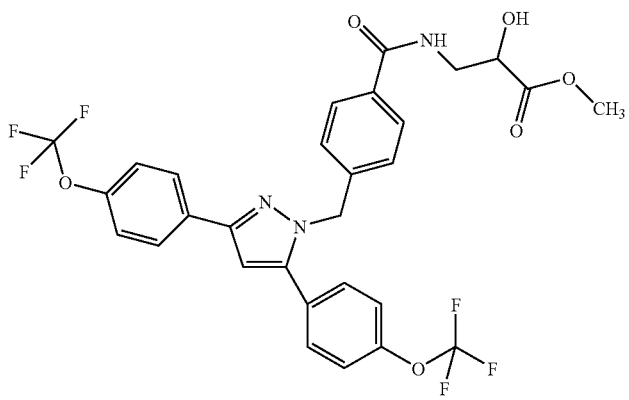 |
| 29 | 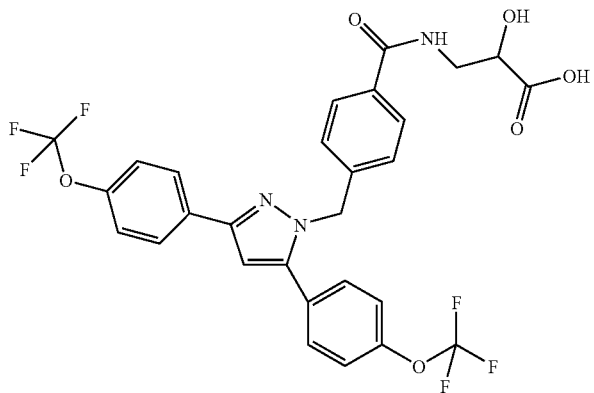 |

-continued

| Cpd No. | Structure |
|---|---|
| 30 | 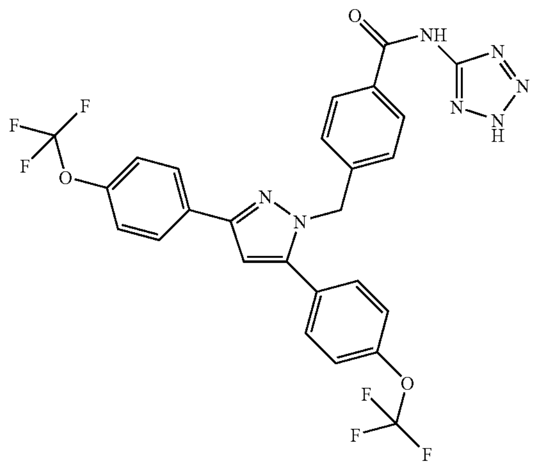 |
| 31 | 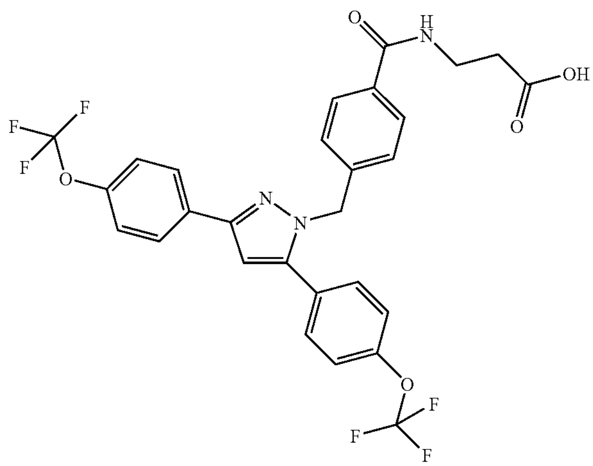 |
| 32 | 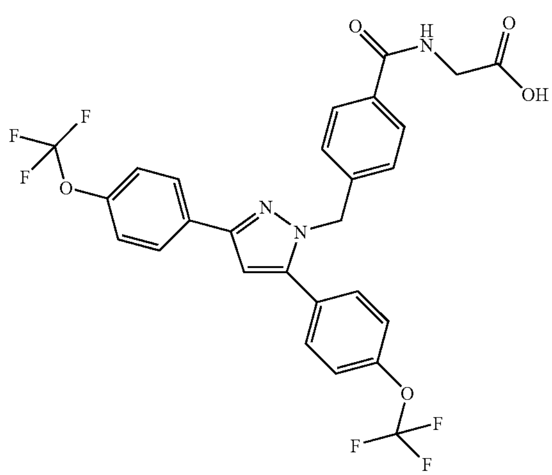 |

-continued
| Cpd No. | Structure |
|---|---|
| 33 | 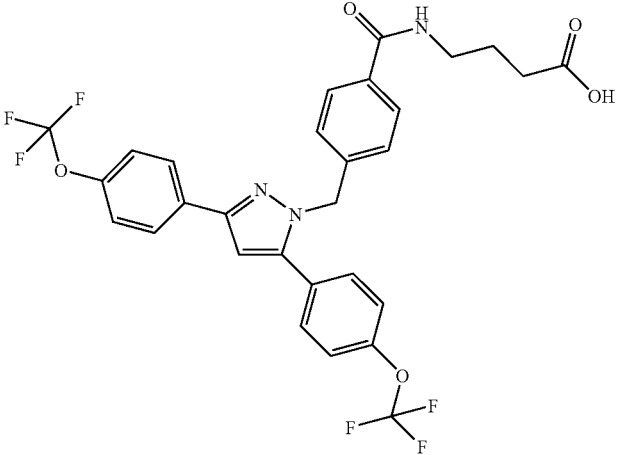 |
| 34 | 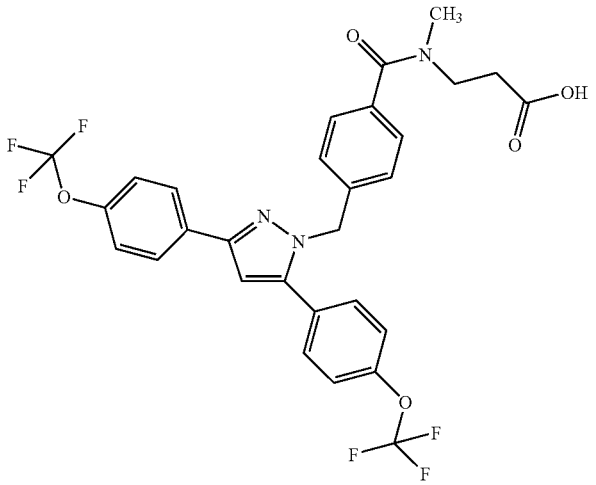 |
| 35 | 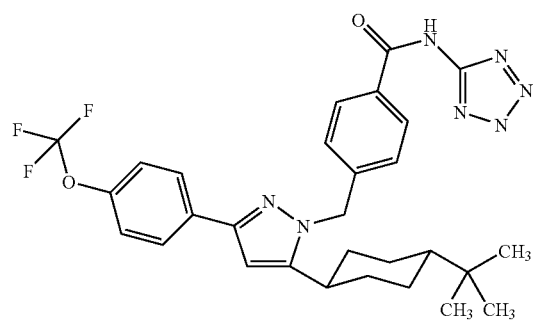 |
| 36 | 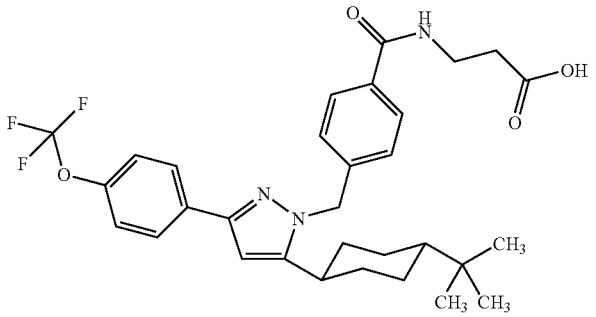 |

| Cpd No. | Structure |
|---|---|
| 37 | 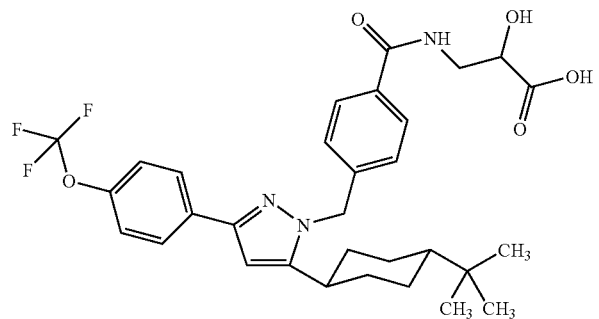 |
| 38 | 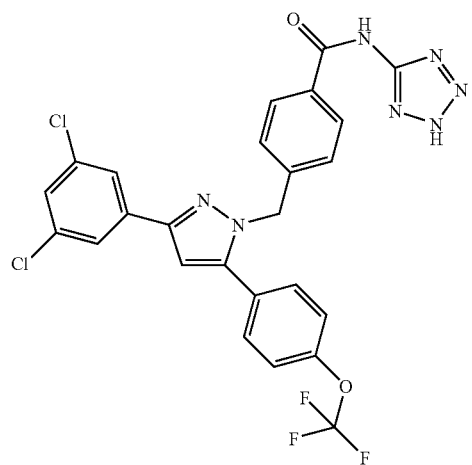 |
| 39 | 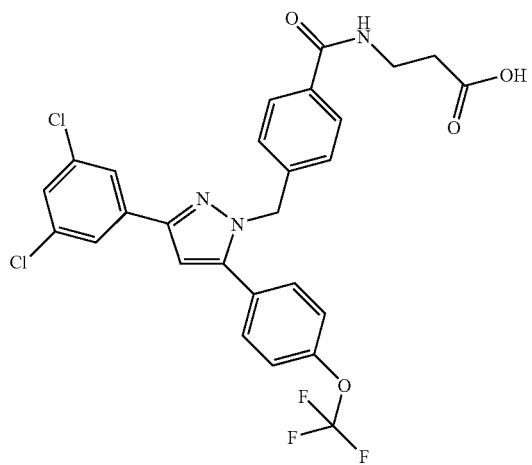 |

-continued
| Cpd No. | Structure |
|---|---|
| 40 | 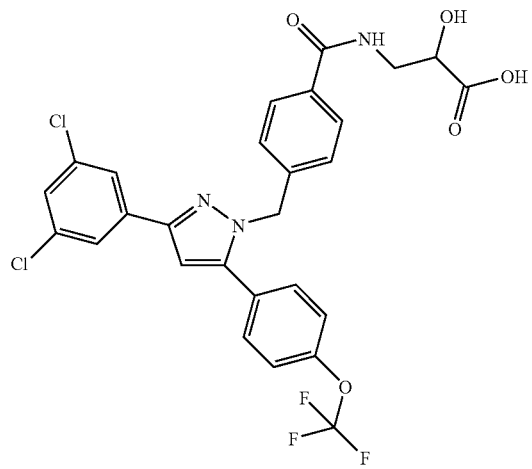 |
| 41 | 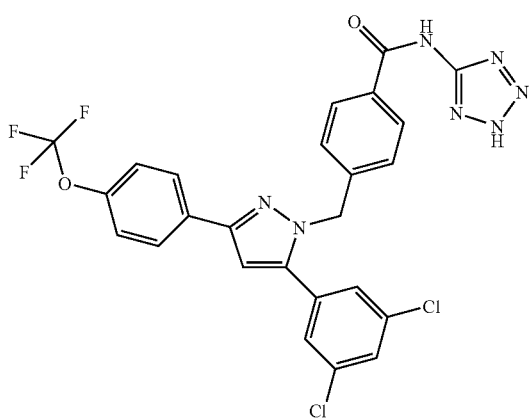 |
| 42 | 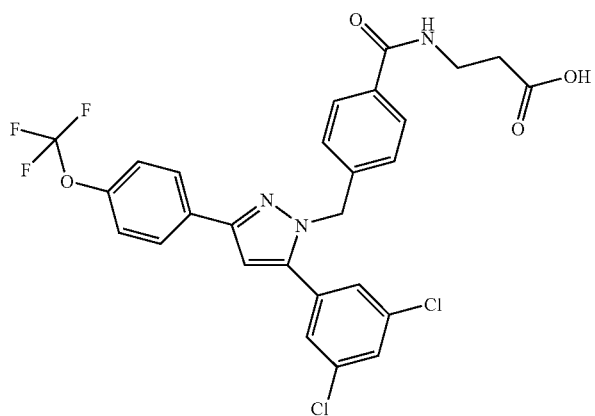 |

-continued
| Cpd No. | Structure |
|---|---|
| 43 | 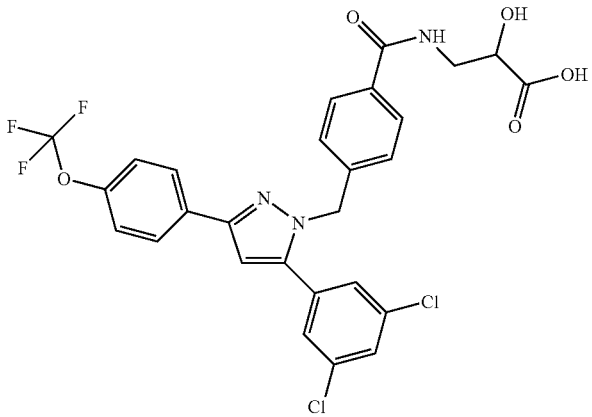 |
| 44 | 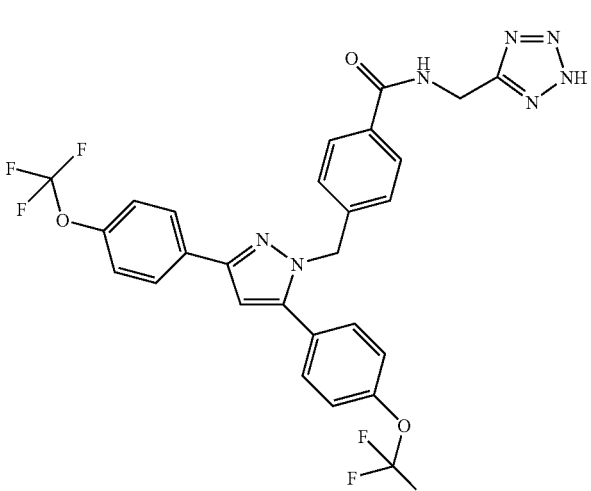 |
| 45 | 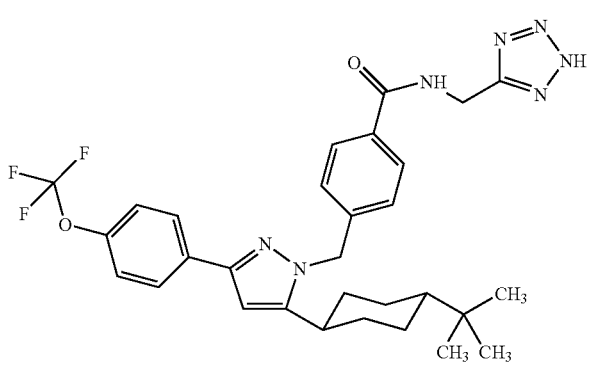 |

-continued
| Cpd No. | Structure |
|---|---|
| 46 | 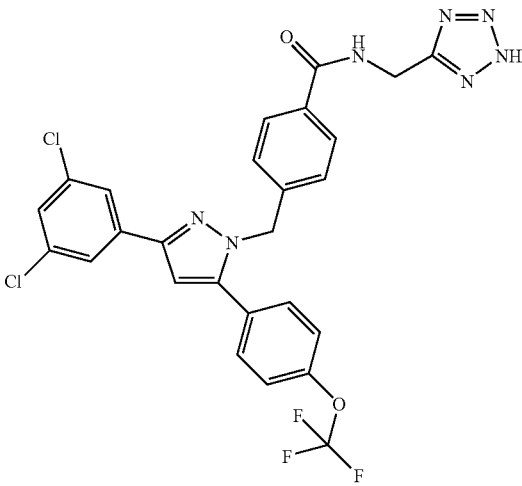 |
| 47 | 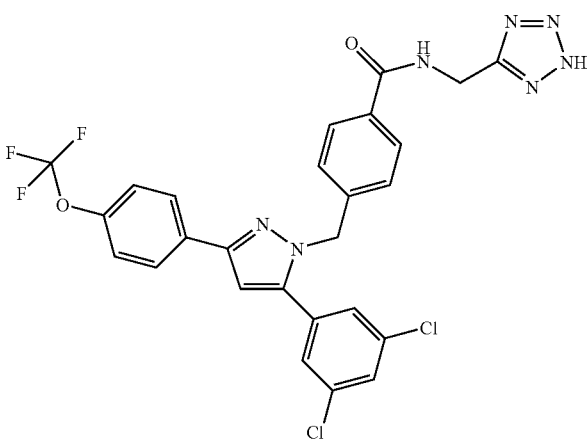 |
| 48 | 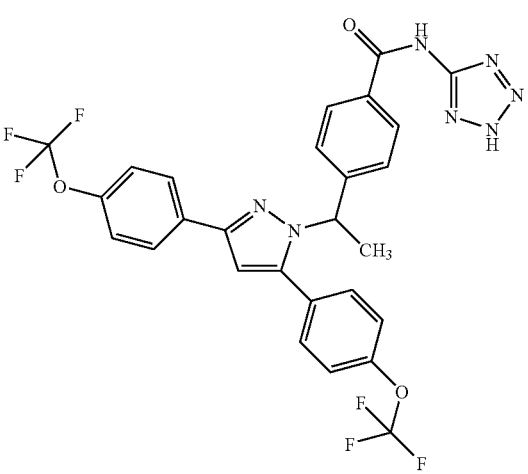 |

-continued

| Cpd No. | Structure |
|---|---|
| 49 | 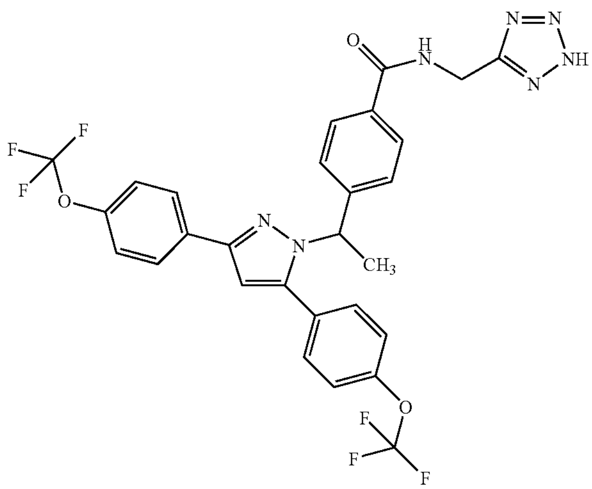 |
| 50 | 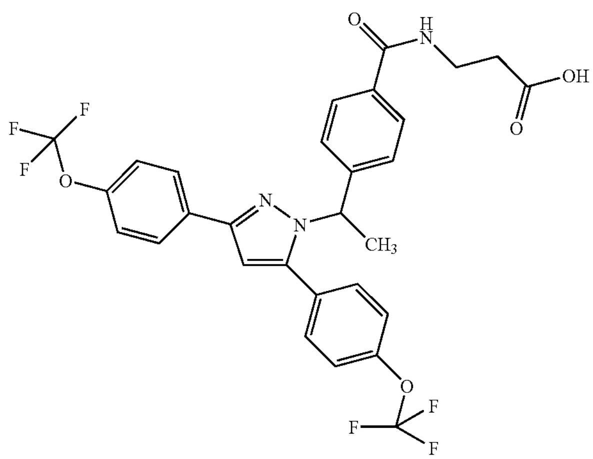 |
| 51 | 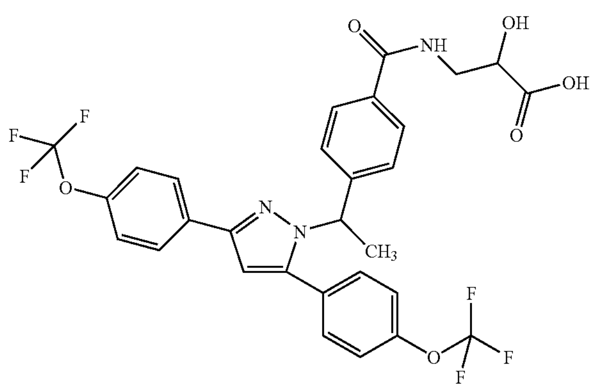 |

| Cpd No. | Structure |
|---|---|
| 52 | 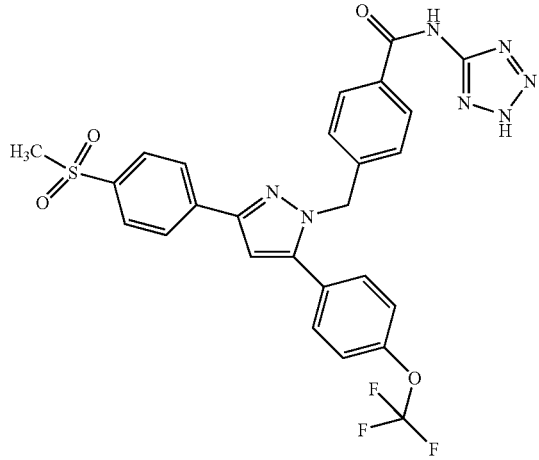 |
| 53 | 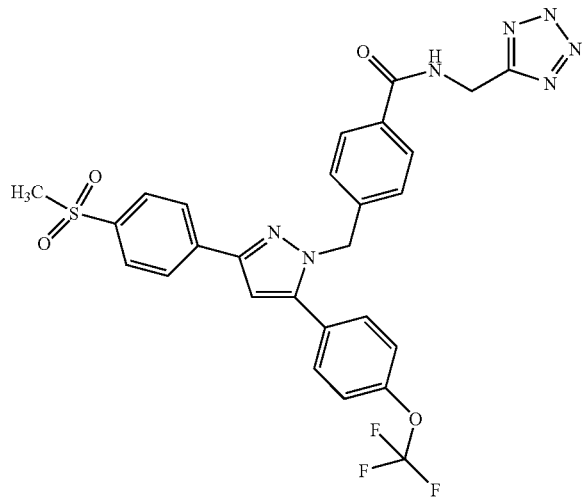 |
| 54 | 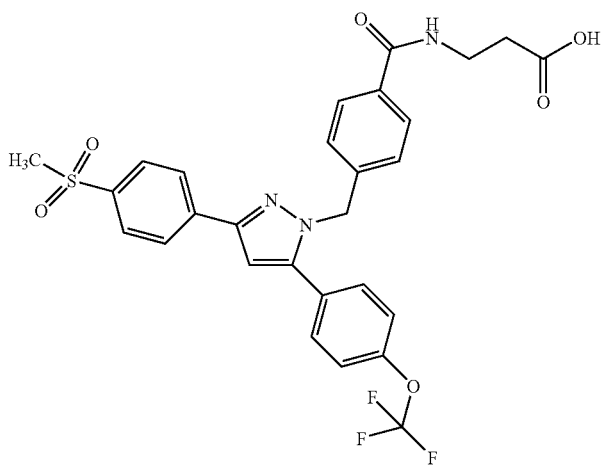 |

-continued
| Cpd No. | Structure |
|---|---|
| 55 | 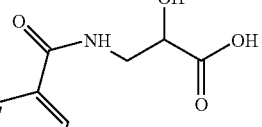 |
| 56 | 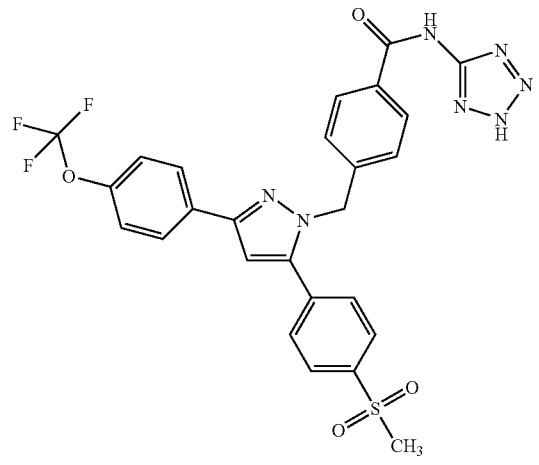 |
| 57 | 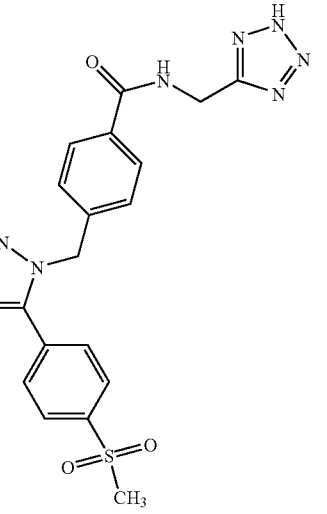 |

-continued

| Cpd No. | Structure |
|---|---|
| 58 | 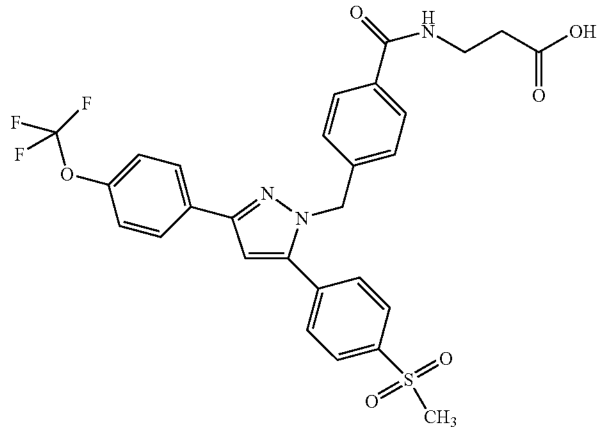 |
| 59 | 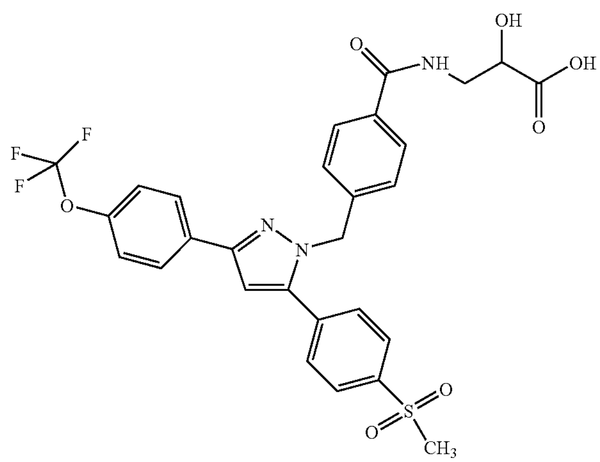 |
| 60 | 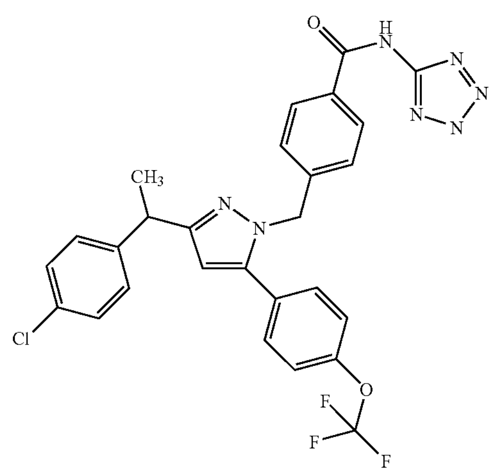 |

-continued
| Cpd No. | Structure |
|---|---|
| 61 | 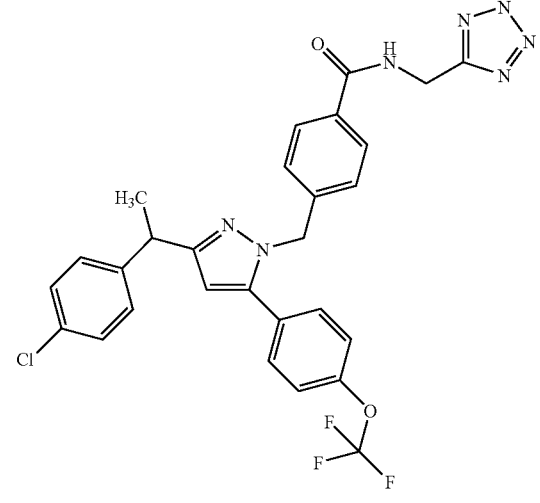 |
| 62 | 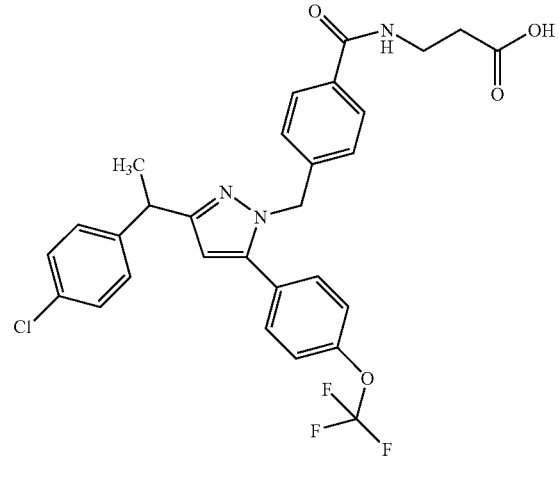 |
| 63 | 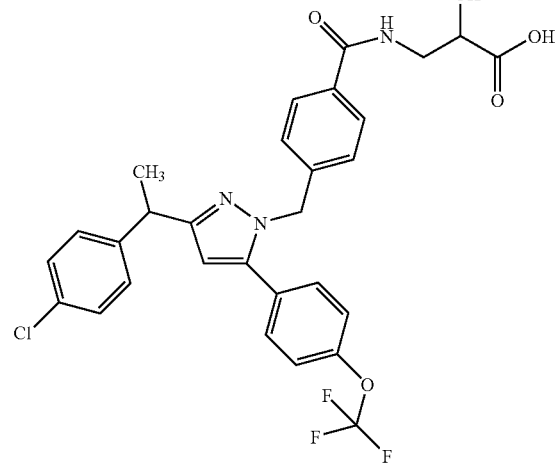 |

-continued
| Cpd No. | Structure |
|---|---|
| 64 | 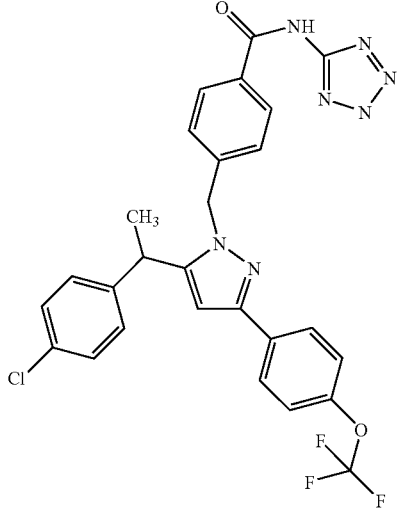 |
| 65 | 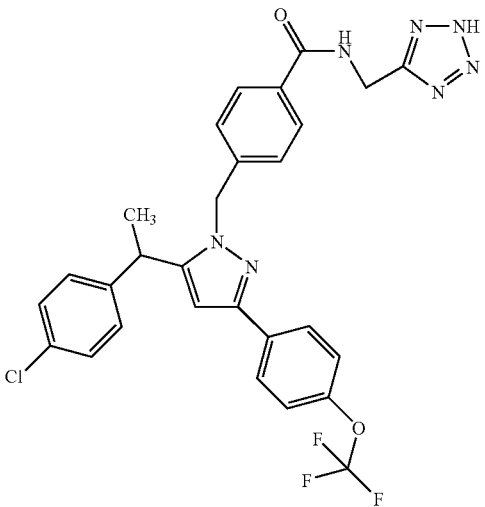 |
| 66 | 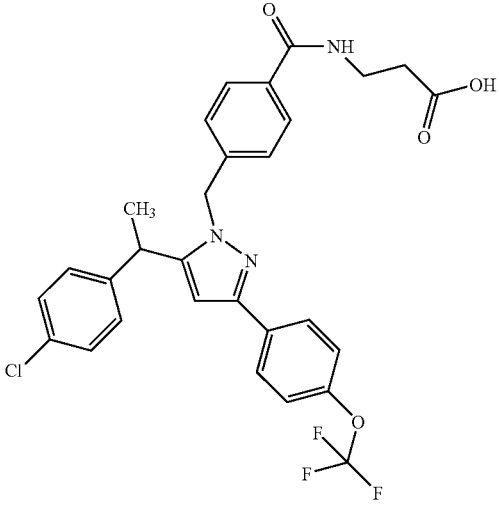 |

-continued
| Cpd No. | Structure |
|---|---|
| 67 | 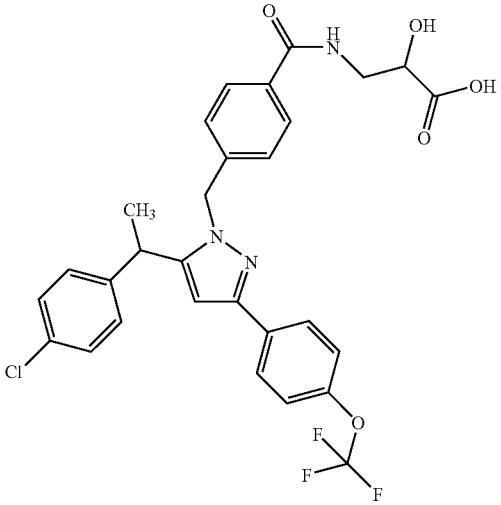 |
| 68 | 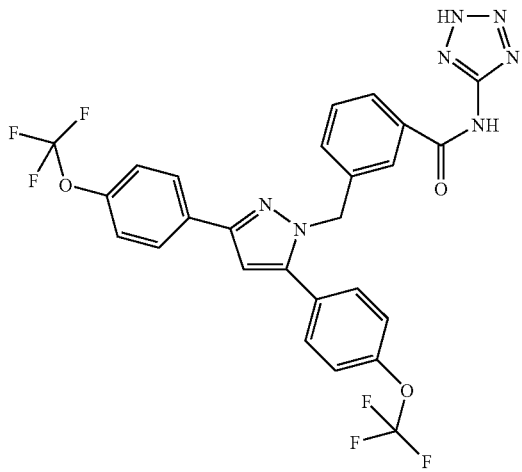 |
| 69 | 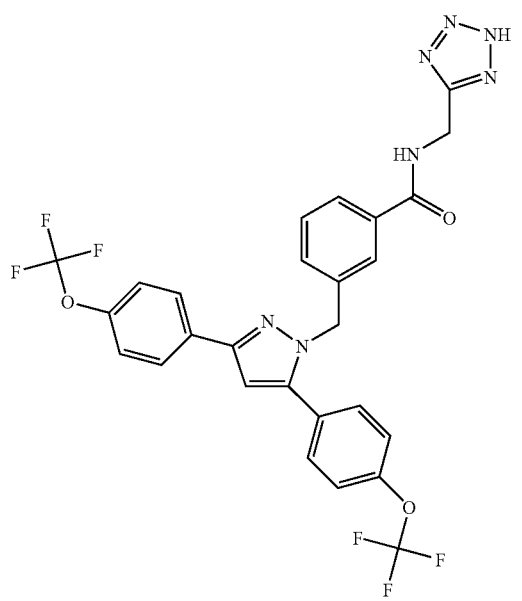 |

-continued

| Cpd No. | Structure |
|---------|-----------|
| 70 | 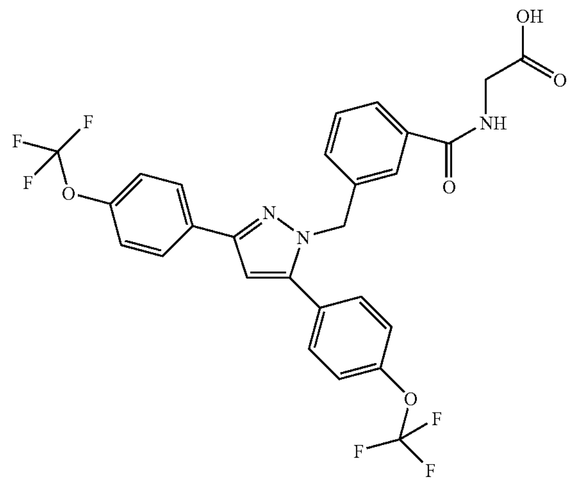 |
| 71 | 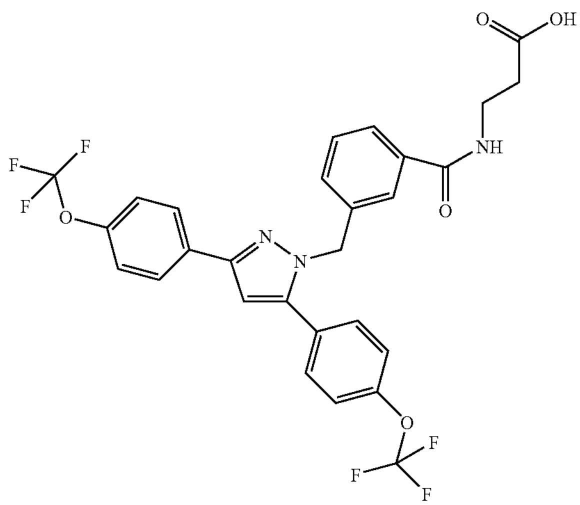 |
| 72 | 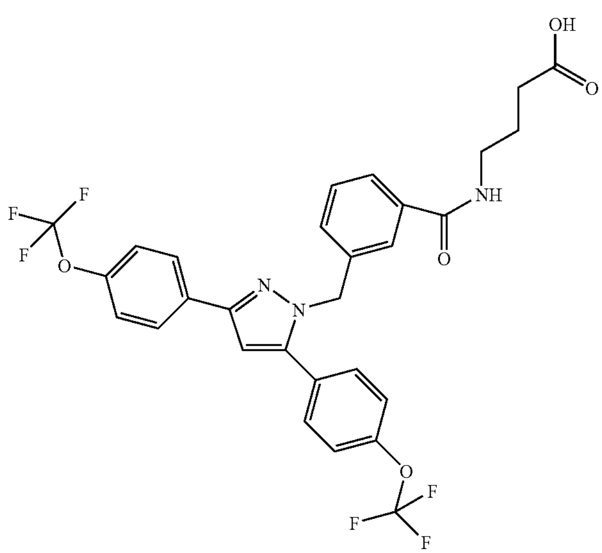 |

-continued

| Cpd No. | Structure |
|---|---|
| 73 | (structure) |
| 75 | (structure) |
| 76 | (structure) |
| 78 | (structure) |

-continued
| Cpd No. | Structure |
|---|---|
| 79 | 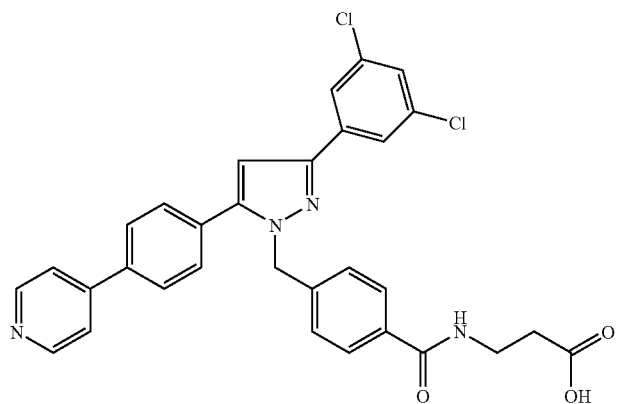 |
| 80 | 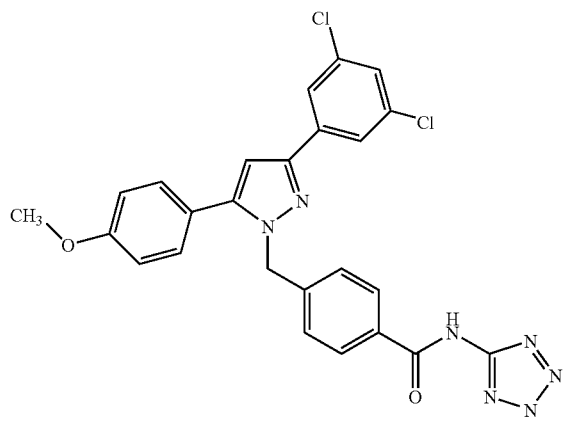 |
| 81 | 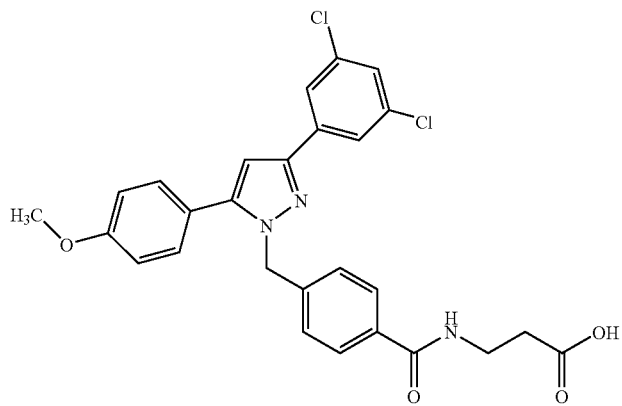 |

-continued

| Cpd No. | Structure |
|---|---|
| 82 | 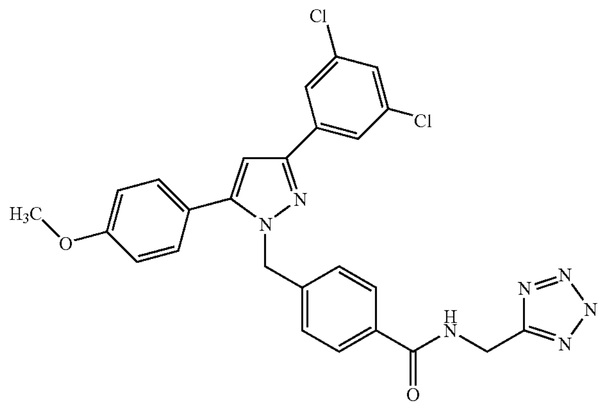 |
| 83 | 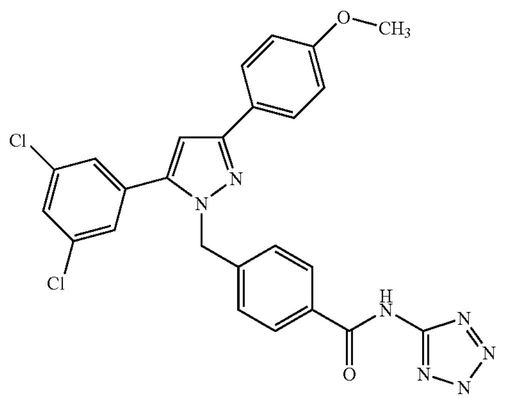 |
| 84 | 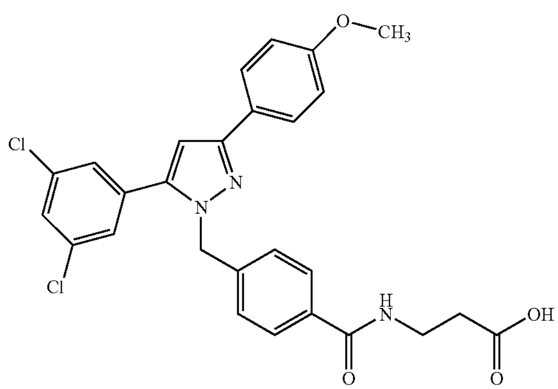 |
| 85 | 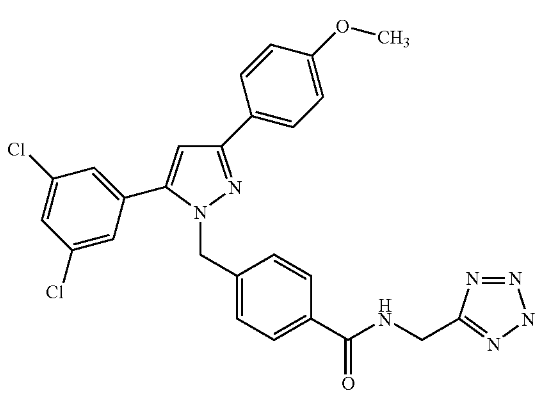 |

-continued
| Cpd No. | Structure |
|---|---|
| 86 | 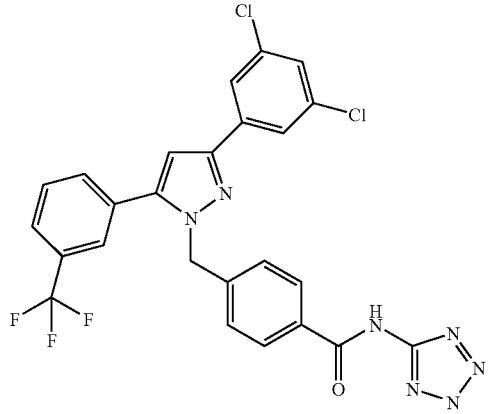 |
| 87 | 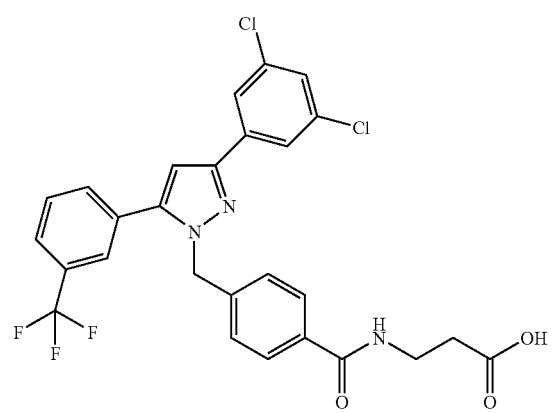 |
| 88 | 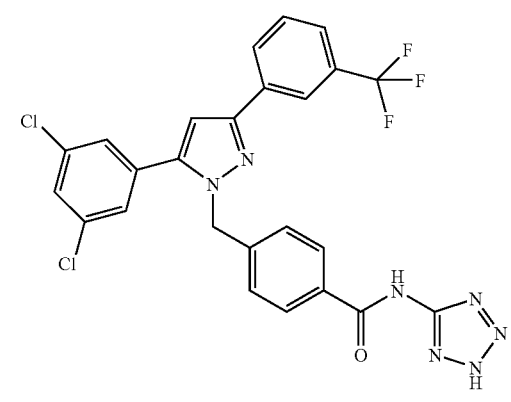 |
| 89 | 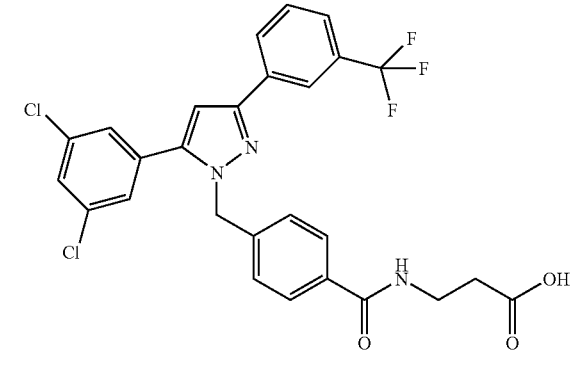 |

-continued
| Cpd No. | Structure |
|---|---|
| 90 | 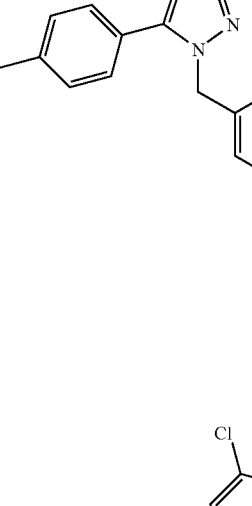 |
| 91 | 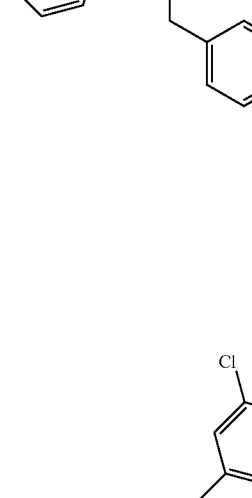 |
| 92 | 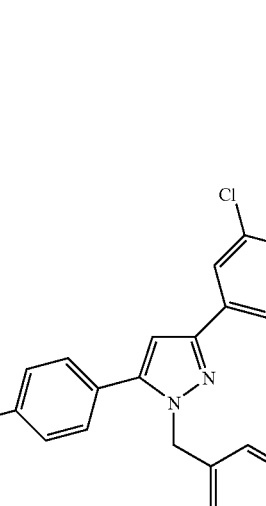 |

| Cpd No. | Structure |
| --- | --- |
| 93 | 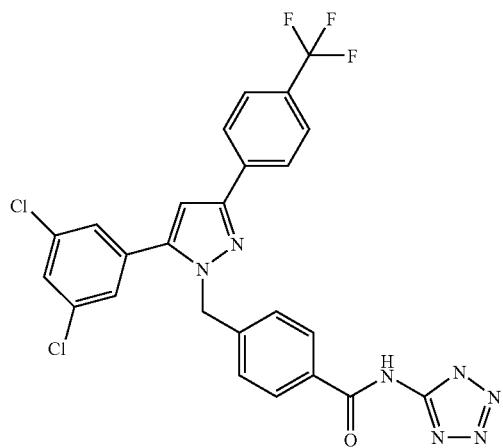 |
| 94 | 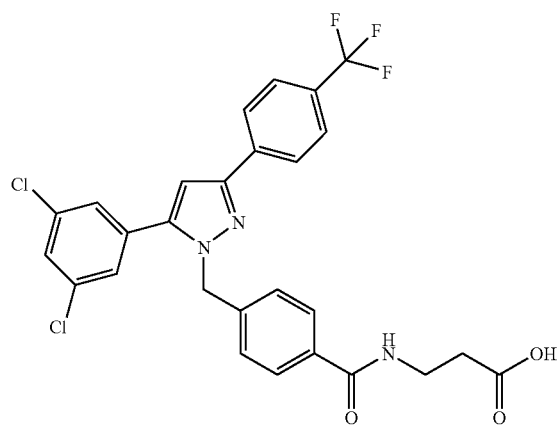 |
| 95 | 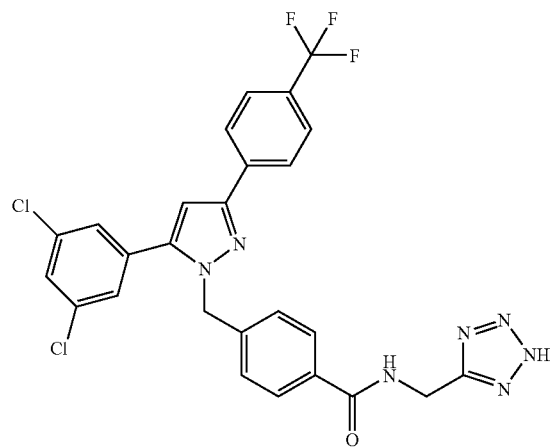 |

-continued
| Cpd No. | Structure |
|---------|-----------|
| 96 | 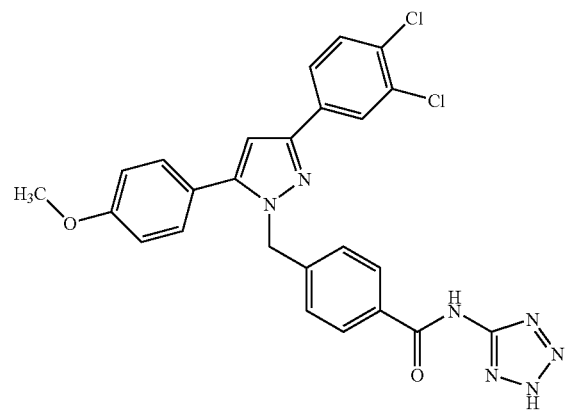 |
| 97 | 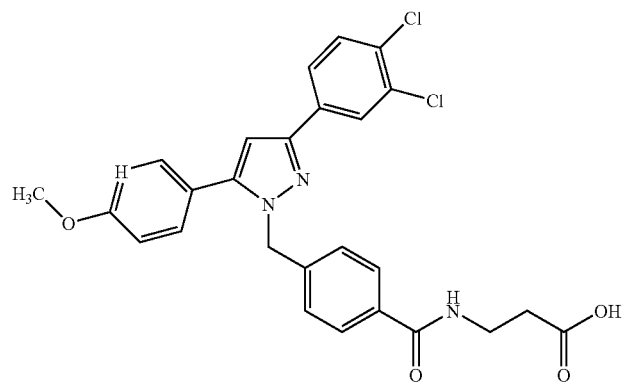 |
| 98 | 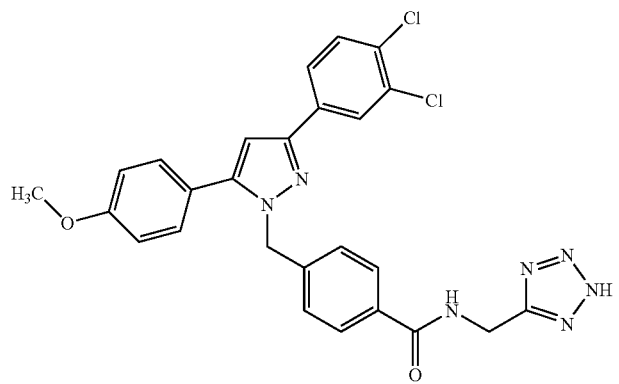 |

-continued
| Cpd No. | Structure |
|---|---|
| 99 | 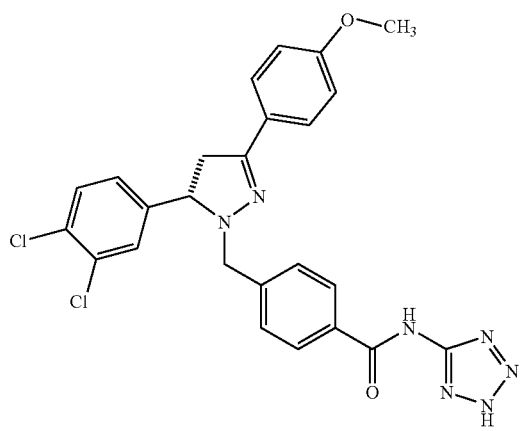 |
| 100 | 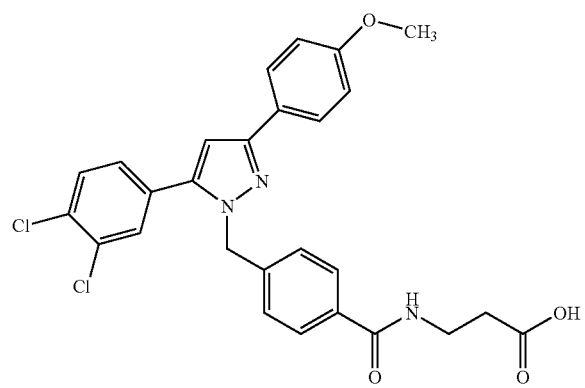 |
| 101 | 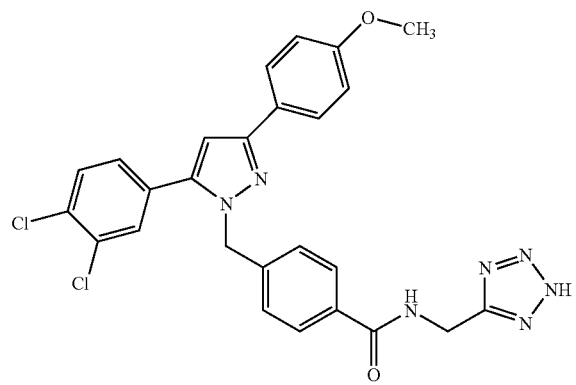 |

-continued

| Cpd No. | Structure |
|---------|-----------|
| 115 | 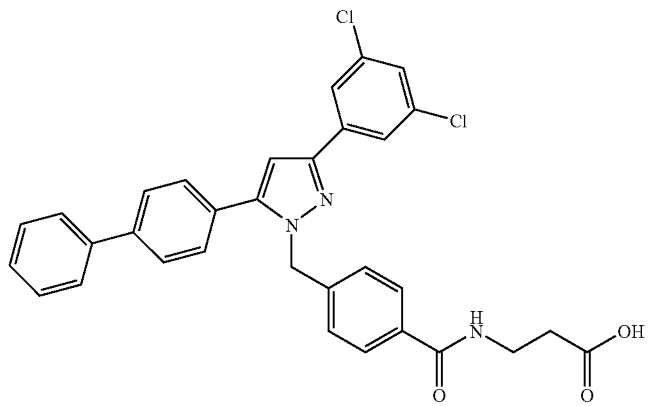 |
| 116 | 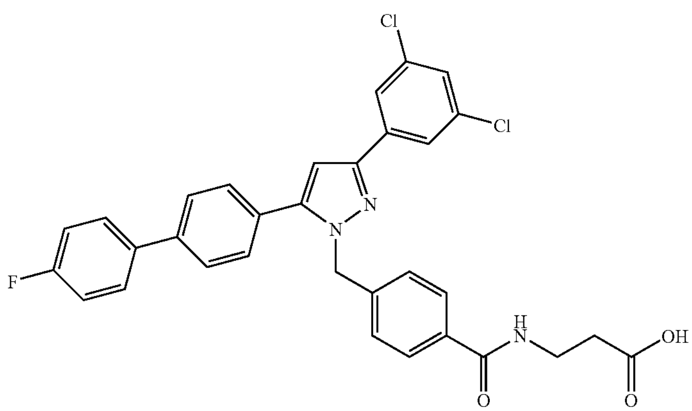 |
| 117 | 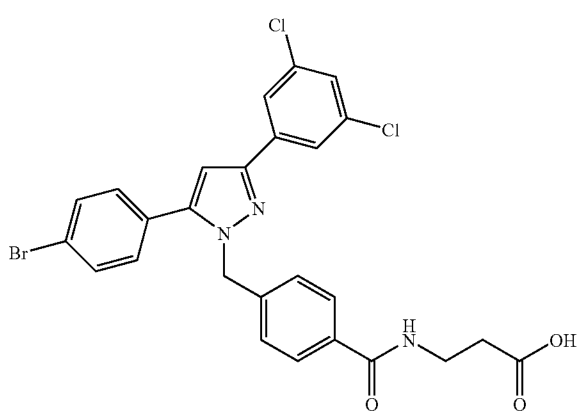 |

-continued
| Cpd No. | Structure |
|---|---|
| 118 | 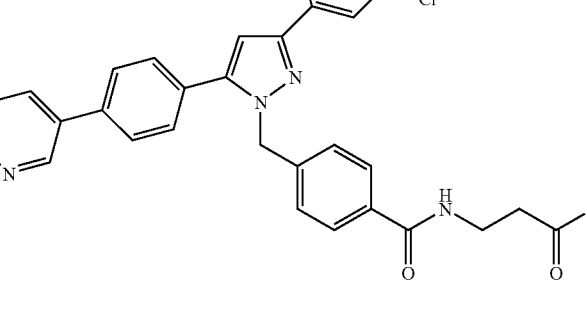 |
| 137 | 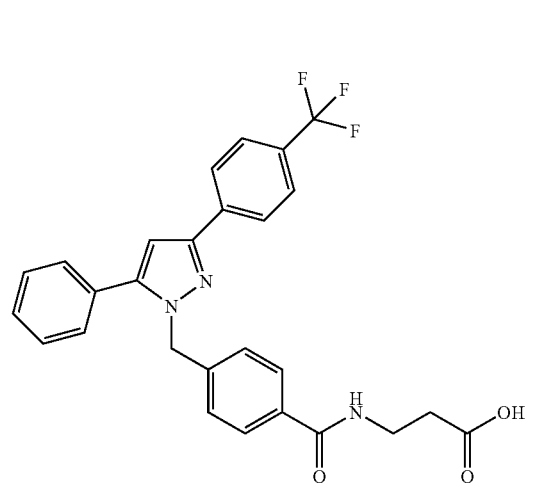 |
| 138 | 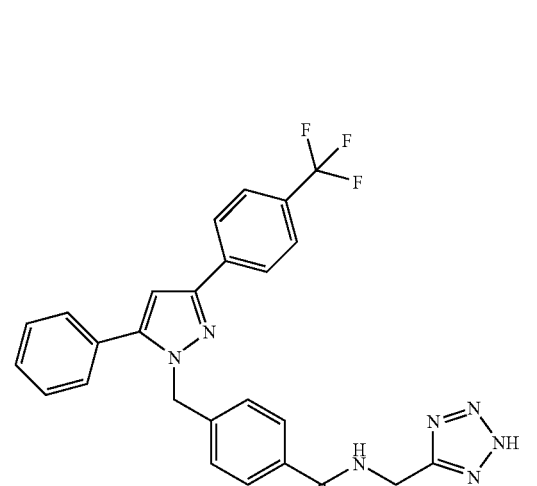 |

-continued
| Cpd No. | Structure |
|---|---|
| 139 | 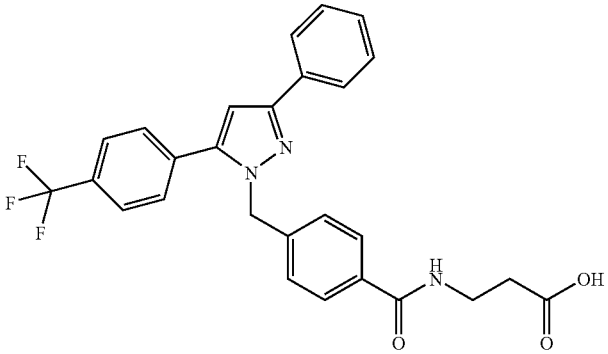 |
| 140 | 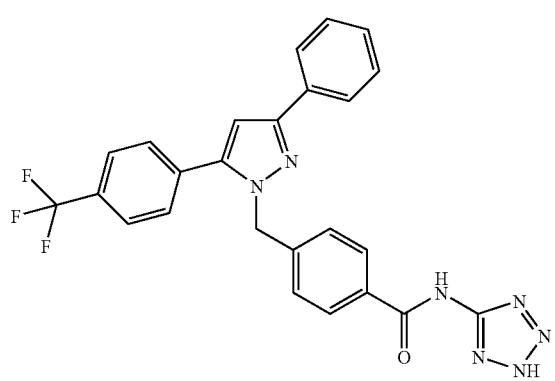 |
| 141 | 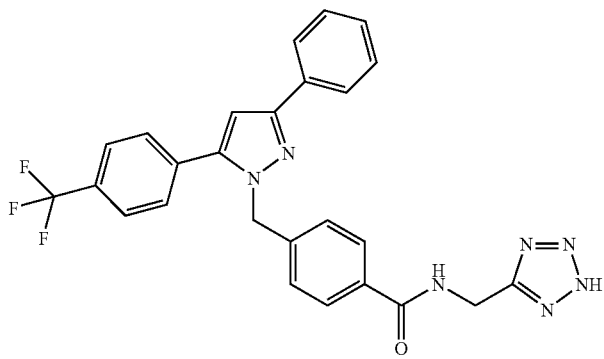 |
| 142 | 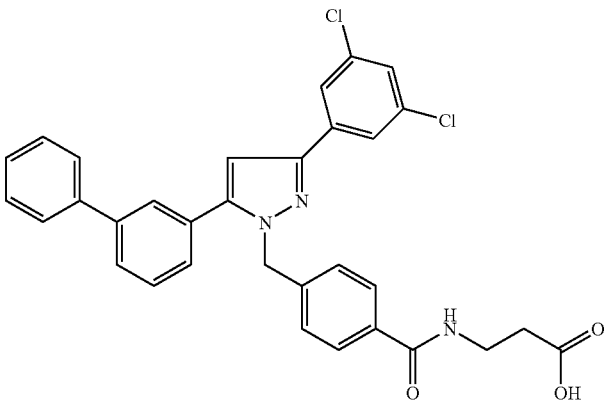 |

-continued
| Cpd No. | Structure |
|---|---|
| 143 | 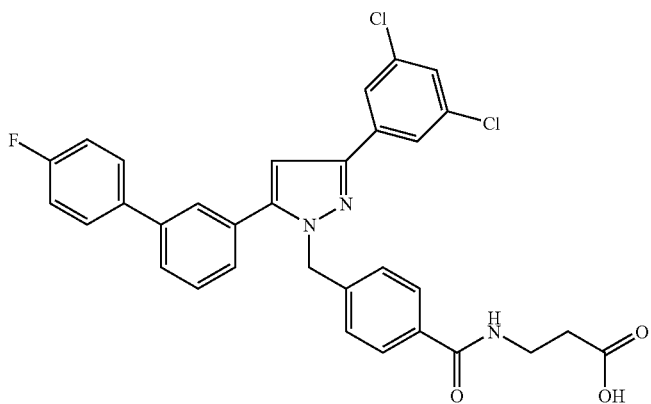 |
| 144 | 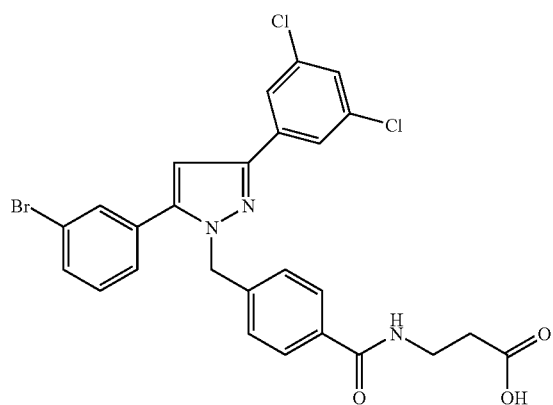 |
| 145 | 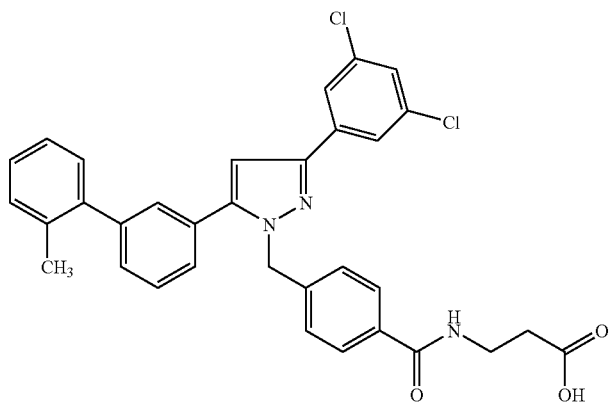 |

-continued
| Cpd No. | Structure |
|---|---|
| 146 | 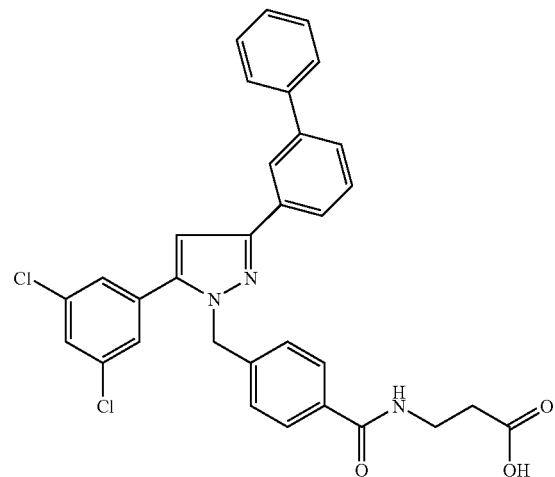 |
| 147 | 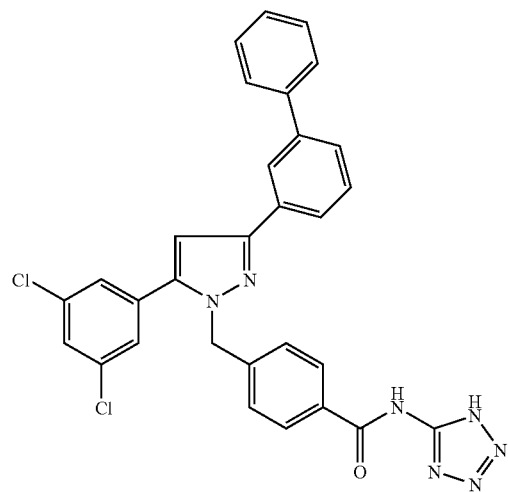 |
| 148 | 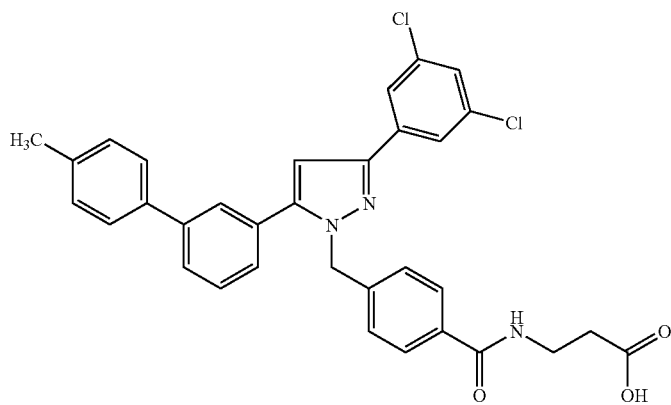 |

-continued
| Cpd No. | Structure |
|---|---|
| 149 | 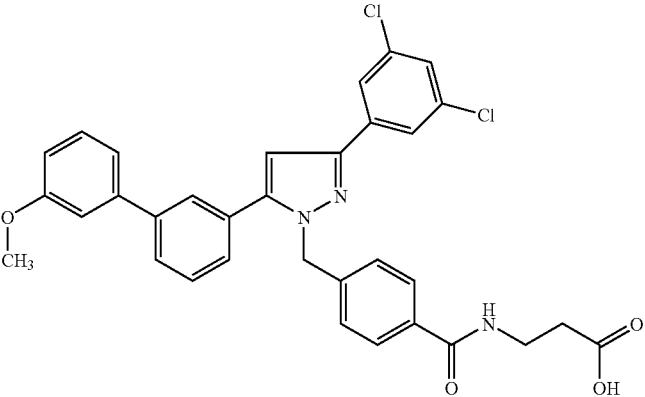 |
| 150 | 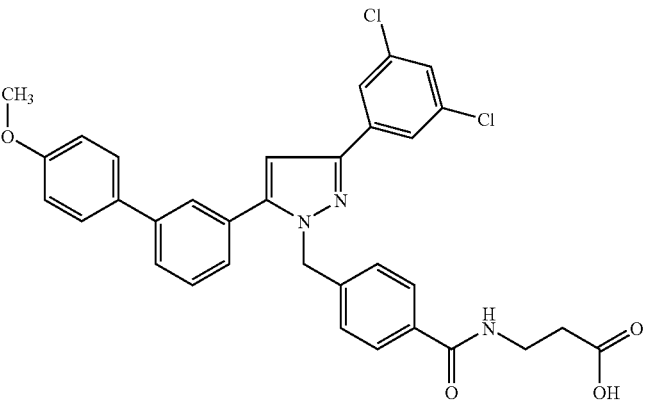 |
| 151 | 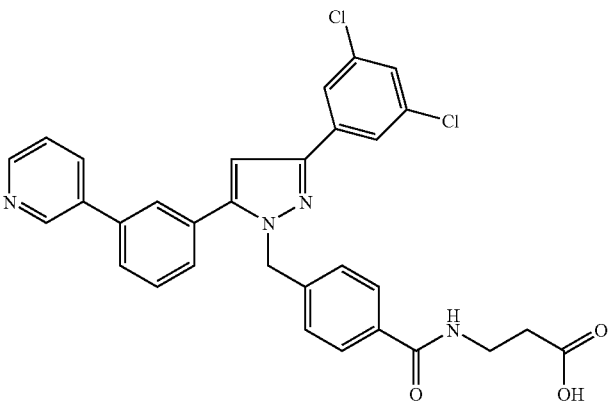 |

| Cpd No. | Structure |
|---|---|
| 152 | 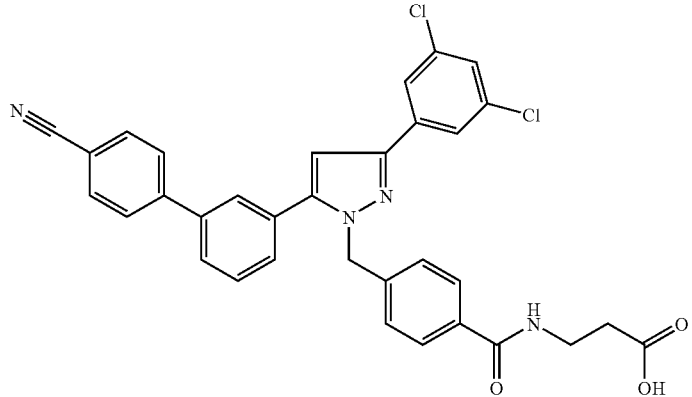 |
| 153 | 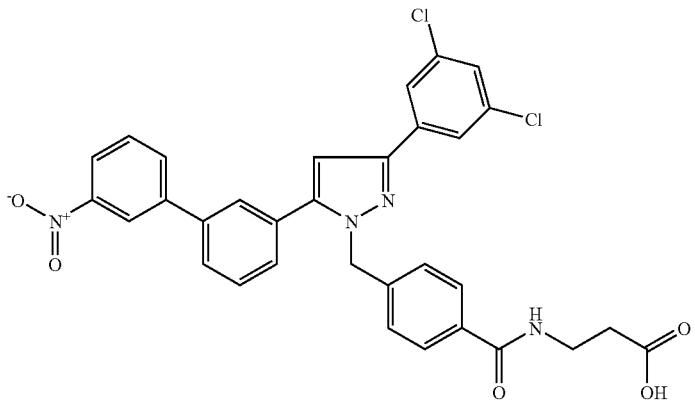 |
| 154 | 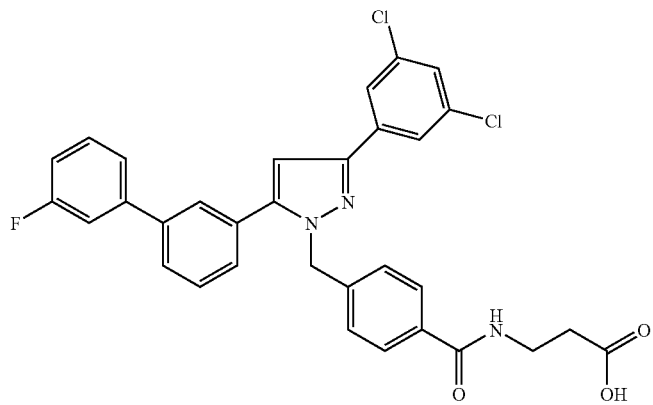 |

-continued
| Cpd No. | Structure |
|---|---|
| 155 | 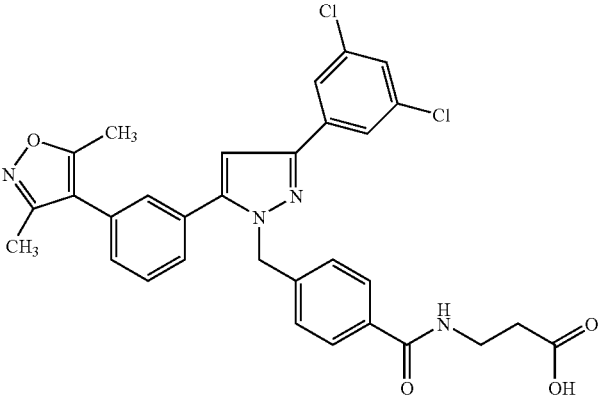 |
| 156 | 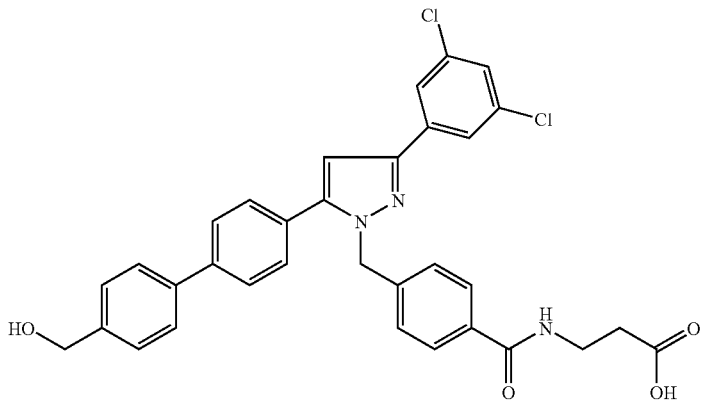 |
| 157 | 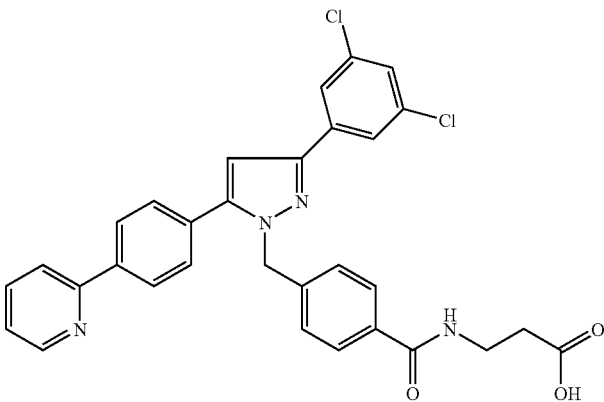 |

-continued
| Cpd No. | Structure |
|---|---|
| 158 | 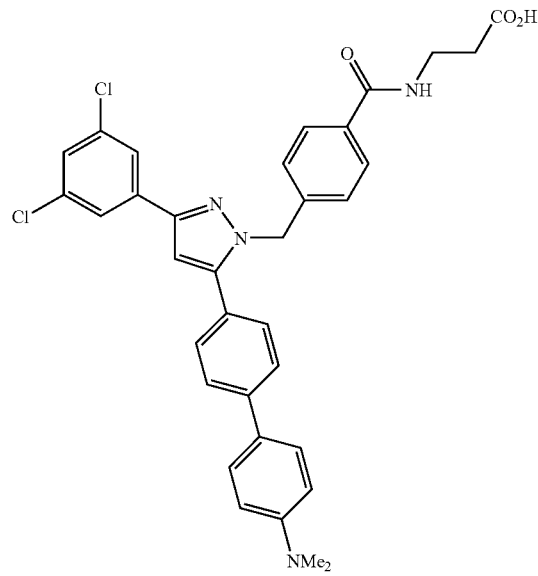 |
| 159 | 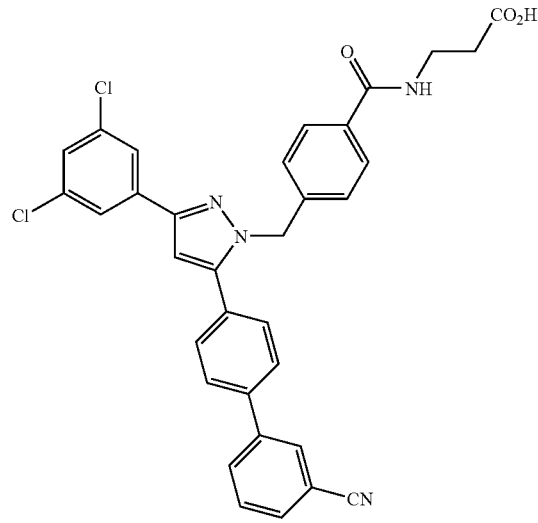 |

-continued
| Cpd No. | Structure |
|---|---|
| 160 | 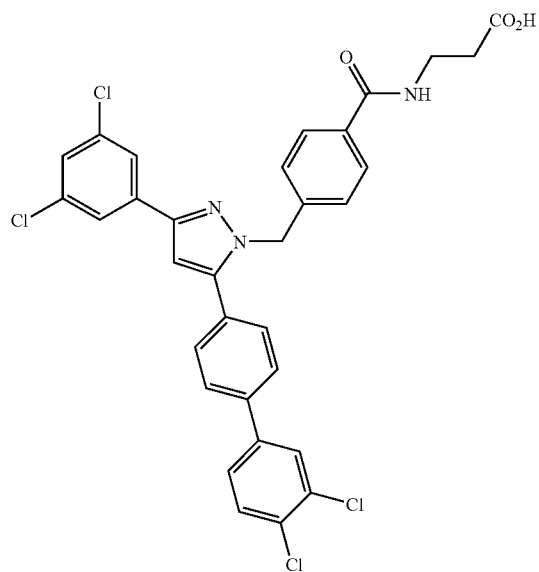 |
| 161 | 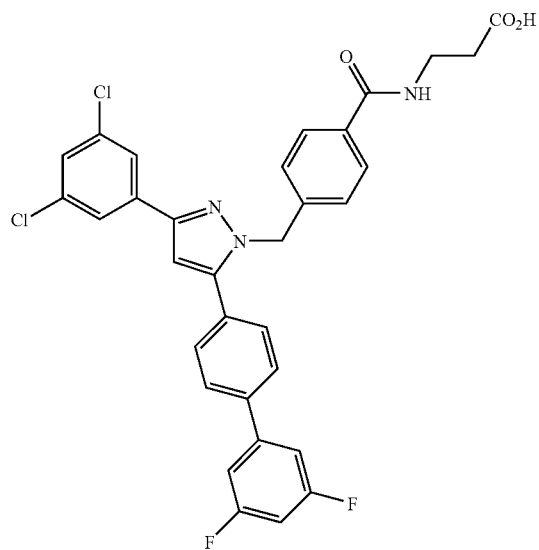 |

| Cpd No. | Structure |
|---|---|
| 162 | 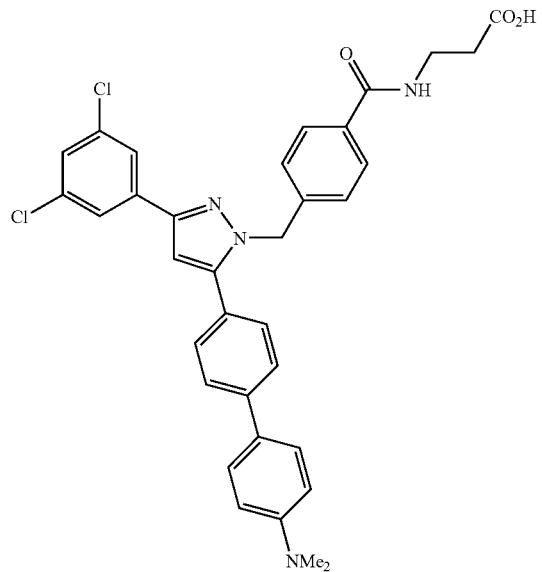 |
| 163 | 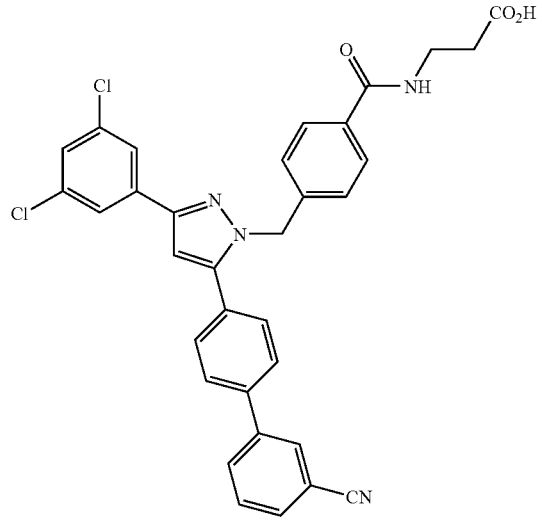 |

-continued
| Cpd No. | Structure |
|---|---|
| 164 | 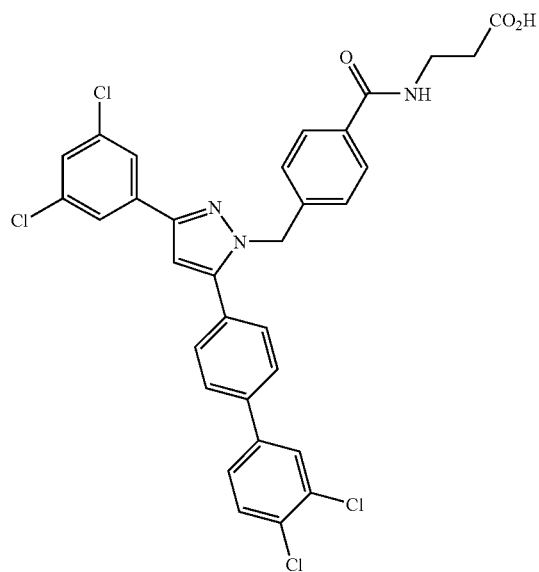 |
| 165 | 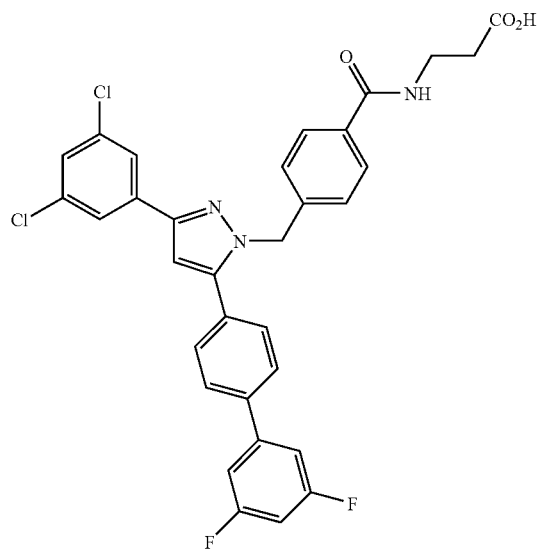 |

-continued
| Cpd No. | Structure |
|---|---|
| 166 | 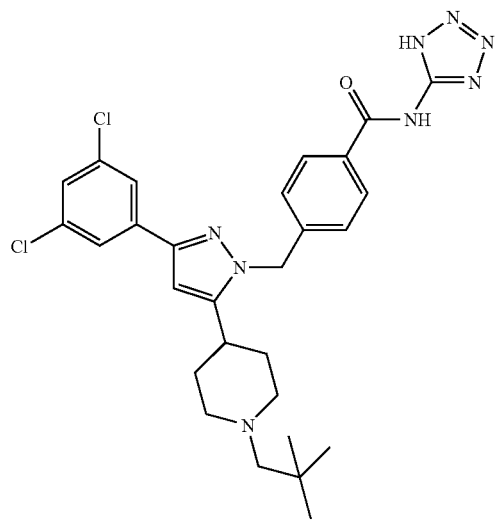 |
| 167 | 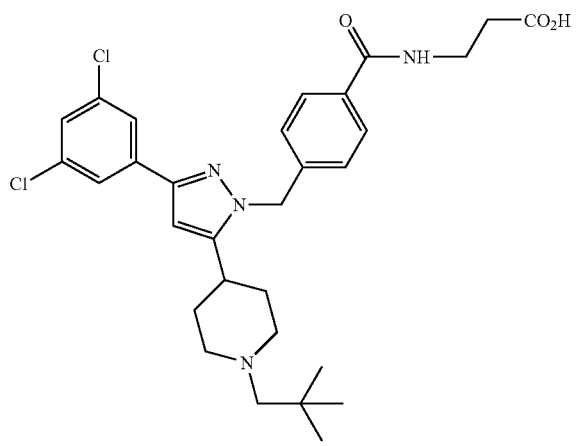 |
| 168 | 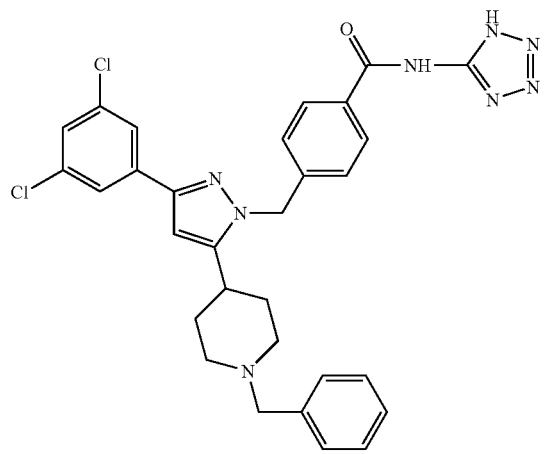 |

-continued
| Cpd No. | Structure |
|---|---|
| 169 | 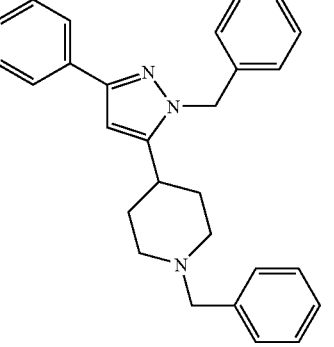 |
| 170 | 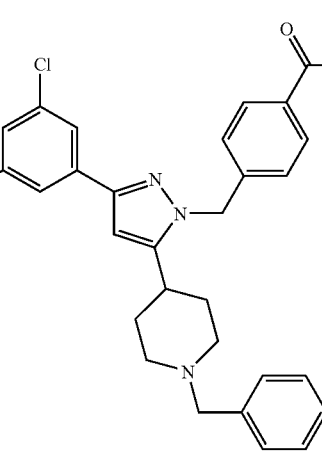 |
| 171 | 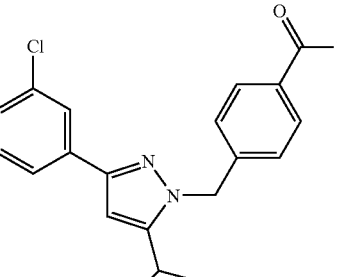 |
or a pharmaceutically acceptable salt thereof.
16. A pharmaceutical composition comprising a compound in accordance with claim 1 or a pharmaceutically acceptable salt thereof in combination with a pharmaceutically acceptable carrier.
* * * * *

UNITED STATES PATENT AND TRADEMARK OFFICE
CERTIFICATE OF CORRECTION

PATENT NO.         : 7,572,922 B2                                          Page 1 of 1
APPLICATION NO. : 10/543290
DATED              : August 11, 2009
INVENTOR(S)        : Parmee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 877 days.

Signed and Sealed this

Twenty-sixth Day of October, 2010

David J. Kappos
*Director of the United States Patent and Trademark Office*